(12) United States Patent
Liu et al.

(10) Patent No.: US 8,389,560 B2
(45) Date of Patent: *Mar. 5, 2013

(54) HCV PROTEASE INHIBITORS

(75) Inventors: Chen-Fu Liu, Taipei (TW);
Kuang-Yuan Lee, Hsinchu (TW);
Pei-Chin Cheng, Xizhou Shiang (TW);
Yo-Chin Liu, Sanchong (TW); Pin Lo,
Sanchong (TW); Kuo-Feng Tseng,
Kaohsiung (TW); Chih-Ming Chen,
Libertyville, IL (US); Chi-Hsin Richard King, Holladay, UT (US); Chu-Chung Lin, Taipei (TW)

(73) Assignee: TaiGen Biotechnology Co., Ltd., Taipei (TW)

( * ) Notice: Subject to any disclaimer, the term of this patent is extended or adjusted under 35 U.S.C. 154(b) by 639 days.

This patent is subject to a terminal disclaimer.

(21) Appl. No.: 12/559,818

(22) Filed: Sep. 15, 2009

(65) Prior Publication Data

US 2011/0065737 A1    Mar. 17, 2011

(51) Int. Cl.
*A61K 31/407*    (2006.01)
*C07D 245/04*    (2006.01)
*C07D 401/12*    (2006.01)

(52) U.S. Cl. .................. 514/411; 540/471; 540/481

(58) Field of Classification Search .................. None
See application file for complete search history.

(56) References Cited

U.S. PATENT DOCUMENTS

| | | | |
|---|---|---|---|
| 4,555,508 | A | 11/1985 | Suh et al. |
| 5,876,984 | A | 3/1999 | Kamigauchi et al. |
| 6,268,207 | B1 | 7/2001 | Bailey |
| 6,323,180 | B1 | 11/2001 | Llinas-Brunet et al. |
| 6,878,722 | B2 | 4/2005 | Campbell et al. |
| 7,566,719 | B2 | 7/2009 | Nakajima et al. |
| 2003/0119752 | A1 | 6/2003 | Farmer et al. |
| 2003/0207861 | A1 | 11/2003 | Arasappan et al. |
| 2003/0224977 | A1 | 12/2003 | Llinas-Brunet et al. |
| 2004/0038872 | A1 | 2/2004 | Campbell et al. |
| 2004/0077551 | A1 | 4/2004 | Campbell et al. |
| 2004/0106559 | A1 | 6/2004 | Wang et al. |
| 2005/0119168 | A1 | 6/2005 | Venkatraman et al. |
| 2005/0153900 | A1 | 7/2005 | Velazquez et al. |
| 2005/0164921 | A1 | 7/2005 | Njoroge et al. |
| 2005/0197299 | A1 | 9/2005 | Babine et al. |
| 2005/0267018 | A1 | 12/2005 | Blatt et al. |
| 2006/0063916 | A1 | 3/2006 | Gallou |
| 2007/0207949 | A1 | 9/2007 | Ghosal et al. |
| 2007/0237818 | A1 | 10/2007 | Malcolm et al. |
| 2008/0039470 | A1 | 2/2008 | Niu et al. |
| 2008/0267917 | A1 | 10/2008 | Niu et al. |
| 2009/0005387 | A1 | 1/2009 | Niu et al. |

FOREIGN PATENT DOCUMENTS

| | | |
|---|---|---|
| WO | WO 00/09543 | 2/2000 |
| WO | 02/18369 | 3/2002 |
| WO | 03/053349 | 7/2003 |
| WO | 03/087092 | 10/2003 |
| WO | 03/099274 | 12/2003 |
| WO | 2004/072243 | 8/2004 |
| WO | 2004/092161 | 10/2004 |
| WO | 2004/092162 | 10/2004 |
| WO | 2004/094452 | 11/2004 |
| WO | 2005/007681 | 1/2005 |
| WO | 2005/028501 | 3/2005 |
| WO | 2005/028502 | 3/2005 |
| WO | 2005/070955 | 8/2005 |
| WO | 2005/116045 | 12/2005 |
| WO | 2006/130607 | 12/2006 |
| WO | WO 2008/002924 | 1/2008 |
| WO | WO2008/022006 | 2/2008 |
| WO | WO2008/134395 | 11/2008 |
| WO | WO 2009055335 A3 * | 7/2009 |

OTHER PUBLICATIONS

Tsantrizos, et al. Angew. Chem. Int. Ed. 42:1355 (2003).*
Mencel et al. "Angiotensin Converting Enzyme Inhibitors. 10. Aryl Sulfonamide Substituted N-[1-Carboxy-3-phenylpropyl]-L-alanynl-L-proline Derivatives as Novel Anithypertensives" J. Med. Chem. 1990, vol. 33, pp. 1606-1615.
Search Report on HCV drug candidates, 36 pages, (Mar. 20, 2008).
Per-Ola Johansson et al. *Potent Inhibitors of the Hepatitis C Virus NS3 Protease: Use of a Novel P2 Cyclopentane-derived Template*, Bioorganic & Medicinal Chemistry 14 (2006) 5136-5151.
Fredrik Thorstensson et al. *Synthesis of Novel Potent Hepatitis C Virus NS3 Protease Inhibitors: Discovery of 4-hydroxy-cyclopent-2-ene-1,2-dicarboxylic Acid as a N-acyl-L-hydroxyproline Bioisostere*, Bioorganic & Medicinal Chemistry 15 (2007) 827-838.
Marcus Bäck et al. *Novel Potent Macrocylic Inhibitors of the Hepatitis C Virus NS3 Protease: Use of Cyclopentane and Cyclopentene P2-motifs*, Bioorganic & Medicinal Chemistry 15 (2007) 7184-7202.
Llinas-Brunet et al. "Structure-Activity Study on a Novel Series of Macrocyclic Inhibitors of the Hepatitis C Virus NS3 Protease Leading to the Discovery of BILN 2061" J. Med. Chem. 47: 1605-1608 (2004).

\* cited by examiner

*Primary Examiner* — Michael Barker
(74) *Attorney, Agent, or Firm* — Occhiuti Rohlicek & Tsao LLP

(57) ABSTRACT

This invention relates to macrocyclic compounds of formula (I) shown in the specification. These compounds can be used to treat hepatitis C virus infection.

28 Claims, No Drawings

HCV PROTEASE INHIBITORS

BACKGROUND

Hepatitis C virus (HCV), a (+)-sense single-stranded RNA virus, is the major causative agent for most cases of non-A, non-B hepatitis. Infection by HCV is a compelling human health problem. See, e.g., WO 05/007681; WO 89/04669; EP 381216; Alberti et al., *J. Hepatology*, 31 (Suppl. 1), 17-24 (1999); Alter, *J. Hepatology*, 31 (Suppl. 1), 88-91 (1999); and Lavanchy, *J. Viral Hepatitis*, 6, 35-47 (1999).

Hepatitis caused by HCV infection is difficult to treat since the virus can quickly mutate and escape the natural immune response. The only anti-HCV therapies currently available are interferon-α, interferon-α/ribavirin combination, and pegylated interferon-α. However, sustained response rates for interferon-α or interferon-α/ribavirin combination were found to be <50% and patients suffer greatly from side effects of these therapeutic agents. See, e.g., Walker, *DDT*, 4, 518-529 (1999); Weiland, *FEMS Microbial. Rev.*, 14, 279-288 (1994); and WO 02/18369. Thus, there remains a need for developing more effective and better-tolerated therapeutic drugs.

An HCV protease necessary for viral replication contains about 3000 amino acids. It includes a nucleocapsid protein (C), envelope proteins (E1 and E2), and several non-structural proteins (NS2, NS3, NS4a, NS5a, and NS5b).

NS3 protein possesses serine protease activity and is considered essential for viral replication and infectivity. The essentiality of the NS3 protease was inferred from the fact that mutations in the yellow fever virus NS3 protease decreased viral infectivity. See, e.g., Chamber et al., *Proc. Natl. Acad. Sci. USA* 87, 8898-8902 (1990). It was also demonstrated that mutations at the active site of the HCV NS3 protease completely inhibited the HCV infection in chimpanzee model. See, e.g., Rice et al., *J. Virol.* 74 (4) 2046-51 (2000). Further, the HCV NS3 protease was found to facilitate proteolysis at the NS3/NS4a, NS4a/NS4b, NS4b/NS5a, NS5a/NS5b junctions and was thus responsible for generating four viral proteins during viral replication. See, e.g., US 2003/0207861. Consequently, the HCV NS3 protease enzyme is an attractive target in treating HCV infection. Potential NS3 HCV protease inhibitors can be found in WO 02/18369, WO 00/09558, WO 00/09543, WO 99/64442, WO 99/07733, WO 99/07734, WO 99/50230, WO 98/46630, WO 98/17679, WO 97/43310, U.S. Pat. No. 5,990,276, Dunsdon et al., *Biorg. Med. Chem. Lett.* 10, 1571-1579 (2000); Llinas-Brunet et al., *Biorg. Med. Chem. Lett.* 10, 2267-2270 (2000); and S. LaPlante et al., *Biorg. Med. Chem. Lett.* 10, 2271-2274 (2000).

SUMMARY

This invention is based on unexpected discoveries that certain macrocyclic compounds block activity of NS3-4A proteases, decrease HCV RNA levels, inhibit HCV protease mutants resistant to other inhibitors, and show a prolonged half-life in the blood system.

In one aspect, this invention relates to compounds of formula (I):

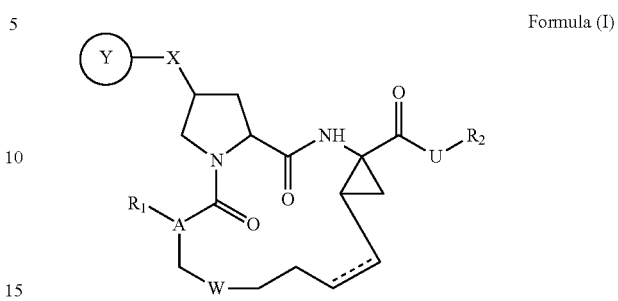

Formula (I)

wherein $R_1$ is —H, —OH, $C_{1-6}$ alkyl, $C_{1-6}$ alkoxyl, $C_{3-10}$ cycloalkyl, $C_{1-10}$ heterocycloalkyl, aryl, heteroaryl, —Z—R, or —NH—Z—R; in which R is H, or is a moiety selected from $C_{1-6}$ alkyl, $C_{3-10}$ cycloalkyl, $C_{1-10}$ heterocycloalkyl, aryl, and heteroaryl, each of which is optionally mono-, di- or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl; and Z is —C(O)—, —C(O)O—, —C(O)C(O)O—, —C(O)C(O)NH—, —C(O)NR'—, —OC(S)—, —C(S)NR'—, or —C(NH)O—, R' being H, $C_{1-6}$ alkyl, $C_{3-10}$ cycloalkyl, $C_{1-10}$ heterocycloalkyl, aryl, or heteroaryl; $R_2$ is H, or is a moiety selected from $C_{1-6}$ alkyl, $C_{3-10}$ cycloalkyl, $C_{1-10}$ heterocycloalkyl, aryl, and heteroaryl, each of which is optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl; A is N or CH; U is —O—, —NH—, —NH(CO)—, —NHS(O)—, or —NHSO$_2$—; W is —(CH$_2$)$_m$—, —NH(CH$_2$)$_n$—, —(CH$_2$)$_n$NH—, —O(CH$_2$)$_n$—, —(CH$_2$)$_n$O—, —S(CH$_2$)$_n$—, —(CH$_2$)$_n$S—, —S(O)—, —SO(CH$_2$)$_n$—, —(CH$_2$)$_n$S(O)—, —SO$_2$(CH$_2$)$_n$—, or —(CH$_2$)$_n$SO$_2$—, m being 1, 2, or 3 and n being 0, 1, or 2; X is —O—, —S—, —NH—, or —OCH$_2$—; Y is

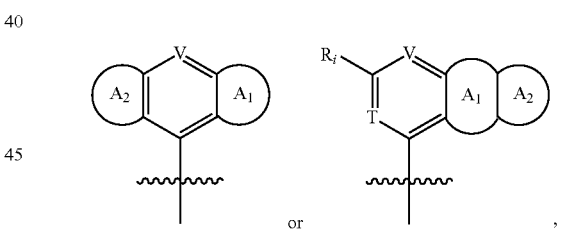

or in which each of V and T, independently, is —CH— or —N—; each of $A_1$ and $A_2$, independently, is a moiety selected from $C_{4-10}$ cycloalkyl, $C_{1-10}$ heterocycloalkyl, aryl, and heteroaryl, each of which is optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl; and $R_i$ is H, halo, nitro, cyano, or amino, or is a moiety selected from $C_{1-6}$ alkyl, $C_{1-6}$ alkoxyl, $C_{2-6}$ alkenyl, $C_{2-6}$ alkynyl, $C_{3-10}$ cycloalkyl, $C_{1-10}$ heterocycloalkyl, aryl, and heteroaryl, each of $C_{1-6}$ alkyl, $C_{1-6}$ alkoxyl, $C_{2-6}$ alkenyl, and $C_{2-6}$ alkynyl being optionally mono-, di- or tri-substituted with halo, nitro, cyano, amino, $C_{1-6}$ alkyl, $C_{1-6}$ alkoxyl, $C_{2-6}$ alkenyl, $C_{2-6}$ alkynyl, $C_{3-10}$ cycloalkyl, $C_{1-10}$ heterocycloalkyl, aryl, or heteroaryl, and each of $C_{3-10}$ cycloalkyl, $C_{1-10}$ heterocycloalkyl, aryl, and heteroaryl being optionally mono-, di- or tri-substituted with halo, nitro, cyano, amino, $C_{1-6}$ alkyl, $C_{1-6}$ alkoxyl, $C_{2-6}$ alkenyl, $C_{2-6}$ alkynyl, $C_{3-10}$ cycloalkyl, $C_{1-10}$ heterocycloalkyl, aryl, or heteroaryl, or optionally fused with $C_{3-10}$ cycloalkyl, $C_{1-10}$ heterocycloalkyl, aryl, or heteroaryl; and ═══ is a single bond or a double bond.

The groups assigned to variables U, W, X, and Z are bivalent. Each of the groups is presented above in the same orientation as that in which the variable is presented in the formula. Take for example the group —NHSO— assigned to the variable U, which, as shown in the formula, is interposed between C═O and $R_2$. The N atom in this —NHS(O)— group is bonded to C═O and the S atom bonded to $R_2$. As another example, the group —C(O)O— assigned to the variable Z is interposed between NH and R (i.e., —NH—Z—R). The C atom in —C(O)O— is bonded to NH and the O atom bonded to R.

Referring to Formula (I), a subset of the compounds feature that $R_1$ is —NH—Z—R, in which Z is —C(O)—, —C(O)O—, —C(O)C(O)O—, or —C(O)C(O)NH—; $R_2$ is

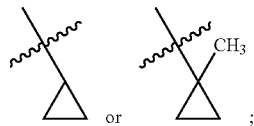

X is O; A is CH; W is —$CH_2CH_2$—, —$OCH_2$—, —$SCH_2$—, or —$SOCH_2$—; U is —$NHSO_2$—; ═══ is a double bond; or Y is

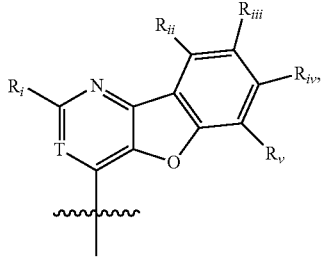

in which T is CH or N; $R_i$ is phenyl or thioazolyl optionally substituted with halo, amino, $C_{1-6}$ alkyl, or $C_{1-6}$ alkoxyl; and each of $R_{ii}$, $R_{iii}$, $R_{iv}$, and $R_v$, independently, is H, halo, nitro, cyano, amino, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl. Examples of $R_1$ are —NH—C(O)O-t-Bu, —NH—C(O)O-cyclopentyl, and —NH—C(O)-furyl.

Another subset of the compounds feature that Y is

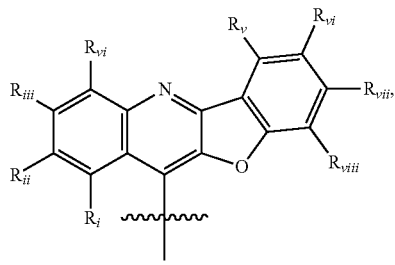

-continued

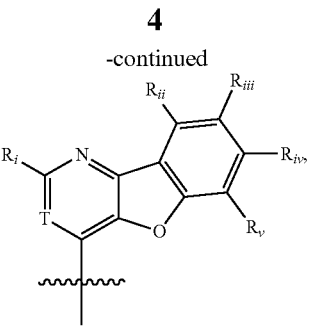

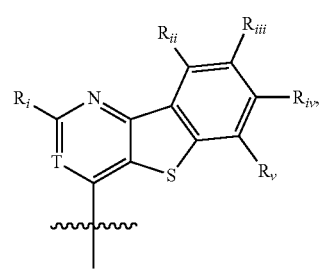

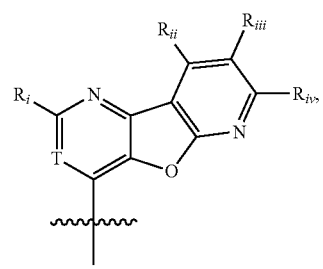

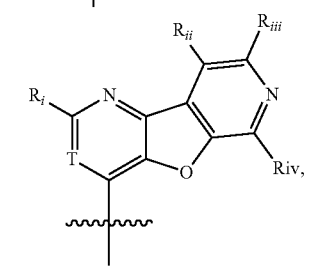

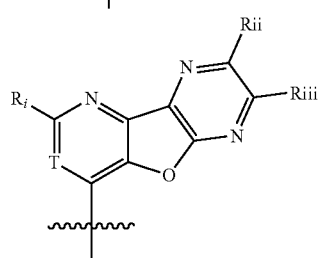

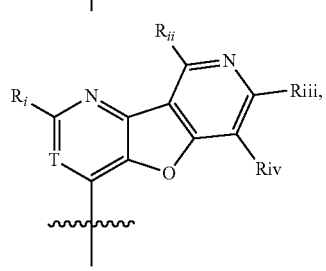

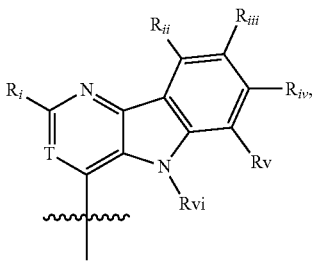

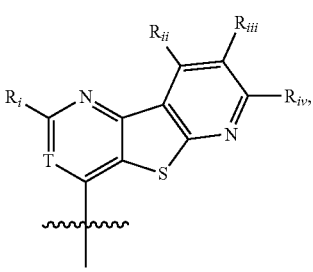

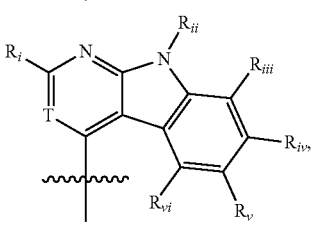

wherein each of $R_i$, $R_{ii}$, $R_{iii}$, $R_{iv}$, $R^v$, and $R_{vi}$, independently, is H, halo, nitro, cyano, amino, $C_{1-6}$ alkyl, $C_{1-6}$ alkoxyl, $C_{2-6}$ alkenyl, $C_{2-6}$ alkynyl, $C_{3-10}$ cycloalkyl, $C_{1-10}$ heterocycloalkyl, aryl, or heteroaryl, each of cycloalkyl, heterocycloalkyl, aryl, and heteroaryl being optionally mono-, di- or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl; and optionally fused with $C_{3-10}$ cycloalkyl, $C_{1-10}$ heterocycloalkyl, aryl, or heteroaryl.

In the above compounds, $R_i$ can be, e.g.,

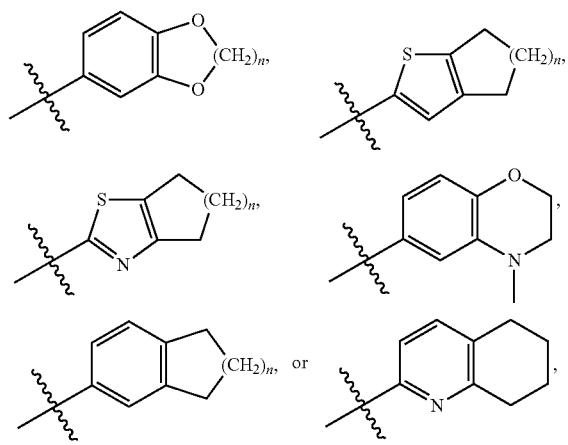

in which the n is 1 or 2.

The compounds of this invention may also feature that ≡ is a single bond, $R_2$ is

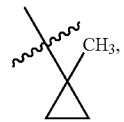 [SMILES: *C1(C)CC1]

or $R_1$ is —H, —OH, $C_{1-6}$ alkyl, $C_{1-6}$ alkoxyl, $C_{3-10}$ cycloalkyl, $C_{1-10}$ heterocycloalkyl, aryl, heteroaryl, or —Z—R.

The term "alkyl" refers to a saturated, linear or branched hydrocarbon moiety, such as —$CH_3$ or —$CH(CH_3)_2$. The term "alkoxy" refers to an —O—($C_{1-6}$ alkyl) radical. The term "alkenyl" refers to a linear or branched hydrocarbon moiety that contains at least one double bond, such as —CH=CH—$CH_3$. The term "alkynyl" refers to a linear or branched hydrocarbon moiety that contains at least one triple bond, such as —C≡C—$CH_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. The term "amino" refers to a radical of —$NH_2$, —NH—($C_{1-6}$ alkyl), or —N($C_{1-6}$ alkyl)$_2$.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

Shown below are 281 exemplary compounds of this invention.
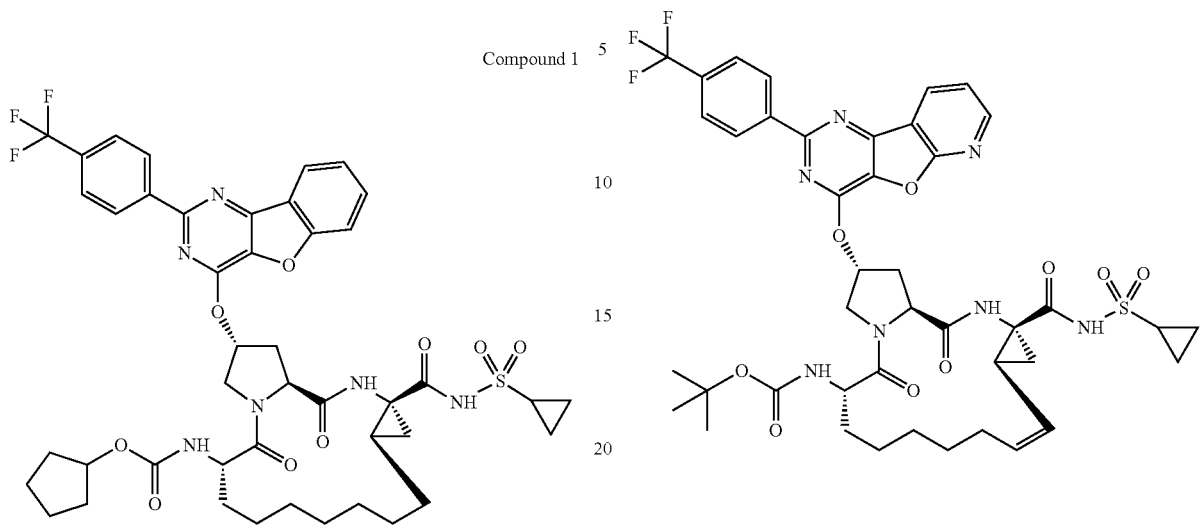
Compound 1
Compound 2
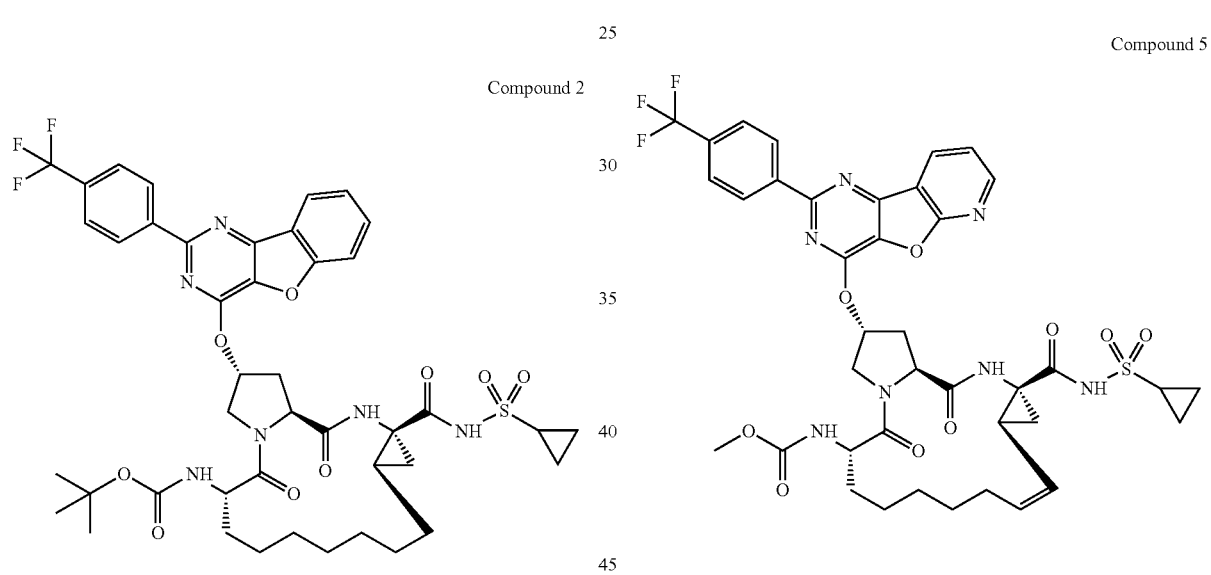
Compound 3
Compound 4
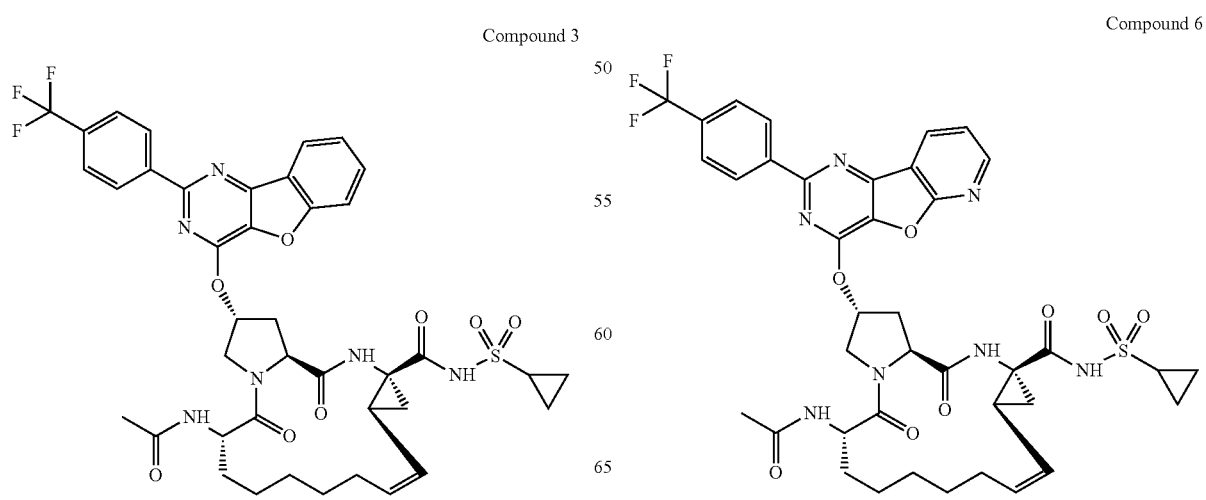
Compound 5
Compound 6

Compound 7
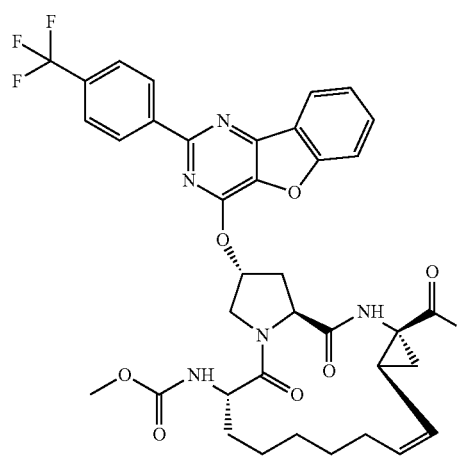
Compound 10
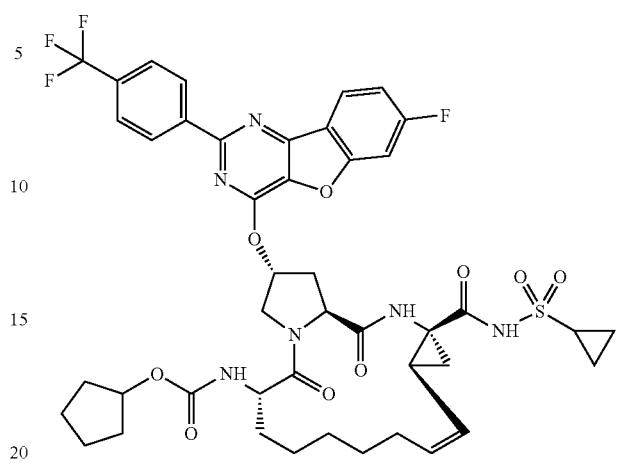
Compound 8
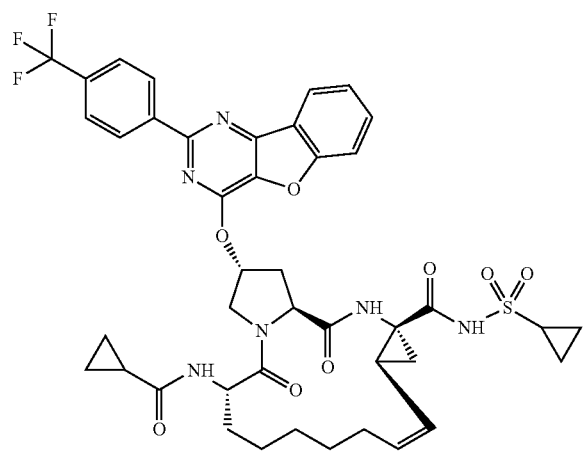
Compound 11
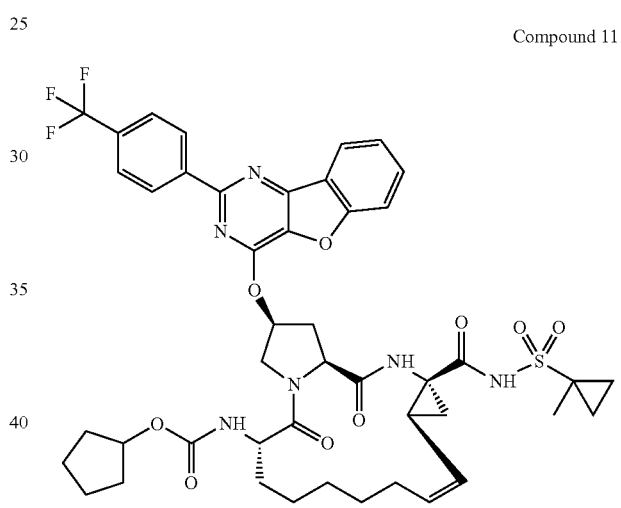
Compound 9
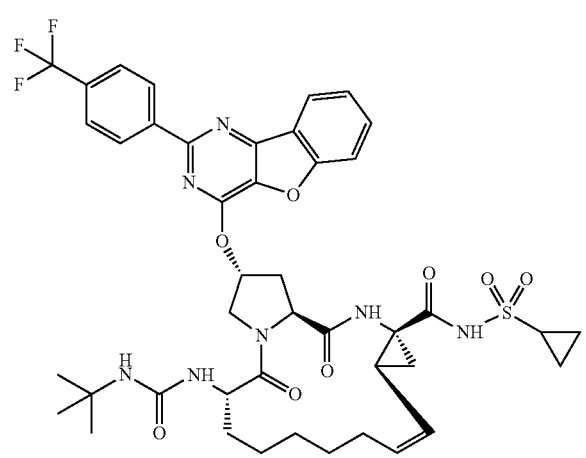
Compound 12
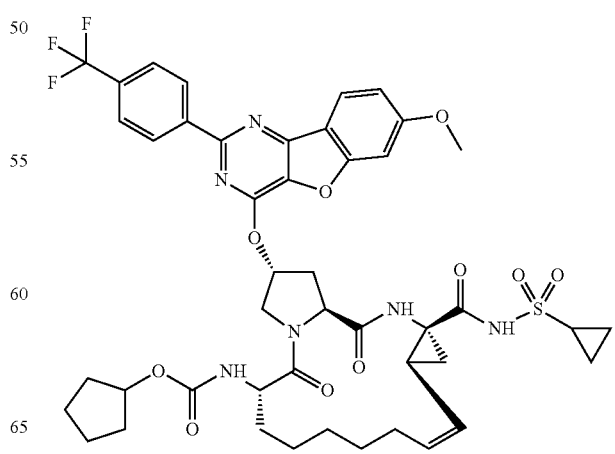

Compound 13
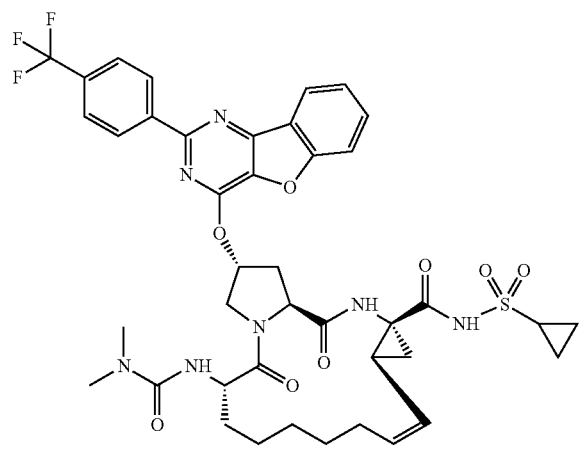
Compound 14
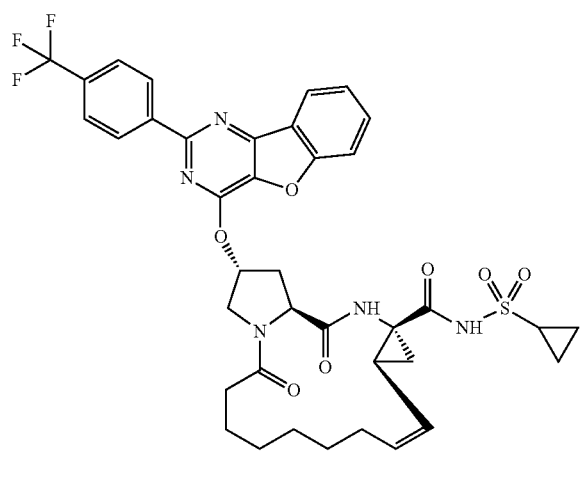
Compound 15
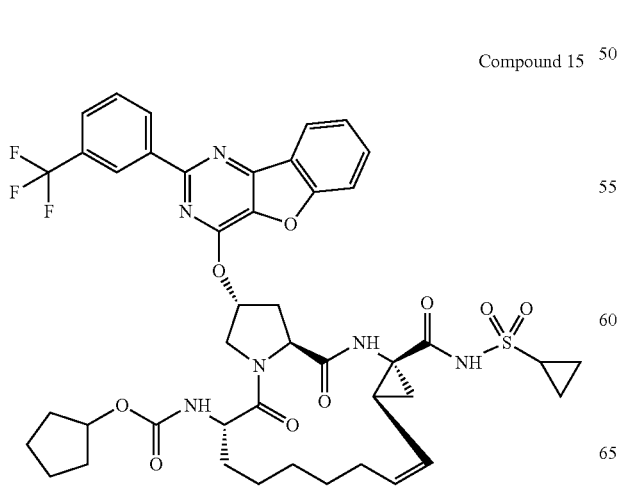
Compound 16
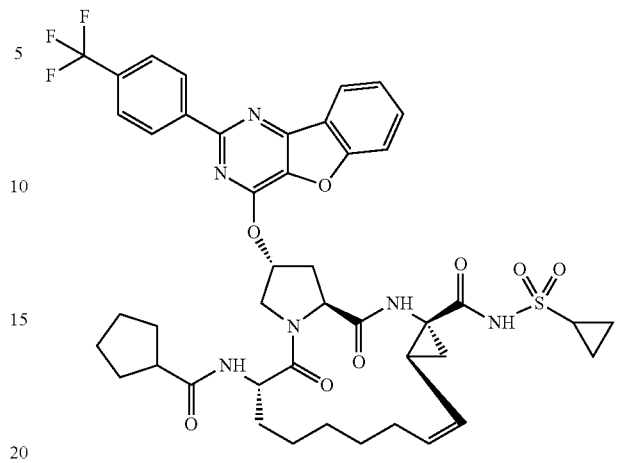
Compound 17
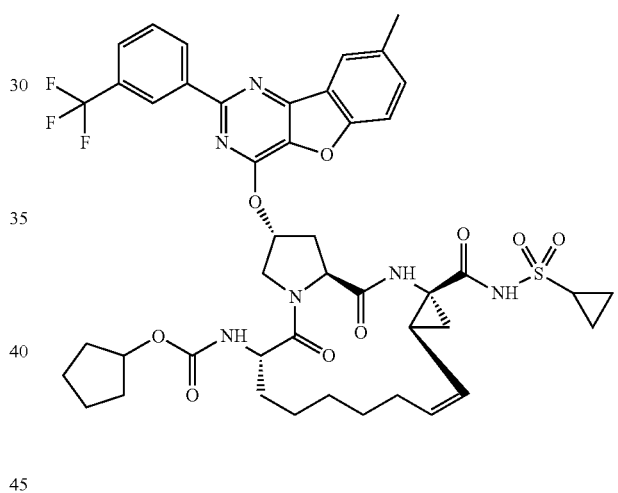
Compound 18
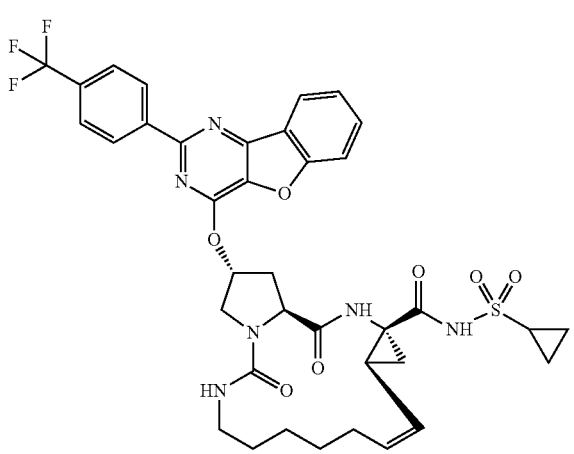

Compound 19
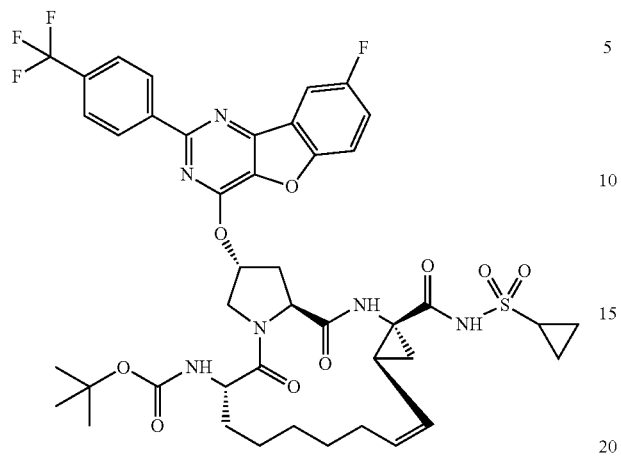
Compound 22
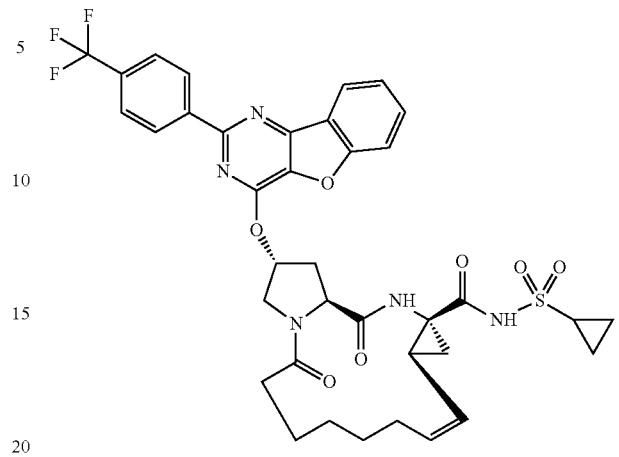
Compound 20
Compound 23
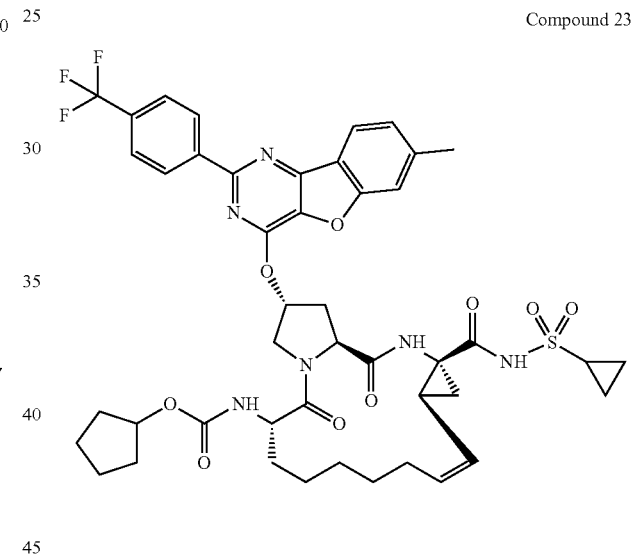
Compound 21
Compound 24
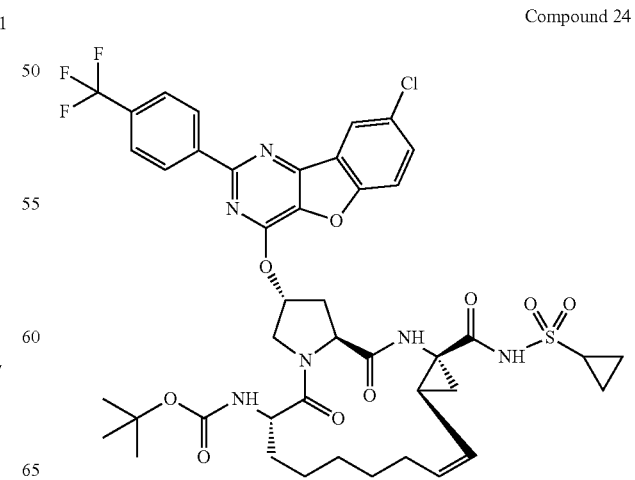

Compound 25
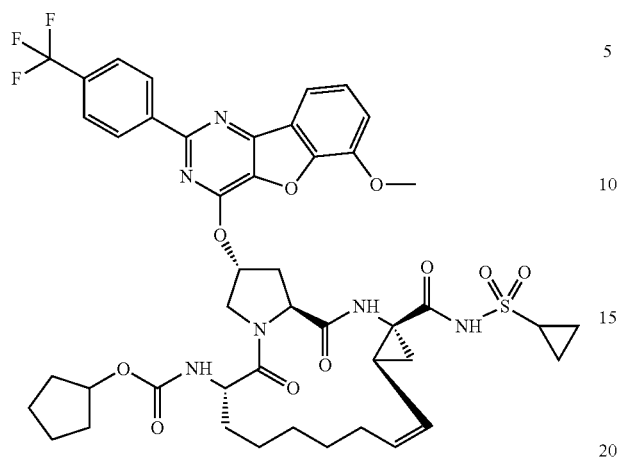
Compound 26
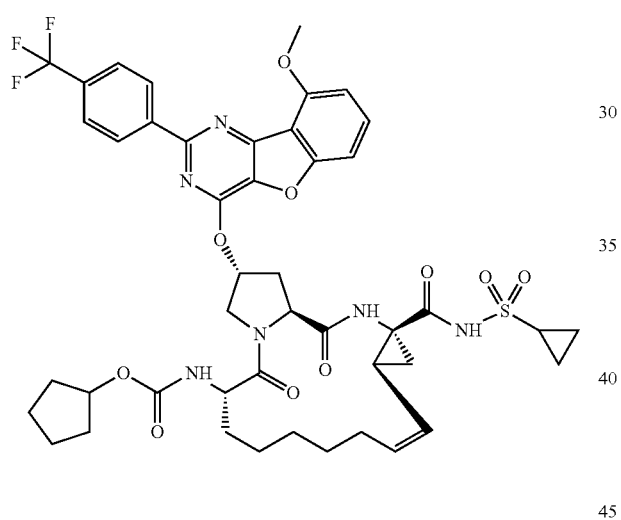
Compound 27
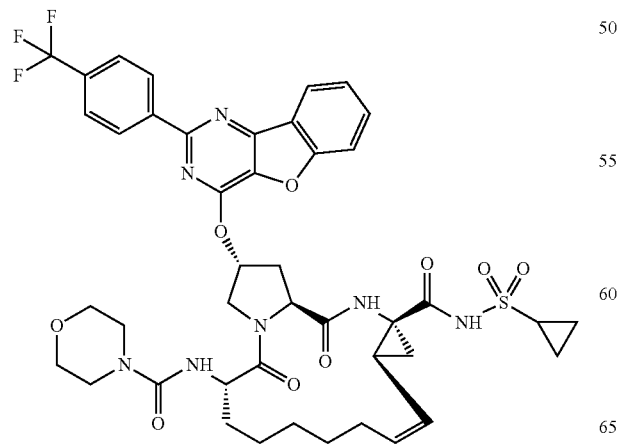
Compound 28
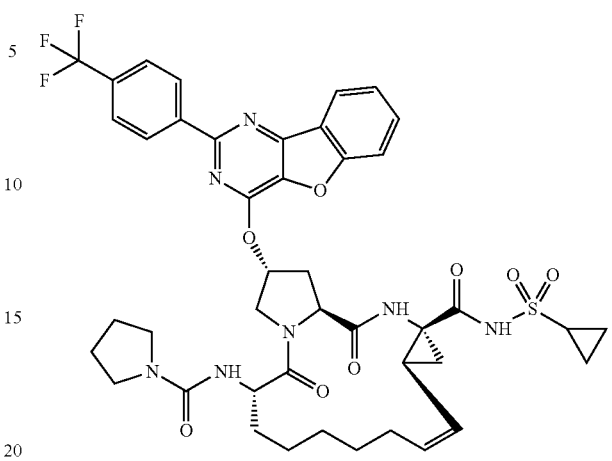
Compound 29
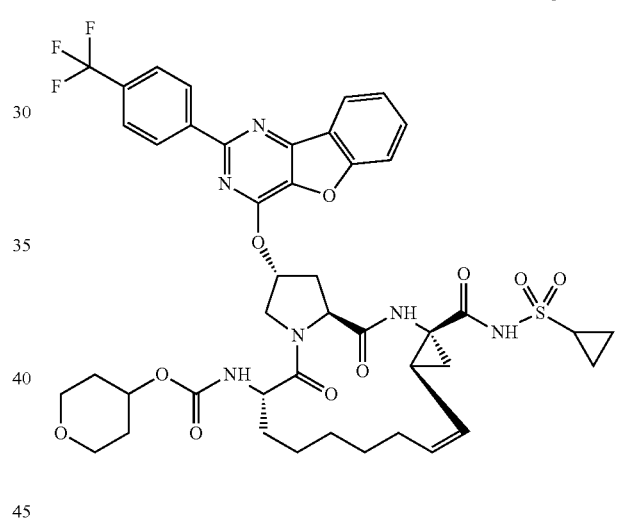
Compound 30
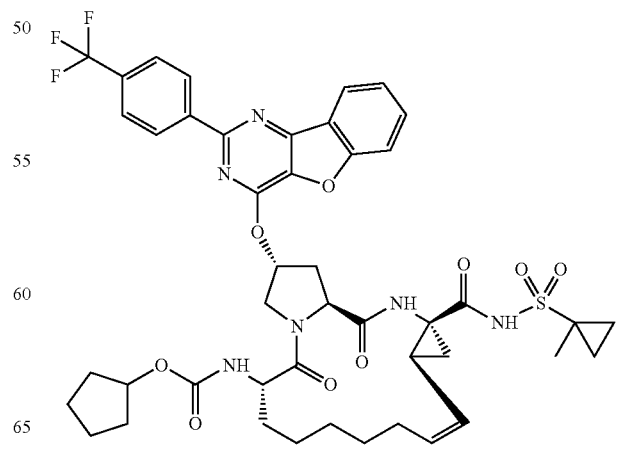

Compound 31
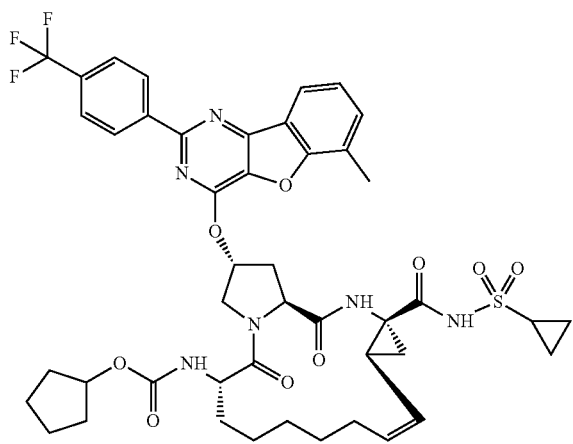
Compound 32
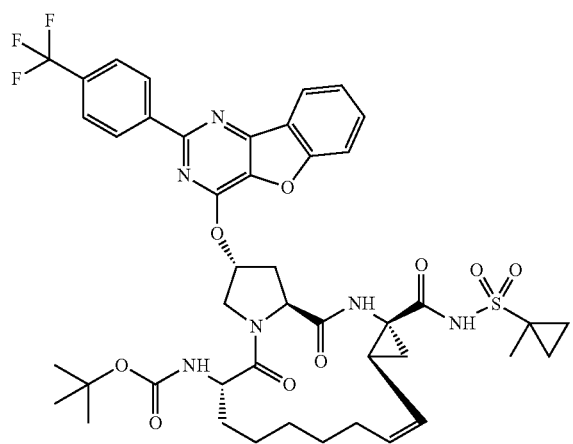
Compound 33
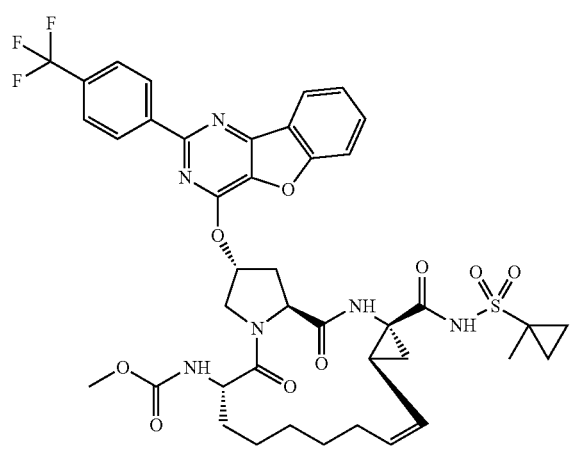
Compound 34
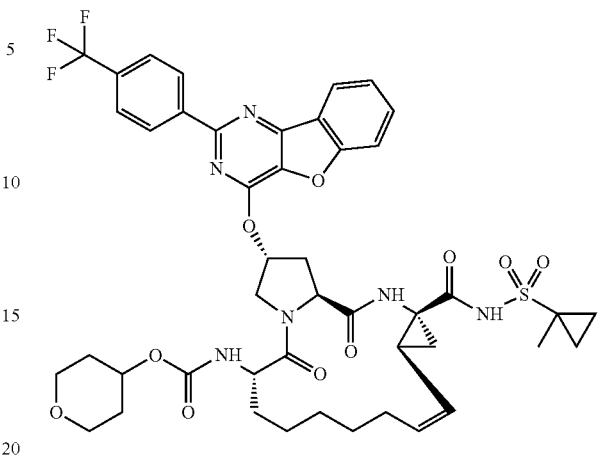
Compound 35
Compound 36
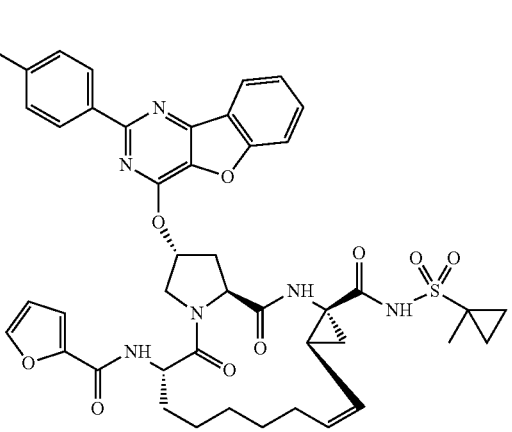

Compound 37
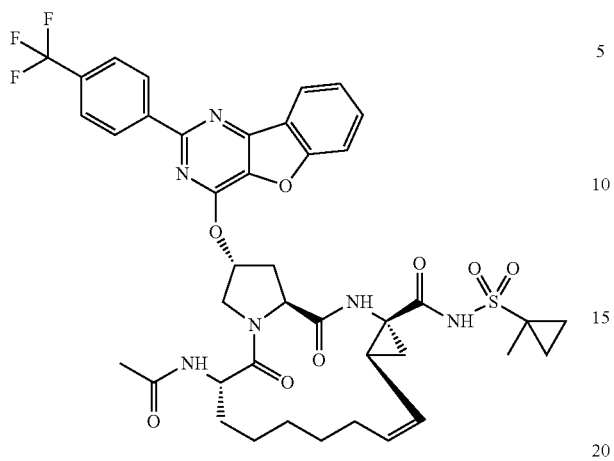
Compound 40
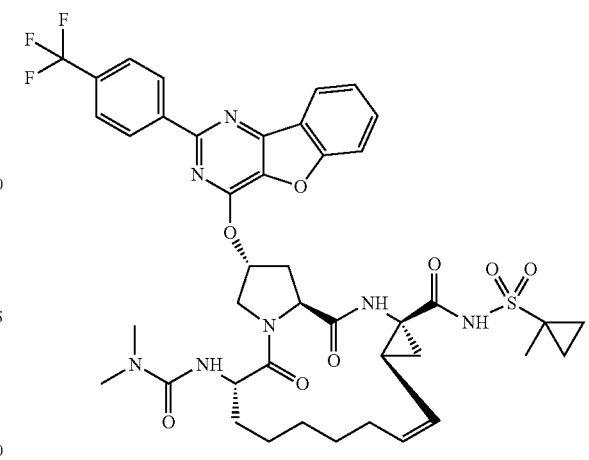
Compound 38
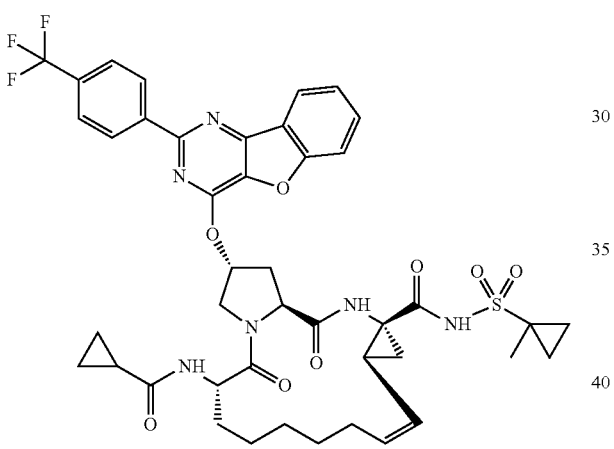
Compound 41
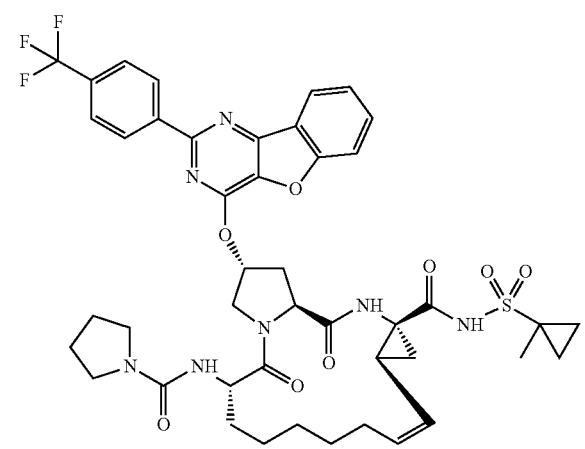
Compound 39
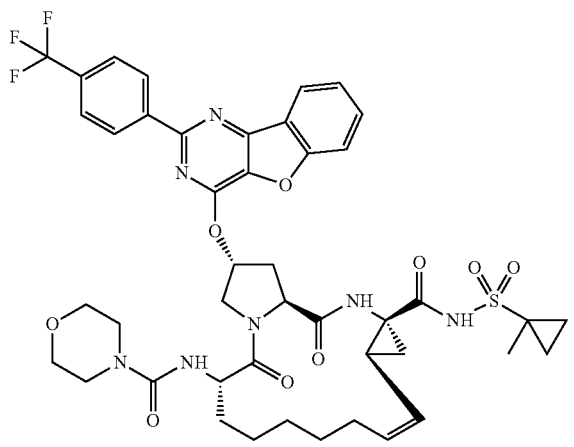
Compound 42

21
-continued
Compound 43
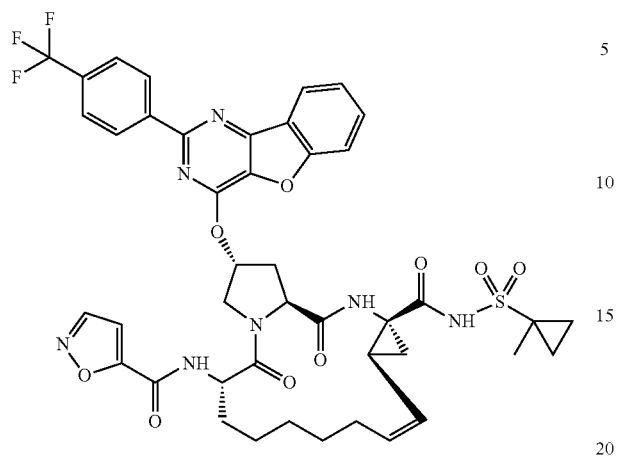
Compound 44
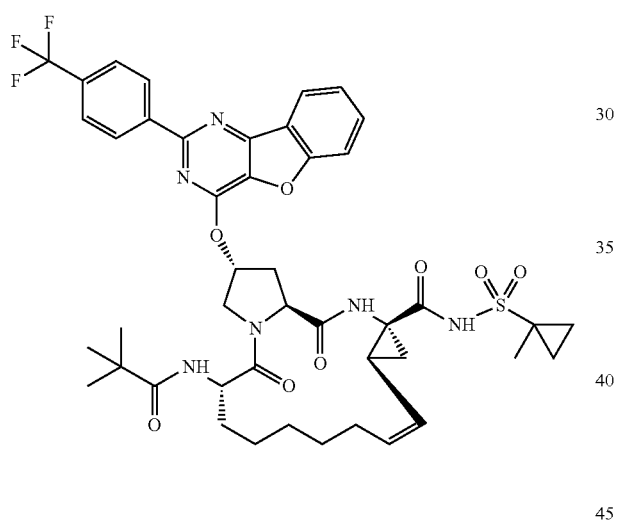
Compound 45
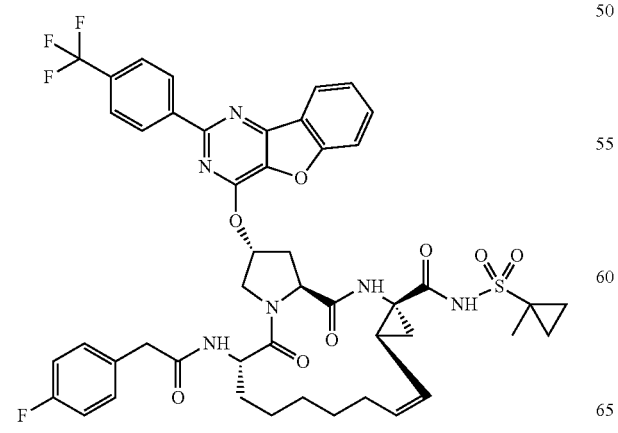
22
-continued
Compound 46
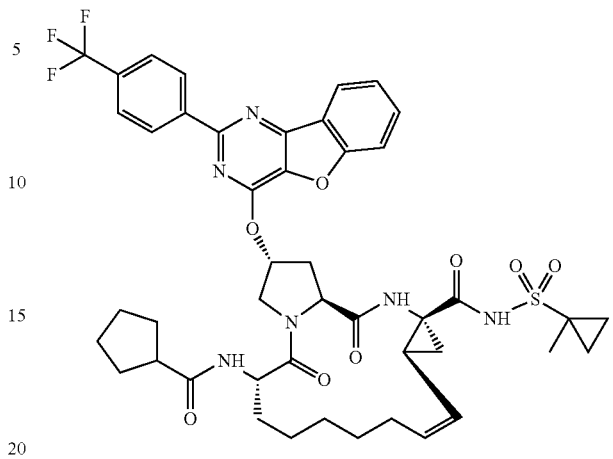
Compound 47
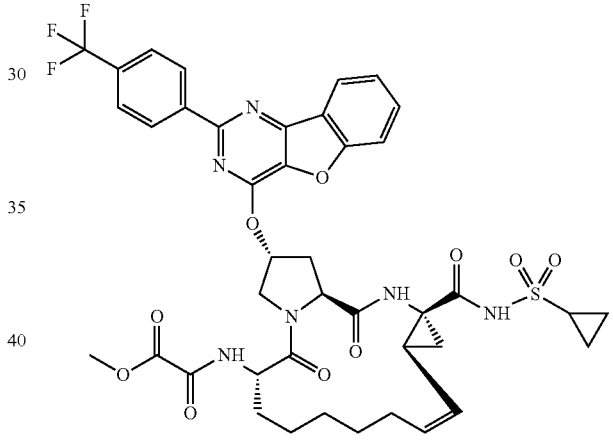
Compound 48
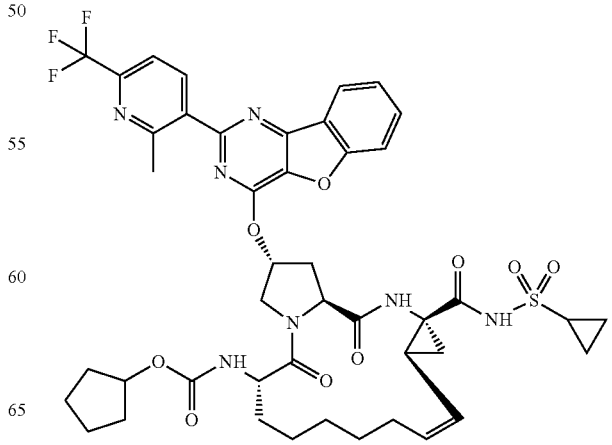

Compound 49
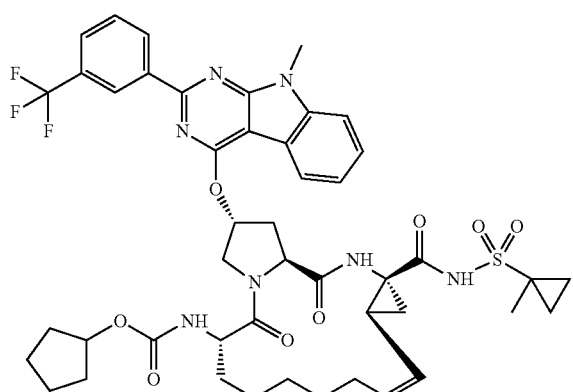
Compound 52
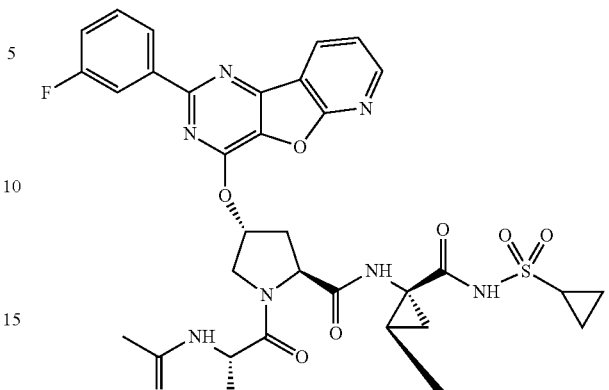
Compound 50
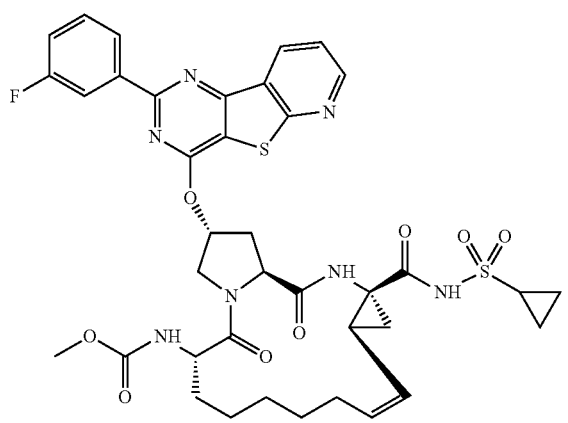
Compound 53
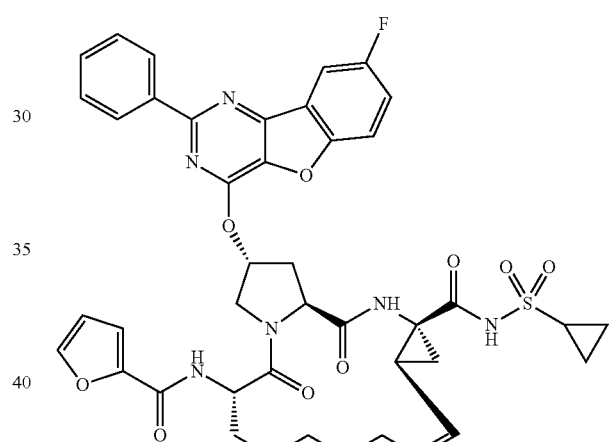
Compound 51
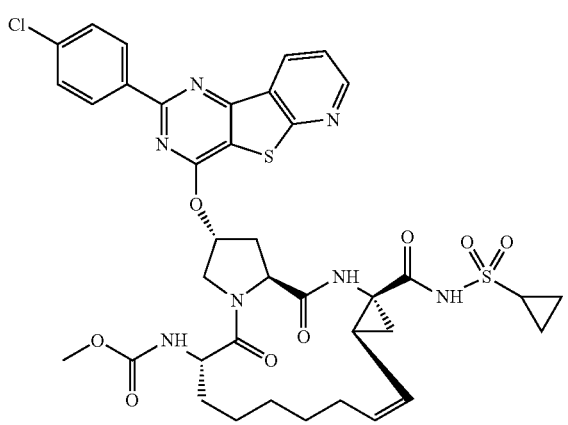
Compound 54
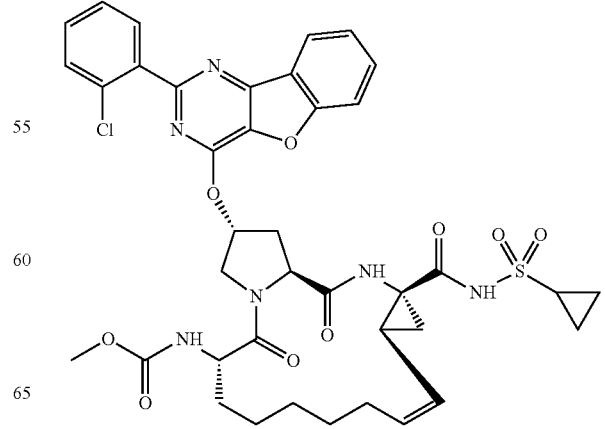

Compound 55
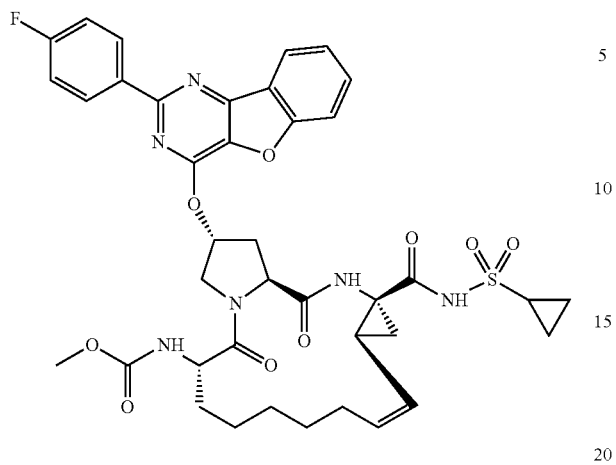
Compound 56
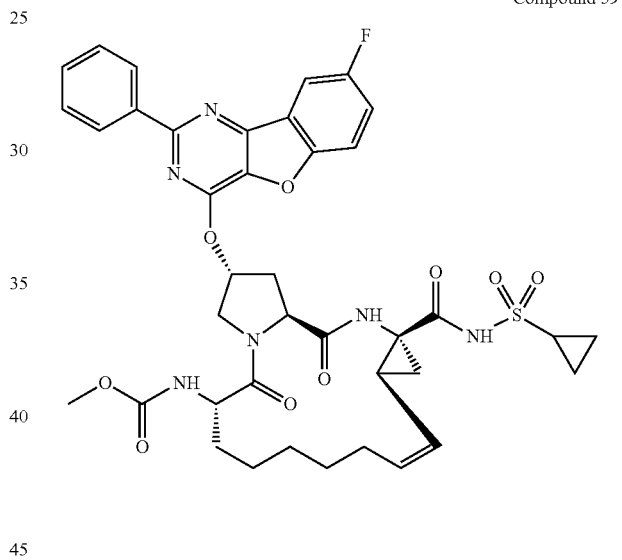
Compound 57
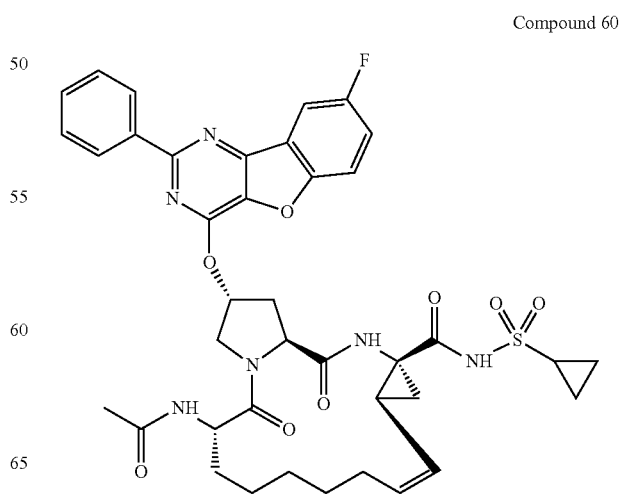
Compound 58
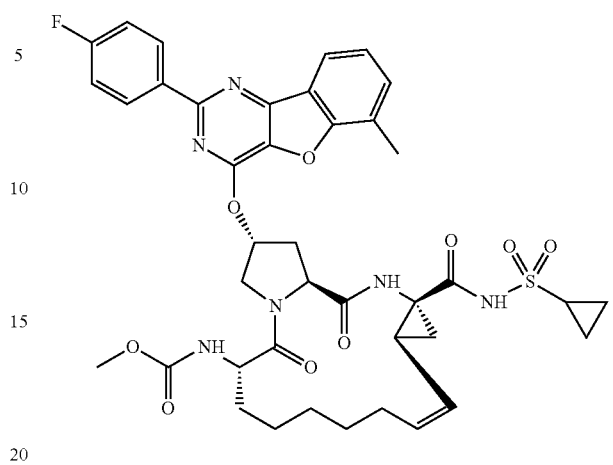
Compound 59
Compound 60

Compound 61
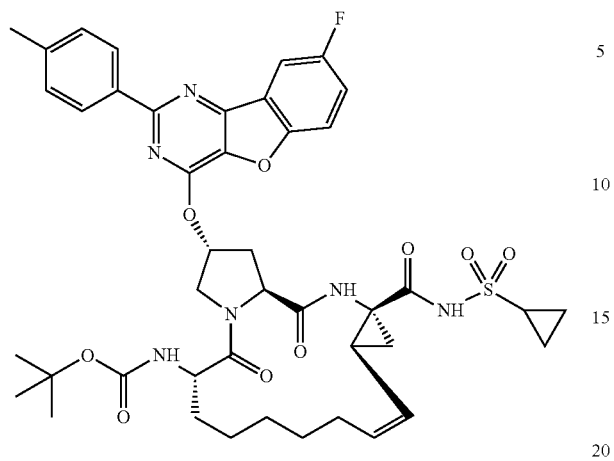
Compound 64
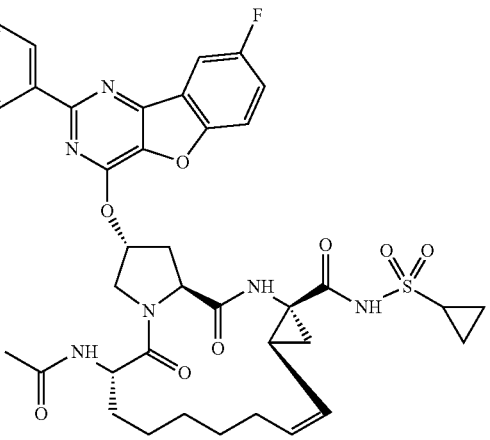
Compound 62
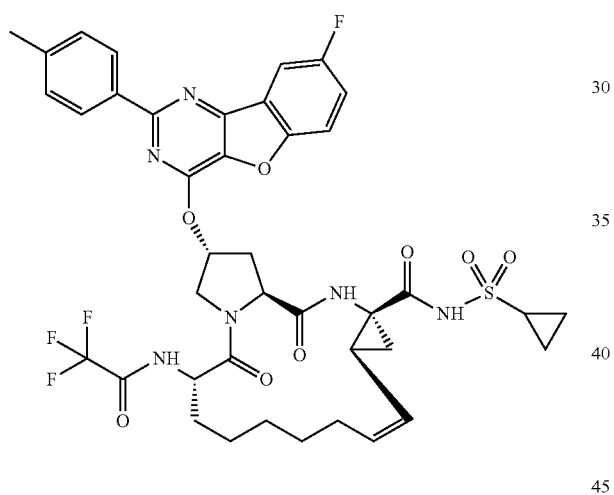
Compound 65
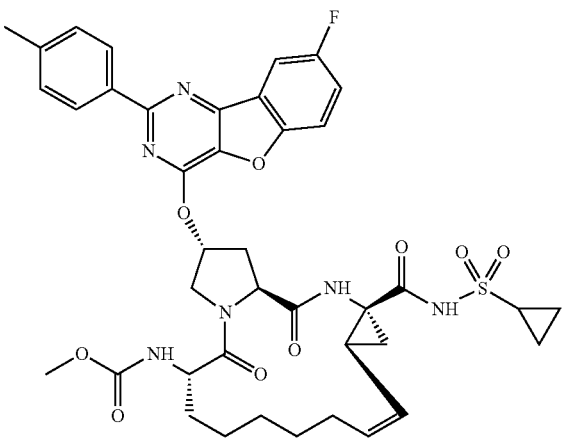
Compound 63
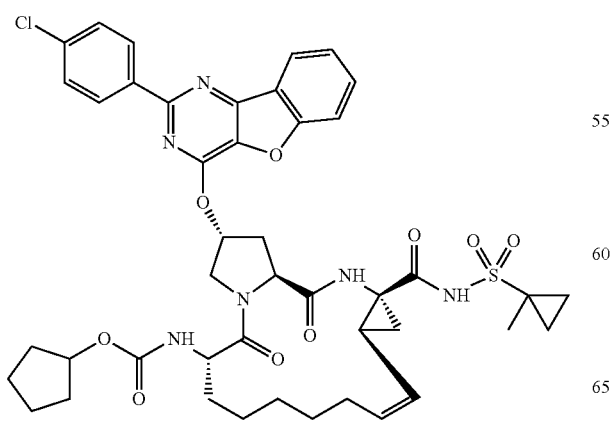
Compound 66
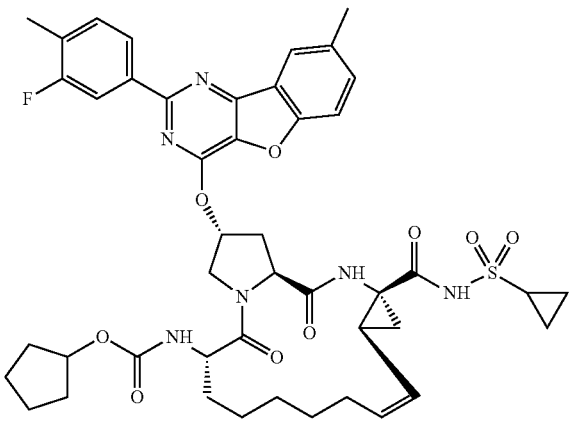

29
-continued
Compound 67
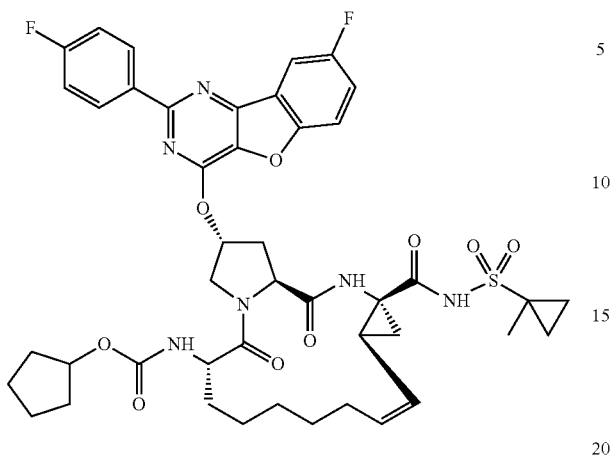
Compound 68
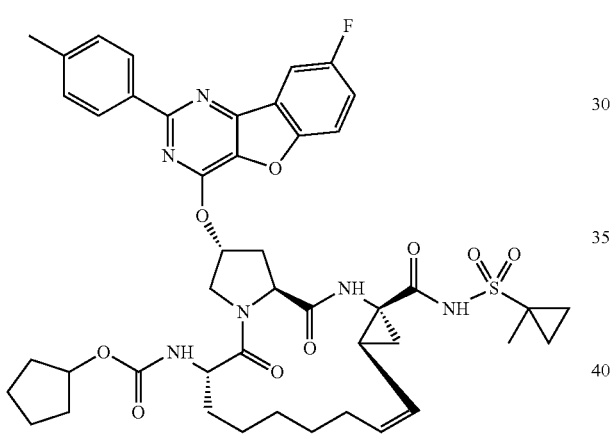
Compound 69
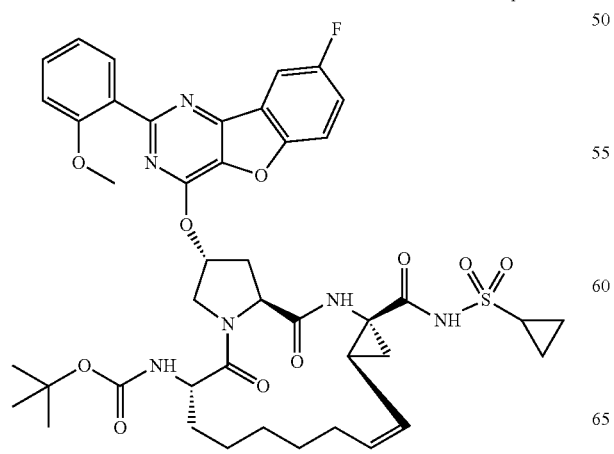
30
-continued
Compound 70
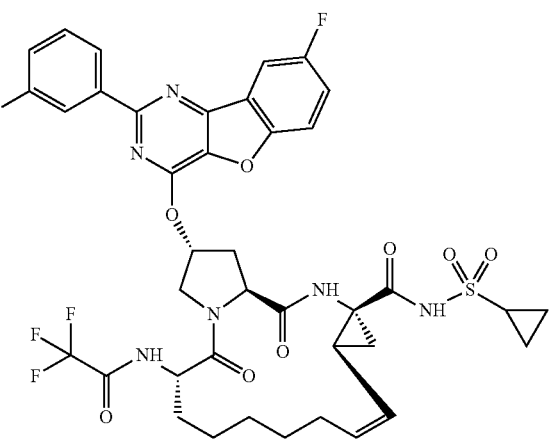
Compound 71
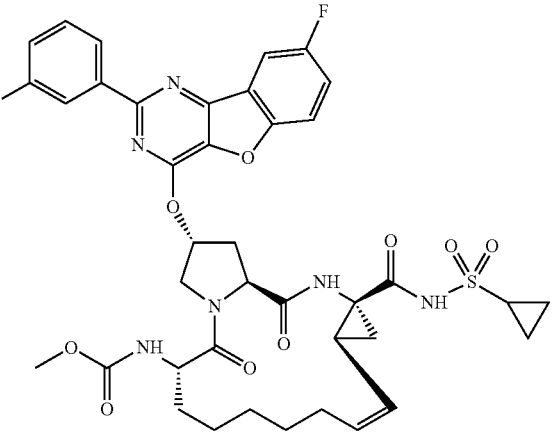
Compound 72
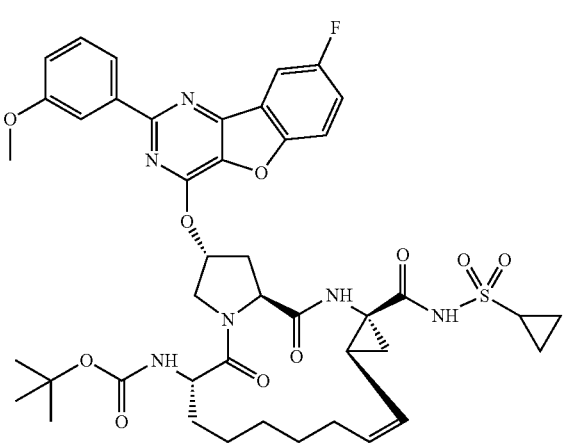

Compound 73
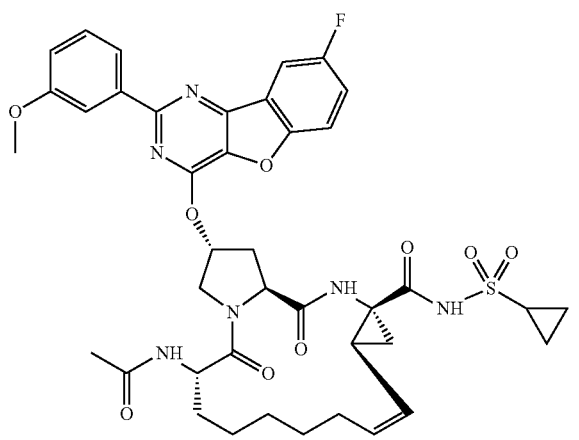
Compound 74
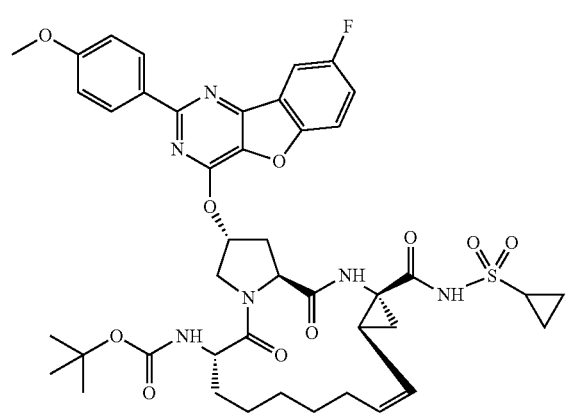
Compound 75
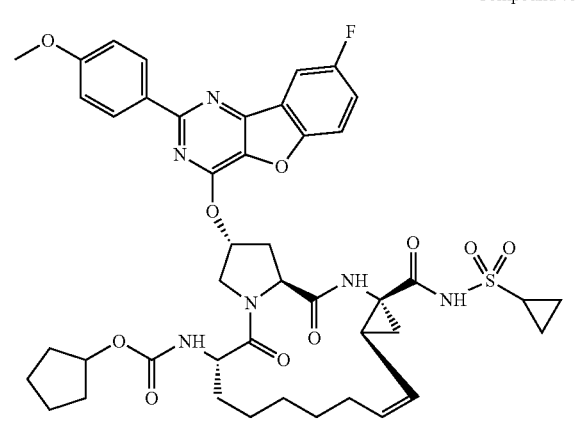
Compound 76
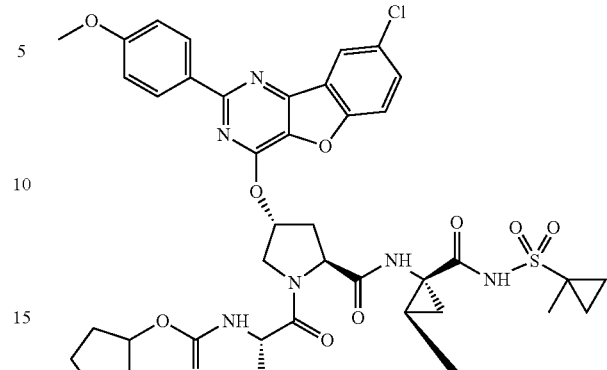
Compound 77
Compound 78
Compound 79
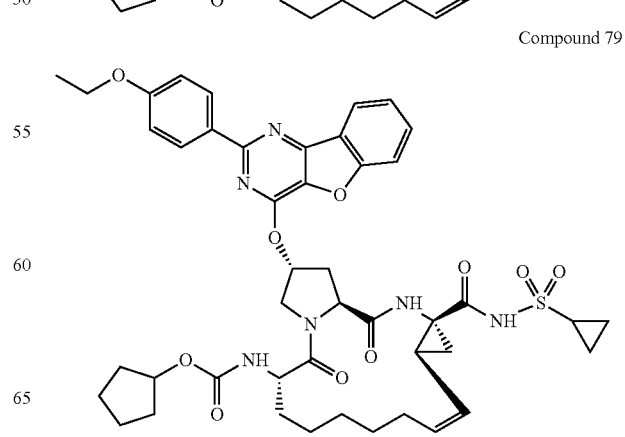

Compound 80
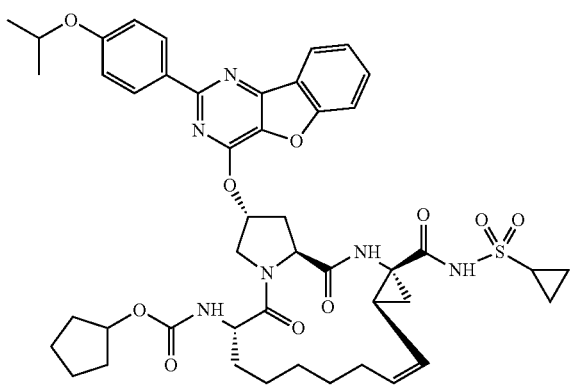
Compound 81
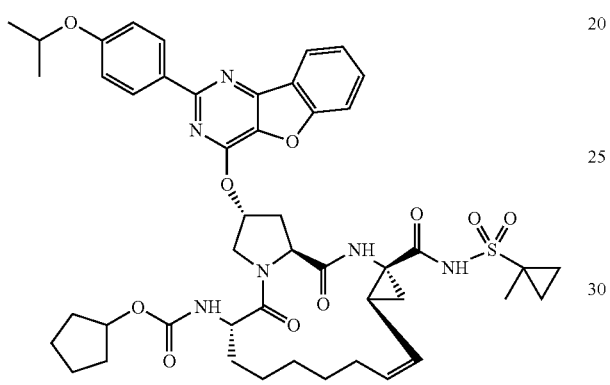
Compound 82
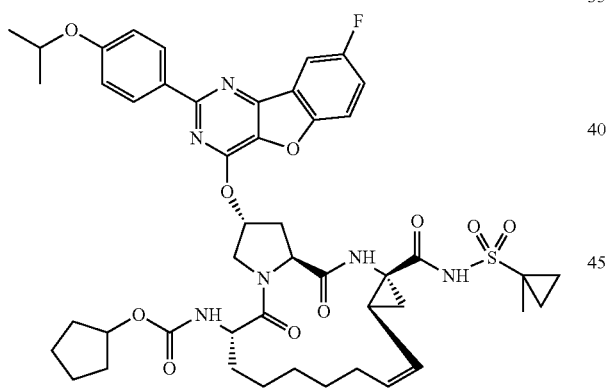
Compound 83
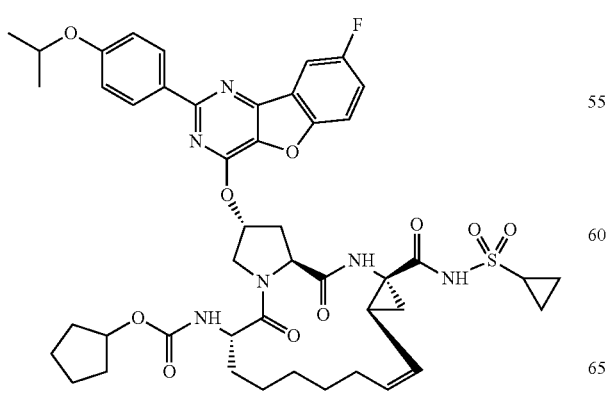
Compound 84
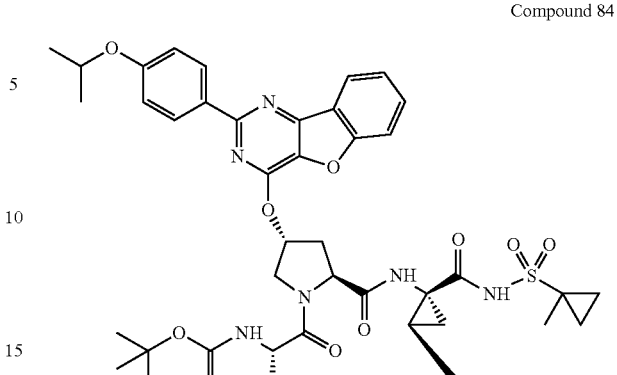
Compound 85
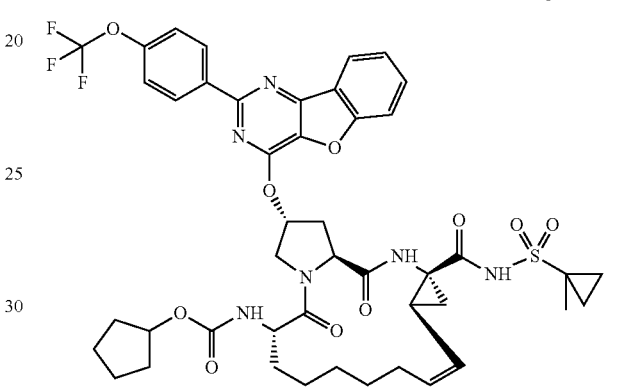
Compound 86
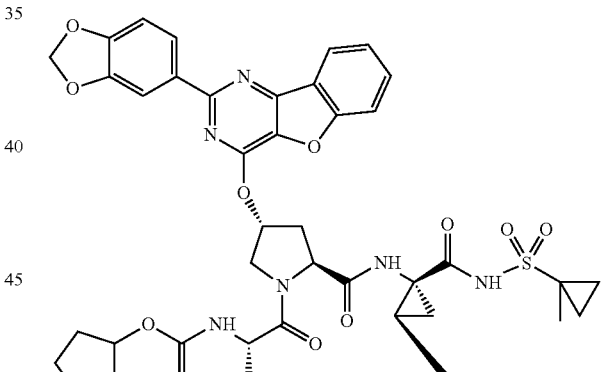
Compound 87
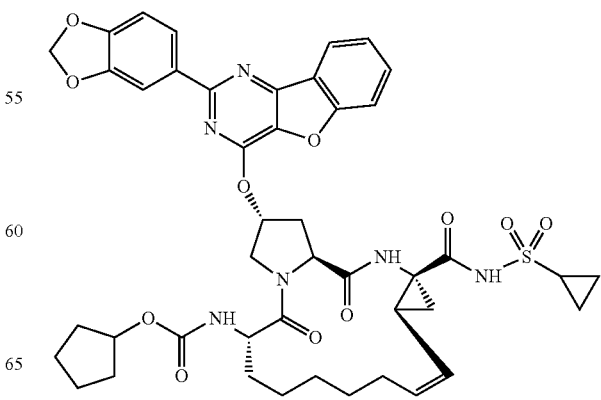

Compound 88
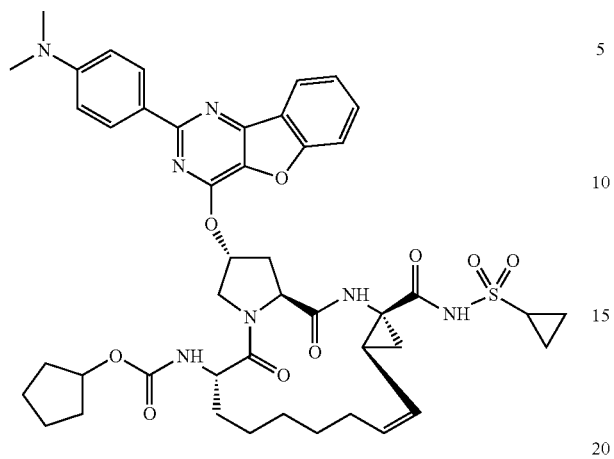
Compound 91
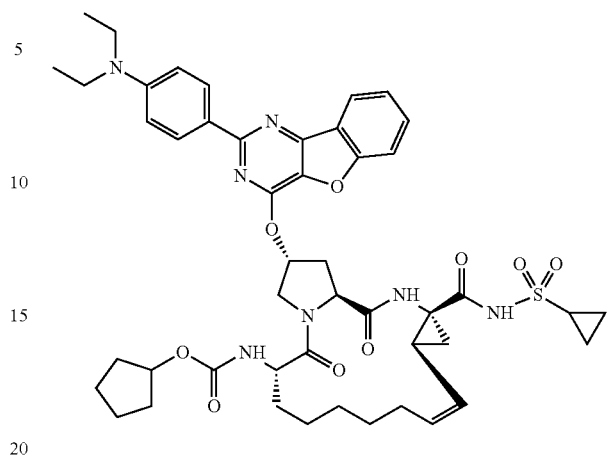
Compound 89
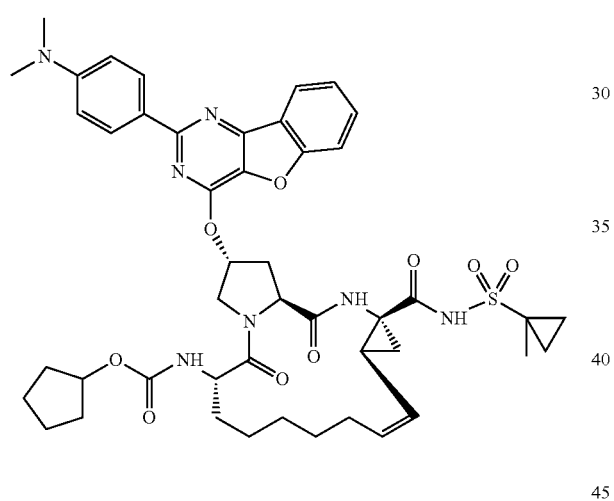
Compound 92
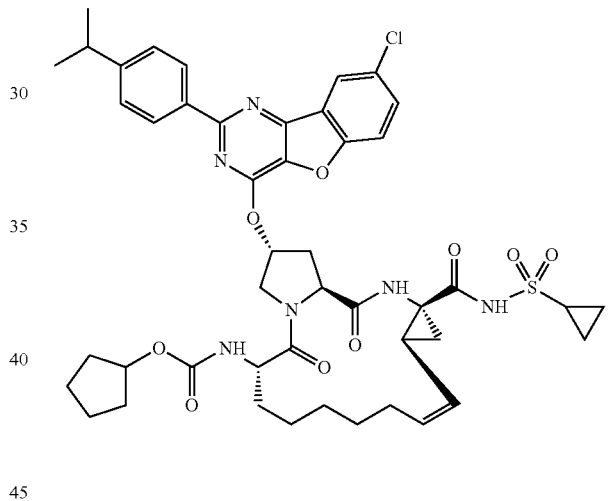
Compound 90
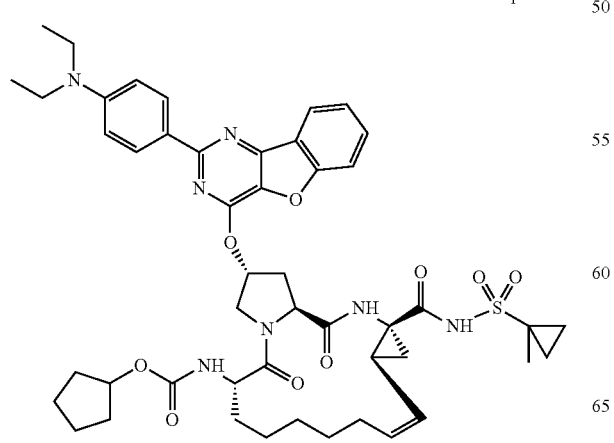
Compound 93
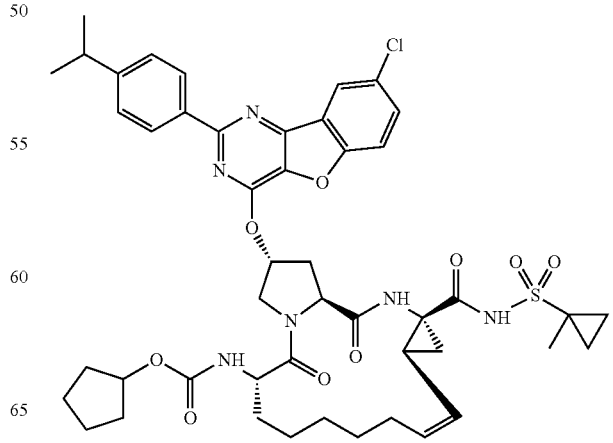

Compound 94
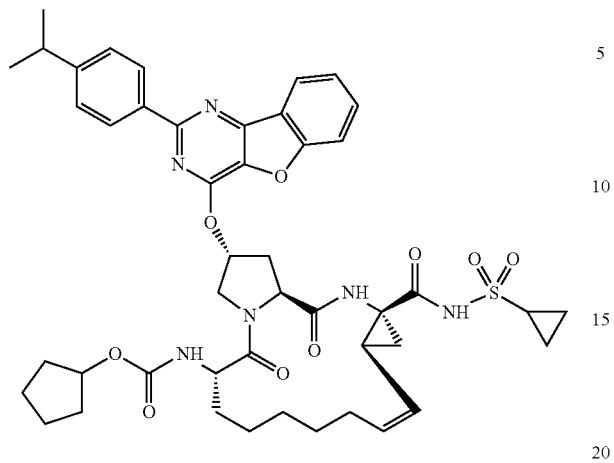
Compound 97
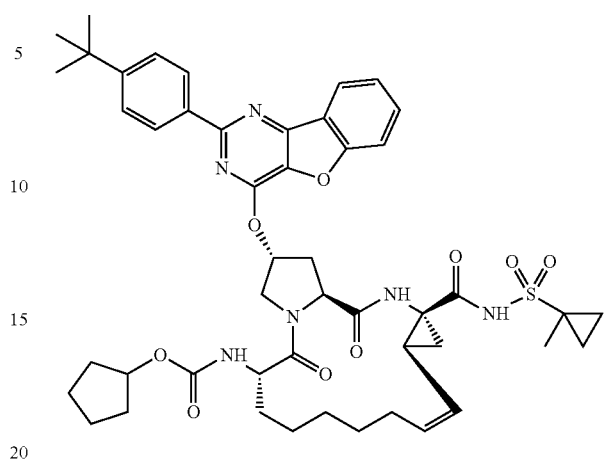
Compound 95
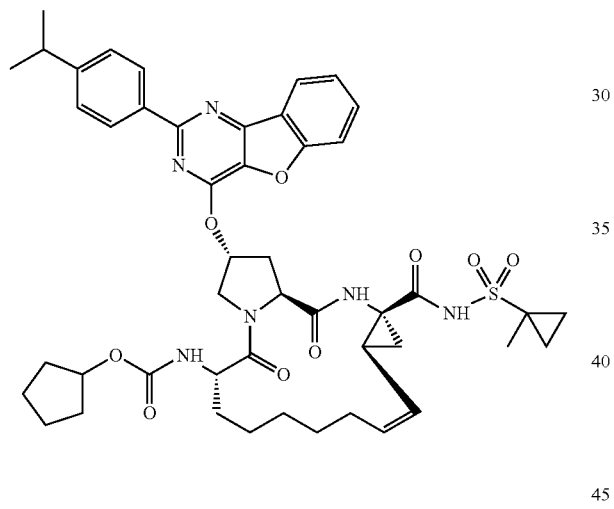
Compound 98
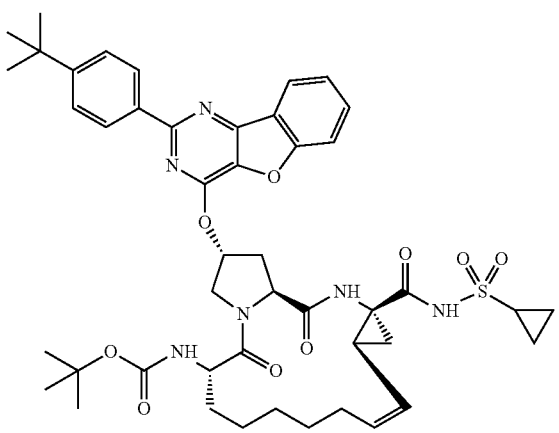
Compound 96
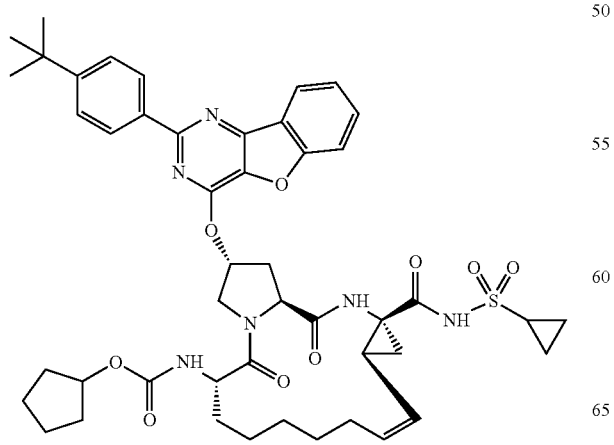
Compound 99
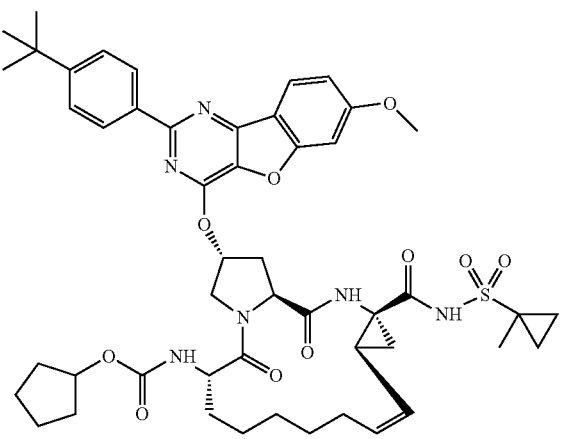

Compound 100
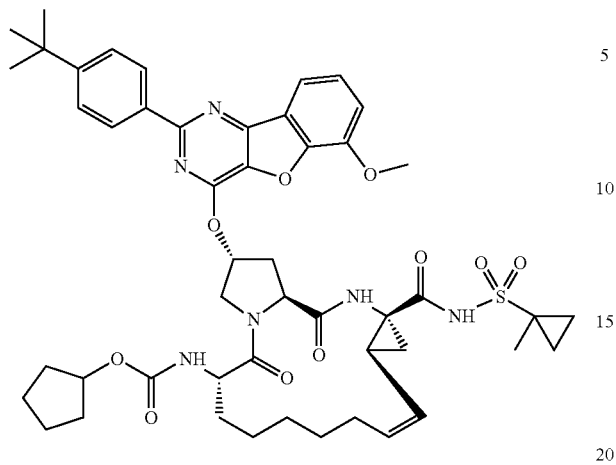
Compound 103
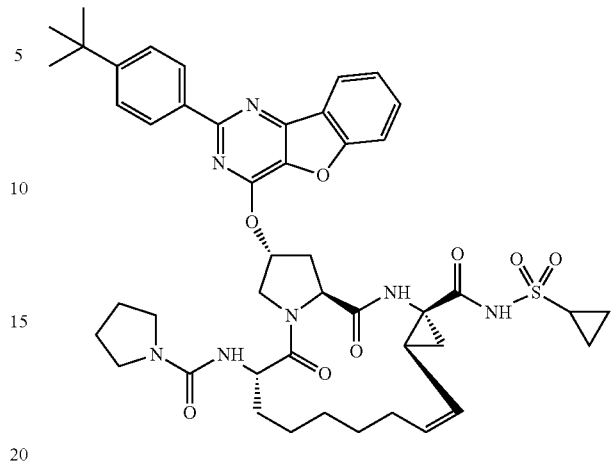
Compound 101
Compound 104
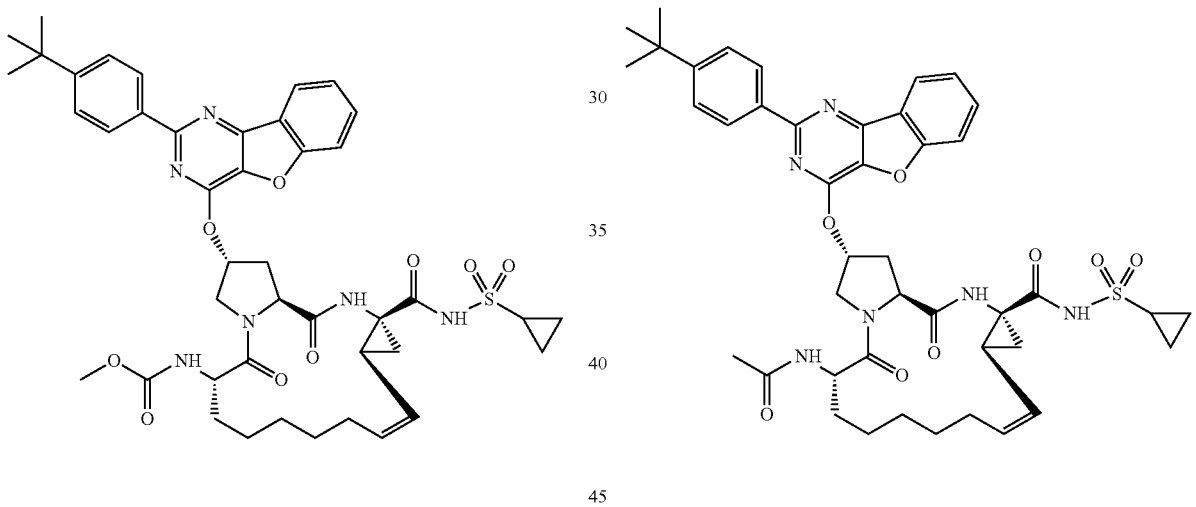
Compound 102
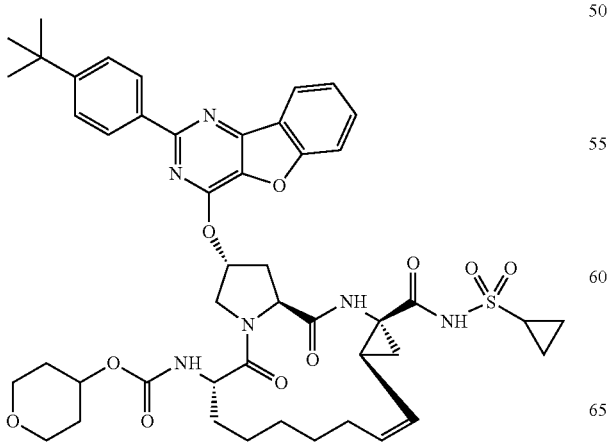
Compound 105

Compound 106
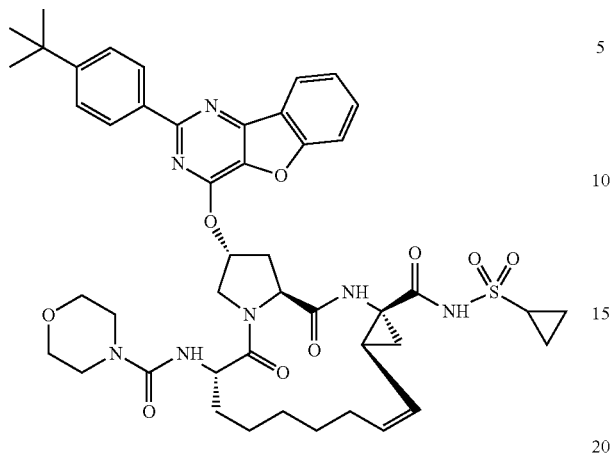
Compound 109
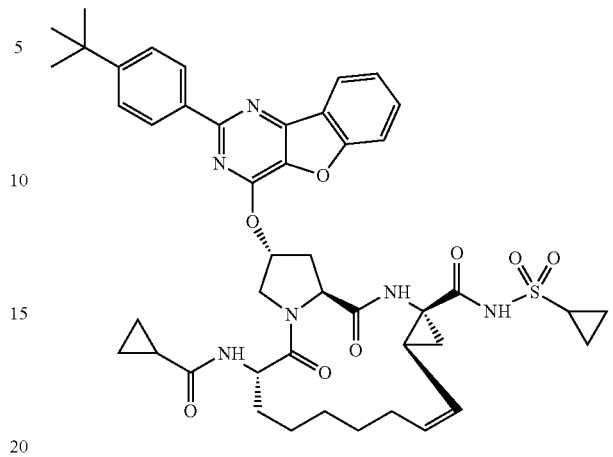
Compound 107
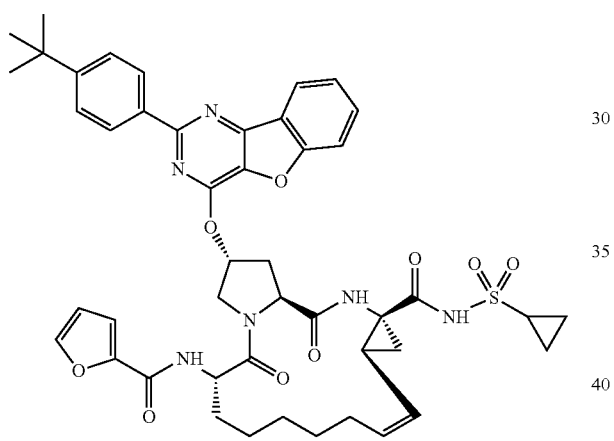
Compound 110
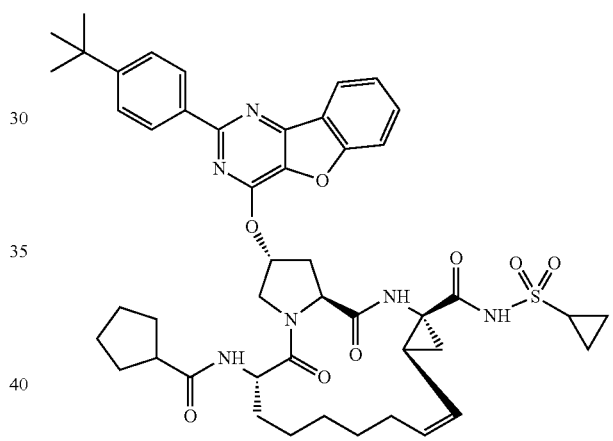
Compound 108
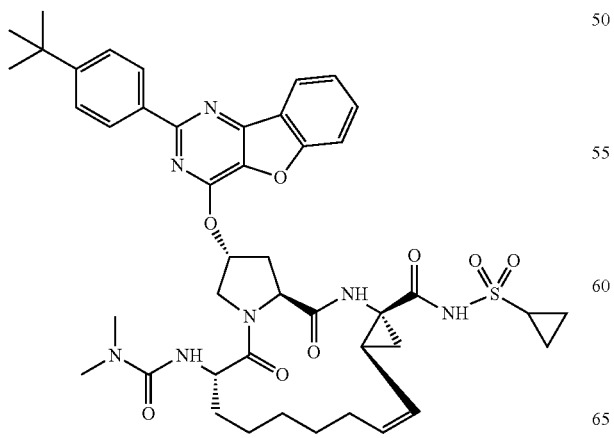
Compound 111
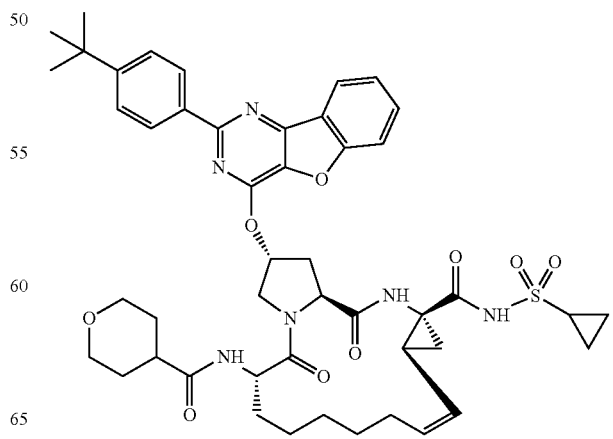

Compound 112
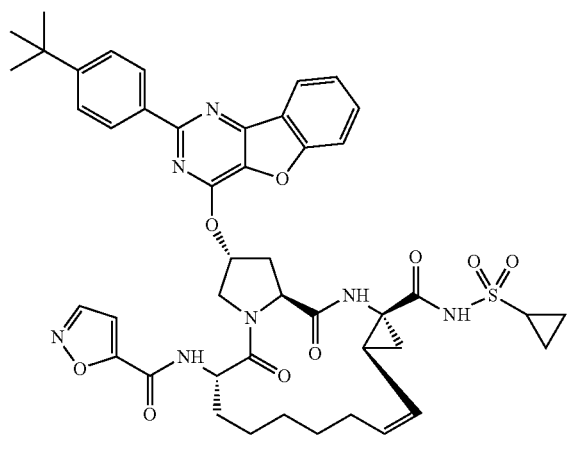
Compound 113
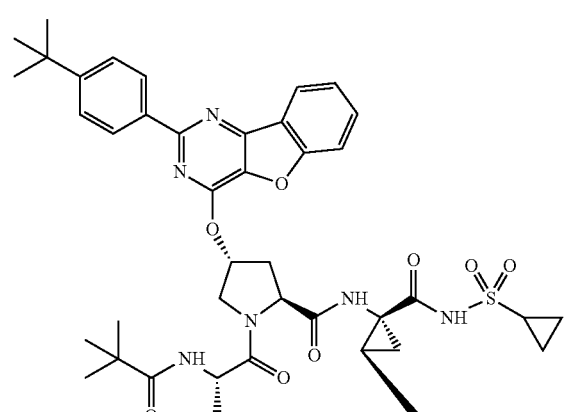
Compound 114
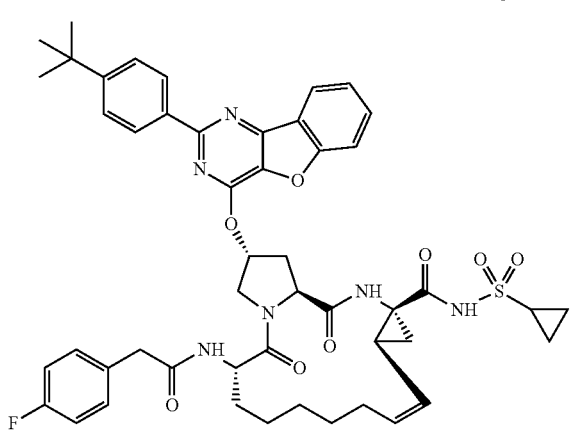
Compound 115
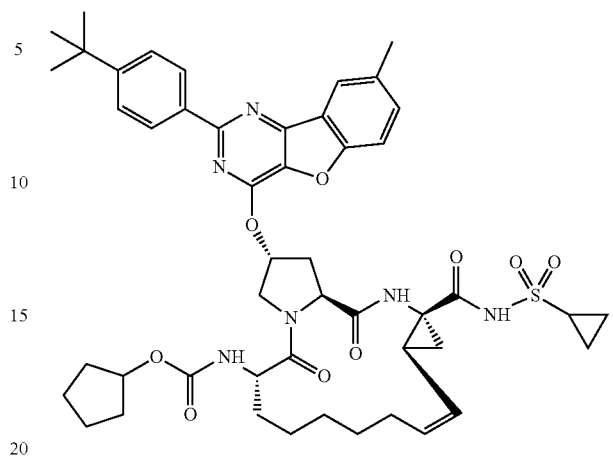
Compound 116
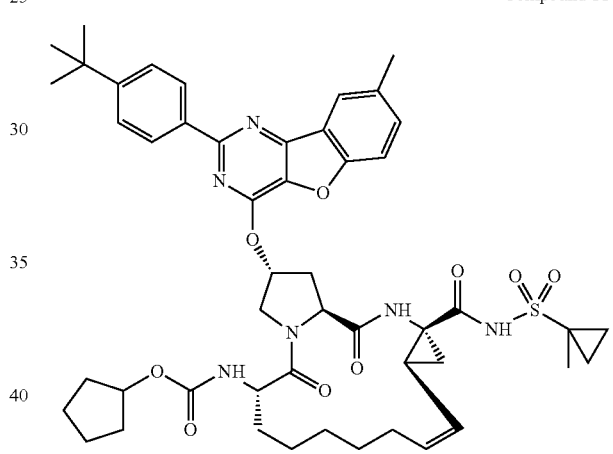
Compound 117
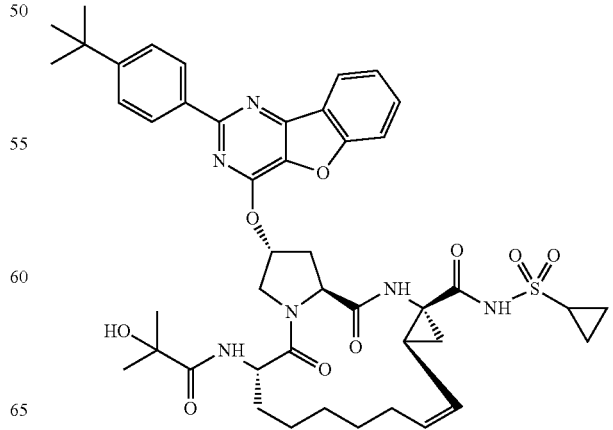

Compound 118
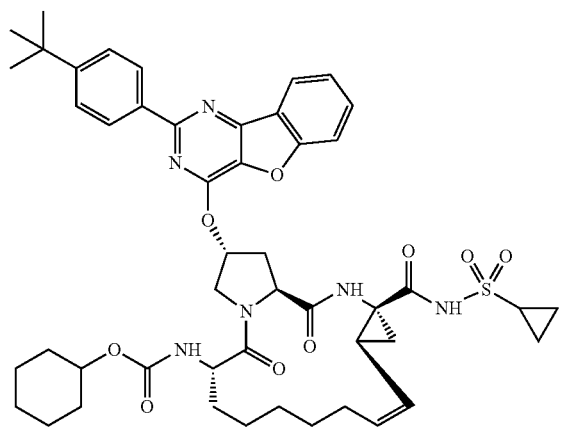
Compound 121
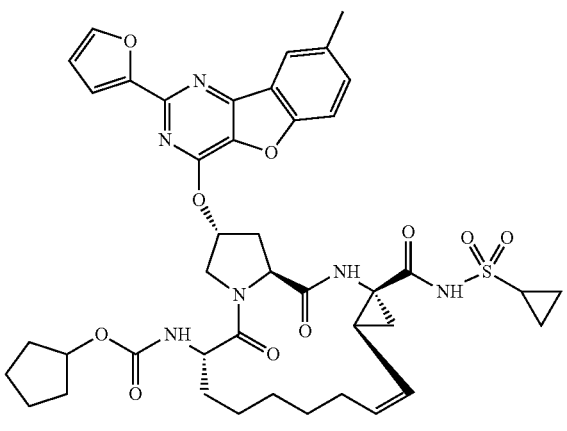
Compound 119
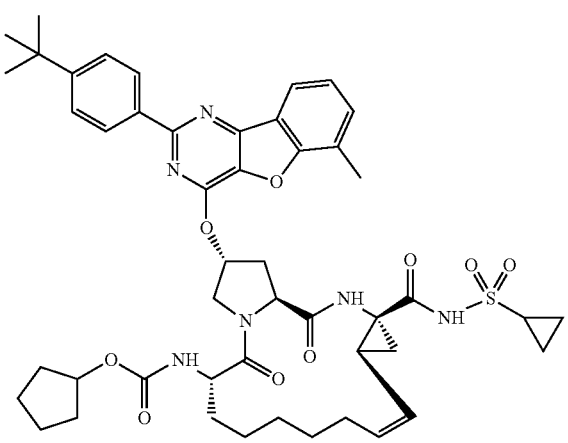
Compound 122
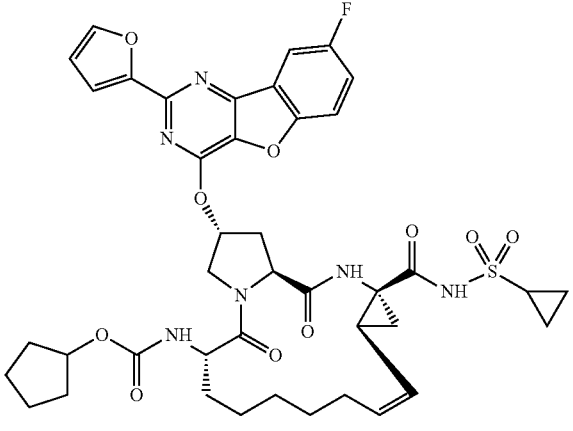
Compound 120
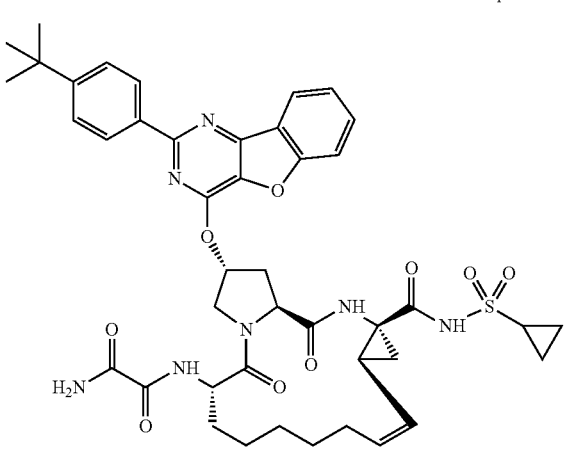
Compound 123
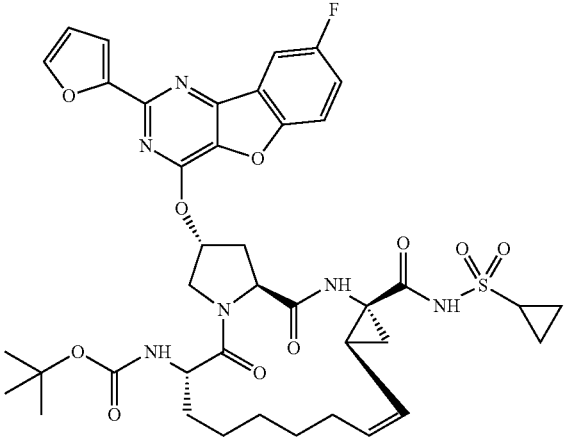

Compound 124
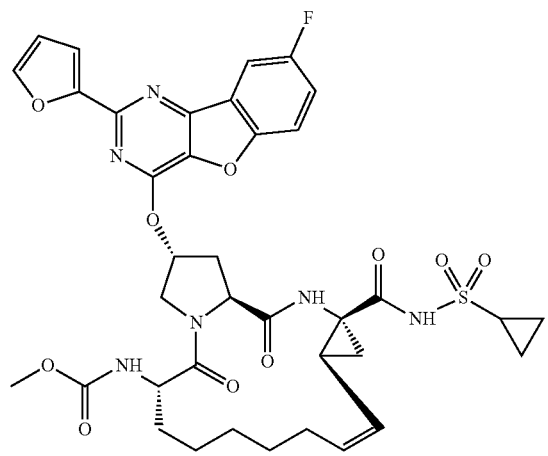
Compound 125
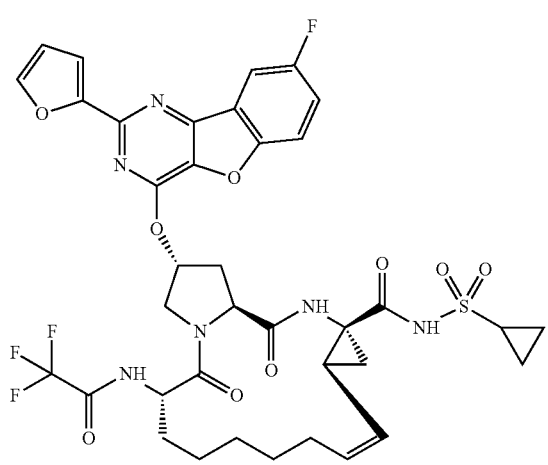
Compound 126
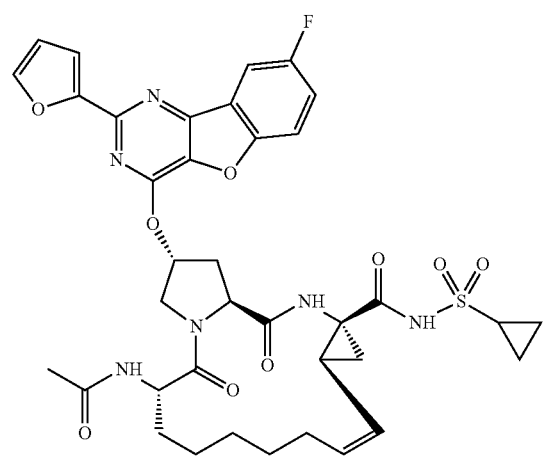
Compound 127
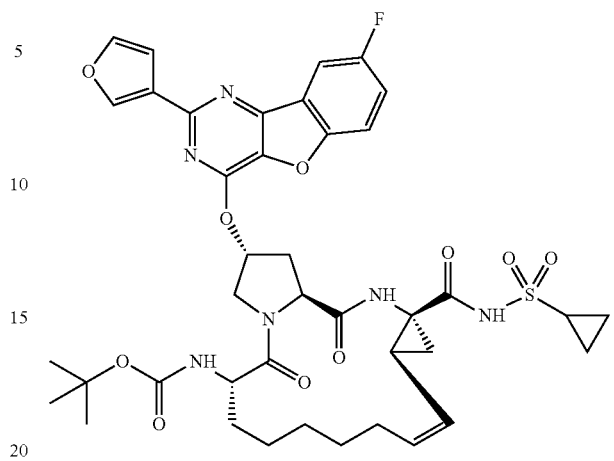
Compound 128
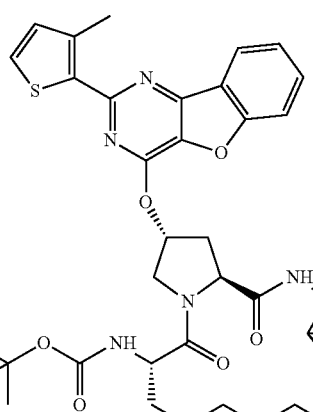
Compound 129
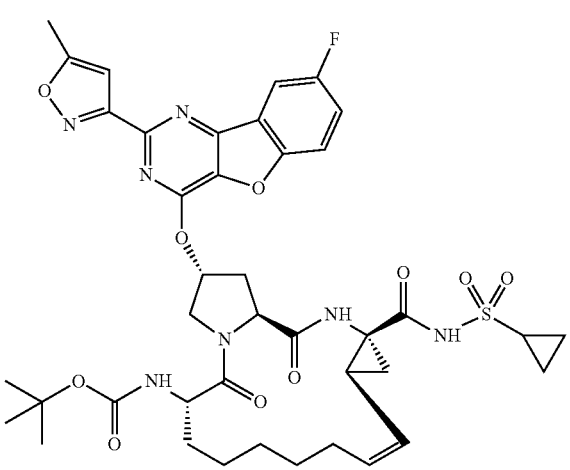

Compound 130
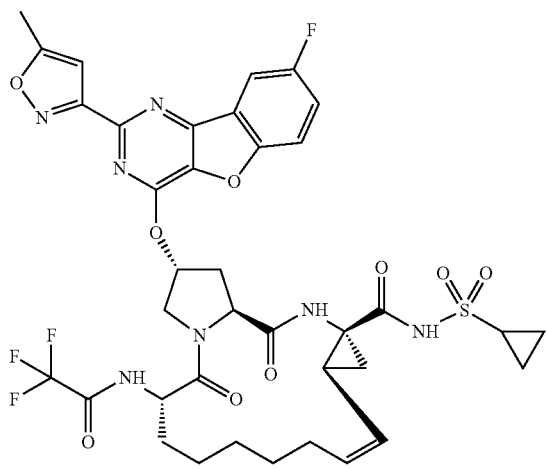
Compound 133
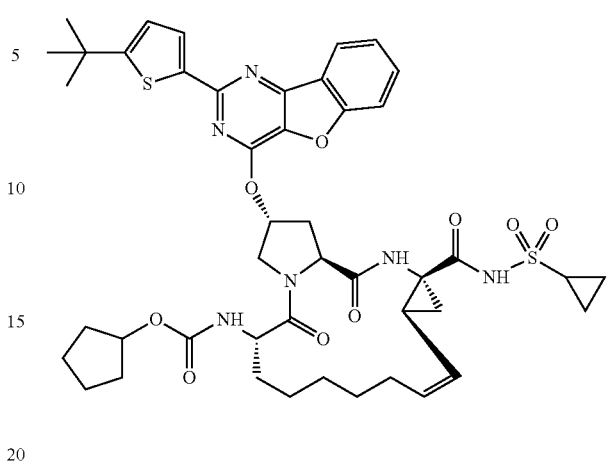
Compound 131
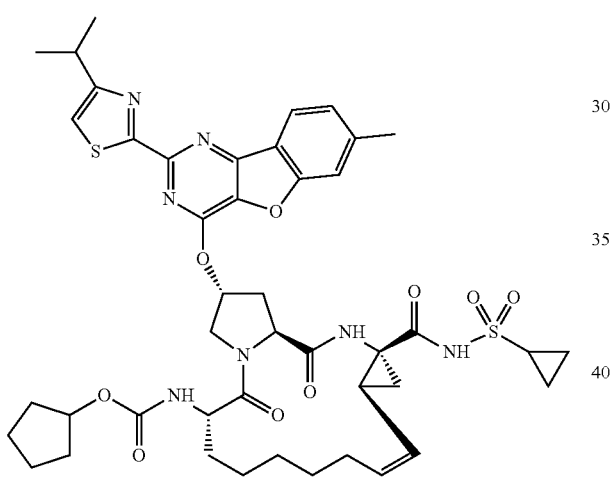
Compound 134
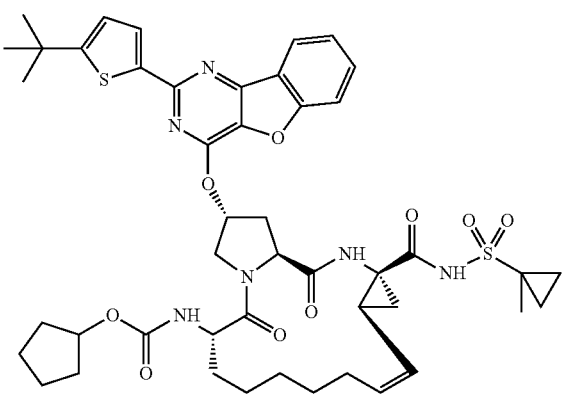
Compound 132
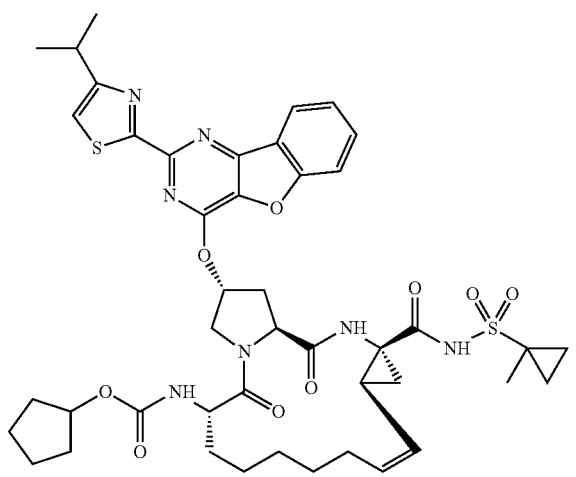
Compound 135
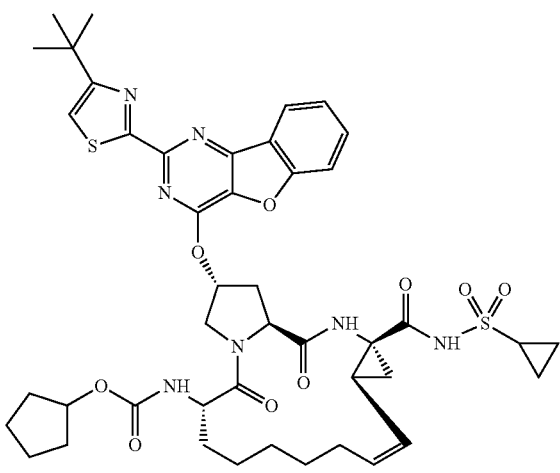

Compound 136
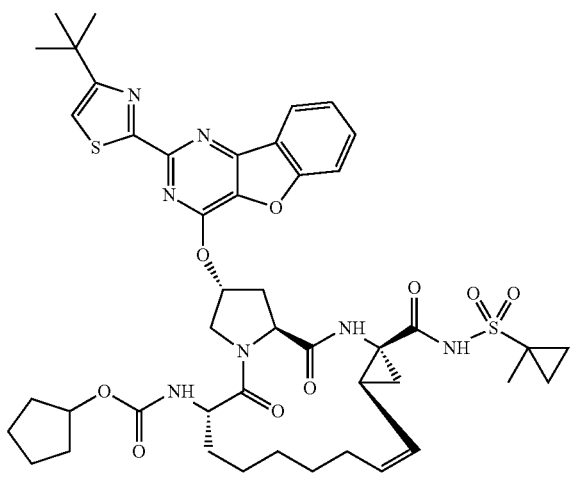
Compound 139
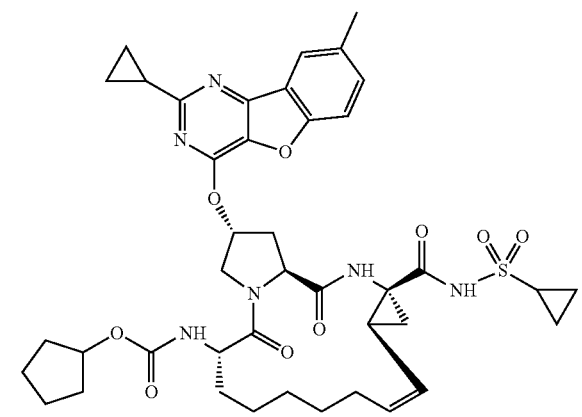
Compound 137
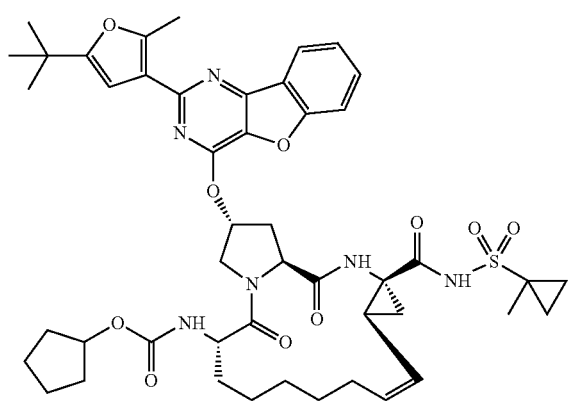
Compound 140
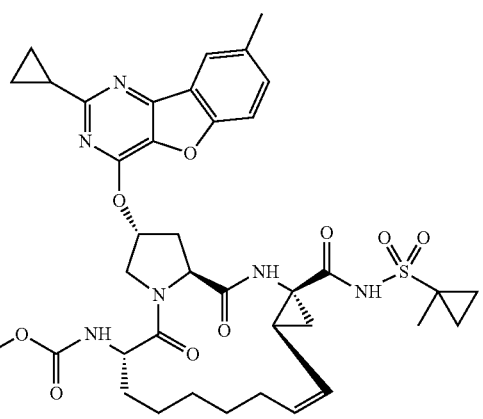
Compound 138
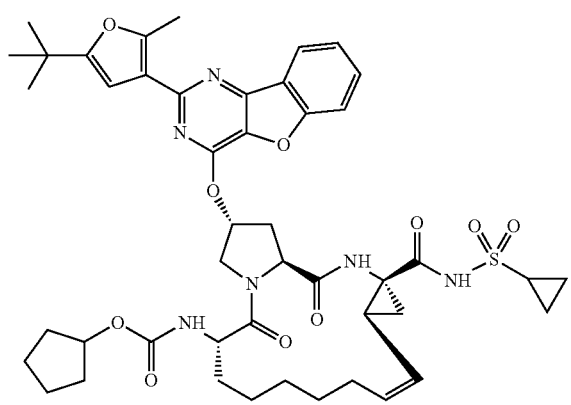
Compound 141
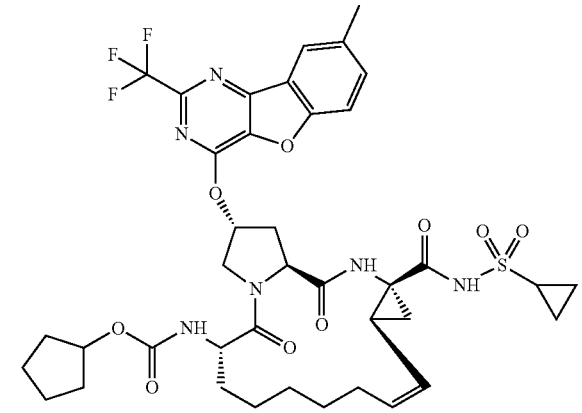

Compound 142
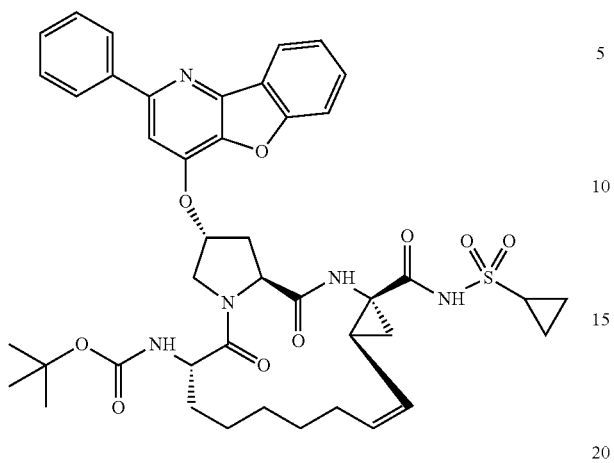
Compound 145
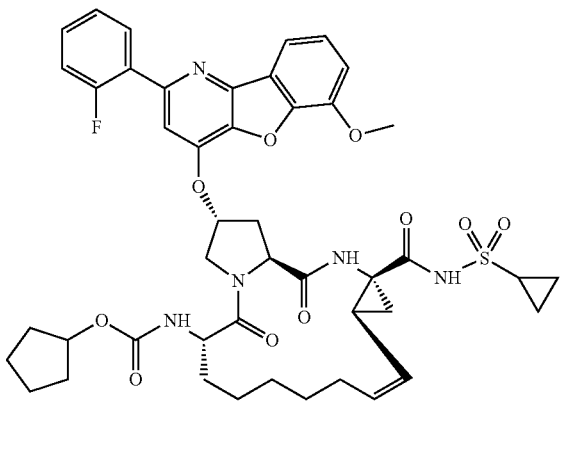
Compound 143
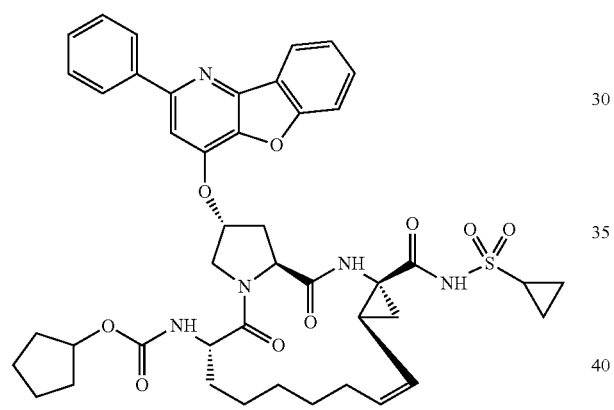
Compound 146
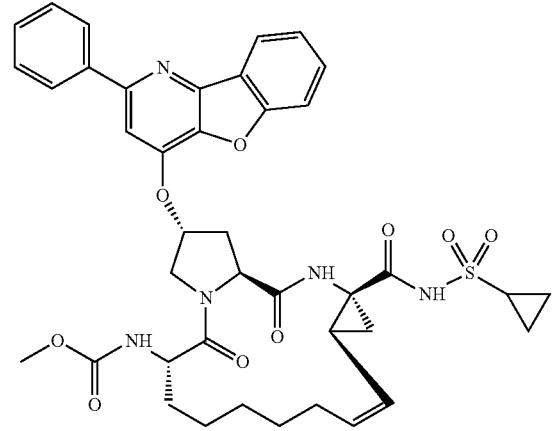
Compound 144
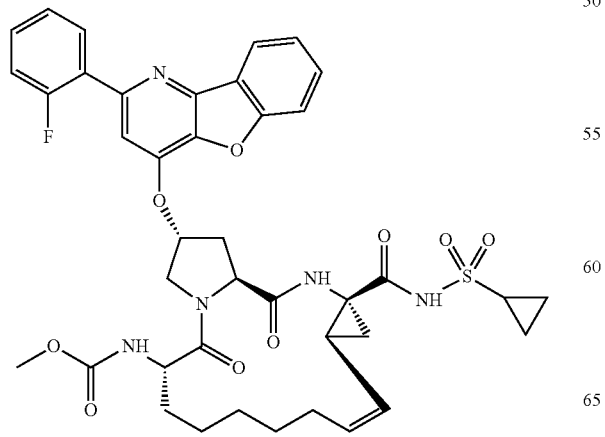
Compound 147
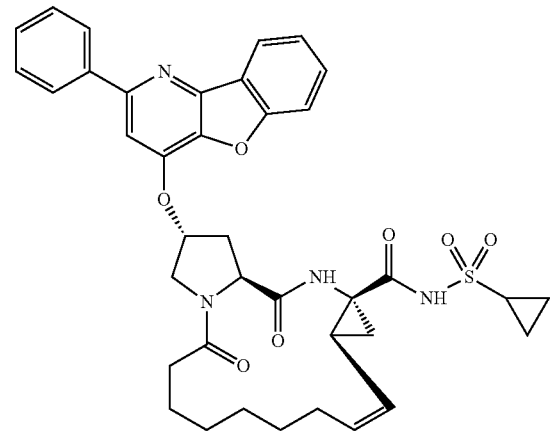

Compound 148
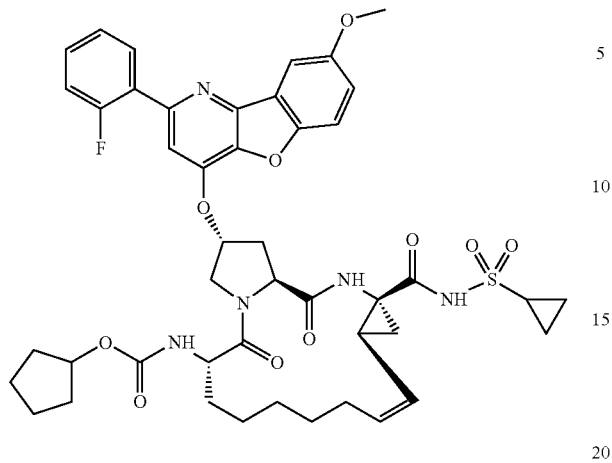
Compound 151
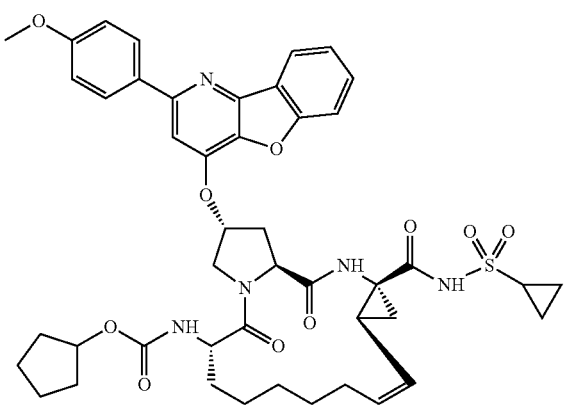
Compound 149
Compound 152
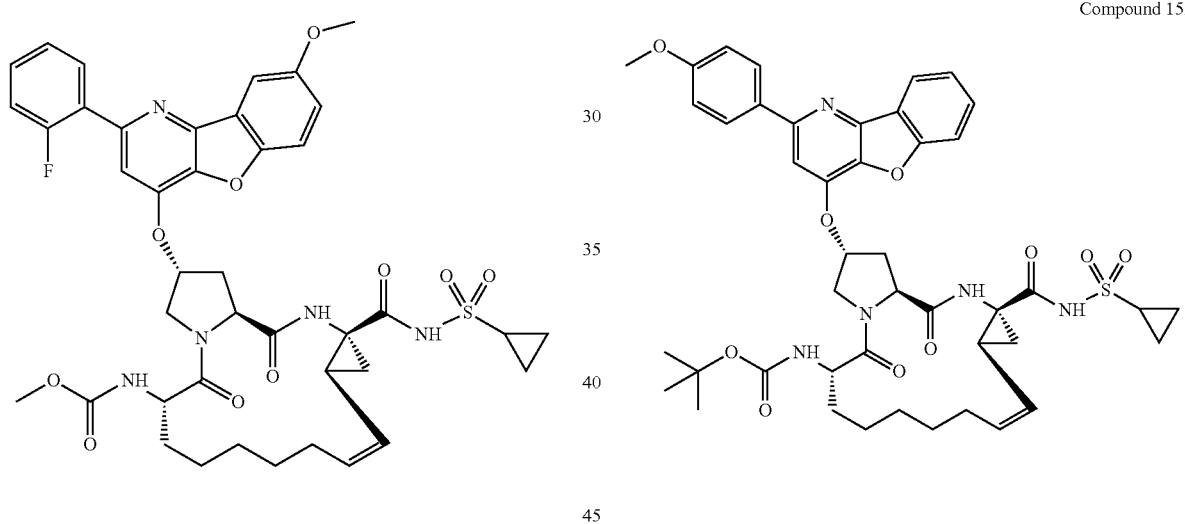
Compound 150
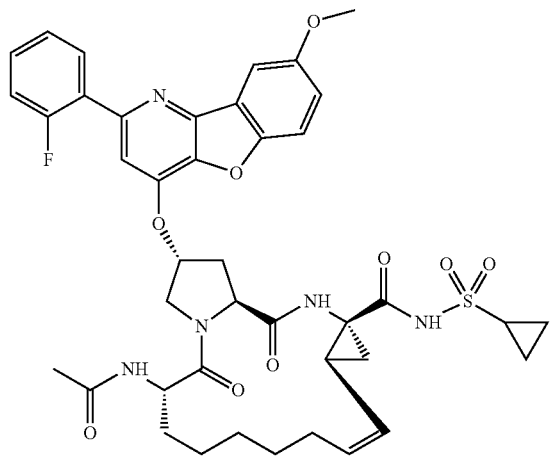
Compound 153

Compound 154
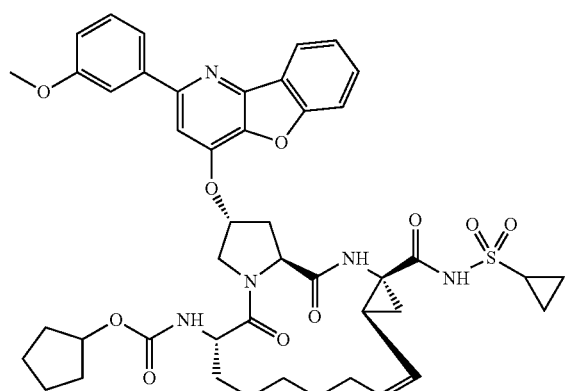
Compound 155
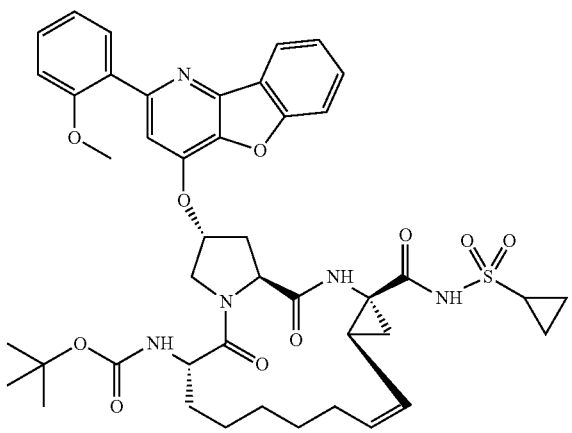
Compound 156
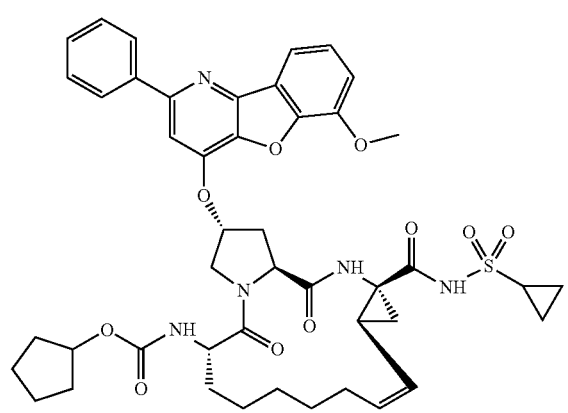
Compound 157
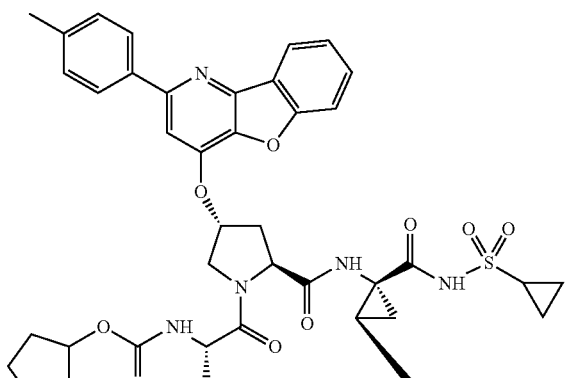
Compound 158
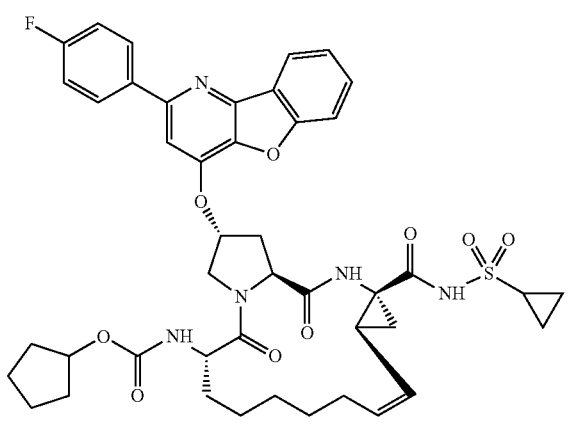
Compound 159
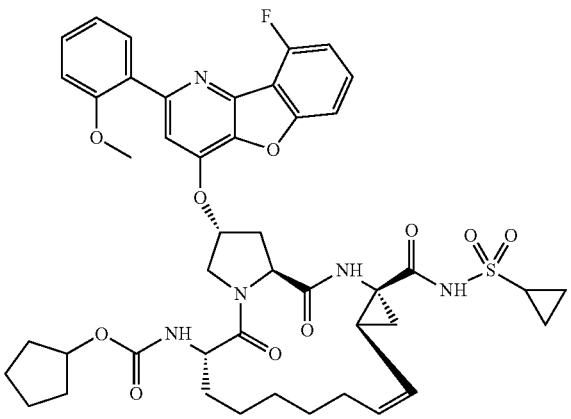

Compound 160
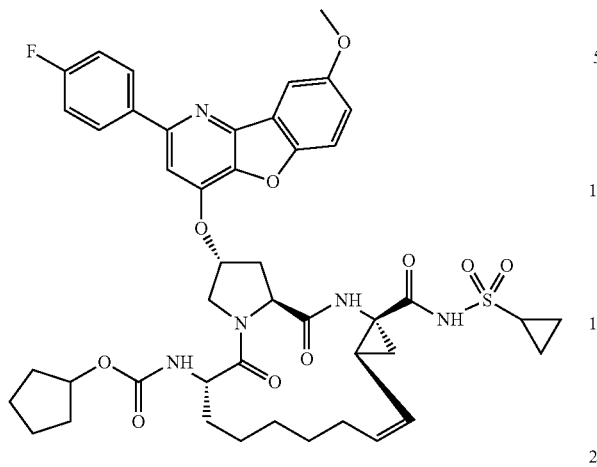
Compound 163
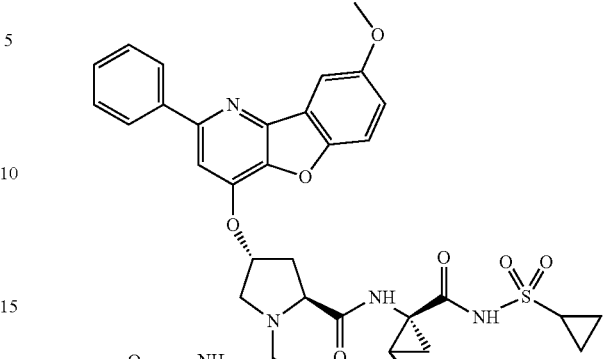
Compound 161
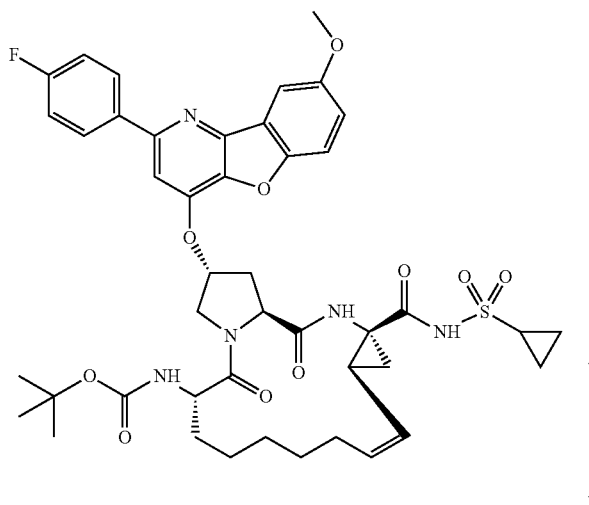
Compound 164
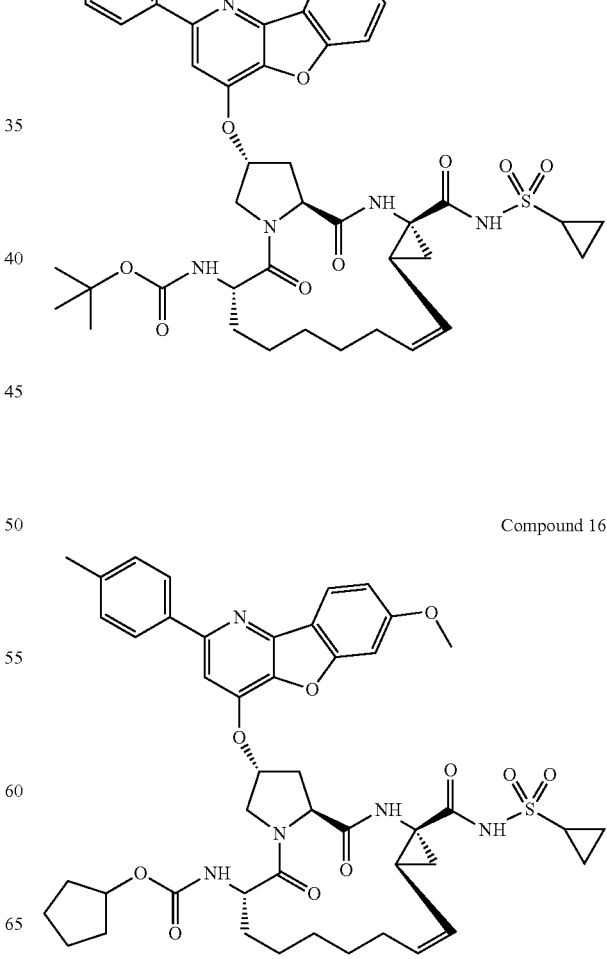
Compound 162
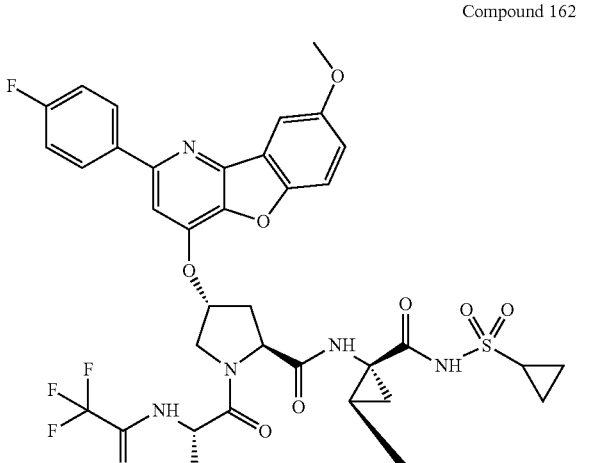
Compound 165

-continued
Compound 166
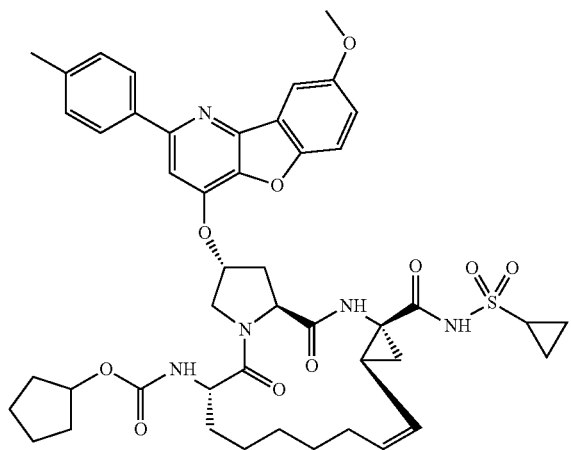
Compound 167
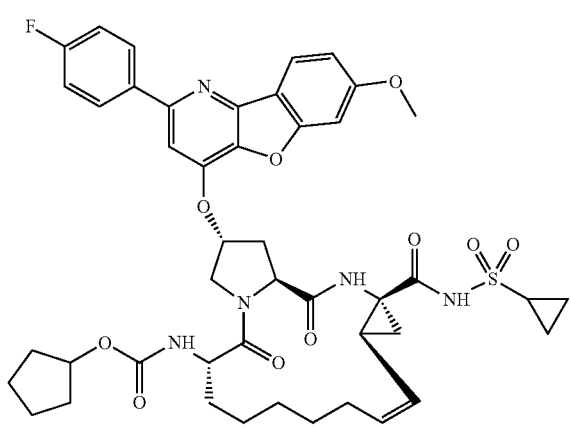
Compound 168
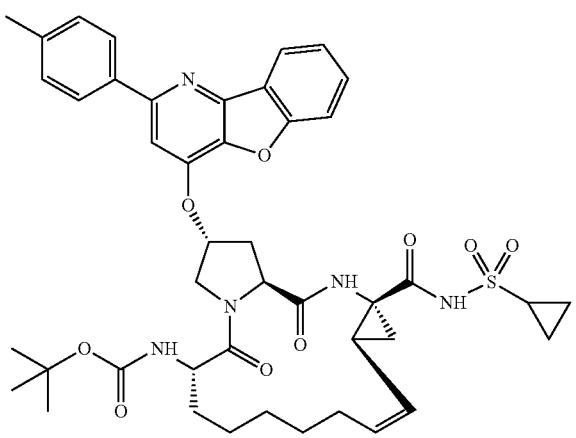
-continued
Compound 169
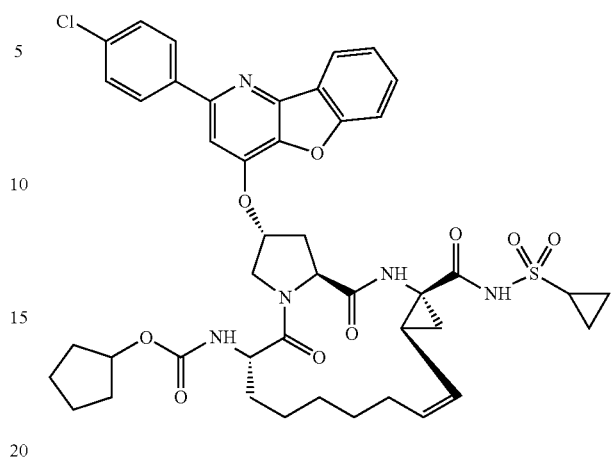
Compound 170
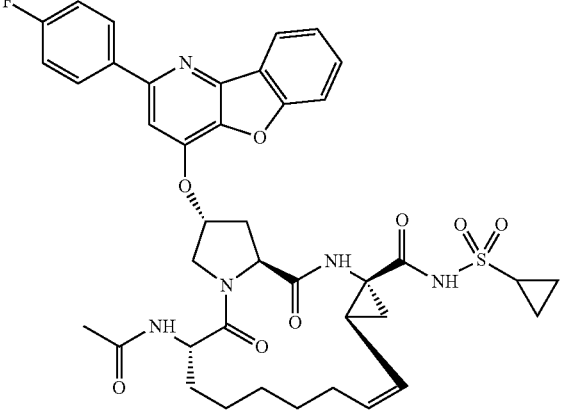
Compound 171
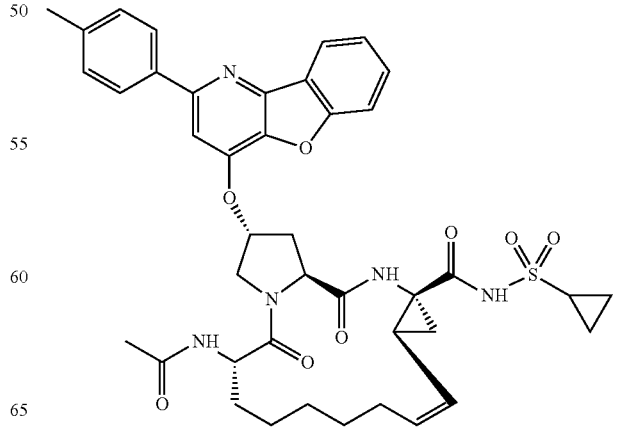

Compound 172
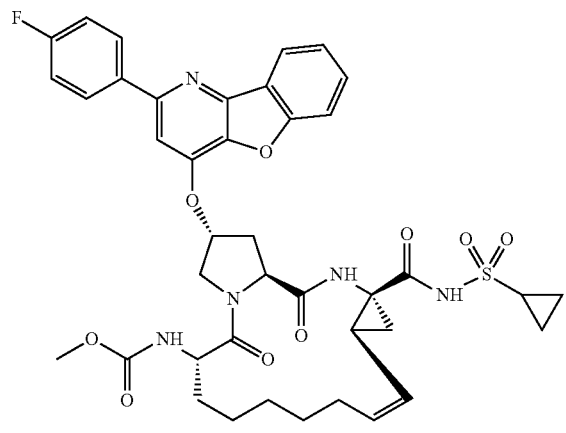
Compound 175
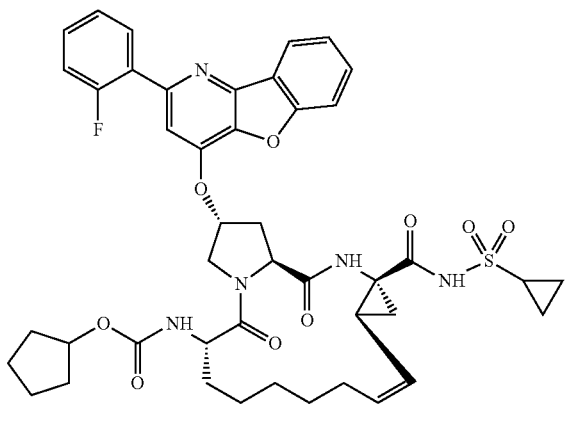
Compound 173
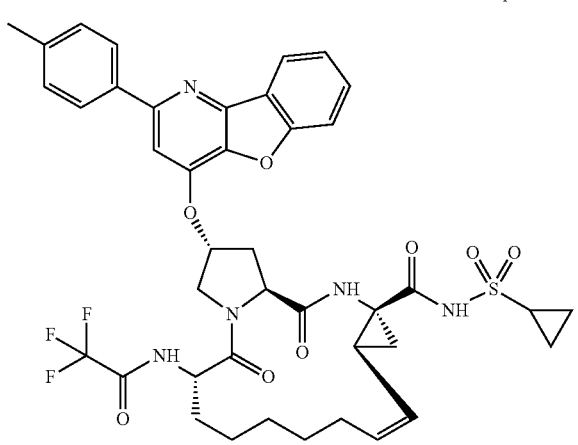
Compound 176
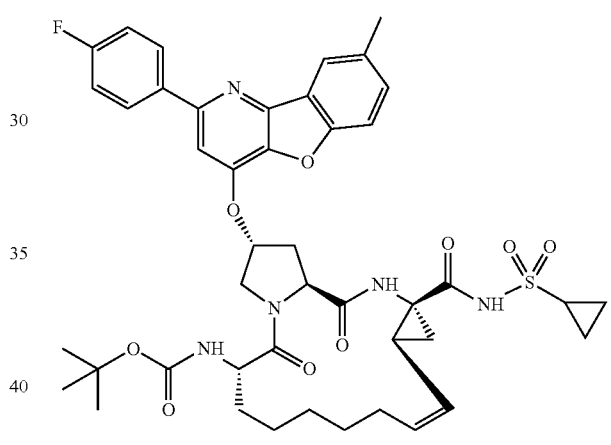
Compound 174
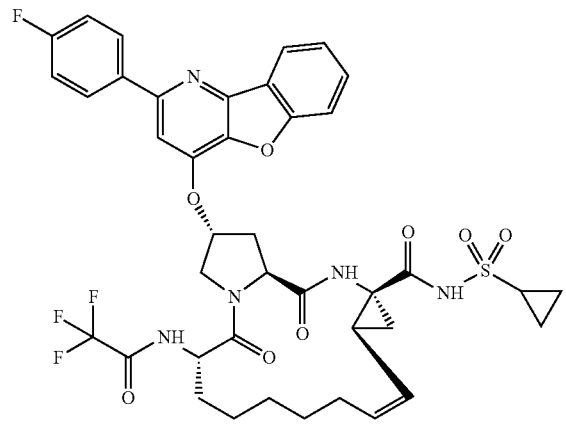
Compound 177
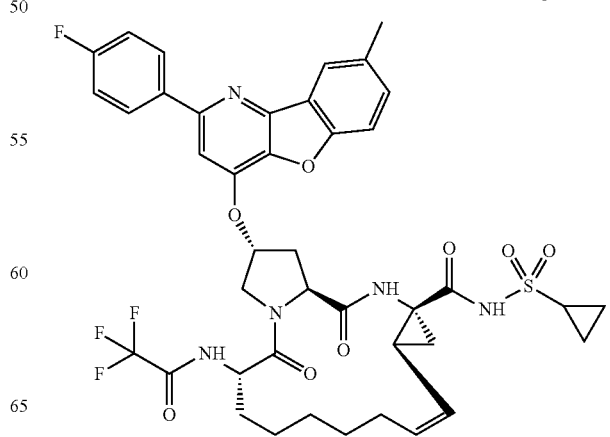

65
-continued
Compound 178
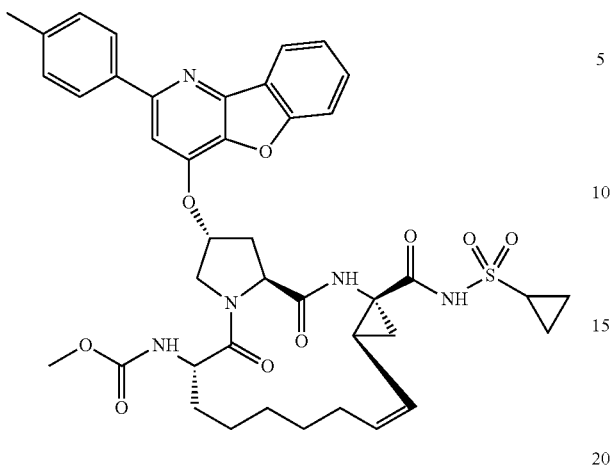
Compound 179
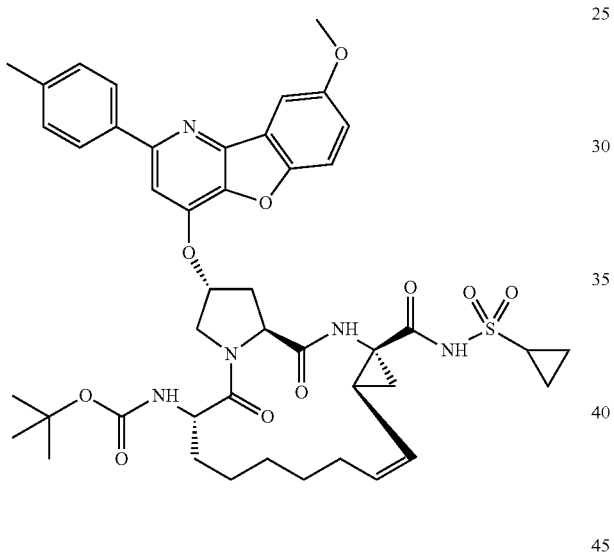
Compound 180
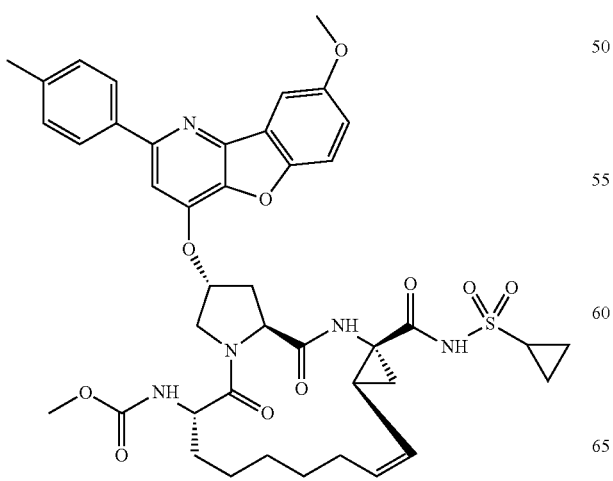
66
-continued
Compound 181
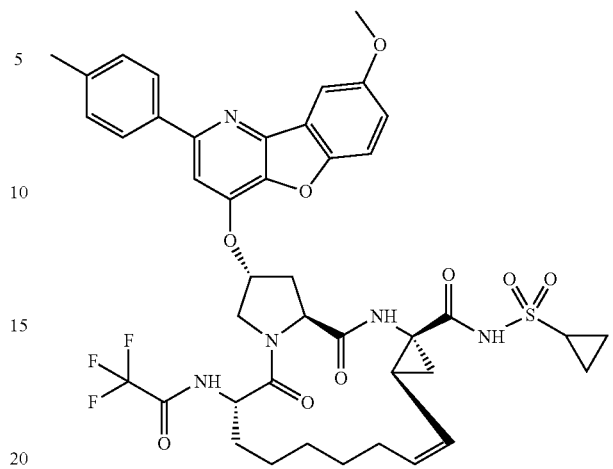
Compound 182
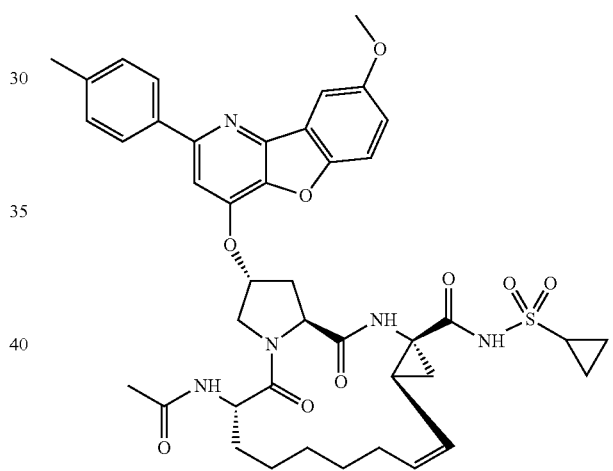
Compound 183
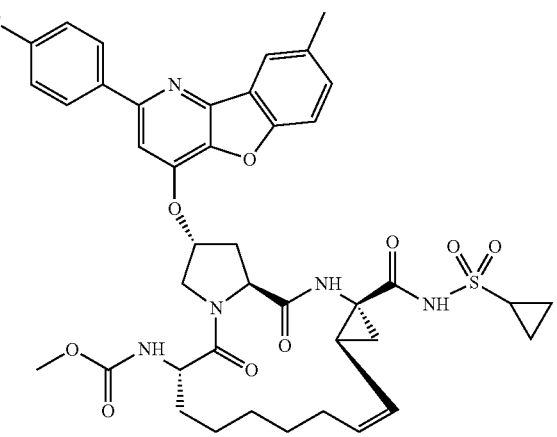

Compound 184
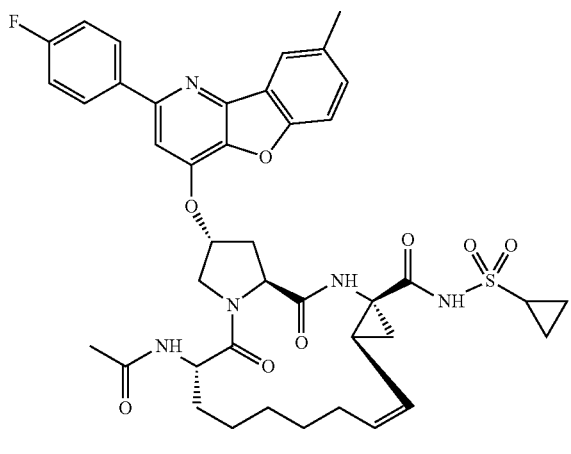
Compound 187
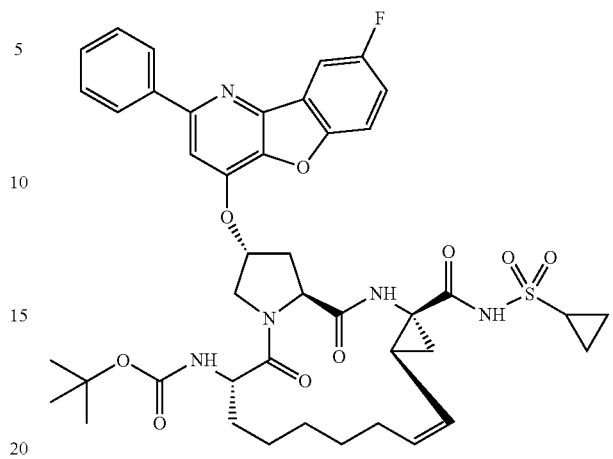
Compound 185
Compound 188
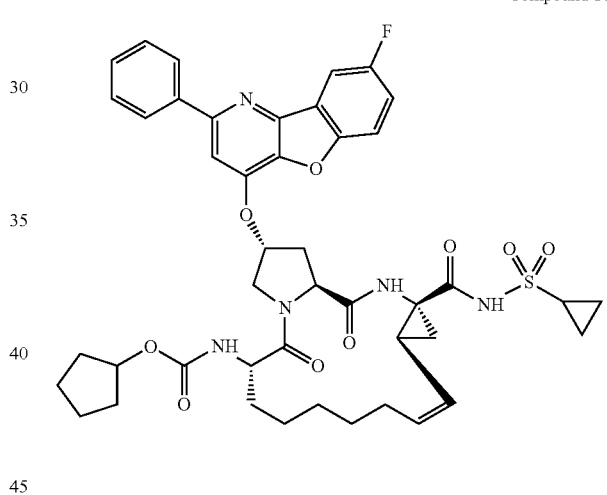
Compound 186
Compound 189
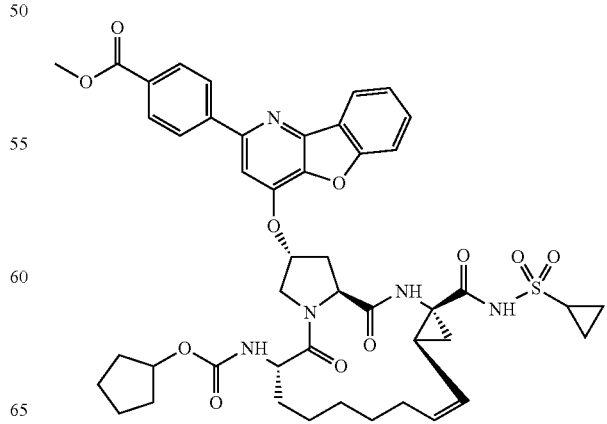

Compound 190
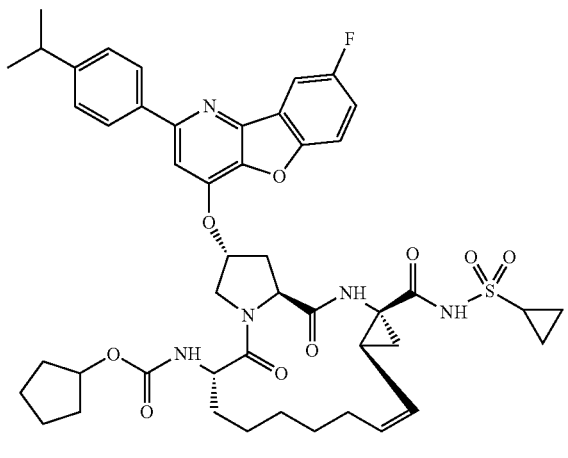
Compound 193
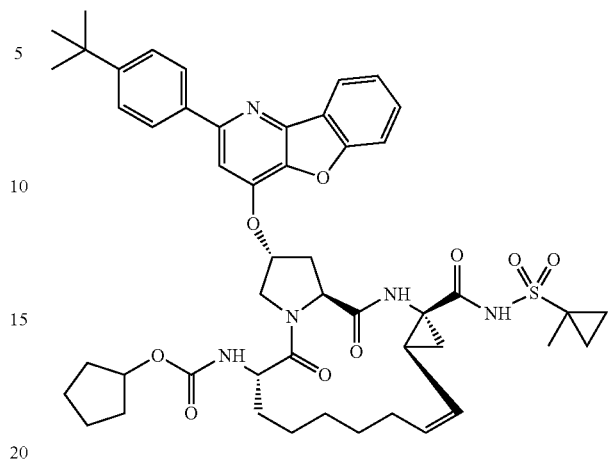
Compound 191
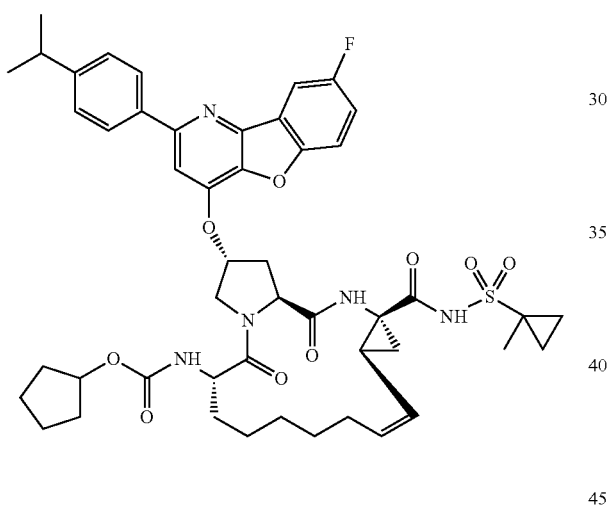
Compound 194
Compound 192
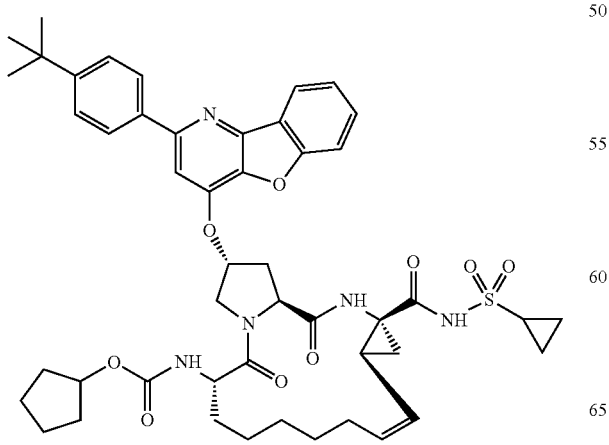
Compound 195
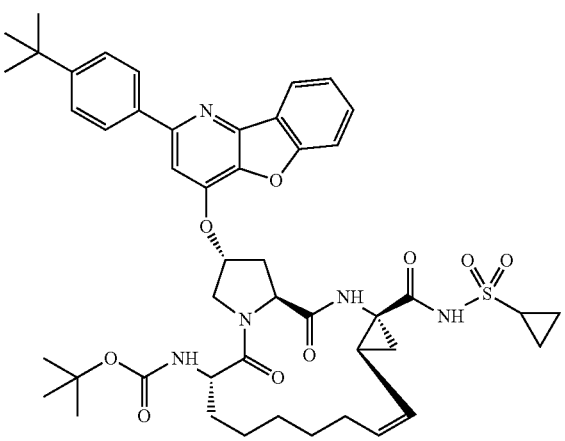

Compound 196
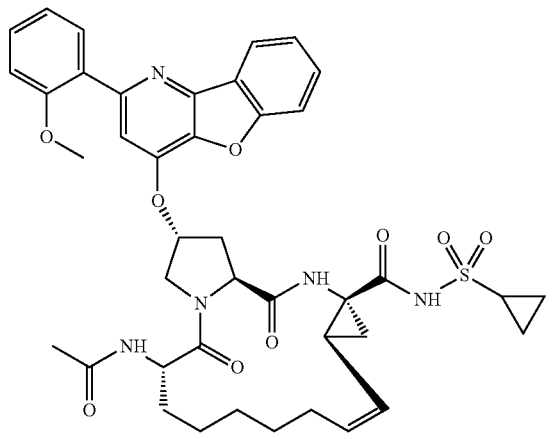
Compound 199
Compound 197
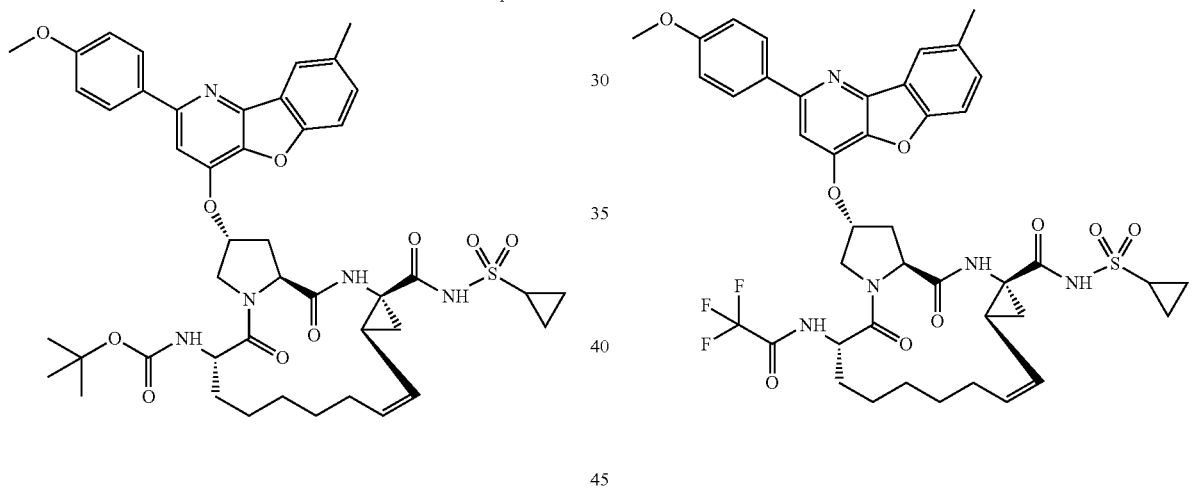
Compound 200
Compound 198
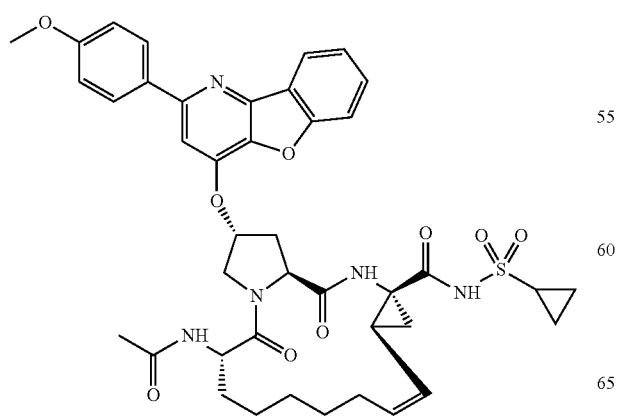
Compound 201
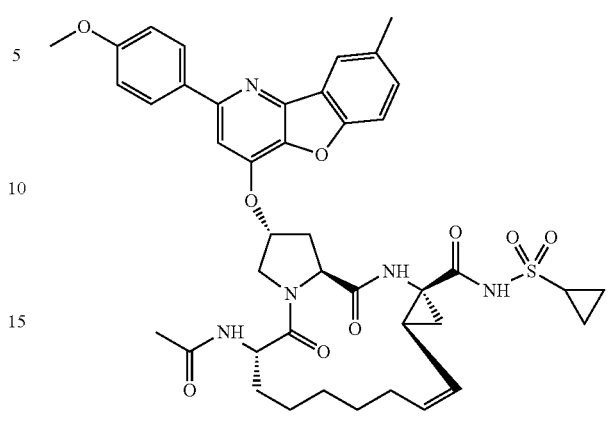

Compound 202
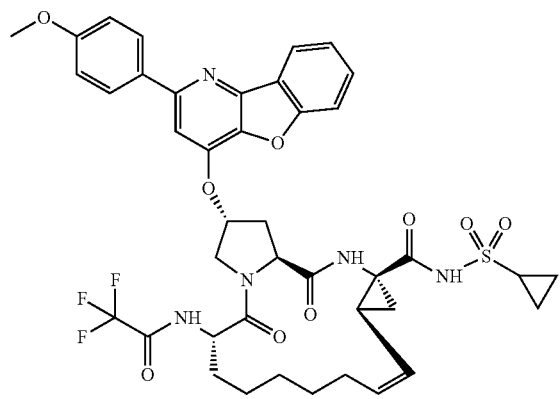
Compound 205
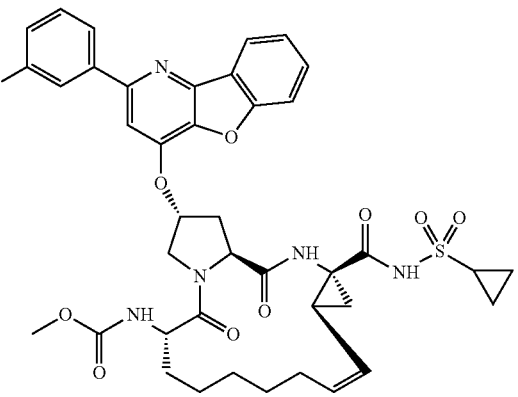
Compound 203
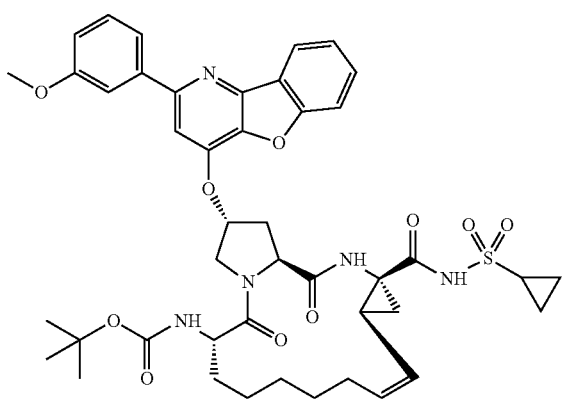
Compound 206
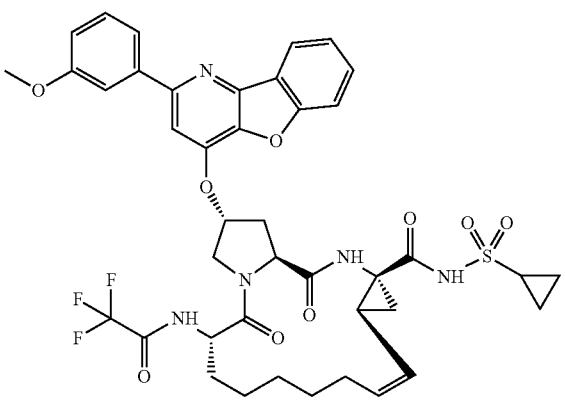
Compound 204
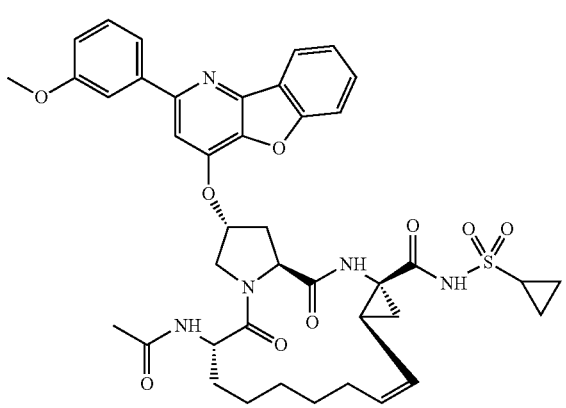
Compound 207
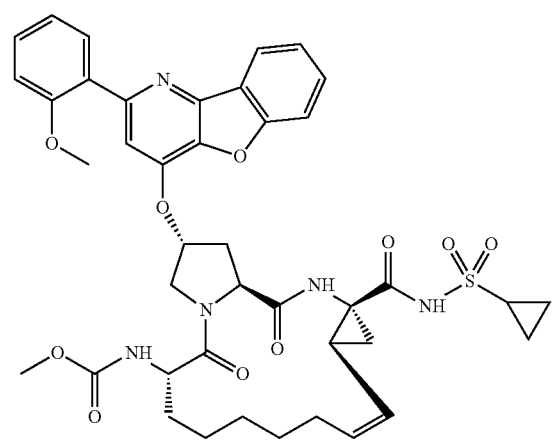

75
-continued
Compound 208
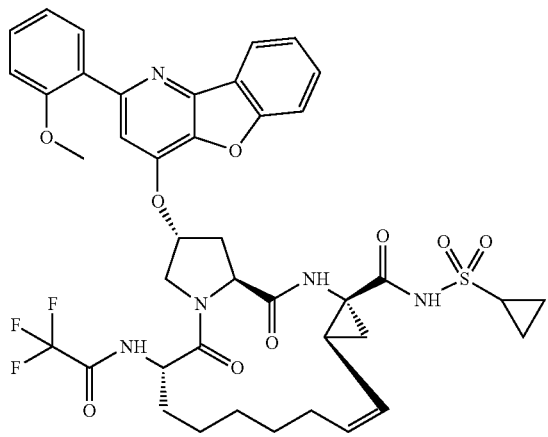
Compound 209
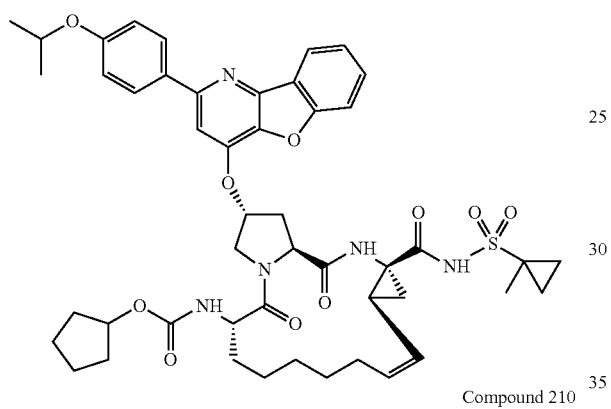
Compound 210
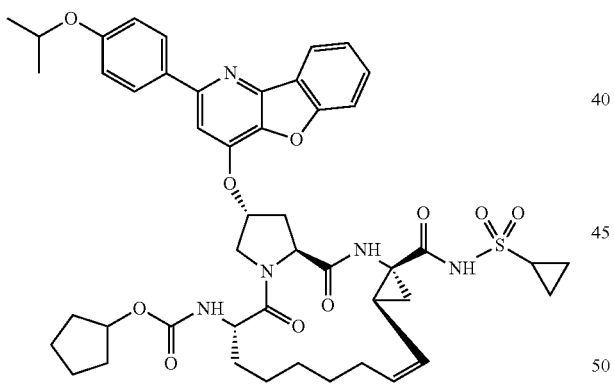
Compound 211
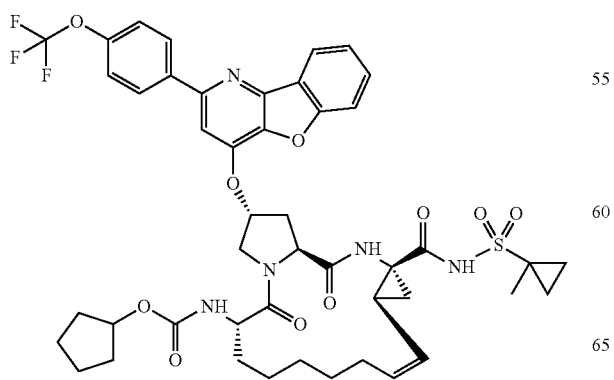
76
-continued
Compound 212
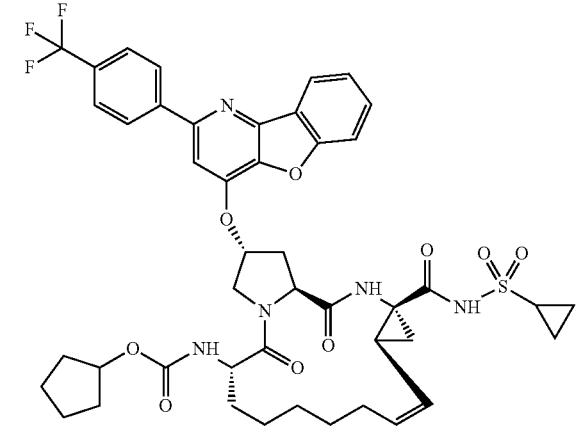
Compound 213
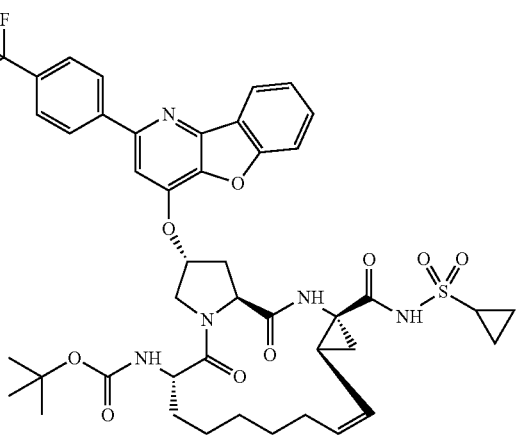
Compound 214
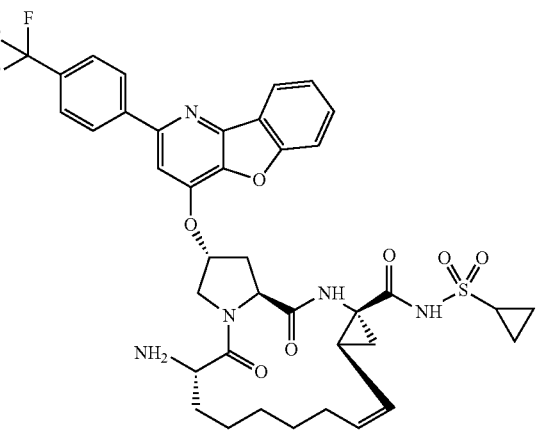

Compound 215
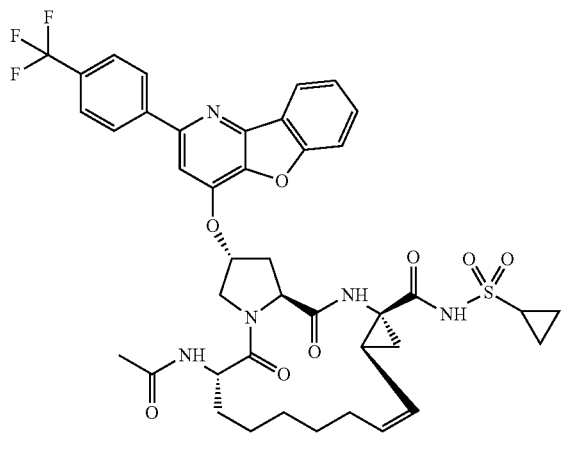
Compound 218
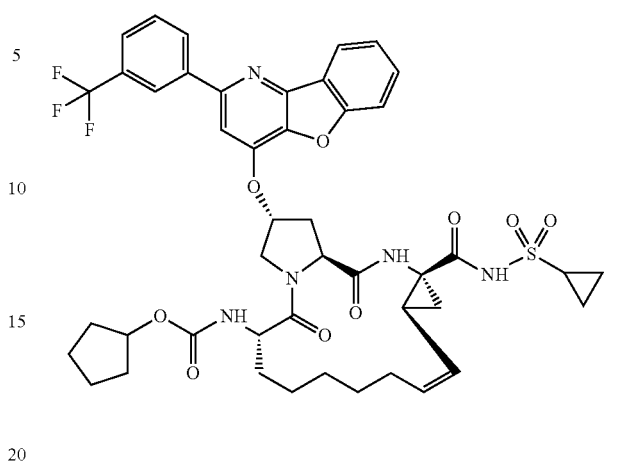
Compound 216
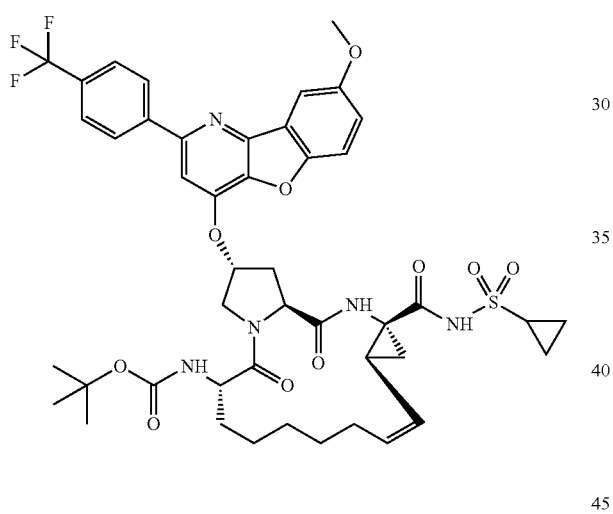
Compound 219
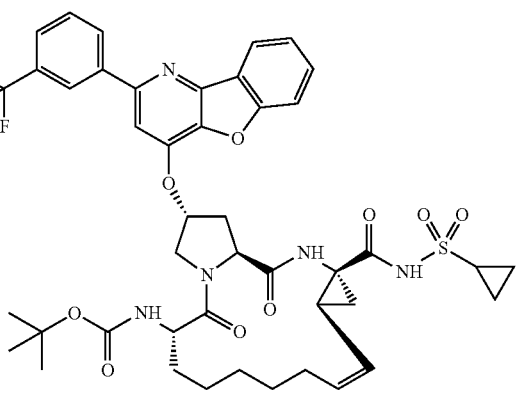
Compound 217
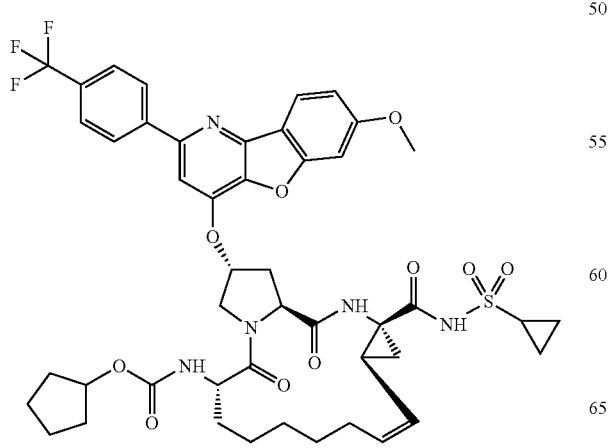
Compound 220
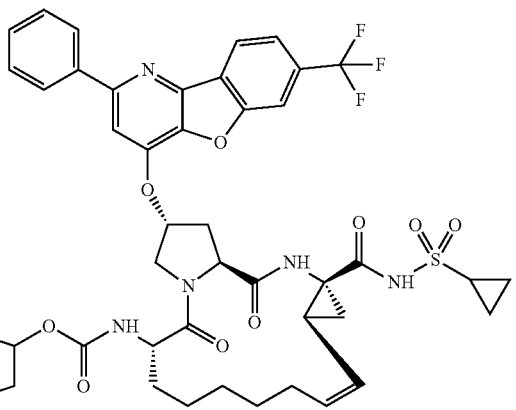

Compound 221
Compound 224
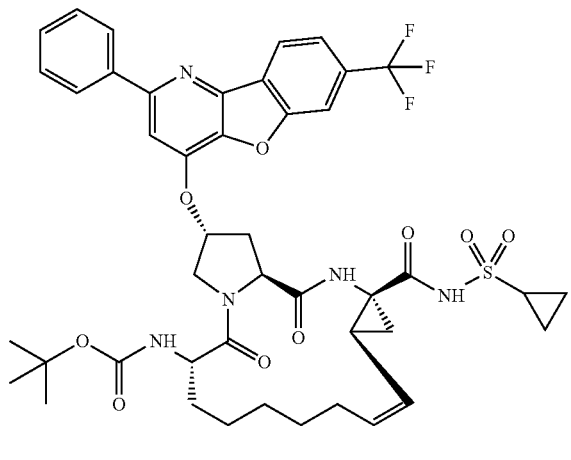
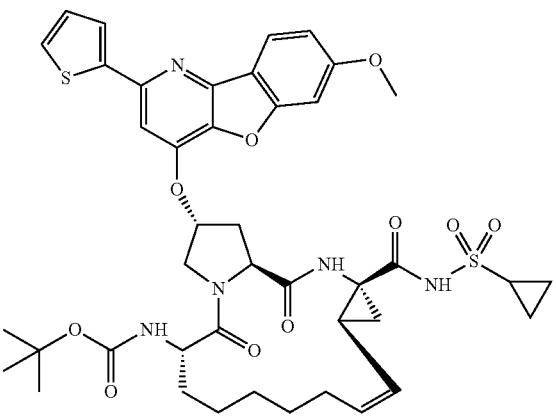
Compound 222
Compound 225
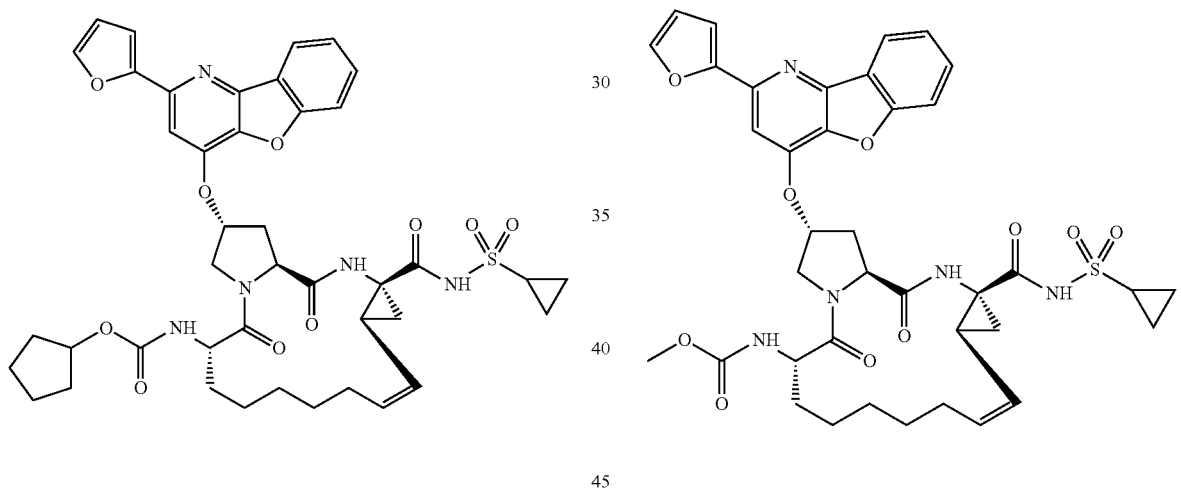
Compound 223
Compound 226
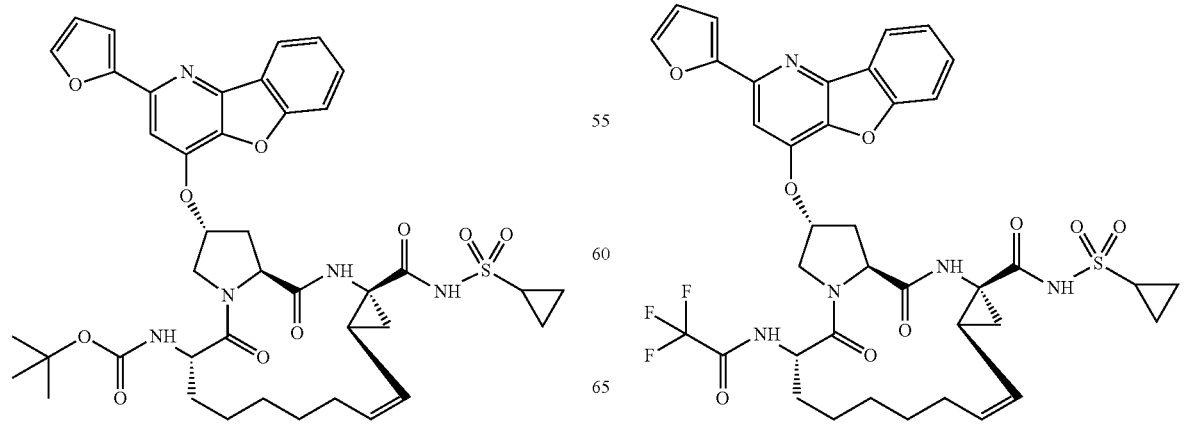

Compound 227
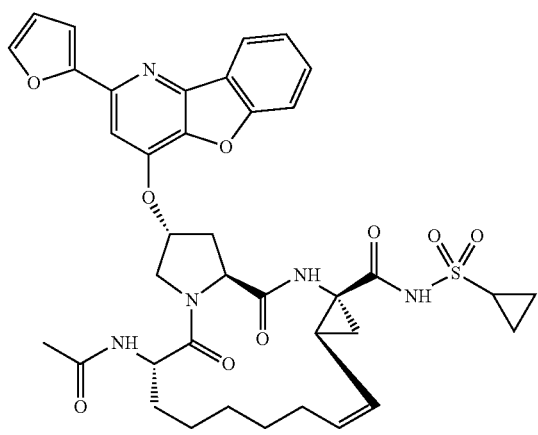
Compound 228
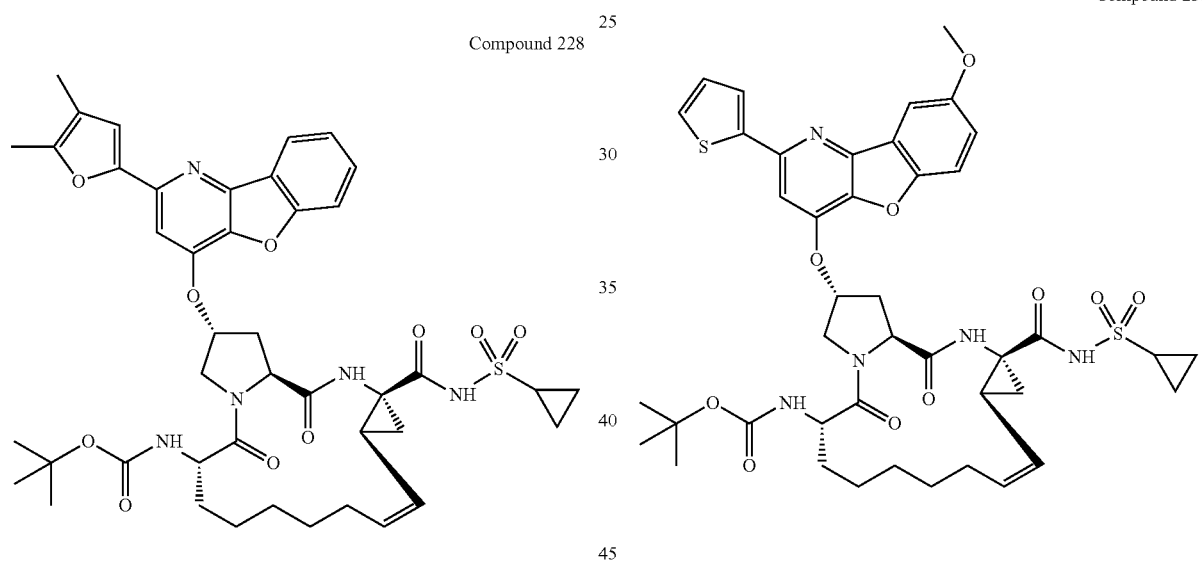
Compound 229
Compound 230
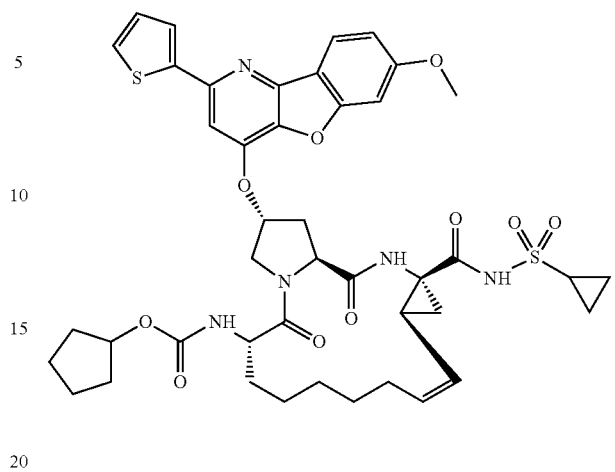
Compound 231
Compound 232
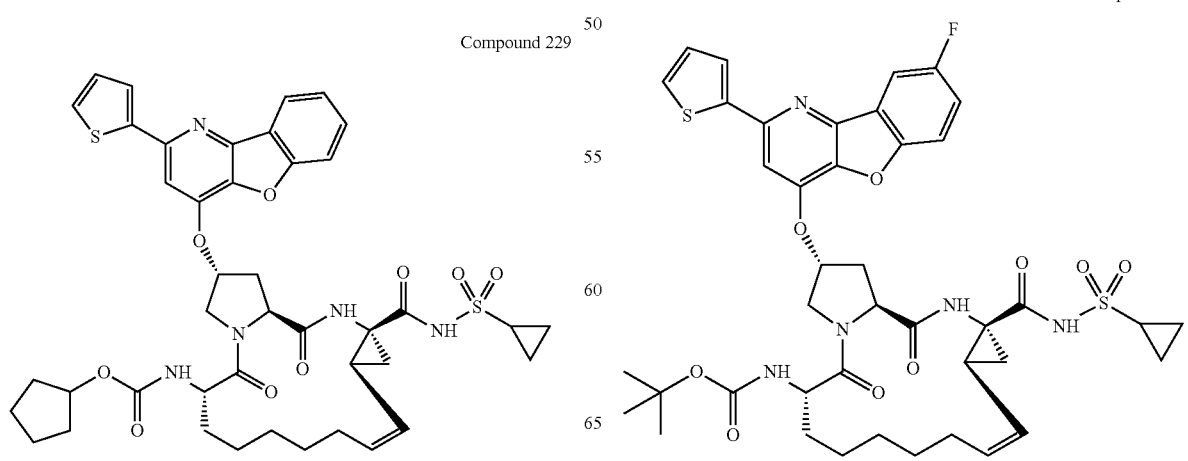

Compound 233
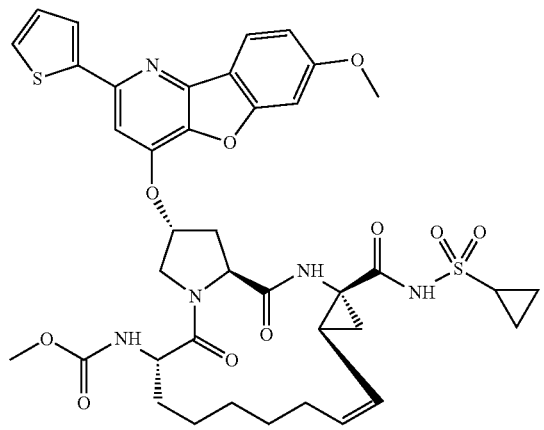
Compound 236
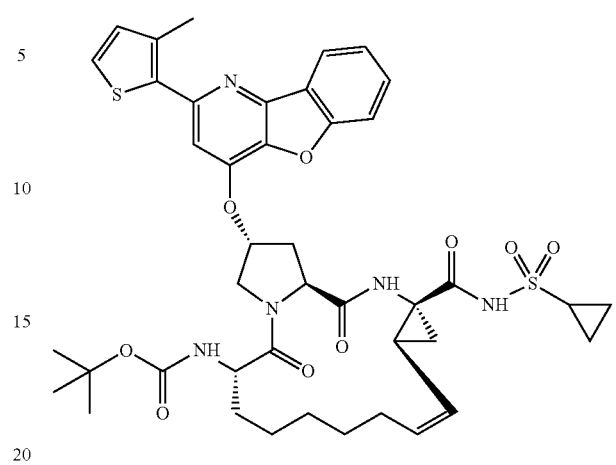
Compound 234
Compound 237
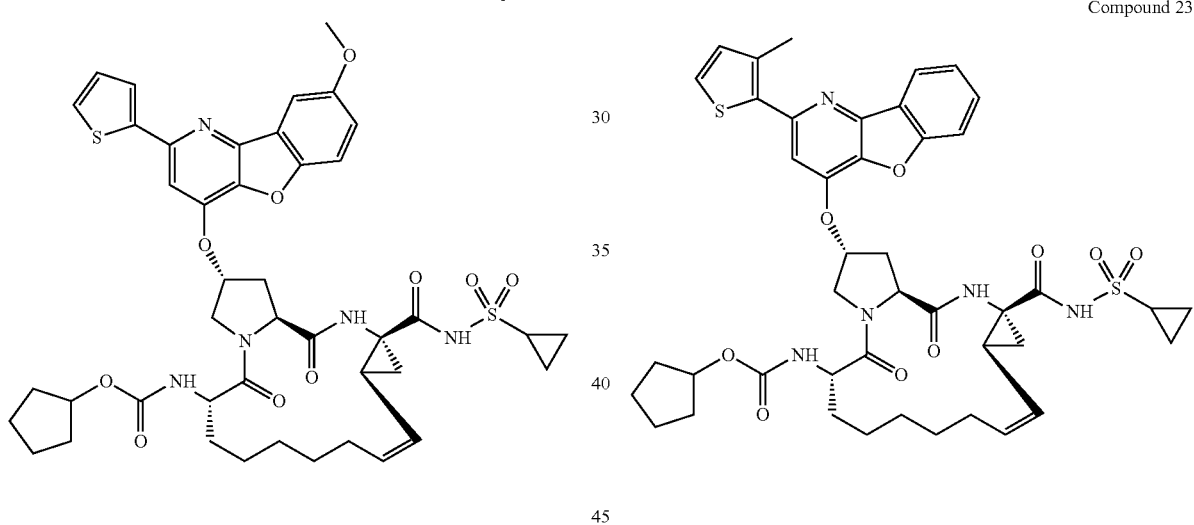
Compound 235
Compound 238
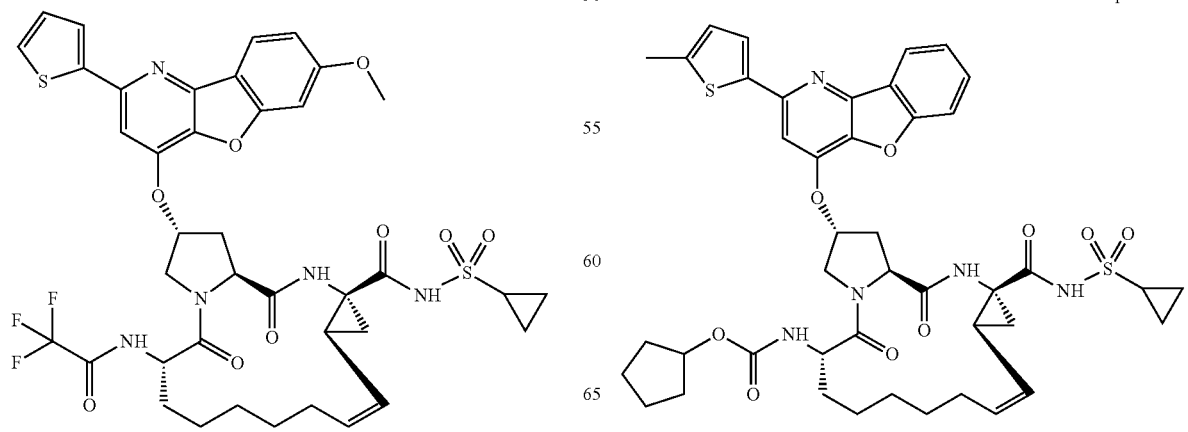

Compound 239
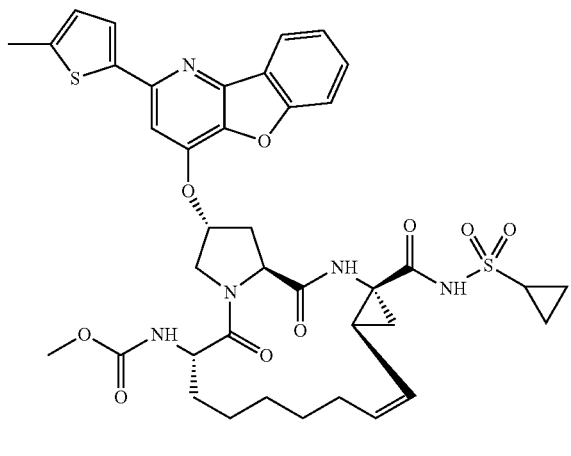
Compound 242
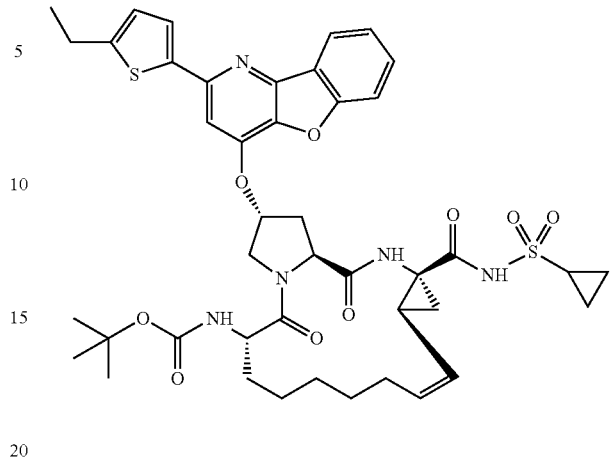
Compound 240
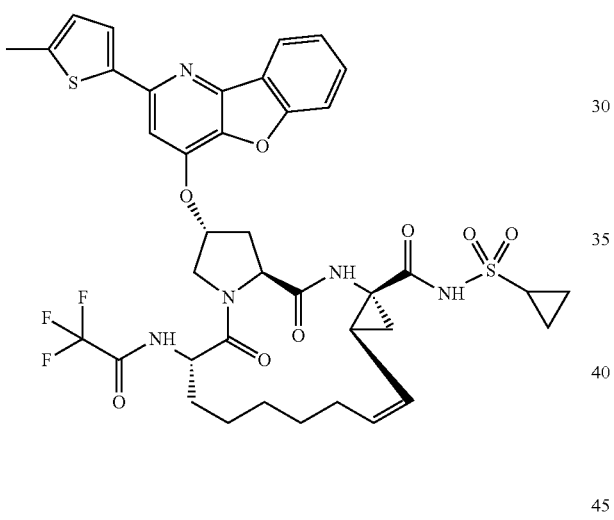
Compound 243
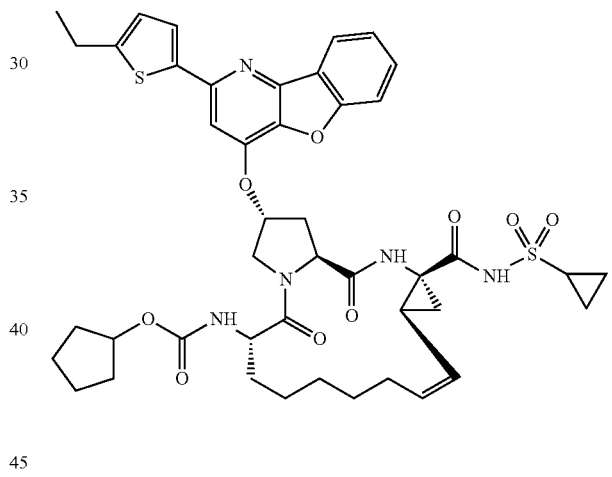
Compound 241
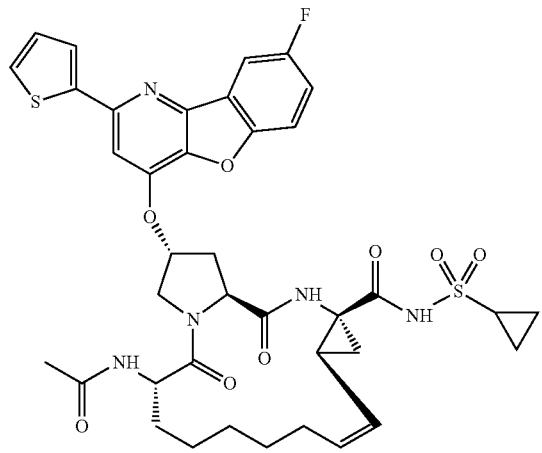
Compound 244
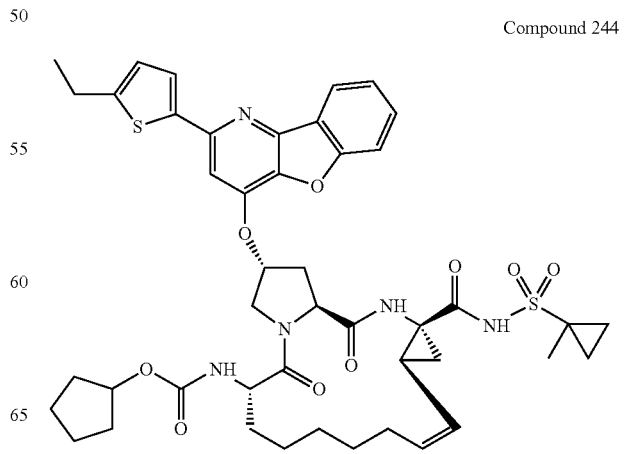

Compound 245
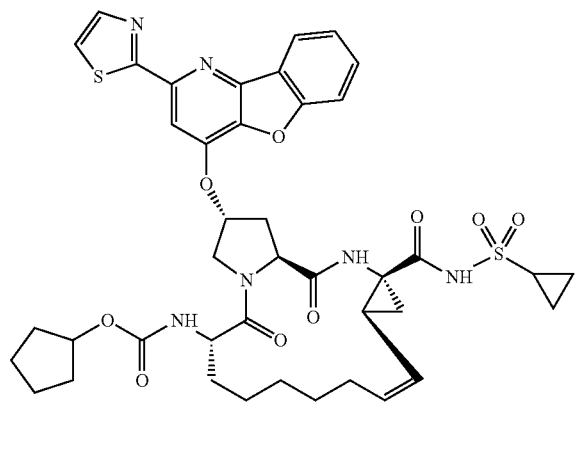
Compound 248
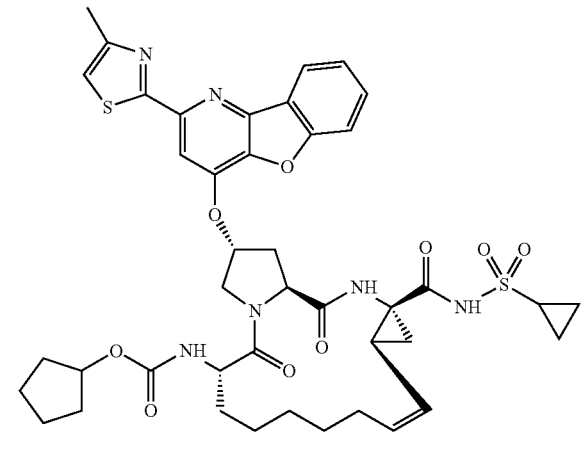
Compound 246
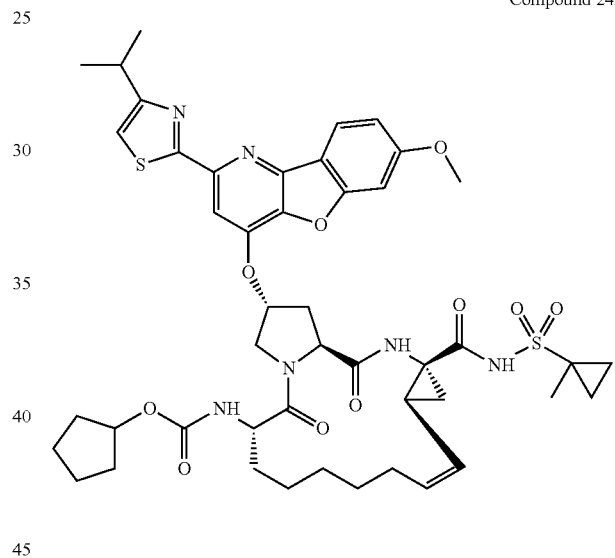
Compound 249
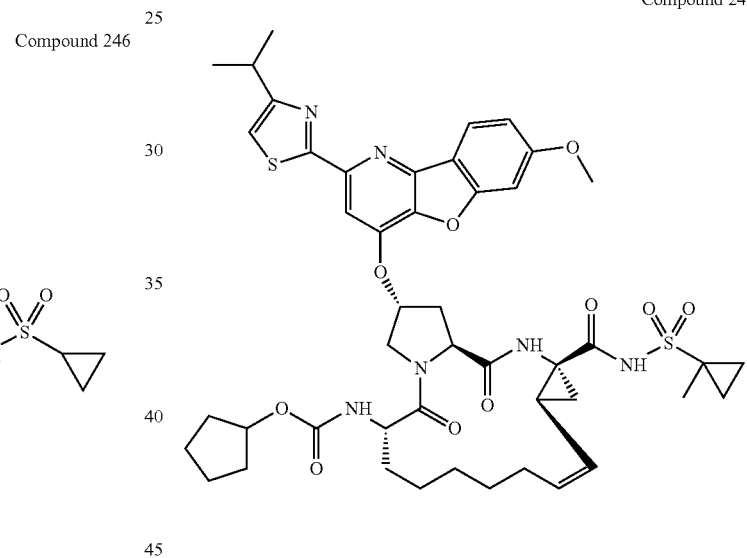
Compound 247
Compound 250
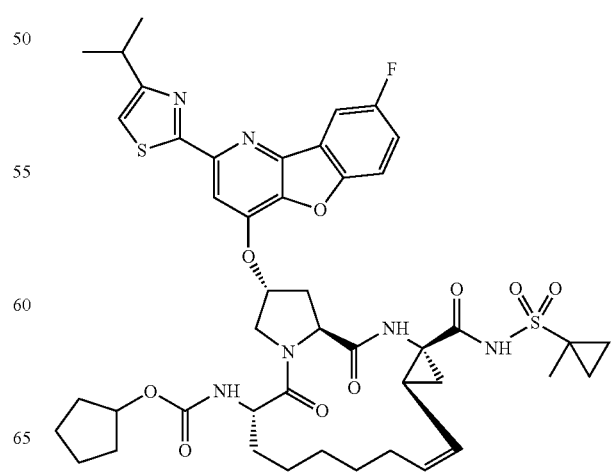

Compound 251
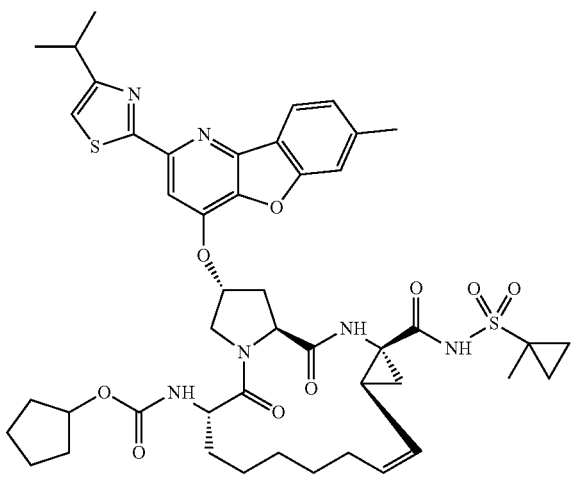
Compound 252
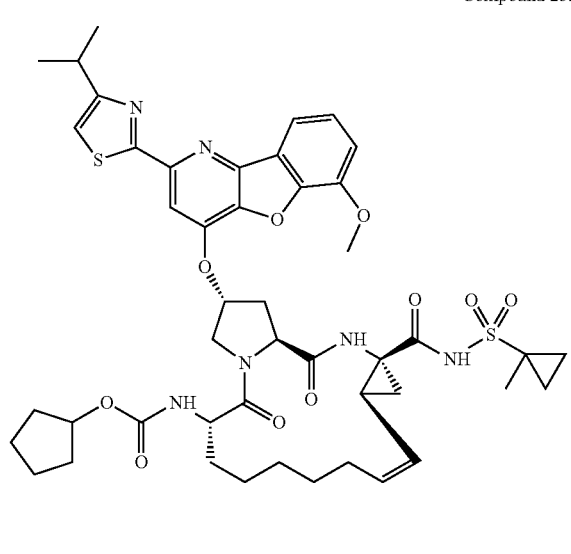
Compound 253
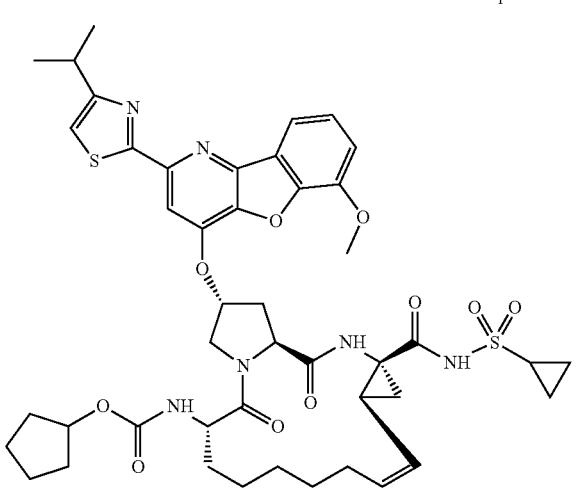
Compound 254
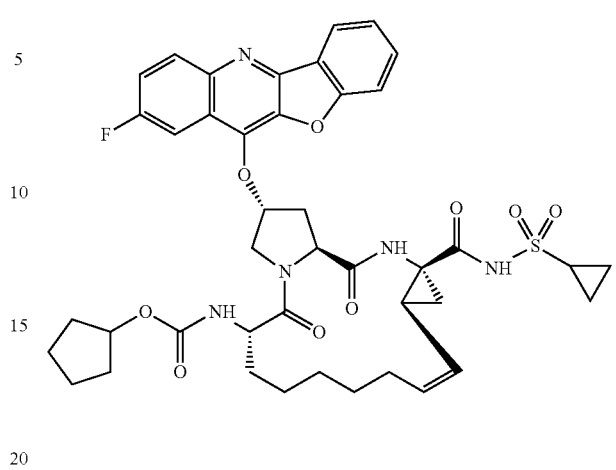
Compound 255
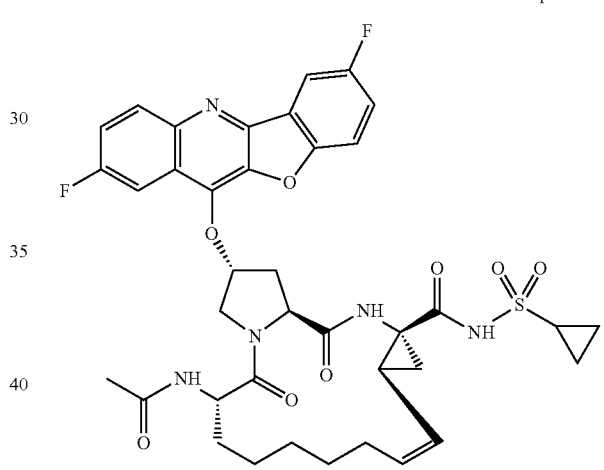
Compound 256
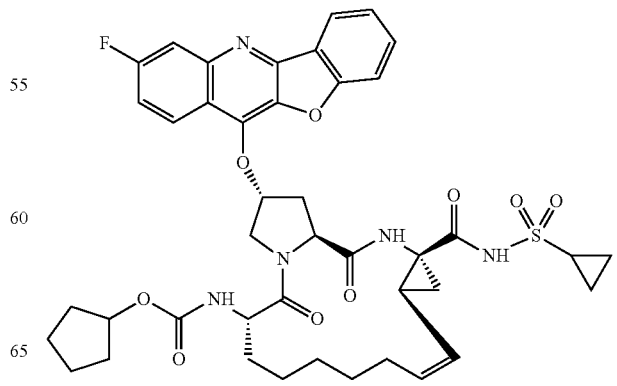

Compound 257
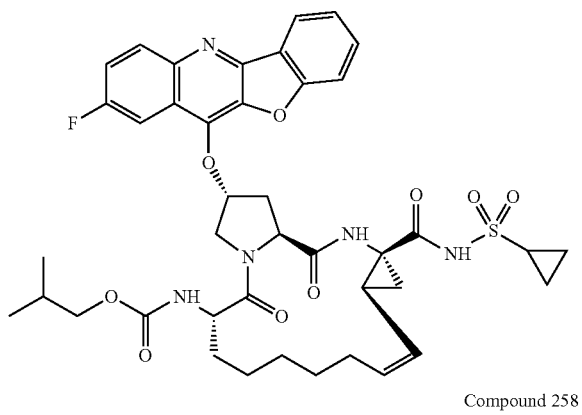
Compound 258
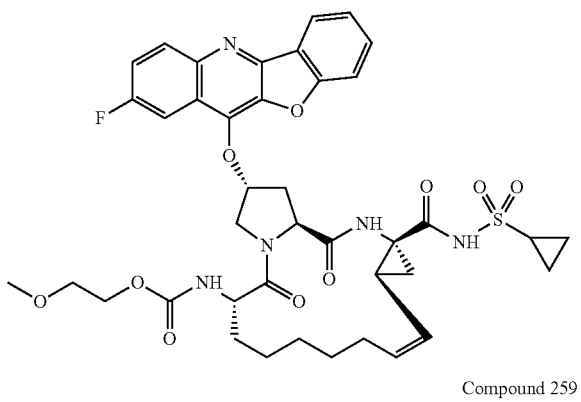
Compound 259
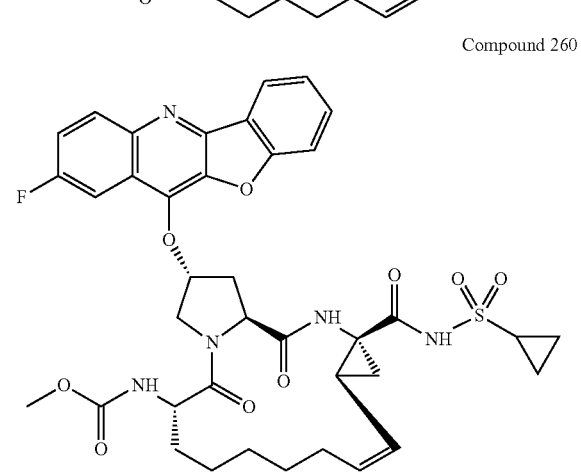
Compound 260
Compound 261
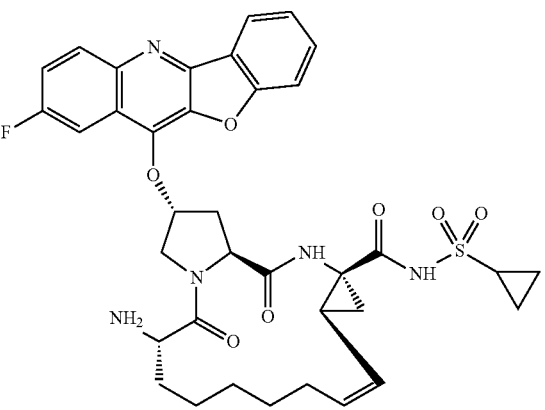
Compound 262
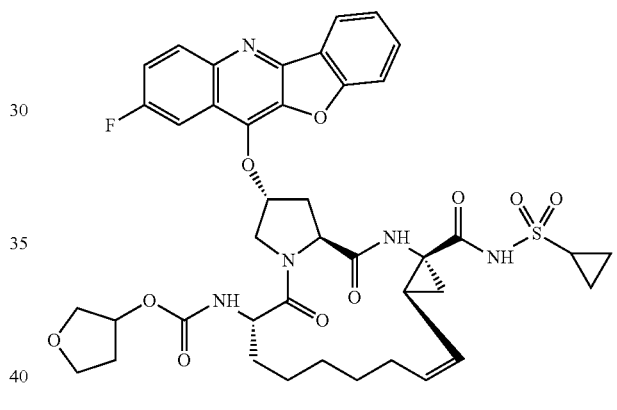
Compound 263
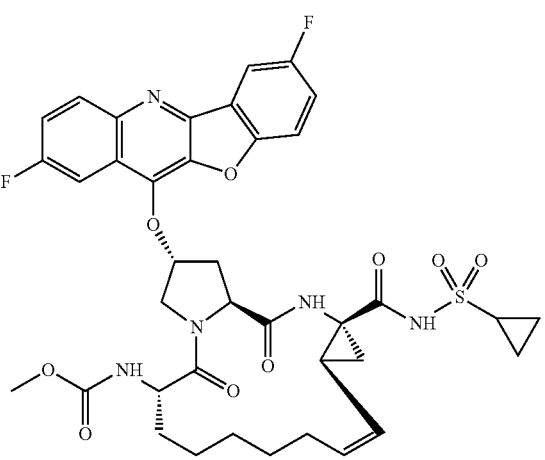

Compound 264
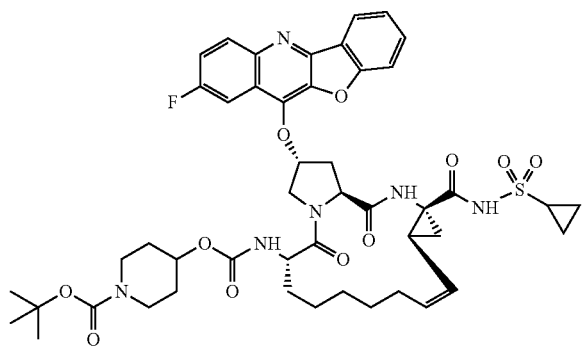
Compound 265
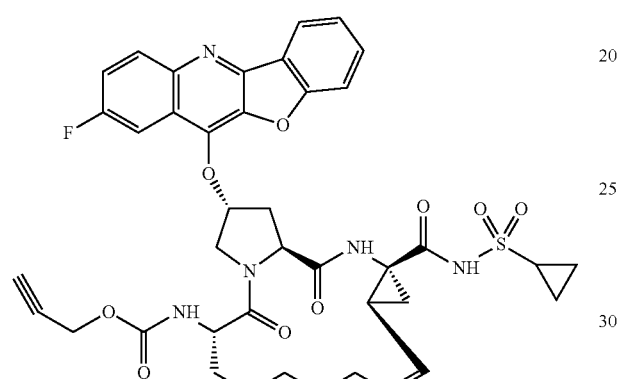
Compound 266
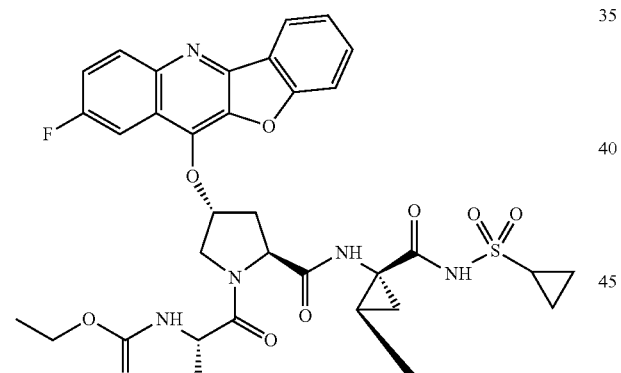
Compound 267
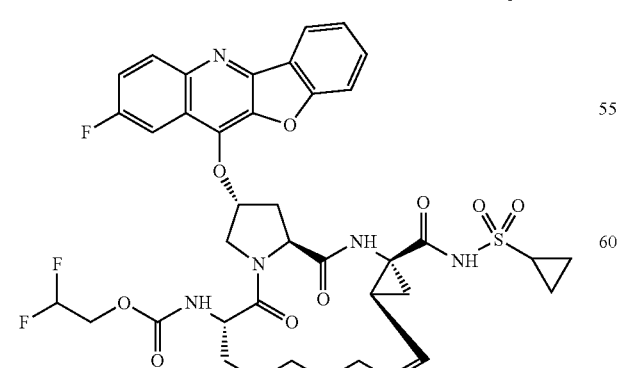
Compound 268
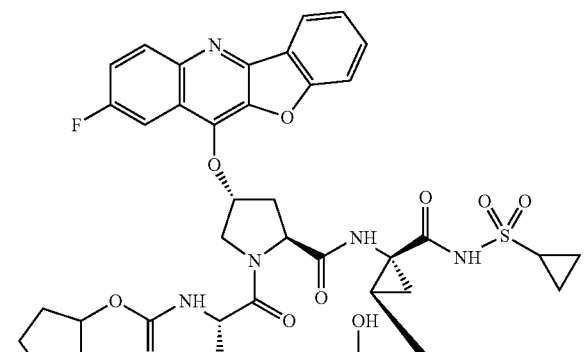
Compound 269
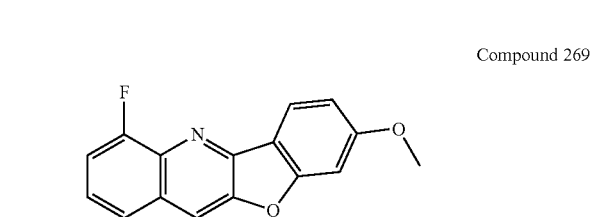
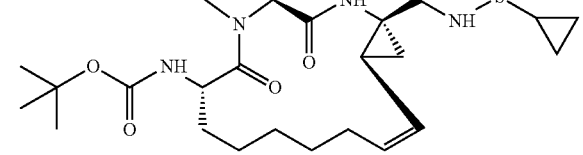
Compound 270
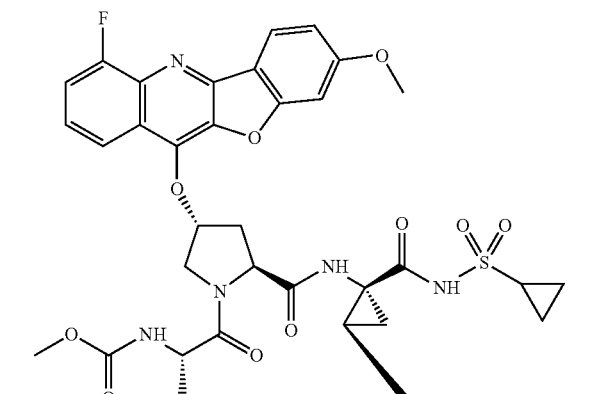

Compound 271
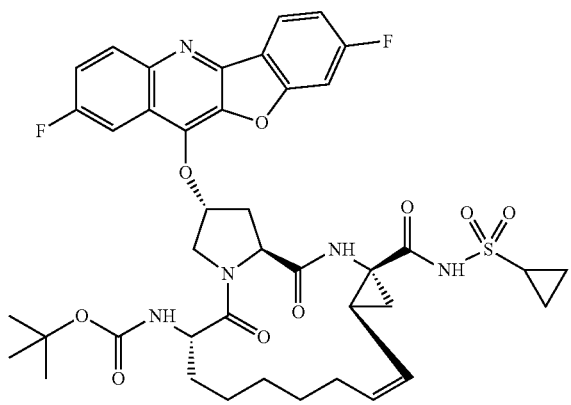
Compound 272
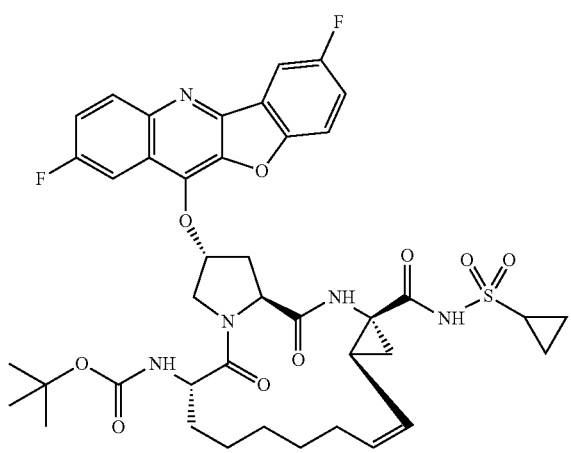
Compound 273
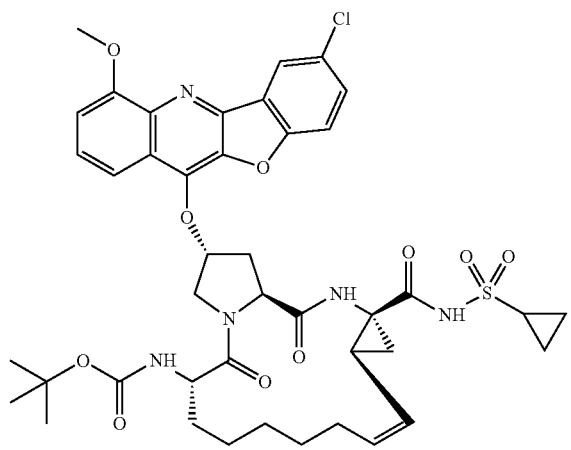
Compound 274
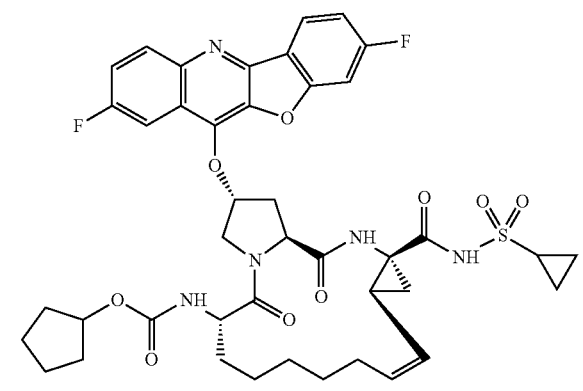
Compound 275
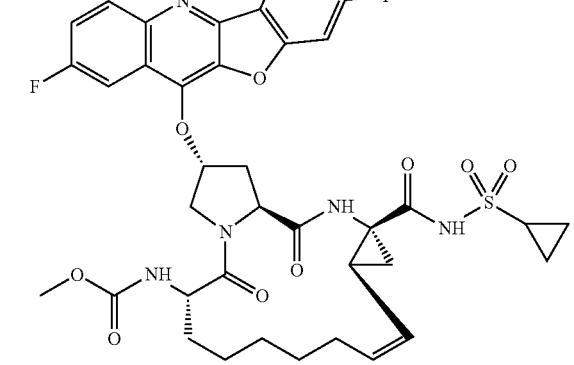
Compound 276
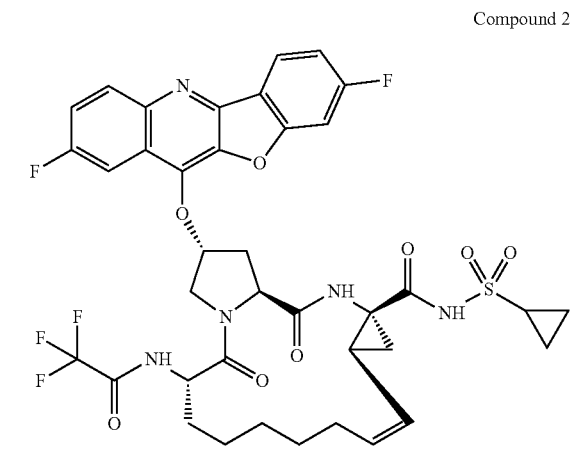

Compound 277

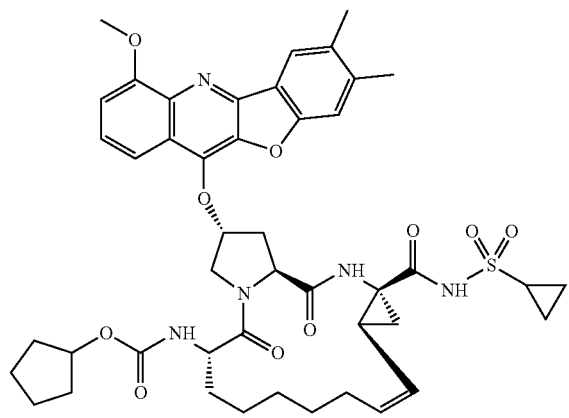

Compound 278

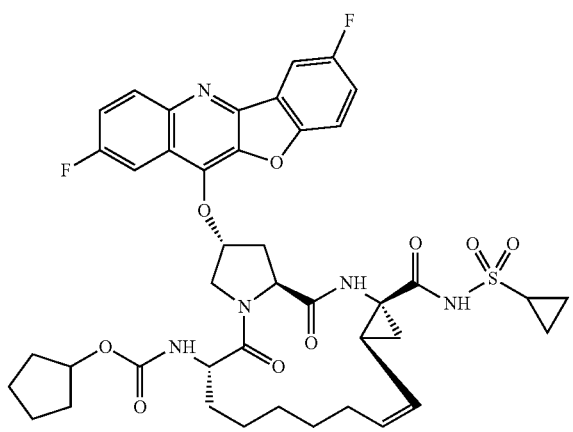

Compound 279

Compound 280

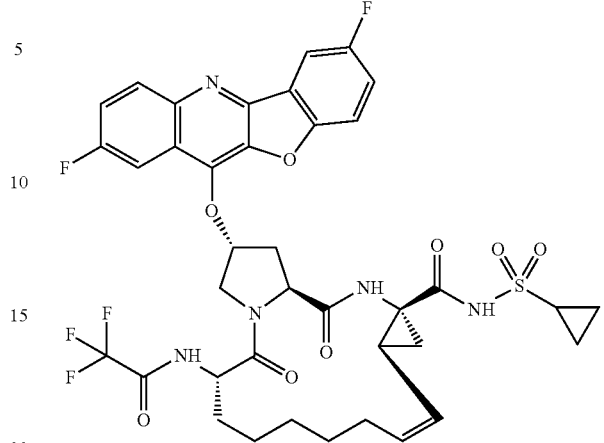

Compound 281

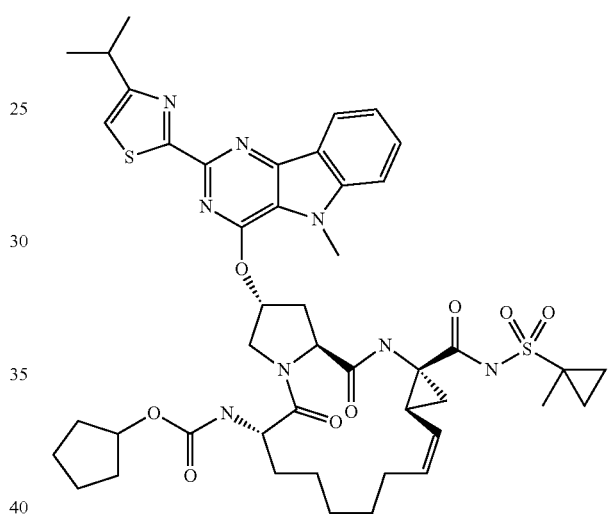

In another aspect, this invention relates to a method for treating hepatitis C virus infection. The method includes administering to a subject in need thereof an effective amount of compound of formula (I) shown above.

In still another aspect, this invention relates to a pharmaceutical composition for use in treating HCV infection. The composition contains an effective amount of at least one of the compounds of formula (I) and a pharmaceutically acceptable carrier. It may include an inhibitor of a target other than HCV NS3 protease in the HCV life cycle, e.g., NS5B polymerase, NS5A, NS4B, or p7.

Examples of such agents include, but are not limited to, N-[3-(1-cyclobutylmethyl-4-hydroxy-2-oxo-1,2-dihydro-quinolin-3-yl)-1,1-dioxo-1,4-dihydro-1l6-benzo[1,2,4]thia-diazin-7-yl]-methanesulfonamide (WO04041818), trans-1,2-di-4-[(phenylacetyl-pyrrolidine-2-(S)-carbonyl)amino]-phenylethylene (WO0401413), and 1-aminoadamantane (Amentadine, Griffin, 2004, J. Gen. Virol. 85: p451). The pharmaceutical composition may also contain an immunomodulatory agent or a second antiviral agent. An immunomodulatory agent refers to an active agent that mediates the immune response. Examples of immunomodulatory agents include, but are not limited to, Nov-205 (Novelos Therapeutics Inc., WO02076490) and IMO-2125 (Idera Pharmaceuticals Inc., WO05001055). An antiviral agent refers to an active agent that kills a virus or suppresses its replication. Examples of antiviral agents include, but are not limited to, ribavirin, ribamidin, interferon-α, pegylated interferon, and HCV protease inhibitors, such as 2-(2-{2-cyclohexyl-2-[(pyrazine-2-carbonyl)-amino]-acetylamino}-3,3-dimethyl-butyryl)-octahydro-cyclopenta[c]pyrrole-1-carboxylic acid (1-cyclopropylaminooxalyl-butyl)-amide (Telaprevir, Vertex Pharmaceuticals Inc., WO02018369), 3-[2-(3-tert-butyl-ureido)-3,3-dimethyl-butyryl]-6,6-dimethyl-3-aza-bicyclo[3.1.0]hexane-2-carboxylic acid (2-carbamoyl-1-cyclobutyl-methyl-2-oxo-ethyl)-amide (Boceprevir, Schering-Plough Research Institute, WO03062265), and 4-fluoro-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.04,6]nonadec-7-en-18-yl ester (ITMN-191, InterMune Inc., US2005/0267018).

Also within the scope of this invention is the use of such a composition for treating HCV infection or for the manufacture of a medicament for the treatment.

The details of one or more embodiments of the invention are set forth in the description below. Other features, objects, and advantages of the invention will be apparent from the description and from the claims.

DETAILED DESCRIPTION

The compounds of this invention can be synthesized from commercially available starting materials by methods well known in the art. For example, one can prepare the compounds of this invention via the route shown in Scheme 1 below:

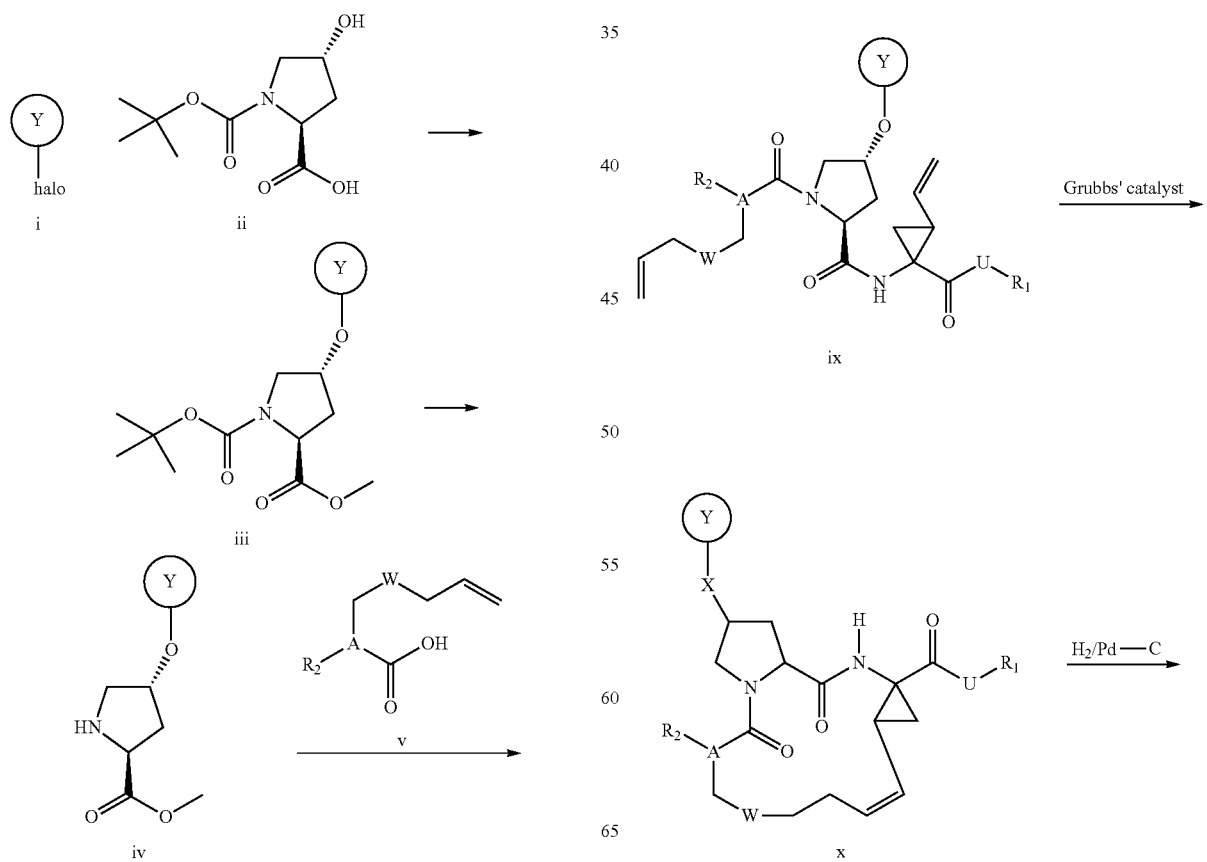

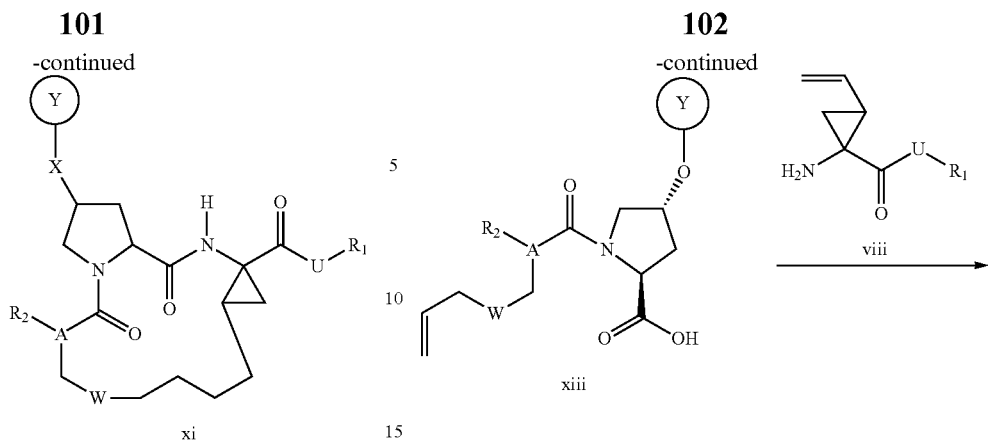

As illustrated in Scheme 1, multicyclic compound (i) is first coupled with N-(t-butoxycarbonyl)-L-proline (ii), followed by methylation, to form intermediate (iii). Intermediate (iii) is deprotected to remove the N-butoxycarbonyl group to produce N-free compound (iv), which is coupled with carboxylic acid (v) to afford intermediate (vi). Intermediate (vi) is hydrolyzed to give acid (vii), which is coupled with amine compound (viii) to provide pyrrolidine compound (ix) having two terminal alkenyl groups. Intermediate (ix) undergoes olefine metathesis in the presence of Grubbs' catalyst to afford desired macrocyclic compound (x). The double bond of macrocyclic analog (xi) can be further hydrogenation in the presence of Pd—C to obtain saturated-macrocyclic compound (xi).

Schemes 2 and 3 below illustrate two alternative synthetic routes to the compounds of this invention.

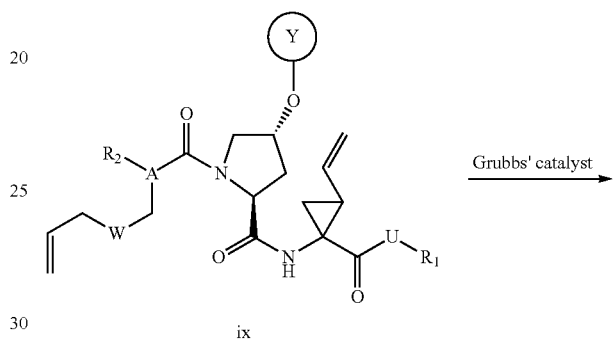

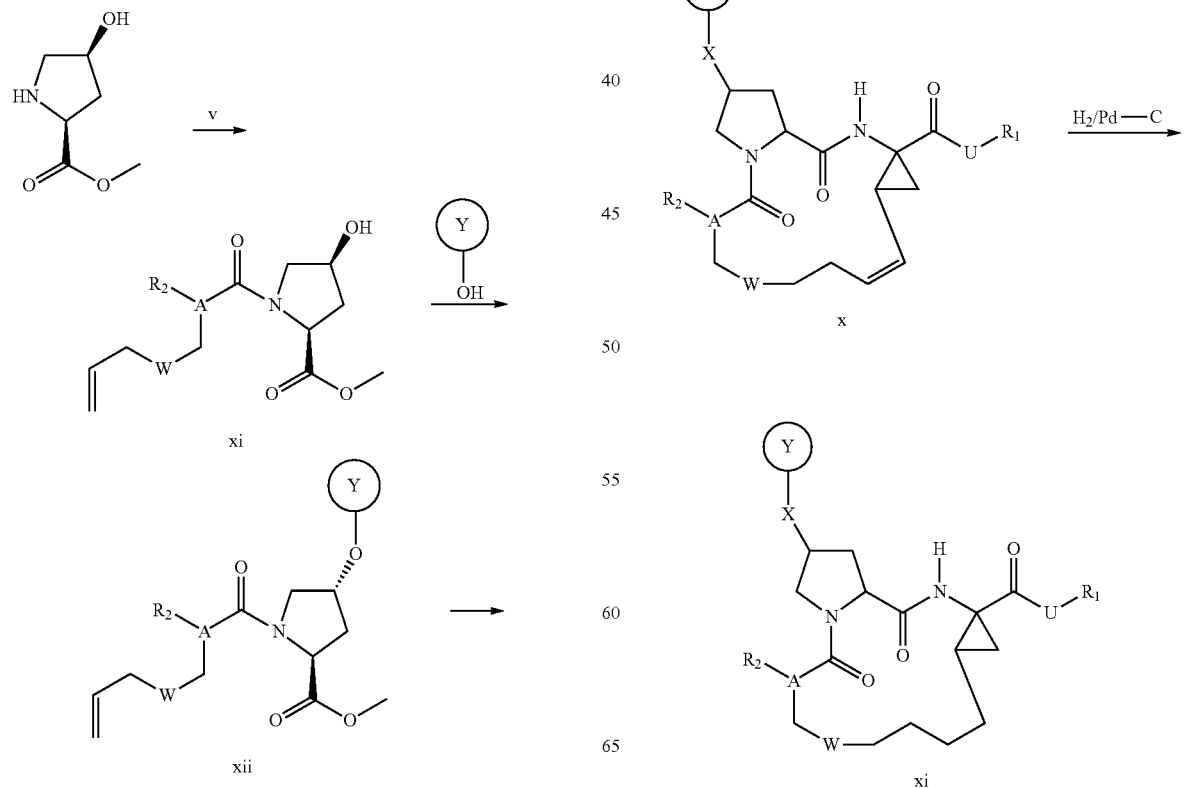

Scheme 3

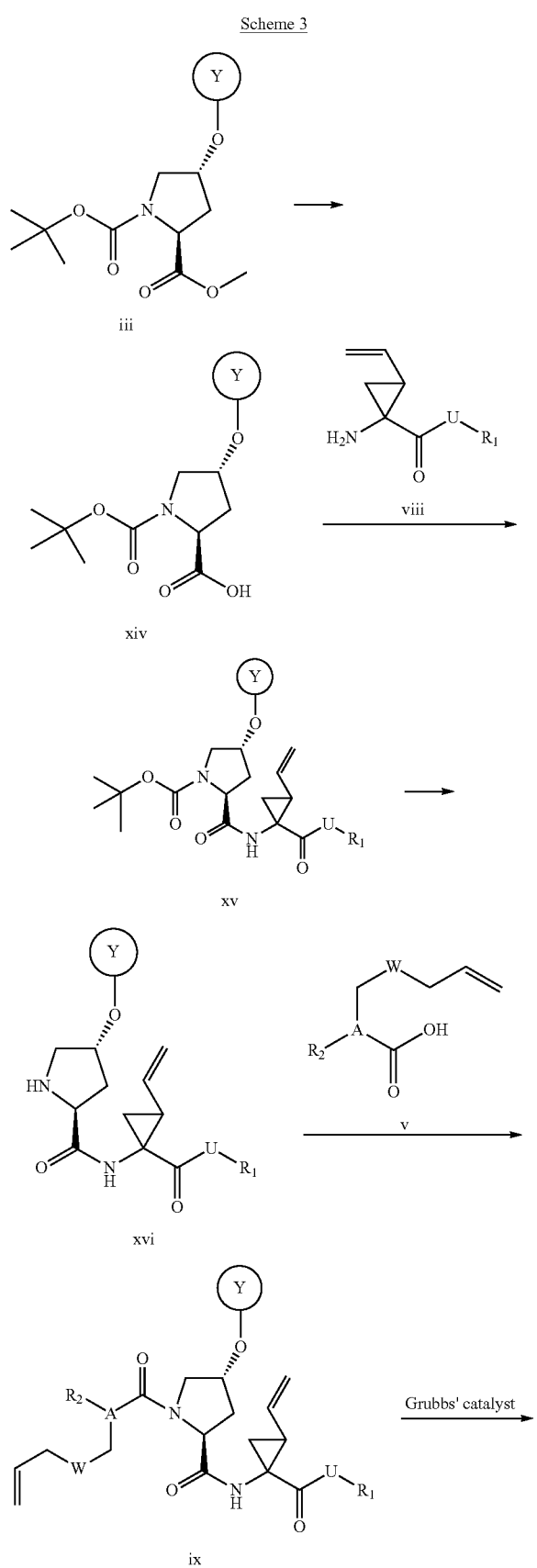

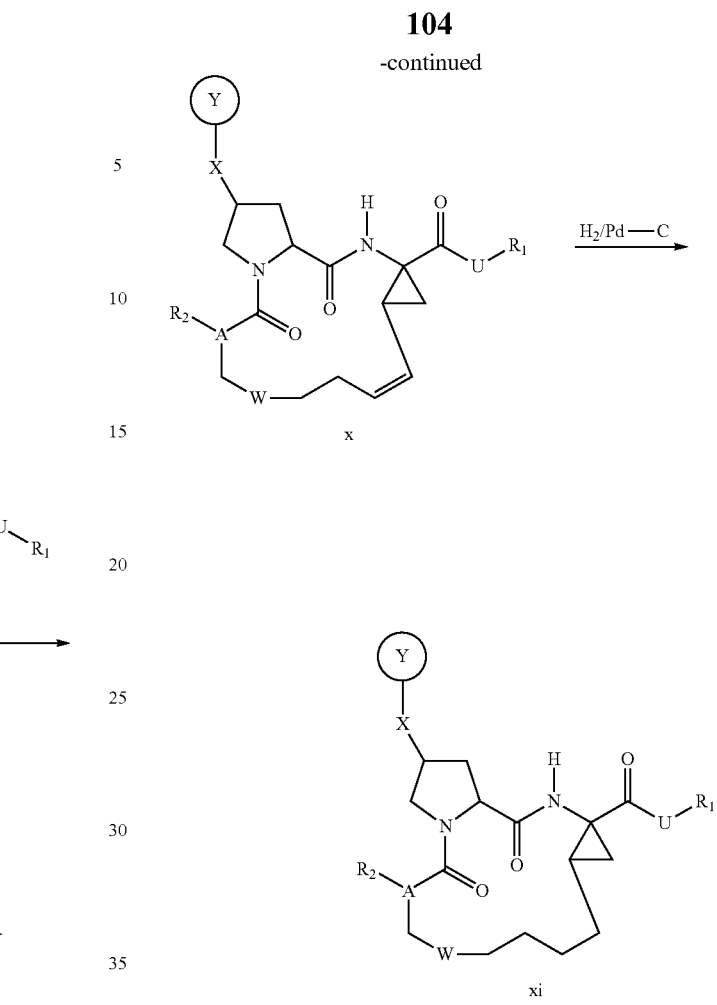

The methods described above may also additionally include steps, either before or after the steps described specifically in Schemes 1-3, to add or remove suitable protecting groups in order to ultimately allow synthesis of the desired compounds. In addition, various synthetic steps may be performed in an alternate sequence or order to give the desired compounds. Synthetic chemistry transformations and protecting group methodologies (protection and deprotection) useful in synthesizing applicable compounds of formula (I) are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Examples 1-281 below provide detailed descriptions of how exemplary compounds 1-281 were actually prepared.

The compounds mentioned herein contain a non-aromatic double bond and asymmetric centers. Thus, they can occur as racemates and racemic mixtures, single enantiomers, individual diastereomers, diastereomeric mixtures, tautomers, and cis- or trans-isomeric forms. All such isomeric forms are contemplated. For example, the compounds of formulas (I) shown above may possess the following stereochemical configurations (II):

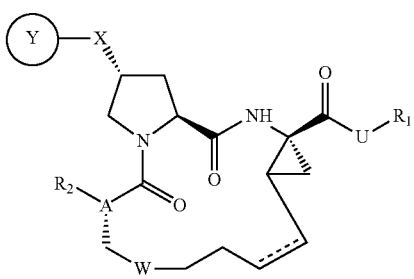
(II)

The compounds described above include the compounds themselves, as well as their salts, prodrugs, and solvates, if applicable. A salt, for example, can be formed between an anion and a positively charged group (e.g., amino) on a compound of formula (I). Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a compound of formula (I). Suitable cations include sodium ion, potassium ion, magnesium ion, calcium ion, and an ammonium cation such as tetramethylammonium ion. The compounds of formula (I) also include those salts containing quaternary nitrogen atoms. Examples of prodrugs include esters and other pharmaceutically acceptable derivatives, which, upon administration to a subject, are capable of providing active compounds of formula (I). A solvate refers to a complex formed between an active compound of formula (I) and a pharmaceutically acceptable solvent. Examples of pharmaceutically acceptable solvents include water, ethanol, isopropanol, ethyl acetate, acetic acid, and ethanolamine.

Also within the scope of this invention is a method of treating HCV infection by administering an effective amount of one or more of the compounds of formula (I) to a patient. The term "treating" or "treatment" refers to administering the compounds to a subject, who has HCV infection, a symptom of it, or a predisposition toward it, with the purpose to confer a therapeutic effect, e.g., to cure, relieve, alter, affect, ameliorate, or prevent the HCV infection, the symptom of it, or the predisposition toward it. The term "an effective amount" refers to the amount of an active compound of this invention that is required to confer a therapeutic effect on the treated subject. Effective doses will vary, as recognized by those skilled in the art, depending on the types of diseases treated, route of administration, excipient usage, and the possibility of co-usage with other therapeutic treatment.

The compounds of this invention can remain in the blood system at an effective level for a prolonged period. Thus, these compounds can be administered at an effective amount once a day to confer the therapeutic effect.

To practice the method of the present invention, a composition having one or more compounds of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active compounds of this invention can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound of this invention. Examples of other carriers include colloidal silicon oxide, magnesium stearate, cellulose, sodium lauryl sulfate, and D&C Yellow # 10.

The compound of this invention can be used to treat HCV along with a second anti-HCV agent, such as an inhibitor of a target other than HCV NS3 protease in the HCV life cycle, another antiviral agent and an immunomodulatory agent. The compound of this invention and the second anti-HCV agent can be administered concurrently or at different times. For concurrent administration, these two agents they may be admixed to form a single dose, or prepared as two separate doses. They are each used at such an amount that their total amount is effective for treating HCV.

The compounds of this invention described above can be preliminarily screened for their efficacy in treating HCV infection by an in vitro assay (see Examples 282 and 283) and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Synthesis of {4-Cyclopropanesulfonylaminocarbonyl-2,15-dioxo-18-[2-(4-trifluoromethyl-phenyl)-benzo[4,5]furo[3,2-d]pyrimidin-4-yloxy]-3,16-diazatricyclo[14.3.0.04,6]nonadec-14-yl}-carbamic acid cyclopentyl ester (Compound 1)

Compound I-3 was first prepared from commercially available 1-t-butoxycarbonylamino-2-vinyl-cyclopropanecarboxylic acid ethyl ester via the route shown below:

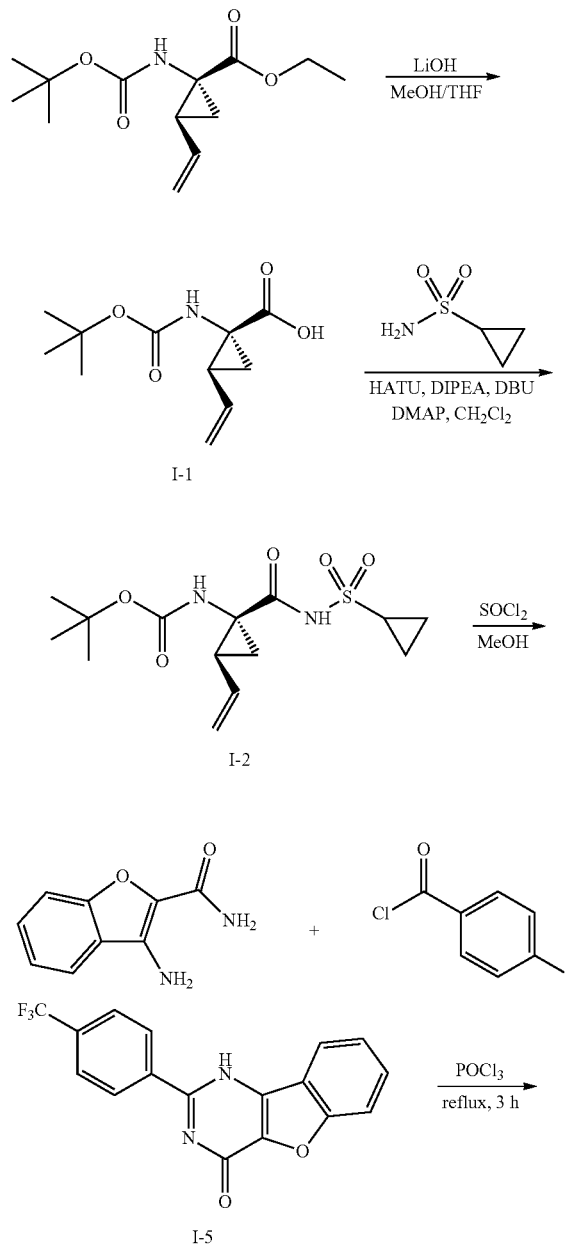

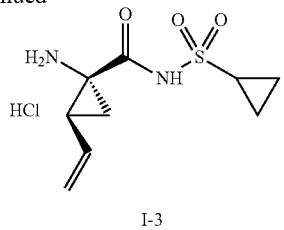

To a solution of 1-t-butoxycarbonylamino-2-vinyl-cyclopropanecarboxylic acid ethyl ester (0.34 g, 1.3 mmol) in THF (5 mL) and methanol (5 mL) was added a suspension of LiOH (0.13 g, 5.3 mmol) in water (1.4 mL). After being stirred overnight at room temperature, the reaction was quenched with 10% HCl (2 mL) and the solvent was removed under vacuum. The resultant solid powder was washed with water (10 mL) to give compound I-1 (0.27 g, 90%). MS m/z 249.9 (M$^+$+23); $^1$H NMR (CDCl$_3$) δ 10.35 (brs, 1H), 5.84-5.71 (m, 1H), 5.29 (d, J=17.4 Hz, 1H), 5.12 (d, J=10.2 Hz, 1H), 2.23-2.14 (m, 1H), 1.87-1.65 (m, 1H), 1.58-1.41 (m, 1H), 1.43 (s, 9H).

A solution of compound I-1 (0.52 g, 2.3 mmol), 2-(1H-7-azabenzotriazol-1-yl)-1,1,3,3-tetramethyl uronium hexafluoro-phosphate methanaminium (HATU, 1.74 g, 4.6 mmol), and 4-dimethylaminopyridine (1.39 g, 11.6 mmol) in CH$_2$Cl$_2$ (40 mL) was stirred at room temperature for 1 hour, followed by slow addition of cyclopropanesulfonamide (0.57 g, 4.7 mmol), diisopropylethylamine (1.81 mL, 14.0 mmol), and 1,8-diazabicyclo[5,4,0]undec-7-ene (1.80 g, 11.7 mmol) over 15 minutes. After the reaction mixture was stirred at room temperature overnight, the solvent was removed under vacuum. The residue was purified by silica gel column chromatography to give compound I-2 (0.51 g, 66%). MS m/z 353.1 (M$^+$+23); $^1$H NMR (CDCl$_3$) δ 9.75 (brs, 1H), 5.64-5.51 (m, 1H), 5.30 (d, J=17.4H), 5.16 (d, J=10.2 Hz, 1H), 2.95-2.89 (m, 1H), 2.19-2.10 (m, 1H), 1.93-1.88 (m, 1H), 1.47 (s, 9H), 1.46-1.38 (m, 1H), 1.32-1.23 (m, 2H), 1.15-1.00 (m, 2H).

To a solution of compound I-2 (0.50 g, 1.5 mmol) in MeOH (8 mL) was added SOCl$_2$ (0.26 g, 2.2 mmol) at room temperature. After the reaction mixture was refluxed for 1 hour, MeOH and SOCl$_2$ was removed under vacuum. The residue was triturated from pentane and filtered to give intermediate I-3 as an off-white solid (0.32 g, 91%). MS m/z (M$^+$+1); $^1$H NMR (CD$_3$COD) δ 5.77-5.65 (m, 1H), 5.43 (d, J=17.4 Hz, 1H), 5.32 (d, J=10.2 Hz, 1H), 3.06-2.97 (m, 1H), 2.45 (dd, J=17.4 Hz, J=7.8, 1H), 2.16 (dd, J=8.0 Hz, J =7.8 Hz, 1H), 1.75 (dd, J=10.1 Hz, J=7.8 Hz, 1H), 1.32-0.86 (m, 4H).

Compound 1 was prepared via the route shown below:

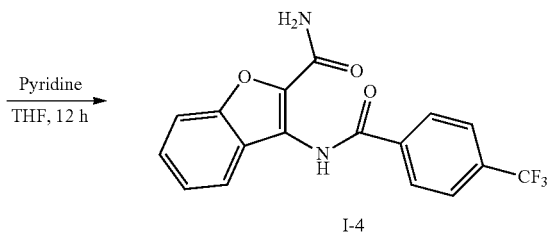

-continued
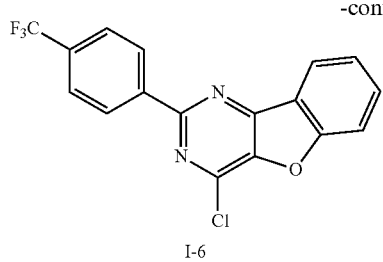
I-6
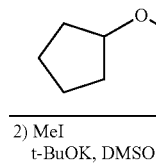
1)
2) MeI
t-BuOK, DMSO
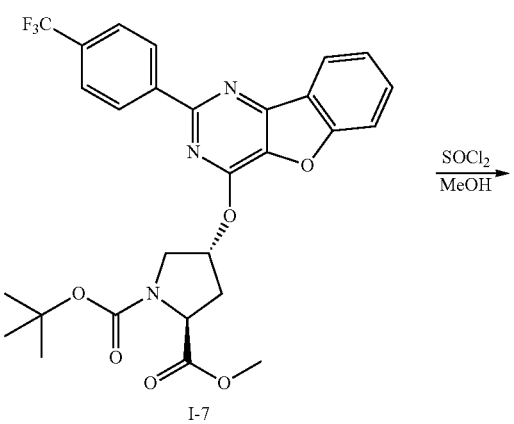
I-7
SOCl₂
MeOH
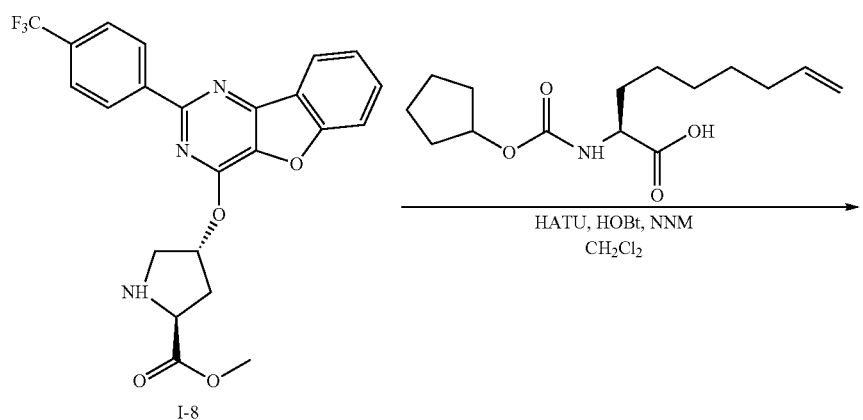
I-8
HATU, HOBt, NNM
CH₂Cl₂
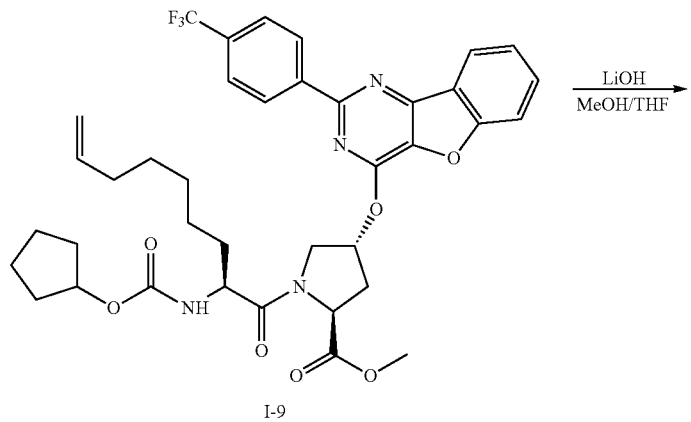
I-9
LiOH
MeOH/THF -continued
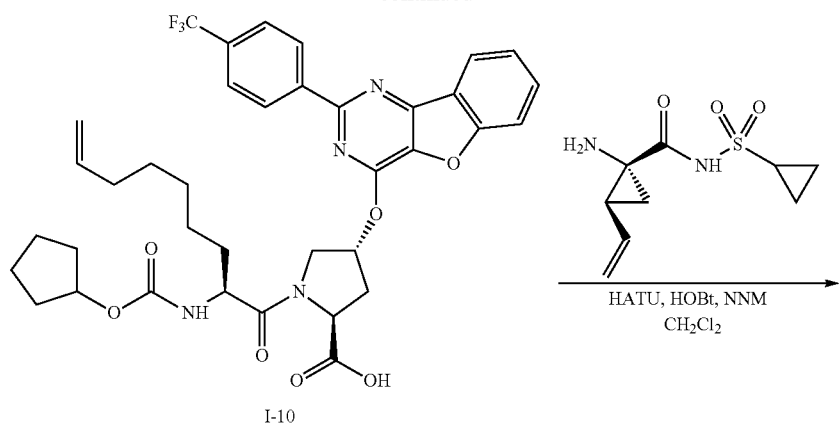
I-10
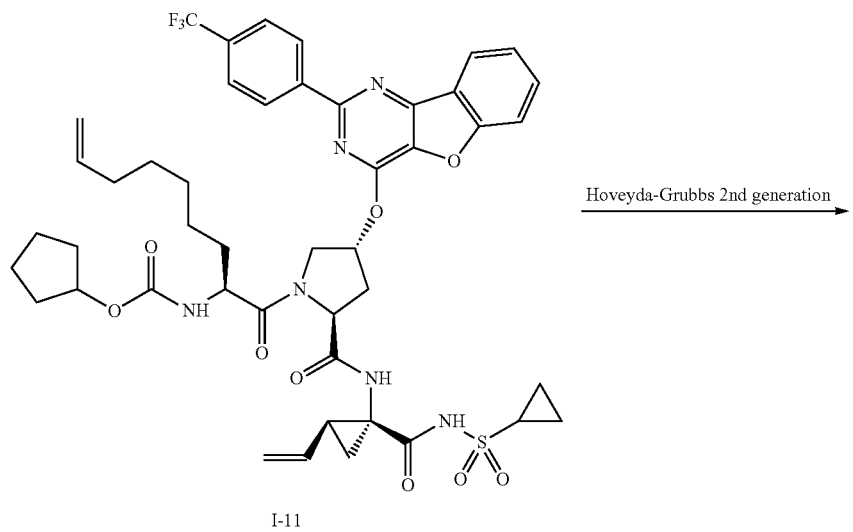
I-11
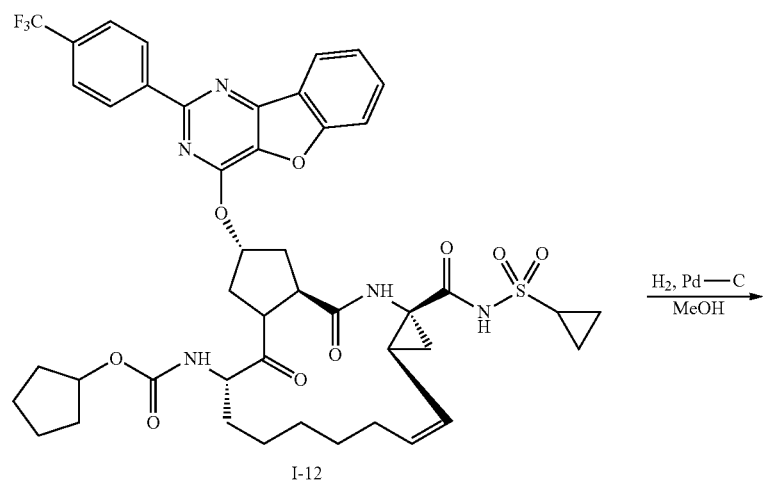
I-12

-continued

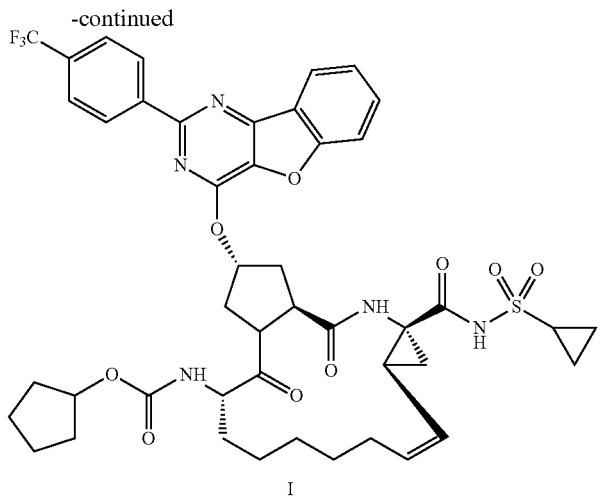

I

A solution of 3-amino-benzofuran-2-carboxylic acid amide (1.00 g, 5.7 mmol) and pyridine (1 mL, 12.26 mmol) in THF (25 mL) was stirred at 0° C. for 10 min. To the resulting solution was slowly added 4-trifluoromethyl-benzoyl chloride (1.48 g, 7.1 mmol). Then the temperature was raised to room temperature and the mixture was stirred for 12 h. After the solvent was removed under reduced pressure, the resulting solid was collected, washed with water, and air-dried to yield I-4 (1.92 g, 96.0%). MS: m/z 349.0 ($M^+$+1).

To a suspension of I-4 (1.92 g, 5.5 mmol) and 2N NaOH (13 mL) in EtOH (25 mL) was heated at 85° C. for 12 h. After cooled, the mixture was acidified and then EtOH was removed. The resulting solid was collected, filtrated, washed with water, and dried to afford I-5 (1.71 g, 95.0%). MS m/z 331 ($M^+$+1).

A solution of I-5 (1.71 g, 5.2 mmol) and excess phosphorus oxychloride ($POCl_3$) was refluxed for 2 hours. After cooled and thoroughly concentrated, the mixture was subjected to extraction with methylene chloride and 10% sodium hydroxide. The organic layer was dried over $MgSO_4$, concentrated, and crystallized from $CH_2Cl_2$ and n-hexane to give compound I-6 (1.49 g, 82%). MS m/z 348.8, 350.9 ($M^+$+1); $^1H$ NMR ($CDCl_3$) δ 8.70 (d, 2H), 8.34 (d, 1H), 7.82-7.75 (m, 4H), 7.57 (ddd, 1H).

To a suspension of boc-trans-4-hydroxy-L-proline (0.53 g, 2.3 mmol) in DMSO (25 mL) was added t-BuOK (0.82 g, 5.1 mmol) at 0° C. After the mixture was allowed to warm to room temperature and stirred for 1 hour, compound I-6 (0.81 g, 2.3 mmol) was added slowly at 10° C. Stirring was continued overnight. Iodomethane (1.02 g, 6.9 mmol) was added and the reaction mixture was stirred at room temperature for additional 30 minutes. The reaction mixture was neutralized to pH 6~7 by 10% HCl aqueous solution and subjected to extraction with methylene chloride. The organic layer was dried over $MgSO_4$, evaporated under vacuum, and purified by silica gel column chromatography to give compound I-7 (1.12 g, 86%). MS m/z 557.8 ($M^+$+1); $^1H$ NMR ($CDCl_3$) δ 8.63 (d, 2H), 8.28 (d, 1H), 7.80-7.74 (m, 2H), 7.70 (d, 2H), 7.51 (ddd, 1H).

To a solution of compound I-7 (1.13 g, 2.0 mmol) in MeOH (20 mL) was added $SOCl_2$ (1.21 g, 9.8 mmol) at room temperature. The reaction mixture was refluxed for 1 hour, and MeOH and $SOCl_2$ were removed. The residue was triturated in pentane. The suspension was filtered to give compound I-8 as an off-white solid (0.87 g, 95%). MS m/z 458.1 ($M^+$+1).

To a solution of HATU (1.12 g, 3.0 mmol), 1-hydroxybenzotriazole (HOBT, 0.41 g, 3.0 mmol), I-8 (0.86 g, 1.9 mmol) and 2-t-butoxycarbonylamino-non-8-enoic acid (1.21 g, 1.9 mmol) in $CH_2Cl_2$ (40 mL) at room temperature was added N-methylmorpholine (NMM, 1.02 g, 9.9 mmol). After stirred overnight, the mixture was concentrated under vacuum. The residue was purified by silica gel column chromatography to give compound I-9 (1.03 g, 73%). MS m/z 711.3 ($M^+$+1).

To a solution of compound I-9 (1.01 g, 1.4 mmol) in THF (20 mL) was added 0.5 M LiOH (5.7 mL, 2.9 mmol) at room temperature. After stirred overnight, the reaction mixture was neutralized by 10% HCl to pH<7 and concentrated under vacuum. The resultant residue was filtered and washed by water to give compound I-10 (0.91 g, 92%). MS: m/z 697.3 ($M^+$+1).

NMM (0.12 g, 1.2 mmol) was added to a solution of compound I-3 (0.28 g, 0.4 mmol), HATU (0.31 g, 0.8 mmol), HOBT (0.08 g, 0.6 mmol) and compound I-10 (0.09 g, 0.4 mmol) in $CH_2Cl_2$ (10 mL) at room temperature. After stirred overnight, the reaction mixture was concentrated under vacuum. The residue was purified by silica gel column chromatography to give compound I-11 (0.10 g, 85%). MS m/z 921.3 ($M^+$+1); $^1H$ NMR ($CDCl_3$) δ 10.24 (s, 1H), 8.61 (d, 2H), 8.26 (d, 1H), 7.77 (d, 2H), 7.73-7.64 (m, 2H), 7.54-7.47 (m, 1H), 7.11 (s, 1H), 6.19 (d, 1H), 5.88-5.70 (m, 2H), 5.38-5.25 (m, 2H), 5.16 (d, 1H), 5.00-4.90 (m, 2H), 4.60 (dd, 1H), 4.88-4.34 (m, 2H), 4.18-4.10 (m, 1H), 2.98-2.89 (m, 1H), 2.68 (dd, 2H), 2.18-1.96 (m, 6H), 1.50-1.32 (m, 7H), 1.28 (s, 9H), 1.09-1.25 (m, 2H).

To a solution of compound I-11 (0.10 g, 0.11 mmol) in $CH_2Cl_2$ (10 mL) was added Hoveyda-Grubbs $2^{nd}$ (35 mg, 0.056 mmol) at room temperature under $N_2$. Then, the reaction mixture was stirred at 40° C. for 24 h to carry out metathesis cyclization. The reaction was quenched and the reaction mixture was purified by column chromatography to give compound I-12 (30 mg, 31%). MS: m/z 893.3 ($M^+$+1); $^1H$ NMR ($CDCl_3$) δ 10.39 (s, 1H), 8.59 (d, 2H), 8.21 (d, 1H), 7.77 (d, 2H), 7.69-7.57 (m, 2H), 7.46 (dd, 1H), 7.20 (s, 1H), 6.12 (s, 1H), 5.69 (q, 1H), 5.12 (d, 1H), 4.97 (dd, 1H), 4.81-4.68 (m, 2H), 4.28-4.07 (m, 2H), 2.96-2.49 (m, 3H), 2.30 (q, 1H), 1.96-1.12 (m, 14H), 1.08 (s, 9H), 0.96-0.82 (m, 2H).

To a solution of compound I-12 (30 mg, 0.034 mmol) in MeOH (10 mL) was added 5% Pd—C (5 mg) at room temperature under $N_2$. Then, the reaction mixture was stirred under hydrogen at room temperature and a pressure of 60 psi for 4 h. The reaction mixture was filtrated and purified by column chromatography to give compound 1 (16.5 mg, 55%). MS: m/z 895.3 (M$^+$+1); $^1$H NMR (CDCl$_3$) δ 10.79 (s, 1H), 8.57 (d, 2H), 8.21 (d, 1H), 7.75 (d, 2H), 7.64 (m, 2H), 7.46 (d, 1H), 7.11 (s, 1H), 6.11 (s, 1H), 5.29 (d, 1H), 4.72 (m, 2H), 4.38 (m, 2H), 4.12 (m, 1H), 3.02-2.58 (m, 3H), 1.98-0.86 (m, 29H).

EXAMPLE 2-141

Syntheses of Compound 2-141

Each of Compounds 2-141 was prepared in a manner similar to those described in Examples 1.

Compound 2: MS: m/z 883.3 (M$^+$+1); $^1$H NMR (CDCl$_3$) δ 10.51 (s, 1H), 8.53 (d, 2H), 8.16 (d, 1H), 7.73 (d, 2H), 7.62 (m, 2H), 7.22 (m, 2H), 6.07 (s, 1H), 5.23 (d, 1H), 4.77 (dd, 1H), 4.49 (d, 1H), 4.35 (m, 1H), 4.13 (m, 1H), 3.02-2.57 (m, 3H), 1.99-0.91 (m, 30H).

Compound 3: MS: m/z 823.2 (M$^+$+1); $^1$H NMR (CDCl$_3$) δ 10.38 (s, 1H), 8.53 (d, 2H), 8.16 (d, 1H), 7.73 (d, 2H), 7.61 (m, 2H), 7.41 (m, 2H), 6.13 (m, 2H), 5.69 (q, 1H), 4.98 (dd, 1H), 4.78 (m, 1H), 4.55 (m, 1H), 4.42 (m, 1H), 4.19 (m, 1H), 2.89 (m, 1H), 2.78 (m, 2H), 2.52 (m, 1H), 2.23 (q, 1H), 1.96-0.84 (m, 15H), 1.90 (s, 3H).

Compound 4: MS: m/z 882.3 (M$^+$+1); $^1$H NMR (CDCl$_3$) δ 10.47 (s, 1H), 8.64 (d, 1H), 8.52 (m, 3H), 7.70 (d, 2H), 7.44 (dd, 1H), 6.07 (s, 1H), 5.63 (q, 1H), 5.01-4.73 (m, 3H), 4.07-4.01 (m, 2H), 2.90-2.22 (m, 4H), 1.97-1.09 (m, 17H), 0.94 (s, 9H), 0.90-0.88 (m, 1H).

Compound 5: MS: m/z 840.2 (M$^+$+1); $^1$H NMR (CDCl$_3$) δ 10.42 (s, 1H), 8.64-8.47 (m, 4H), 7.80 (d, 2H), 7.50-7.27 (m, 2H), 6.15 (s, 1H), 5.69 (q, 1H), 5.23 (d, 1H), 5.02 (dd, 1H), 4.84 (dd, 1H), 4.53 (d, 1H), 4.25-4.11 (m, 2H), 3.32 (s, 3H), 2.93-2.15 (m, 4H), 1.92-0.83 (m, 16H).

Compound 6: MS: m/z 824.2 (M$^+$+1); $^1$H NMR (CDCl$_3$) δ 10.48 (s, 1H), 8.63 (d, 1H), 8.62-8.48 (m, 3H), 7.78 (d, 2H), 7.44-7.40 (m, 1H), 6.16-6.14 (m, 2H), 5.73 (q, 1H), 5.04 (dd, 1H), 4.85 (dd, 1H), 4.55 (s, 1H), 4.51 (s, 1H), 4.15 (d, 1H), 2.93-2.89 (m, 2H), 2.77-2.22 (m, 3H), 1.95-1.85 (m, 1H), 1.79 (s, 3H), 1.76-0.83 (m, 15H).

Compound 7: MS: m/z 839.2 (M$^+$+1); $^1$H NMR (CDCl$_3$) δ 10.39 (s, 1H), 8.46 (d, 2H), 8.15 (d, 1H), 7.71 (d, 2H), 7.62-7.37 (m, 3H), 7.16 (s, 1H), 6.08 (s, 1H), 5.71 (q, 1H), 5.25 (d, 1H), 4.96 (dd, 1H), 4.75 (dd, 1H), 4.44 (d, 1H), 4.35-4.09 (m, 2H), 3.34 (s, 3H), 2.96-2.71 (m, 2H), 2.57 (brs, 1H), 2.28 (q, 1H), 2.08-0.87 (m, 16H).

Compound 8: MS: m/z 849.3 (M$^+$+1); $^1$H NMR (CDCl$_3$) δ 10.54 (s, 1H), 8.45 (d, 2H), 8.06 (d, 1H), 7.71 (d, 2H), 7.57 (m, 3H), 7.35 (s, 1H), 6.28 (d, 1H), 6.04 (s, 1H), 5.71 (q, 1H), 4.96 (dd, 1H), 4.67 (dd, 1H), 4.47 (d, 1H), 4.45 (brs, 1H), 4.11 (m, 1H), 2.92-2.45 (m, 4H), 2.32 (q, 1H), 1.96-0.84 (m, 20H).

Compound 9: MS: m/z 880.3 (M$^+$+1); $^1$H NMR (CDCl$_3$) δ 10.45 (s, 1H), 8.40 (d, 2H), 8.14 (s, 1H), 7.97 (d, 1H), 7.64 (d, 2H), 7.48-7.41 (m, 2H), 7.25-7.20 (m, 1H), 5.96 (s, 1H), 5.63 (q, 1H), 4.92-4.86 (m, 2H), 4.77 (d, 1H), 4.44 (s, 1H), 4.20 (dd, 1H), 4.03 (dd, 1H), 2.90-2.84 (m, 2H), 2.80-2.63 (m, 1H), 2.38-2.32 (m, 1H), 1.98-1.02 (m, 15H), 0.91 (s, 9H), 0.90-0.086 (m, 1H).

Compound 10: MS: m/z 911.2 (M$^+$+1); $^1$H NMR (CDCl$_3$) δ 10.23 (s, 1H), 8.54 (d, 2H), 7.87-7.80 (m, 1H), 7.71 (d, 2H), 7.56 (dd, 1H), 7.33-7.20 (m, 1H), 6.88 (s, 1H), 6.13 (s, 1H), 5.65 (q, 1H), 5.07-4.94 (m, 2H), 4.69 (dd, 1H), 4.57 (d, 1H), 4.43-4.38 (m, 1H), 4.24-4.01 (m, 2H), 2.91-2.80 (m, 2H), 2.74 (s, 3H), 2.65-2.63 (m, 1H), 2.60-2.41 (m, 1H), 2.22 (q, 1H), 1.98-0.86 (m, 20H).

Compound 11: MS: m/z 907.3 (M$^+$+1).

Compound 12: MS: m/z 923.3 (M$^+$+1); $^1$H NMR (CDCl$_3$) δ 10.42 (s, 1H), 8.57 (d, 2H), 8.06 (d, 1H), 7.76 (d, 2H), 7.51 (s, 1H), 7.14-6.93 (m, 2H), 6.13 (s, 1H), 5.80-5.60 (m, 1H), 5.31 (d, 1H), 4.97-4.83 (m, 2H), 4.79 (dd, 1H), 4.64-4.04 (m, 3H), 3.88 (s, 3H), 2.94-2.43 (m, 3H), 2.36-0.86 (m, 25H).

Compound 13: MS: m/z 852.3 (M$^+$+1); $^1$H NMR (CDCl$_3$) δ 10.68 (s, 1H), 8.38 (d, 2H), 7.95 (d, 1H), 7.72-7.58 (m, 3H), 7.47 (d, 2H), 7.24-7.19 (m, 1H), 6.01 (s, 1H), 5.69 (q, 1H), 4.94 (dd, 1H), 4.78 (dd, 1H), 4.70 (d, 1H), 4.46 (d, 1H), 4.22-3.98 (m, 2H), 2.97-2.80 (m, 2H), 2.57 (s, 6H), 2.67-2.41 (m, 1H), 2.23 (q, 1H), 1.85-0.84 (m, 16H).

Compound 14: MS: m/z 766.2 (M$^+$+1); $^1$H NMR (CDCl$_3$) δ 10.30 (s, 1H), 8.62 (m, 2H), 8.24 (m, 1H), 7.77 (d, 2H), 7.67 (m, 2H), 7.48 (m, 1H), 6.90 (s, 1H), 6.18 (s, 1H), 5.72 (q, 1H), 4.98 (dd, 1H), 4.65 (dd, 1H), 4.24 (m, 1H), 4.05 (m, 1H), 2.92 (m, 1H), 2.76 (m, 2H), 2.58-2.28 (m, 4H), 1.94-1.05 (m, 13H), 0.97-0.86 (m, 2H).

Compound 15: MS: m/z 893.3 (M$^+$+1); $^1$H NMR (CDCl$_3$) δ 10.33 (s, 1H), 8.88 (s, 1H), 8.68 (d, 1H), 8.26 (d, 1H), 7.80-7.65 (m, 4H), 7.35-7.26 (m, 1H), 6.98 (d, 1H), 6.20 (d, 1H), 5.71 (q, 1H), 5.18 (d, 1H), 5.00 (dd, 1H), 4.77 (dd, 1H), 4.64 (d, 1H), 4.46 (s, 1H), 4.25 (dd, 1H), 4.15 (dd, 1H), 2.92-2.28 (m, 4H), 2.17-0.82 (m, 24H).

Compound 16: MS: m/z 877.3 (M$^+$+1); $^1$H NMR (CDCl$_3$) δ 10.40 (s, 1H), 8.45 (d, 2H), 8.04 (d, 1H), 7.62 (d, 2H), 7.58-7.50 (m, 2H), 7.44 (s, 1H), 7.35 (dd, 1H), 6.02 (s, 1H), 5.95 (d, 1H), 5.63 (q, 1H), 4.81 (dd, 1H), 4.70 (dd, 1H), 4.49 (d, 1H), 4.42-4.38 (m, 1H), 4.04 (dd, 1H), 2.90-2.20 (m, 6H), 1.96-0.83 (m, 23H).

Compound 17: MS: m/z 907.3 (M$^+$+1); $^1$H NMR (CDCl$_3$) δ 10.42 (s, 1H), 8.73 (s, 1H), 8.62 (d, 1H), 7.96 (s, 1H), 7.71 (d, 1H), 7.64 (dd, 1H), 7.59-7.25 (m, 3H), 6.11 (s, 1H), 5.62 (q, 1H), 5.21 (d, 1H), 4.99 (dd, 1H), 4.79 (dd, 1H), 4.61 (d, 1H), 4.52 (s, 1H), 4.25-4.10 (m, 2H), 2.95-2.51 (m, 3H), 2.47 (s, 3H), 2.31 (q, 1H), 2.03-0.91 (m, 24H).

Compound 18: MS: m/z 767.2 (M$^+$+1); $^1$H NMR (CDCl$_3$) δ 10.38 (s, 1H), 8.49 (d, 2H), 8.15 (d, 1H), 7.77 (d, 2H), 7.64-7.58 (m, 2H), 7.41-7.32 (m, 1H), 7.29 (s, 1H), 6.08 (s, 1H), 5.78 (q, 1H), 5.08 (dd, 1H), 4.66 (dd, 1H), 4.42 (d, 1H), 4.09-4.06 (m, 1H), 3.85-3.62 (m, 4H), 2.93-2.45 (m, 4H), 2.04-0.87 (m, 13H).

Compound 19: MS: m/z 899.3 (M$^+$+1); $^1$H NMR (CDCl$_3$) δ 10.28 (s, 1H), 8.51 (d, 2H), 7.80 (dd, 1H), 7.70 (d, 2H), 7.51-7.42 (m, 1H), 7.37-7.23 (m, 1H), 6.97 (s, 1H), 6.06 (s, 1H), 5.63 (q, 1H), 4.96-4.85 (m, 2H), 4.75-4.63 (m, 2H), 4.09-4.02 (m, 2H), 2.93-2.43 (m, 4H), 2.21 (q, 1H), 1.96-0.76 (m, 24H).

Compound 20: MS: m/z 895.3 (M$^+$+1); $^1$H NMR (CDCl$_3$) δ 10.42 (s, 1H), 8.43 (d, 2H), 7.81 (s, 1H), 7.67 (d, 2H), 7.51 (s, 1H), 7.35-7.28 (m, 2H), 5.92 (s, 1H), 5.57 (q, 1H), 5.19 (d, 1H), 4.88-4.61 (m, 3H), 4.14-4.00 (m, 2H), 2.83-2.41 (m, 4H), 2.38 (s, 3H), 2.24 (q, 1H), 1.96-1.16 (m, 15H), 1.05 (s, 9H), 0.97-0.78 (m, 1H).

Compound 21: MS: m/z 923.3 (M$^+$+1); $^1$H NMR (CDCl$_3$) δ 10.33 (s, 1H), 8.50 (d, 2H), 7.67 (d, 2H), 7.59 (s, 1H), 7.41 (d, 1H), 7.34 (s, 1H), 7.16 (d, 1H), 6.06 (s, 1H), 5.64 (q, 1H), 5.23 (d, 1H), 4.94 (dd, 1H), 4.87 (dd, 1H), 4.58-4.42 (m, 2H), 4.30-4.02 (m, 2H), 3.84 (s, 3H), 2.88-2.44 (m, 4H), 2.21 (q, 1H), 1.84-0.78 (m, 23H).

Compound 22: MS: m/z 752.2 (M$^+$+1); $^1$H NMR (CDCl$_3$) δ 10.76 (s, 1H), 8.61 (d, 2H), 8.25 (m, 1H), 7.79 (d, 2H), 7.67 (d, 2H), 7.52 (m, 1H), 6.70 (s, 1H), 6.19 (s, 1H), 5.69 (q, 1H), 5.08 (m, 1H), 4.65 (dd, 1H), 4.23 (dd, 1H), 4.02 (m, 1H), 3.05-1.98 (m, 7H), 1.96-0.82 (m, 13H).

Compound 23: MS: m/z 907.3 (M$^+$+1); $^1$H NMR (CDCl$_3$) δ 10.40 (s, 1H), 8.56 (d, 2H), 8.08 (d, 1H), 7.73 (d, 2H), 7.29

(s, 1H), 7.26-7.20 (m, 2H), 6.13 (s, 1H), 5.71 (q, 1H), 5.22 (d, 1H), 4.95 (dd, 1H), 4.82-4.73 (m, 1H), 4.63-4.51 (m, 1H), 4.33-4.06 (m, 2H), 2.96-2.51 (m, 4H), 2.53 (s, 3H), 2.24 (q, 1H), 1.96-0.94 (m, 24H).

Compound 24: MS: m/z 916.3 (M$^+$+1); $^1$H NMR (CDCl$_3$) δ 10.37 (s, 1H), 8.48 (d, 2H), 8.08 (s, 1H), 7.68 (d, 2H), 7.50-7.37 (m, 3H), 6.01 (s, 1H), 5.59 (q, 1H), 5.13 (d, 1H), 4.83 (dd, 1H), 4.74-4.63 (m, 2H), 4.15 (dd, 1H), 4.05 (d, 1H), 2.94-2.41 (m, 4H), 2.21 (q, 1H), 1.89-1.14 (m, 14H), 1.03 (s, 9H), 0.96-0.85 (m, 1H).

Compound 25: MS: m/z 923.3 (M$^+$+1).

Compound 26: MS: m/z 923.3 (M$^+$+1); $^1$H NMR (CDCl$_3$) δ 1035 (s, 1H), 8.50 (d, 2H), 7.69 (d, 2H), 7.52 (dd, 1H), 7.40 (s, 1H), 7.12 (d, 1H), 6.75 (d, 1H), 6.05 (s, 1H), 5.63 (q, 1H), 5.27 (d, 1H), 4.97-4.83 (m, 1H), 4.75 (dd, 1H), 4.42 (brs, 1H), 4.28-4.08 (m, 2H), 4.08 (s, 3H), 2.91-2.38 (m, 4H), 2.23 (q, 1H), 1.96-0.82 (m, 24H).

Compound 27: MS: m/z 894.3 (M$^+$+1); $^1$H NMR (CDCl$_3$) δ 10.38 (s, 1H), 8.47 (d, 2H), 8.08 (d, 1H), 7.62 (d, 2H), 7.58-7.54 (m, 2H), 7.40-7.33 (m, 1H), 7.31 (s, 1H), 6.07 (s, 1H), 5.63 (q, 1H), 4.95 (dd, 1H), 4.83 (d, 1H), 4.87 (dd, 1H), 4.58 (d, 1H), 4.31-4.19 (m, 1H), 4.09 (dd, 1H), 3.40-3.32 (m, 4H), 3.01-2.41 (m, 8H), 2.19 (q, 1H), 1.92-0.83 (m, 15H).

Compound 28: MS: m/z 878.3 (M$^+$+1); $^1$H NMR (CDCl$_3$) δ 10.56 (s, 1H), 8.41 (d, 2H), 8.02 (d, 1H), 7.74 (s, 1H), 7.68 (d, 2H), 7.53-7.47 (m, 2H), 7.35-7.32 (m, 1H), 6.01 (s, 1H), 5.62 (q, 1H), 4.90 (dd, 1H), 4.78 (dd, 1H), 4.59-4.43 (m, 2H), 4.35-4.25 (m, 1H), 4.05 (dd, 1H), 3.61-3.49 (m, 1H), 3.01-2.45 (m, 8H), 2.21 (q, 1H), 1.85-0.83 (m, 18H).

Compound 29: MS: m/z 909.3 (M$^+$+1); $^1$H NMR (CDCl$_3$) δ 10.27 (s, 1H), 8.53 (d, 2H), 8.16 (d, 1H), 7.67 (d, 2H), 7.64-7.43 (m, 4H), 6.03 (s, 1H), 5.61 (q, 1H), 5.22-5.19 (m, 1H), 4.87 (dd, 1H), 4.66 (dd, 1H), 4.57 (d, 1H), 4.19-4.01 (m, 3H), 3.71-3.42 (m, 4H), 3.19-2.97 (m, 2H), 2.91-2.43 (m, 4H), 2.20 (q, 1H), 1.95-0.81 (m, 17H).

Compound 30: MS: m/z 906.3 (M$^+$+1); $^1$H NMR (CDCl$_3$) δ 10.18 (s, 1H), 8.62 (d, 2H), 8.25 (d, 1H), 7.78 (d, 2H), 7.70-7.61 (m, 2H), 7.55-7.46 (m, 1H), 7.01 (1H), 6.18 (1H), 5.71 (q, 1H), 5.12 (d, 1H), 5.02 (dd, 1H), 4.77 (dd, 1H), 4.64 (d, 1H), 4.53-4.43 (1H), 4.31-4.18 (m, 2H), 2.83-2.44 (m, 3H), 2.28 (q, 1H), 1.95-1.22 (m, 23H), 0.83 (s, 3H).

Compound 31: MS: m/z 907.3 (M$^+$+1); $^1$H NMR (CDCl$_3$) δ 10.39 (s, 1H), 8.57 (d, 2H), 8.05 (d, 1H), 7.77 (d, 2H), 7.42-7.26 (m, 3H), 6.15 (s, 1H), 5.69 (q, 1H), 5.29 (d, 1H), 4.96 (dd, 1H), 4.78 (dd, 1H), 4.63-4.56 (m, 1H), 4.40-4.13 (m, 3H), 2.91-2.64 (m, 3H), 2.62 (s, 3H), 2.56-2.22 (m, 2H), 1.89-0.96 (m, 23H).

Compound 32: MS: m/z 895.2 (M$^+$+1); $^1$H NMR (CDCl$_3$) δ 10.45 (s, 1H), 8.60 (d, 2H), 8.22 (d, 1H), 7.55 (d, 2H), 7.67-7.60 (m, 2H), 7.45 (dd, 1H), 7.20 (s, 1H), 6.12 (s, 1H), 5.65 (q, 1H), 5.13 (d, 1H), 4.97 (dd, 1H), 4.81-4.71 (m, 2H), 4.14-4.10 (m, 2H), 2.82-2.45 (m, 3H), 2.27 (q, 1H), 1.97-1.21 (m, 14H), 1.08 (s, 9H), 0.89-0.80 (m, 4H).

Compound 33: MS: m/z 853.3 (M$^+$+1); $^1$H NMR (CDCl$_3$) δ 10.22 (s, 1H), 8.58 (s, 1H), 8.48 (d, 2H), 8.08 (d, 1H), 7.57 (d, 2H), 7.53-7.44 (m, 2H), 7.39-7.26 (m, 1H), 6.05 (s, 1H), 5.65 (q, 1H), 5.21 (d, 1H), 4.95 (dd, 1H), 4.82 (dd, 1H), 4.40 (d, 1H), 4.21-4.03 (m, 2H), 3.27 (s, 3H), 2.81-2.40 (m, 3H), 2.22 (q, 1H), 1.95-1.20 (m, 15H), 0.81 (s, 3H).

Compound 34: MS: m/z 923.3 (M$^+$+1); $^1$H NMR (CDCl$_3$) δ 10.17 (s, 1H), 8.61 (d, 2H), 8.25 (d, 1H), 7.80 (d, 2H), 7.65-7.50 (m, 2H), 7.41 (dd, 1H), 6.97 (s, 1H), 6.18 (s, 1H), 5.72 (q, 1H), 5.15 (d, 1H), 5.05 (dd, 1H), 4.77 (dd, 1H), 4.65 (d, 1H), 4.29-4.10 (m, 2H), 3.78-3.52 (m, 2H), 3.23-3.03 (m, 2H), 2.79-2.85 (m, 2H), 2.56 (brs, 1H), 2.27 (q, 1H), 1.98-1.19 (m, 20H), 0.88 (s, 3H).

Compound 35: MS: m/z 894.2 (M$^+$+1); $^1$H NMR (CDCl$_3$) δ 10.45 (s, 1H), 8.47 (d, 2H), 8.12 (s, 1H), 8.05 (d, 1H), 7.70 (d, 2H), 7.53-7.46 (m, 2H), 7.31-7.22 (m, 1H), 6.03 (s, 1H), 5.70 (q, 1H), 5.03-4.84 (m, 4H), 4.24 (d, 1H), 2.95-2.47 (m, 3H), 2.38 (q, 1H), 1.94-1.11 (m, 25H), 0.85 (s, 3H).

Compound 36: MS: m/z 889.3 (M$^+$+1); $^1$H NMR (CDCl$_3$) δ 10.26 (s, 1H), 8.47 (d, 2H), 8.07 (d, 1H), 7.65 (d, 2H), 7.57 (s, 1H), 7.55-7.42 (m, 2H), 7.38-7.27 (m, 2H), 6.82 (d, 1H), 6.62 (d, 2H), 5.63 (dd, 1H), 6.15 (s, 1H), 5.63 (q, 1H), 4.92 (dd, 1H), 4.74-4.59 (m, 2H), 4.42 (d, 1H), 4.17 (dd, 1H), 2.79-2.42 (m, 3H), 2.23 (q, 1H), 1.95-1.05 (m, 15H), 0.76 (s, 3H).

Compound 37: MS: m/z 837.3 (M$^+$+1); $^1$H NMR (CDCl$_3$) δ 10.16 (s, 1H), 8.48 (d, 2H), 8.11 (d, 1H), 7.69 (d, 2H), 7.58 (d, 2H), 7.36 (dd, 1H), 7.17 (s, 1H), 6.15 (s, 1H), 6.04 (d, 1H), 5.64 (q, 1H), 4.94 (dd, 1H), 4.67 (dd, 1H), 4.47 (dd, 1H), 4.41 (d, 1H), 4.12 (dd, 1H), 2.78-2.68 (m, 1H), 2.43 (brs, 1H), 2.22 (q, 1H), 1.98-1.64 (m, 7H), 1.53-1.11 (m, 12H), 0.78 (s, 3H).

Compound 38: MS: m/z 863.3 (M$^+$+1); $^1$H NMR (CDCl$_3$) δ 10.52 (s, 1H), 8.38 (d, 2H), 7.92 (d, 1H), 7.88 (s, 1H), 7.65 (d, 2H), 7.58-7.52 (m, 2H), 7.35-7.21 (m, 1H), 6.19 (d, 1H), 5.92 (s, 1H), 5.71 (q, 1H), 5.01 (dd, 1H), 4.81 (dd, 1H), 4.62 (d, 1H), 4.37 (brs, 1H), 4.11-4.01 (m, 1H), 2.98-2.87 (m, 1H), 2.74-2.52 (m, 2H), 2.33 (q, 1H), 1.98-1.19 (m, 16H), 0.88 (s, 3H), 0.68-0.41 (m, 4H).

Compound 39: MS: m/z 908.3 (M$^+$+1); $^1$H NMR (CDCl$_3$) δ 10.26 (s, 1H), 8.48 (d, 2H), 8.15 (d, 1H), 7.67 (d, 2H), 7.57-7.46 (m, 2H), 7.39-7.35 (m, 2H), 6.07 (s, 1H), 5.62 (q, 1H), 4.98-4.86 (m, 2H), 4.77 (dd, 1H), 4.58 (d, 1H), 4.02 (dd, 1H), 3.38-3.24 (m, 4H), 2.99-2.81 (m, 4H), 2.82-2.42 (m, 3H), 2.19 (q, 1H), 1.88-1.04 (m, 15H), 0.92-0.72 (m, 4H).

Compound 40: MS: m/z 866.3 (M$^+$+1); $^1$H NMR (CDCl$_3$) δ 10.51 (s, 1H), 8.37 (d, 2H), 7.91 (d, 1H), 7.69 (s, 1H), 7.61 (d, 2H), 7.53-7.42 (m, 2H), 7.23-7.14 (m, 1H), 6.01 (s, 1H), 5.67 (q, 1H), 4.94 (dd, 1H), 4.72 (dd, 1H), 4.61 (d, 1H), 4.43 (d, 1H), 4.30-4.02 (m, 2H), 2.94-2.60 (m, 3H), 2.57 (s, 6H), 2.20 (q, 1H), 1.80-1.15 (m, 15H), 0.77 (s, 3H).

Compound 41: MS: m/z 892.3 (M$^+$+1); $^1$H NMR (CDCl$_3$) δ 10.40 (s, 1H), 8.51 (d, 2H), 8.16 (d, 1H), 7.85 (d, 2H), 7.65 (s, 1H), 7.58 (d, 1H), 7.41-7.37 (m, 1H), 6.14 (s, 1H), 5.59 (q, 1H), 4.99 (dd, 1H), 4.80 (dd, 1H), 4.62 (d, 1H), 4.57 (d, 1H), 4.45-4.37 (m, 1H), 4.17 (dd, 1H), 3.75-3.65 (m, 2H), 3.60-3.48 (m, 2H), 2.80-2.45 (m, 3H), 2.24 (q, 1H), 1.89-1.41 (m, 20H), 0.8 (s, 3H).

Compound 42: MS: m/z 907.3 (M$^+$+1); $^1$H NMR (CDCl$_3$) δ 10.20 (s, 1H), 8.43 (d, 2H), 8.10 (d, 1H), 7.65 (d, 2H), 7.60-7.55 (m, 2H), 7.39-7.35 (m, 1H), 7.25 (s, 1H), 6.05 (s, 1H), 5.98 (d, 1H), 5.66 (q, 1H), 4.93 (dd, 1H), 4.72 (dd, 1H), 4.52-4.42 (m, 2H), 4.08 (dd, 1H), 3.78-3.60 (m, 2H), 3.21-3.11 (m, 2H), 3.81-2.43 (br, 3H), 2.19-2.05 (m, 2H), 1.85-1.09 (m, 19H), 0.77 (s, 3H).

Compound 43: MS: m/z 890.3 (M$^+$+1); $^1$H NMR (CDCl$_3$) δ 10.16 (s, 1H), 8.55 (d, 2H), 8.21 (d, 1H), 8.14 (s, 1H), 7.68 (d, 2H), 7.58-7.41 (m, 4H), 7.21 (s, 1H), 6.40 (s, 1H), 6.18 (s, 1H), 5.63 (q, 1H), 4.95 (dd, 1H), 4.78-4.62 (m, 2H), 4.44 (d, 1H), 4.16 (dd, 1H), 2.69-2.44 (m, 3H), 2.24 (q, 1H), 1.98-1.15 (m, 15H), 0.79 (s, 3H).

Compound 44: MS: m/z 879.3 (M$^+$+1); $^1$H NMR (CDCl$_3$) δ 10.22 (s, 1H), 8.59 (d, 2H), 8.22 (d, 1H), 7.76 (d, 2H), 7.75-7.60 (m, 2H), 7.48-7.42 (m, 1H), 7.17 (s, 1H), 6.20 (s, 1H), 6.16 (d, 1H), 5.71 (q, 1H), 5.02 (dd, 1H), 4.77 (dd, 1H), 4.60-4.52 (m, 2H), 4.20 (dd, 1H), 2.79-2.45 (m, 3H), 2.21 (q, 1H), 1.96-1.07 (m, 15H), 1.03 (s, 9H), 0.82 (s, 3H).

Compound 45: MS: m/z 933.3 (M$^+$+1); $^1$H NMR (CDCl$_3$) δ 10.22 (s, 1H), 8.56 (d, 2H), 8.19 (d, 1H), 7.88 (d, 2H), 7.69-7.42 (m, 3H), 7.19 (s, 1H), 6.81-6.62 (m, 4H), 6.11 (s, 1H), 5.68 (q, 1H), 5.00 (dd, 1H), 4.77 (dd, 1H), 4.55 (d, 2H), 4.41-4.12 (m, 2H), 2.82-2.42 (m, 3H), 2.28 (q, 1H), 2.01-1.11 (m, 15H), 0.83 (s, 1H).

Compound 46: MS: m/z 891.3 (M$^+$+1); $^1$H NMR (CDCl$_3$) δ 10.34 (s, 1H), 8.35 (d, 2H), 7.94 (d, 1H), 7.66 (s, 1H), 7.62 (d, 2H), 7.54-7.46 (m, 2H), 7.22 (dd, 1H), 5.93-5.84 (m, 2H), 5.61 (q, 1H), 4.92 (dd, 1H), 4.87 (dd, 1H), 4.58 (d, 1H), 4.41-4.36 (m, 1H), 4.04 (dd, 1H), 2.82-2.75 (m, 1H), 2.65-2.50 (m, 2H), 2.24 (q, 1H), 1.80-1.00 (m, 24H), 0.81 (s, 3H).

Compound 47: MS: m/z 867.3 (M$^+$+1); $^1$H NMR (CDCl$_3$) δ 10.35 (s, 1H), 8.54 (d, 2H), 8.18 (d, 1H), 7.86 (d, 1H), 7.66 (d, 2H), 7.61 (m, 2H), 7.46 (m, 2H), 6.13 (s, 1H), 5.67 (q, 1H), 4.94 (dd, 1H), 4.77 (m, 1H), 4.61 (m, 1H), 4.40 (d, 1H), 4.20 (m, 1H), 3.72 (s, 3H), 2.91 (m, 1H), 2.72-2.39 (m, 3H), 2.25 (q, 1H), 1.96-0.82 (m, 15H).

Compound 48: MS: m/z 908.2 (M$^+$+1); $^1$H NMR (CDCl$_3$) δ 10.28 (s, 1H), 8.44 (d, 1H), 8.23 (d, 1H), 7.67 (m, 3H), 7.52 (m, 1H), 7.07 (s, 1H), 6.04 (s, 1H), 5.68 (q, 1H), 5.12 (d, 1H), 4.98 (dd, 1H), 4.79-4.68 (m, 2H), 4.34 (s, 1H), 4.20 (dd, 1H), 4.00 (m, 1H), 2.95 (s, 3H), 2.93 (m, 1H), 2.72 (m, 2H), 2.52 (m, 1H), 2.26 (q, 1H), 1.94-0.82 (23H).

Compound 49: MS: m/z 920.2 (M$^+$+1).

Compound 50: MS: m/z 806.2 (M$^+$+1); $^1$H NMR (CDCl$_3$) δ 10.47 (s, 1H), 8.77-8.53 (m, 2H), 8.19 (d, 1H), 8.13 (d, 1H), 7.73 (s, 1H), 7.53-7.30 (m, 2H), 7.26-7.18 (m, 1H), 6.07 (s, 1H), 5.70-5.40 (m, 2H), 4.98-4.61 (m, 2H), 4.40-4.03 (m, 3H), 3.47 (s, 3H), 2.95-2.90 (m, 1H), 2.87-2.50 (m, 3H), 2.20 (dd, 1H), 2.10-1.86 (m, 3H), 1.61-1.08 (m, 11H), 0.96 (m, 1H).

Compound 51: MS: m/z 822.3, 824.3 (M$^+$+1); $^1$H NMR (CDCl$_3$) δ 10.42 (s, 1H), 8.69-8.44 (m, 3H), 8.34 (d, 2H), 7.65 (s, 1H), 7.42-7.30 (m, 3H), 6.04 (s, 1H), 5.70-5.45 (m, 2H), 4.91-4.63 (m, 2H), 4.35-4.03 (m, 3H), 3.42 (s, 3H), 2.84 (s, 1H), 2.72-2.50 (m, 3H), 2.22 (dd, 1H), 2.19 (m, 3H), 1.54-0.78 (m, 11H).

Compound 52: MS: m/z 774.2 (M$^+$+1); $^1$H NMR (CDCl$_3$) δ 10.33 (s, 1H), 8.65-8.58 (m, 1H), 8.46 (d, 1H), 8.18 (d, 1H), 8.06 (d, 1H), 7.46-7.38 (m, 3H), 7.19-7.11 (m, 1H), 6.13 (s, 1H), 6.04 (d, 1H), 5.66 (dd, 1H), 5.27-5.08 (m, 1H), 5.07-4.67 (m, 2H), 4.52-4.39 (m, 2H), 4.13-4.09 (m, 1H), 3.62-3.60 (m, 1H), 2.95-2.10 (m, 4H), 1.98 (s, 3H), 1.90-0.81 (m, 14H).

Compound 53: MS: m/z 825.3 (M$^+$+1).

Compound 54: MS: m/z 805.3, 807.3 (M$^+$+1); $^1$H NMR (CDCl$_3$) δ 10.46 (s, 1H), 8.28-8.19 (m, 1H), 7.98 (s, 1H), 7.88-7.85 (m, 1H), 7.63-7.39 (m, 6H), 6.07 (s, 1H), 5.67-5.46 (m, 2H), 4.96-4.79 (m, 2H), 4.41-4.09 (m, 3H), 3.37 (s, 3H), 2.97-0.88 (m, 20H).

Compound 55: MS: m/z 789.2 (M$^+$+1); $^1$H NMR (CDCl$_3$) δ 10.61 (s, 1H), 8.49 (s, 1H), 8.39-8.24 (m, 2H), 8.05-7.94 (m, 2H), 7.56-7.04 (m, 5H), 5.90 (s, 1H), 5.47 (br, 1H), 4.93-4.69 (br, 2H), 4.40-4.07 (m, 3H), 3.46 (s, 1H), 3.23 (s, 3H), 2.91-2.07 (m, 11H), 1.99-1.54 (m, 4H), 1.32-0.81 (m, 5H).

Compound 56: MS: m/z 839.3, 843.3 (M$^+$+1); $^1$H NMR (CDCl$_3$) δ 10.27 (s, 1H), 8.24 (d, 1H), 7.89 (d, 1H), 7.63 (d, 1H), 7.56 (s, 1H), 7.52-7.40 (m, 2H), 7.14 (brs, 1H), 6.08 (s, 1H), 5.69 (q, 1H), 5.30 (brs, 1H), 4.97 (dd, 1H), 4.74 (dd, 1H), 4.46 (d, 1H), 4.40-4.22 (m, 1H), 4.13-4.08 (m, 1H), 3.36 (s, 3H), 2.99-2.05 (m, 5H), 1.90-1.10 (m, 15H), 0.99-0.88 (m, 1H).

Compound 57: MS: m/z 827.2 (M$^+$+1); $^1$H NMR (CDCl$_3$) δ 10.17 (s, 1H), 8.42 (d, 2H), 7.84 (d, 1H), 7.49-7.41 (m, 4H), 7.28 (m, 1H), 7.13 (brs, 1H), 6.16 (s, 1H), 5.63 (q, 1H), 4.95 (m, 1H), 4.70 (dd, 1H), 4.63 (m, 1H), 4.31-4.11 (m, 2H), 2.97-2.70 (m, 3H), 2.50-1.06 (m, 17H), 0.91 (m, 1H).

Compound 58: MS: m/z 803.3 (M$^+$+1).

Compound 59: MS: m/z 789.2 (M$^+$+1); $^1$H NMR (CDCl$_3$) δ 10.39 (s, 1H), 8.53-8.41 (m, 3H), 7.81 (d, 1H), 7.59-7.42 (m, 4H), 7.26 (m, 1H), 7.18 (s, 1H), 6.17 (s, 1H), 5.17 (q, 1H), 5.28 (dd, 1H), 4.95 (dd, 1H), 4.75 (m, 1H), 4.43 (d, 1H), 4.38-4.04 (m, 2H), 3.40 (s, 3H), 2.96-2.67 (m, 3H), 2.60-2.41 (m, 1H), 2.37-2.22 (m, 1H), 1.99-0.85 (m, 14H).

Compound 60: MS: m/z 773.2 (M$^+$+1); $^1$H NMR (CDCl$_3$) δ 10.33 (s, 1H), 8.46 (d, 2H), 7.88-7.84 (m, 1H), 7.60-7.50 (m, 4H), 7.35-7.17 (m, 3H), 6.20 (s, 1H), 6.08 (d, 1H), 5.72 (q, 1H), 4.98 (dd, 1H), 4.72 (dd, 1H), 4.56 (m, 1H), 4.41 (d, 1H), 4.21 (m, 1H), 2.94-2.90 (m, 1H), 2.80-2.77 (m, 1H), 2.55-2.52 (m, 1H), 2.23 (q, 1H), 1.98-1.90 (m, 1H), 1.84 (s, 3H), 1.80-0.80 (m, 16H).

Compound 61: MS: m/z 845.3 (M$^+$+1); $^1$H NMR (CDCl$_3$) δ 10.41 (s, 1H), 8.34 (d, 2H), 7.84 (d, 1H), 7.53-7.44 (m, 1H), 7.40-7.33 (m, 3H), 7.19 (s, 1H), 6.14 (s, 1H), 5.71 (q, 1H), 5.15 (d, 1H), 4.98 (dd, 1H), 4.89-4.80 (m, 2H), 4.25-4.19 (m, 2H), 2.95-2.90 (m, 1H), 2.88-2.42 (m, 3H), 2.44 (s, 3H), 2.29 (m, 1H), 1.98-1.20 (m, 14H), 1.11 (s, 9H), 1.00-0.87 (1H).

Compound 62: MS: m/z 841.2 (M$^+$+1); $^1$H NMR (CDCl$_3$) δ 10.21 (s, 1H), 8.35 (d, 2H), 7.89 (d, 1H), 7.60-7.57 (m, 1H), 7.33 (d, 2H), 7.17 (d, 1H), 7.05 (s, 1H), 6.22 (s, 1H), 5.68 (q, 1H), 4.97 (dd, 1H), 4.77-4.64 (m, 2H), 4.33-4.17 (m, 2H), 2.93-2.74 (m, 3H), 2.44 (s, 3H), 2.21 (m, 1H), 1.95-0.91 (m, 17H).

Compound 63: MS: m/z 903.3; 905.3 (M$^+$+1); $^1$H NMR (CDCl$_3$) δ 10.18 (s, 1H), 8.45 (d, 2H), 8.23 (d, 1H), 7.64 (m, 2H), 7.49 (d, 3H), 7.01 (s, 1H), 6.17 (s, 1H), 5.72 (q, 1H), 5.13 (d, 1H), 4.99 (dd, 1H), 4.77 (dd, 1H), 4.58 (d, 1H), 4.53 (brs, 1H), 4.27 (m, 1H), 4.14 (m, 1H), 2.83-2.44 (m, 3H), 2.27 (q, 1H), 1.95-1.22 (m, 23H), 0.83 (s, 3H).

Compound 64: MS: m/z 787.3 (M$^+$+1); $^1$H NMR (CDCl$_3$) δ 10.45 (s, 1H), 8.25 (d, 2H), 7.75 (d, 1H), 7.67 (s, 1H), 7.53-7.52 (m, 1H), 7.26 (d, 2H), 6.29 (d, 1H), 6.19 (s, 1H), 5.67 (q, 1H), 4.94 (dd, 1H), 4.75 (dd, 1H), 4.52 (brs, 1H), 4.42 (d, 1H), 4.10-4.18 (m, 1H), 2.89-2.50 (m, 3H), 2.43 (s, 3H), 2.35-2.20 (m, 1H), 1.98-1.85 (m, 1H), 1.82 (s, 3H), 1.62-0.81 (m, 16H).

Compound 65: MS: m/z 803.2 (M$^+$+1); $^1$H NMR (CDCl$_3$) δ 10.46 (s, 1H), 8.30 (d, 1H), 8.17 (d, 2H), 7.63 (d, 1H), 7.55 (s, 1H), 7.45-7.41 (m, 1H), 7.25-7.20 (m, 2H), 5.97 (s, 1H), 5.65-5.59 (m, 1H), 5.36 (d, 1H), 4.91-4.87 (m, 1H), 4.73 (dd, 1H), 4.37-4.05 (m, 3H), 3.30 (s, 3H), 2.84-2.47 (m, 3H), 2.38 (s, 3H), 2.40-2.16 (m, 1H), 1.90-0.87 (m, 16H).

Compound 66: MS: m/z 871.3 (M$^+$+1); $^1$H NMR (CDCl$_3$) δ 10.42 (s, 1H), 8.19-8.02 (m, 2H), 7.93 (s, 1H), 7.67 (s, 1H), 7.47-7.26 (m, 3H), 6.05 (s, 1H), 5.62 (q, 1H), 5.34 (d, 1H), 4.96-4.42 (m, 4H), 4.36-4.10 (m, 2H), 2.95-2.90 (m, 1H), 2.77 (s, 3H), 2.76-2.48 (m, 3H), 2.35 (s, 3H), 2.30-0.87 (m, 24H).

Compound 67: MS: m/z 875.3 (M$^+$+1).

Compound 68: TG-2379: MS: m/z 871.3 (M$^+$+1); $^1$H NMR (CDCl$_3$) δ 10.33 (s, 1H), 8.34 (d, 2H), 7.85 (d, 1H), 7.73 (s, 1H), 7.54-7.46 (m, 1H), 7.38-7.22 (m, 3H), 6.12 (s, 1H), 5.65 (q, 1H), 5.35 (d, 1H), 4.93 (dd, 1H), 4.78 (dd, 1H), 4.62-4.50 (m, 2H), 4.32-4.08 (m, 2H), 2.81-2.42 (m, 3H), 2.40 (s, 3H), 2.26 (q, 1H), 1.93-1.11 (m, 23H), 0.80 (s, 3H).

Compound 69: MS: m/z 861.3 (M$^+$+1).

Compound 70: MS: m/z 857.2 (M$^+$+1); $^1$H NMR (CDCl$_3$) δ 10.23 (s, 1H), 8.09 (s, H), 8.05 (s, 1H), 7.96 (dd, 1H), 7.58 (dd, 1H), 7.47-7.19 (m, 3H), 7.06 (d, 1H), 6.21 (s, 1H), 5.69 (q, 1H), 4.95 (dd, 1H), 4.81-4.60 (m, 2H), 4.35-4.17 (m, 2H), 3.94 (s, 3H), 2.92-2.41 (m, 3H), 2.23 (q, 1H), 1.92-0.82 (m, 17H).

Compound 71: MS: m/z 819.2 (M$^+$+1); $^1$H NMR (CDCl$_3$) δ 10.36 (s, 1H), 8.01-7.81 (m, 3H), 7.71 (d, 1H), 7.34-7.22 (m, 3H), 6.96 (d, 1H), 6.01 (s, 1H), 5.61 (q, 1H), 5.27 (dd, 1H), 4.90 (dd, 1H), 4.69 (dd, 1H), 4.38 (d, 1H), 4.22-4.03 (m, 2H), 3.87 (s, 3H), 3.28 (s, 3H), 2.86-2.42 (m, 3H), 2.20 (q, 1H), 1.97-0.88 (m, 16H).

Compound 72: MS: m/z 861.3 (M$^+$+1); $^1$H NMR (CDCl$_3$) δ 10.38 (s, 1H), 8.10-7.98 (m, 2H), 7.86 (d, 1H), 7.54-7.22 (m, 3H), 7.20 (s, 1H), 7.06 (d, 1H), 6.10 (s, 1H), 5.70 (q, 1H), 5.29 (d, 1H), 4.97 (dd, 1H), 4.79-4.67 (m, 2H), 4.18-4.04 (m, 2H), 3.94 (s, 3H), 2.95-2.57 (m, 3H), 2.28 (q, 1H), 1.91-0.87 (m, 25H).

Compound 73: MS: m/z 803.2 (M$^+$+1); $^1$H NMR (CDCl$_3$) δ 10.37 (s, 1H), 8.12-8.96 (m, 2H), 7.85 (d, 1H), 7.56-7.26 (m, 4H), 7.05 (d, 1H), 6.19-6.15 (m, 2H), 5.71 (q, 1H), 4.96 (dd, 1H), 4.74 (s, 1H), 4.53-4.42 (m, 2H), 4.19 (d, 1H), 3.93 (s, 3H), 2.91-2.20 (m, 4H), 2.10-0.82 (m, 19H).

Compound 74: MS: m/z 861.3 (M$^+$+1); $^1$H NMR (CDCl$_3$) δ 10.42 (s, 1H), 8.39 (d, 2H), 7.81 (d, 1H), 7.50-7.26 (m, 3H), 7.00 (d, 2H), 6.05 (s, 1H), 5.65 (q, 1H), 5.21 (d, 1H), 4.95 (dd, 1H), 4.84 (dd, 1H), 4.68 (d, 1H), 4.21-4.07 (m, 2H), 3.90 (s, 3H), 2.90-2.45 (m, 4H), 2.22 (q, 1H), 1.98-1.20 (m, 14H), 1.13 (s, 9H), 0.99-0.84 (m, 1H).

Compound 75: MS: m/z 887.3 (M$^+$+1); $^1$H NMR (CDCl$_3$) δ 10.33 (s, 1H), 8.38 (d, 2H), 7.82 (d, 1H), 7.61 (s, 1H), 7.59-7.43 (m, 1H), 7.35-7.20 (m, 1H), 7.01 (d, 2H), 6.07 (s, 1H), 5.68 (q, 1H), 5.42 (d, 1H), 4.98 (dd, 1H), 4.75 (dd, 1H), 4.58 (s, 1H), 4.38-4.13 (m, 3H), 3.88 (s, 3H), 2.86 (br, 2H), 2.59-2.11 (m, 2H), 1.96-1.20 (m, 22H), 0.92-0.78 (m, 4H).

Compound 76: MS: m/z 903.3, 905.3 (M$^+$+1).

Compound 77: MS: m/z 887.3 (M$^+$+1).

Compound 78: MS: m/z 883.4 (M$^+$+1); $^1$H NMR (CDCl$_3$) δ 10.19 (s, 1H), 8.46 (d, 2H), 8.25 (d, 1H), 7.62 (m, 2H), 7.46 (m, 1H), 7.04 (d, 2H), 6.96 (s, 1H), 6.19 (s, 1H), 5.73 (q, 1H), 5.15 (d, 1H), 5.02 (dd, 1H), 4.77 (m, 1H), 4.58 (m, 2H), 4.30 (m, 1H), 4.15 (m, 3H), 2.79 (m, 2H), 2.54 (m, 1H), 2.26 (q, 1H), 1.92-0.83 (m, 26H), 0.83 (s, 3H).

Compound 79: MS: m/z 869.4 (M$^+$+1); $^1$H NMR (CDCl$_3$) δ 10.36 (s, 1H), 8.44 (d, 2H), 8.24 (d, 1H), 7.60 (m, 2H), 7.44 (m, 1H), 7.04 (s, 1H), 7.00 (d, 2H), 6.16 (s, 1H), 5.71 (q, 1H), 5.21 (d, 1H), 4.97 (dd, 1H), 4.74 (m, 1H), 4.57 (m, 2H), 4.30 (m, 1H), 4.15 (m, 3H), 2.91 (m, 1H), 2.75 (m, 2H), 2.56 (m, 1H), 2.26 (q, 1H), 1.92-0.83 (m, 26H).

Compound 80: MS: m/z 883.4 (M$^+$+1); $^1$H NMR (CDCl$_3$) δ 10.42 (s, 1H), 8.43 (d, 2H), 8.23 (d, 1H), 7.61-7.39 (m, 4H), 7.03 (d, 2H), 6.18 (s, 1H), 5.71 (q, 1H), 5.30 (d, 1H), 4.96 (dd, 1H), 4.79-4.57 (m, 4H), 4.41-4.22 (m, 1H), 4.15-4.08 (m, 1H), 2.96-2.67 (m, 3H), 2.57-2.42 (m, 1H), 2.25 (q, 1H), 1.98-0.87 (m, 29H).

Compound 81: MS: m/z 897.4 (M$^+$+1); $^1$H NMR (CDCl$_3$) δ 10.31 (s, 1H), 8.42 (d, 2H), 8.21 (d, 1H), 7.57-7.25 (m, 4H), 7.02 (d, 2H), 6.14 (s, 1H), 5.67-5.64 (m, 1H), 5.40 (d, 1H), 5.03-4.93 (m, 1H), 4.79-4.54 (m, 4H), 4.39-4.12 (m, 2H), 2.77-2.72 (m, 2H), 2.54 (br, 1H), 2.26 (q, 1H), 2.03-1.24 (m, 29H), 0.80 (s, 3H).

Compound 82: MS: m/z 915.2 (M$^+$+1); $^1$H NMR (CDCl$_3$) δ 10.29 (s, 1H), 8.38 (d, 2H), 7.74 (d, 1H), 7.57-7.24 (m, 3H), 7.27 (d, 2H), 6.14 (s, 1H), 5.66 (q, 1H), 5.32 (d, 1H), 4.98 (dd, 1H), 4.76 (dd, 1H), 4.71-4.48 (m, 3H), 4.39-4.08 (m, 2H), 2.85-2.42 (m, 3H), 2.31 (q, 1H), 2.03-1.24 (m, 29H), 0.80 (s, 3H).

Compound 83: MS: m/z 901.2 (M$^+$+1); $^1$H NMR (CDCl$_3$) δ 10.42 (s, 1H), 8.46 (d, 2H), 7.82 (d, 1H), 7.54 (dd, 1H), 7.42 (s, 1H), 7.32 (m, 1H), 6.98 (d, 2H), 6.14 (s, 1H), 5.65 (q, 1H), 5.33 (d, 1H), 4.97 (dd, 1H), 4.76 (dd, 1H), 4.71-4.50 (m, 3H), 4.41-4.08 (m, 2H), 2.93-2.42 (m, 4H), 2.31 (q, 1H), 2.03-0.80 (m, 29H).

Compound 84: MS: m/z 885.3 (M$^+$+1); $^1$H NMR (CDCl$_3$) δ 10.26 (s, 1H), 8.42 (d, 2H), 8.23 (d, 1H), 7.58 (m, 2H), 7.44 (dd, 1H), 7.22 (s, 1H), 7.01 (d, 2H), 6.17 (s, 1H), 5.67 (q, 1H), 5.16 (d, 1H), 4.98 (dd, 1H), 4.75 (dd, 1H), 4.62 (m, 2H), 4.38-4.08 (m, 2H), 2.80-2.42 (m, 3H), 2.32 (q, 1H), 1.96-1.20 (m, 21H), 1.13 (s, 9H), 0.81 (m, 3H).

Compound 85: MS: m/z 923.2 (M$^+$+1).

Compound 86: MS: m/z 883.2 (M$^+$+1); $^1$H NMR (CDCl$_3$) δ 10.41 (s, 1H), 8.19 (d, 1H), 8.06 (d, 1H), 7.95 (s, 1H), 7.61-7.41 (m, 4H), 6.92 (d, 1H), 6.12 (s, 1H), 6.04 (s, 2H), 5.67 (q, 1H), 5.35 (d, 1H), 4.97 (dd, 1H), 4.77 (dd, 1H), 4.58 (d, 1H), 4.36-4.11 (m, 2H), 2.85-2.43 (m, 3H), 2.27 (q, 1H), 1.98-1.21 (m, 24H), 0.81 (s, 3H).

Compound 87: MS: m/z 869.2 (M$^+$+1); $^1$H NMR (CDCl$_3$) δ 10.36 (s, 1H), 8.17 (d, 1H), 7.97 (d, 1H), 7.88 (s, 1H), 7.58-7.32 (m, 4H), 6.85 (d, 1H), 6.02 (s, 1H), 5.98 (s, 2H), 5.59 (q, 1H), 5.37 (d, 1H), 4.87 (d, 1H), 4.68 (dd, 1H), 4.52-4.02 (m, 3H), 2.90-2.38 (m, 4H), 2.23 (q, 1H), 1.91-0.88 (m, 24H).

Compound 88: MS: m/z 868.5 (M$^+$+1).

Compound 89: MS: m/z 882.5 (M$^+$+1).

Compound 90: MS: m/z 910.3 (M$^+$+1); $^1$H NMR (CDCl$_3$) δ 10.32 (s, 1H), 8.34 (d, 2H), 8.22 (d, 1H), 7.61-7.43 (m, 3H), 7.44 (dd, 1H), 6.76 (d, 2H), 6.14 (s, 1H), 5.62 (q, 1H), 5.39 (d, 1H), 4.96 (dd, 1H), 4.72 (dd, 1H), 4.63 (brs, 1H), 4.55 (d, 1H), 4.41-4.04 (m, 2H), 3.42 (q, 4H), 2.80-2.42 (m, 3H), 2.32 (q, 1H), 1.98-1.17 (m, 29H), 0.83 (s, 3H).

Compound 91: MS: m/z 896.3 (M$^+$+1); $^1$H NMR (CDCl$_3$) δ 10.46 (s, 1H), 8.33 (d, 2H), 8.21 (d, 1H), 7.62-7.43 (m, 3H), 7.43 (dd, 1H), 6.77 (d, 2H), 6.13 (s, 1H), 5.65 (q, 1H), 5.39 (d, 1H), 4.93 (dd, 1H), 4.73 (dd, 1H), 4.64 (brs, 1H), 4.53 (d, 1H), 4.43-4.05 (m, 2H), 3.43 (q, 4H), 2.94-2.42 (m, 4H), 2.29 (q, 1H), 2.14-0.83 (m, 29H).

Compound 92: MS: m/z 901.4, 903.4 (M$^+$+1); $^1$H NMR (CDCl$_3$) δ 10.40 (s, 1H), 8.36 (d, 2H), 8.23 (s, 1H), 7.58-7.26 (m, 5H), 6.15 (s, 1H), 5.65 (q, 1H), 5.19 (d, 1H), 4.96 (dd, 1H), 4.77 (dd, 1H), 4.62-4.52 (m, 2H), 4.33-4.08 (m, 2H), 3.01-2.42 (m, 5H), 2.25 (q, 1H), 1.96-0.89 (m, 29H).

Compound 93: MS: m/z 915.4, 917.4 (M$^+$+1); $^1$H NMR (CDCl$_3$) δ 10.27 (s, 1H), 8.38 (d, 2H), 8.22 (s, 1H), 7.59-7.34 (m, 5H), 6.13 (s, 1H), 5.70 (q, 1H), 5.29 (d, 1H), 4.98 (dd, 1H), 4.78 (dd, 1H), 4.62-4.55 (m, 2H), 4.35-4.08 (m, 2H), 3.04-2.96 (m, 1H), 2.80-2.43 (m, 3H), 2.25 (q, 1H), 1.97-1.20 (m, 29H), 0.81 (s, 3H).

Compound 94: MS: m/z 867.4 (M$^+$+1).

Compound 95: MS: m/z 881.3 (M$^+$+1); $^1$H NMR (CDCl$_3$) δ 10.31 (s, 1H), 8.41 (d, 2H), 8.22 (d, 1H), 7.63-7.21 (m, 4H), 7.20 (d, 2H), 6.16 (s, 1H), 5.65 (q, 1H), 5.38 (d, 1H), 4.94 (dd, 1H), 4.80 (dd, 1H), 4.65-4.56 (m, 2H), 4.38-4.12 (m, 2H), 3.08-2.92 (m, 1H), 2.83-2.67 (m, 2H), 2.59-2.41 (m, 1H), 2.25 (q, 1H), 1.98-1.08 (,m, 28H), 0.95-0.86 (m, 4H).

Compound 96: MS: m/z 881.4 (M$^+$+1); $^1$H NMR (CDCl$_3$) δ 10.47 (s, 1H), 8.40 (d, 2H), 8.23 (d, 1H), 7.76 (s, 1H), 7.62-7.41 (m, 5H), 6.13 (s, 1H), 5.65 (q, 1H), 5.33 (d, 1H), 5.03-4.87 (m, 2H), 4.78 (dd, 1H), 4.57 (d, 1H), 4.38-4.04 (m, 2H), 2.95-2.43 (m, 4H), 2.21 (q, 1H), 2.01-1.37 (m, 20H), 1.33 (s, 9H), 1.21-0.86 (m, 3H).

Compound 97: MS: m/z 895.4 (M$^+$+1); $^1$H NMR (CDCl$_3$) δ 10.30 (s, 1H), 8.40 (d, 2H), 8.23 (d, 1H), 7.59-7.43 (m, 5H), 6.98 (d, 1H), 6.16 (s, 1H), 5.65 (q, 1H), 5.41 (d, 1H), 4.98 (dd, 1H), 4.79 (q, 1H), 4.62-4.52 (m, 1H), 4.36-4.09 (m, 3H), 2.75 (brs, 2H), 2.59-2.56 (m, 1H), 2.28 (q, 1H), 1.91-1.18 (m, 31H), 0.89-0.78 (m, 4H).

Compound 98: MS: m/z 869.4 (M$^+$+1); $^1$H NMR (CDCl$_3$) δ 10.41 (s, 1H), 8.42 (d, 2H), 8.23 (d, 1H), 7.62-7.43 (m, 5H), 7.44 (dd, 1H), 6.17 (s, 1H), 5.64 (q, 1H), 5.17 (d, 1H), 4.97 (dd, 1H), 4.77-4.63 (m, 2H), 4.21-4.10 (m, 2H), 2.94-2.55 (m, 4H), 2.27 (q, 1H), 1.89-1.15 (m, 23H), 1.10 (s, 9H), 0.98-0.87 (m, 1H).

Compound 99: MS: m/z 925.4 (M$^+$+1); $^1$H NMR (CDCl$_3$) δ 10.28 (s, 1H), 8.37 (d, 2H), 8.03 (d, 1H), 7.50 (d, 2H), 7.48 (s, 1H), 7.01-6.92 (m, 2H), 6.13 (s, 1H), 5.65 (q, 1H), 5.39 (d, 1H), 4.98 (dd, 1H), 4.88 (dd, 1H), 4.64 (s, 1H), 4.53 (d, 1H), 4.41-4.23 (m, 1H), 4.19-4.11 (m, 1H), 3.88 (s, 3H), 2.78-2.42 (m, 3H), 2.26 (q, 1H), 2.04-1.18 (m, 31H), 0.89-0.78 (m, 4H).

Compound 100: MS: m/z 925.4 (M$^+$+1); $^1$H NMR (CDCl$_3$) δ 10.23 (s, 1H), 8.35 (d, 2H), 7.77 (d, 1H), 7.48 (d, 2H), 7.38-7.22 (m, 1H), 7.04-6.81 (m, 2H), 6.16 (s, 1H), 5.68 (q, 1H), 5.21 (d, 1H), 4.99 (dd, 1H), 4.78 (dd, 1H), 4.57 (d, 1H), 4.22-4.03 (m, 3H), 4.00 (s, 3H), 2.80-2.43 (m, 3H), 2.31 (q, 1H), 1.96-1.20 (m, 31H), 0.95-0.78 (m, 4H).

Compound 101: MS: m/z 827.3 (M$^+$+1).

Compound 102: MS: m/z 897.4 (M$^+$+1); $^1$H NMR (CDCl$_3$) δ 10.30 (s, 1H), 8.39 (d, 2H), 8.20 (d, 1H), 7.59-7.37 (m, 5H), 7.14 (s, 1H), 6.04 (s, 1H), 5.61 (q, 1H), 5.21 (d, 1H), 4.87 (dd, 1H), 4.77 (dd, 1H), 4.57 (d, 1H), 4.19-4.07 (m, 4H), 3.67-3.42 (m, 2H), 3.17-2.40 (m, 6H), 2.20 (q, 1H), 1.93-0.78 (m, 27H).

Compound 103: MS: m/z 866.3 (M$^+$+1); $^1$H NMR (CDCl$_3$) δ 10.45 (s, 1H), 8.31 (d, 2H), 8.12 (d, 1H), 7.51-7.42 (m, 5H), 7.32-7.25 (m, 1H), 6.09 (s, 1H), 5.61 (q, 1H), 4.90 (dd, 1H), 4.81 (dd, 1H), 4.59 (d, 1H), 4.50-4.36 (m, 2H), 4.13 (dd, 1H), 3.69-3.27 (m, 3H), 3.10 (brs, 4H), 2.90-2.41 (m, 4H), 2.19 (q, 1H), 1.98-0.78 (m, 25H).

Compound 104: MS: m/z 811.3 (M$^+$+1); $^1$H NMR (CDCl$_3$) δ 10.38 (s, 1H), 8.38 (d, 2H), 8.19 (d, 1H), 7.60-7.31 (m, 5H), 7.32-7.25 (m, 1H), 6.15 (s, 1H), 5.65 (q, 1H), 4.88 (dd, 1H), 4.70 (dd, 1H), 4.57 (dd, 1H), 4.40 (d, 1H), 4.21-4.05 (m, 2H), 2.95-2.41 (m, 4H), 2.22 (q, 1H), 2.01 (s, 3H), 1.98-0.79 (m, 24H).

Compound 105: MS: m/z 868.4 (M$^+$+1); $^1$H NMR (CDCl$_3$) δ 10.57 (s, 1H), 8.37 (d, 2H), 8.15 (d, 1H), 8.09 (s, 1H), 7.58-7.51 (m, 4H), 7.27 (dd, 1H), 6.09 (s, 1H), 5.61 (q, 1H), 4.98-4.79 (m, 4H), 4.44 (s, 1H), 4.10 (dd, 1H), 3.79-3.68 (m, 2H), 2.92-2.45 (m, 4H), 2.24 (q, 1H), 1.98-0.88 (m, 32H).

Compound 106: MS: m/z 882.4 (M$^+$+1); $^1$H NMR (CDCl$_3$) δ 10.37 (s, 1H), 8.35 (d, 2H), 8.16 (d, 1H), 7.56-7.48 (m, 2H), 7.42 (d, 2H), 7.36-7.33 (m, 1H), 7.30 (s, 1H), 6.09 (s, 1H), 5.63 (q, 1H), 4.97-4.86 (m, 2H), 4.76 (dd, 1H), 4.58 (d, 1H), 4.28-4.11 (m, 2H), 3.39-3.25 (m, 4H), 3.01-2.82 (m, 5H), 2.75-2.44 (m, 2H), 2.16 (q, 1H), 1.95-0.76 (m, 25H).

Compound 107: MS: m/z 863.3 (M$^+$+1); $^1$H NMR (CDCl$_3$) δ 10.34 (s, 1H), 8.33 (d, 2H), 8.32 (d, 1H), 7.59-7.40 (m, 6H), 7.37 (s, 1H), 6.81 (d, 1H), 6.65 (d, 1H), 6.25 (s, 1H), 6.13 (s, 1H), 5.62 (q, 1H), 4.87 (dd, 1H), 4.69-4.52 (m, 2H), 4.42 (d, 1H), 4.18 (dd, 1H), 2.95-2.40 (m, 4H), 2.24-0.78 (m, 25H).

Compound 108: MS: m/z 840.4 (M$^+$+1); $^1$H NMR (CDCl$_3$) δ 10.67 (s, 1H), 8.32 (d, 2H), 8.19 (d, 1H), 7.77 (s, 1H), 7.58-7.44 (m, 4H), 7.34-7.25 (m, 1H), 6.14 (s, 1H), 5.77 (q, 1H), 4.98 (dd, 1H), 4.78-4.71 (m, 2H), 4.44 (d, 1H), 4.29 (brs, 1H), 4.11-4.05 (m, 1H), 2.96-2.72 (m, 2H), 2.64 (s, 6H), 2.41 (br, 1H), 2.20 (q, 1H), 1.96-0.78 (m, 25H).

Compound 109: MS: m/z 837.4 (M$^+$+1); $^1$H NMR (CDCl$_3$) δ 10.49 (s, 1H), 8.35-8.25 (m, 3H), 7.71 (s, 1H), 7.55-7.41 (m, 4H), 7.26 (s, 1H), 6.19 (d, 1H), 6.01 (s, 1H), 5.63 (q, 1H), 4.88 (dd, 1H), 4.71 (brs, 1H), 4.56 (d, 1H), 4.39 (brs, 1H), 4.06 (d, 1H), 2.81-2.45 (m, 4H), 2.23 (q, 1H), 1.99-1.64 (m, 4H), 1.58-0.77 (m, 21H), 0.51 (brs, 4H).

Compound 110: MS: m/z 865.4 (M$^+$+1); $^1$H NMR (CDCl$_3$) δ 10.39 (s, 1H), 8.29 (d, 2H), 8.15 (d, 1H), 7.56-7.42 (m, 5H), 7.36-7.24 (m, 1H), 6.05 (s, 1H), 5.98 (d, 1H), 5.64 (q, 1H), 4.87 (dd, 1H), 4.69 (dd, 1H), 4.55 (d, 1H), 4.42 (dd, 1H), 4.04 (dd, 1H), 2.81-2.05 (m, 5H), 1.95-1.71 (m, 4H), 1.57-0.76 (m, 29H).

Compound 111: MS: m/z 881.4 (M$^+$+1); $^1$H NMR (CDCl$_3$) δ 10.29 (s, 1H), 8.33 (d, 2H), 8.30 (s, 1H), 7.58-7.41 (m, 4H), 7.39 (dd, 1H), 7.22 (s, 1H), 6.10 (s, 1H), 5.98 (d, 1H), 5.62 (q, 1H), 4.91 (dd, 1H), 4.68 (dd, 1H), 4.46-4.40 (m, 2H), 4.05 (dd, 1H), 3.79-3.62 (m, 2H), 3.21-3.09 (m, 2H), 2.88-2.40 (m, 3H), 2.22-1.72 (m, 6H), 1.47-0.78 (m, 25H).

Compound 112: MS: m/z 864.3 (M$^+$+1); $^1$H NMR (CDCl$_3$) δ 10.29 (s, 1H), 8.38 (d, 2H), 8.23 (d, 1H), 8.09 (s, 1H), 7.57-7.45 (m, 5H), 7.41 (dd, 1H), 7.28 (s, 1H), 6.42 (s, 1H), 6.15 (s, 1H), 5.62 (q, 1H), 4.86 (dd, 1H), 4.75-4.66 (m, 2H), 4.49 (d, 1H), 4.17 (dd, 1H), 2.83-2.43 (m, 3H), 2.25 (q, 1H), 1.99-0.78 (m, 25H).

Compound 113: MS: m/z 853.4 (M$^+$+1); $^1$H NMR (CDCl$_3$) δ 10.34 (s, 1H), 8.36 (d, 2H), 8.30 (d, 1H), 7.62-7.46 (m, 4H), 7.41-7.36 (m, 1H), 7.17 (s, 1H), 6.19 (s, 1H), 6.17 (d, 1H), 5.68 (q, 1H), 4.92 (dd, 1H), 4.73 (dd, 1H), 4.58-4.43 (m, 2H), 4.19 (dd, 1H), 2.89-2.43 (m, 3H), 2.22 (q, 1H), 1.99-1.82 (m, 6H), 1.59-0.83 (m, 28H).

Compound 114: MS: m/z 907.3 (M$^+$+1); $^1$H NMR (CDCl$_3$) δ 10.30 (s, 1H), 8.39 (d, 2H), 8.21 (d, 1H), 7.56 (dd, 1H), 7.48 (d, 2H), 7.40 (dd, 1H), 7.24 (s, 1H), 7.18 (d, 2H), 7.03 (d, 2H), 6.92 (s, 1H), 6.06 (s, 1H), 5.74 (d, 1H), 5.61 (q, 1H), 4.87 (dd, 1H), 4.70 (dd, 1H), 4.42 (d, 1H), 4.31 (dd, 1H), 4.08 (dd, 1H), 2.84-2.79 (m, 1H), 2.65-2.43 (m, 2H), 2.23 (q, 1H), 1.88-1.62 (m, 6H), 1.49-0.78 (m, 19H).

Compound 115: MS: m/z 895.4 (M$^+$+1); $^1$H NMR (CDCl$_3$) δ 10.42 (s, 1H), 8.40 (d, 2H), 8.01 (s, 1H), 7.55 (d, 2H), 7.46-7.32 (m, 3H), 6.13 (s, 1H), 5.61 (q, 1H), 5.32 (brs, 1H), 5.01-4.87 (m, 1H), 4.89 (dd, 1H), 4.62-4.55 (m, 2H), 4.34-4.08 (m, 2H), 2.94-2.55 (m, 4H), 2.50 (s, 3H), 2.23 (q, 1H), 1.95-1.10 (m, 32H).

Compound 116: MS: m/z 909.4 (M$^+$+1); $^1$H NMR (CDCl$_3$) δ 10.29 (s, 1H), 8.40 (d, 2H), 8.01 (s, 1H), 7.55 (d, 2H), 7.47-7.26 (m, 3H), 6.14 (s, 1H), 5.69 (q, 1H), 5.37 (d, 1H), 4.99 (dd, 1H), 4.78 (dd, 1H), 4.60 (d, 1H), 4.40-4.05 (m, 3H), 2.80-2.51 (m, 3H), 2.50 (s, 3H), 2.29 (q, 1H), 1.98-1.12 (m, 32H), 0.82 (s, 3H).

Compound 117: MS: m/z 855.2 (M$^+$+1); $^1$H NMR (CDCl$_3$) δ 10.08 (s, 1H), 8.22 (d, 2H), 8.03 (d, 2H), 7.44-7.18 (m, 3H), 7.26-7.17 (m, 1H), 7.13 (d, 1H), 6.12 (s, 1H), 5.65 (q, 1H), 4.89 (dd, 1H), 4.77 (dd, 1H), 4.49 (d, 1H), 4.42-4.36 (m, 1H), 4.13 (dd, 1H), 3.16 (s, 1H), 2.84-2.46 (m, 4H), 2.16 (q, 1H), 1.95-0.77 (m, 31H).

Compound 118: MS: m/z 895.4 (M$^+$+1).

Compound 119: MS: m/z 895.4 (M$^+$+1).

Compound 120: MS: m/z 840.2 (M$^+$+1); $^1$H NMR (CDCl$_3$) δ 10.26 (s, 1H), 8.38 (d, 2H), 8.20 (d, 1H), 8.00 (d, 1H), 7.61-7.54 (m, 2H), 7.50 (d, 2H), 7.41-7.35 (m, 1H), 7.15 (s, 1H), 6.72 (d, 1H), 6.10 (d, 1H), 5.63 (q, 1H), 5.27 (d, 1H), 4.89 (dd, 1H), 4.68 (dd, 1H), 4.51-4.42 (m, 2H), 4.12 (dd, 1H), 2.84-2.43 (m, 4H), 2.22 (q, 1H), 1.98-0.84 (m, 24H).

Compound 121: MS: m/z 829.3 (M$^+$+1).

Compound 122: MS: m/z 833.3 (M$^+$+1).

Compound 123: MS: m/z 821.3 (M$^+$+1); $^1$H NMR (CDCl$_3$) δ 10.27 (s, 1H), 7.90 (dd, 1H), 7.60 (s, 1H), 7.27 (dd, 1H), 7.32-7.20 (m, 2H), 6.91 (s, 1H), 6.53 (dd, 1H), 6.03 (s, 1H), 5.64 (q, 1H), 4.98-4.89 (m, 2H), 4.71-4.58 (m, 2H), 4.14-4.03 (m, 2H), 2.86-2.80 (m, 1H), 2.67-2.40 (m, 2H), 2.22 (q, 1H), 1.98-1.10 (m, 15H), 1.05 (s, 9H), 0.98-0.82 (m, 1H).

Compound 124: MS: m/z 779.2 (M$^+$+1); $^1$H NMR (CDCl$_3$) δ 10.31 (s, 1H), 7.93 (dd, 1H), 7.70 (s, 1H), 7.65-7.55 (dd, 1H), 7.41-7.26 (m, 2H), 7.04 (s, 1H), 6.61 (s, 1H), 6.15 (s, 1H), 5.72 (q, 1H), 5.37 (d, 1H), 5.01-4.91 (m, 1H), 4.77 (dd, 1H), 4.46 (d, 1H), 4.37-4.09 (m, 2H), 3.36 (s, 3H), 2.92-2.53 (m, 3H), 2.23 (q, 1H), 1.99-0.86 (m, 16H).

Compound 125: MS: m/z 817.2 (M$^+$+1); $^1$H NMR (CDCl$_3$) δ 10.28 (s, 1H), 7.98 (d, 1H), 7.66 (s, 1H), 7.60 (dd, 1H), 7.40-7.09 (m, 3H), 6.11 (s, 1H), 6.60 (s, 1H), 6.17 (s, 1H), 5.72 (q, 1H), 4.99 (dd, 1H), 4.76-4.67 (m, 2H), 4.31-4.18 (m, 2H), 2.91-2.75 (m, 2H), 2.45 (br, 1H), 2.22-0.84 (m, 17H).

Compound 126: MS: m/z 763.2 (M++1); ¹H NMR (CDCl₃) δ 10.29 (s, 1H), 7.81 (dd, 1H), 7.60 (s, 1H), 7.52 (dd, 1H), 7.35-7.18 (m, 3H), 6.52 (d, 1H), 6.13-6.01 (m, 2H), 5.61 (q, 1H), 4.83 (dd, 1H), 4.62 (dd, 1H), 4.45 (dd, 1H), 4.38 (d, 1H), 4.17 (dd, 1H), 2.85-2.79 (m, 1H), 2.67 (d, 1H), 2.41 (m, 1H), 2.21-0.84 (m, 20H).

Compound 127: MS: m/z 821.3 (M++1); ¹H NMR (CDCl₃) δ 10.37 (s, 1H), 8.15 (s, 1H), 7.79 (d, 1H), 7.45-7.42 (m, 3H), 7.35-7.25 (m, 1H), 7.01 (s, 1H), 5.89 (s, 1H), 5.54 (q, 1H), 5.19 (d, 1H), 4.85 (dd, 1H), 4.67 (dd, 1H), 4.54 (d, 1H), 4.20 (dd, 1H), 4.04 (d, 1H), 2.91-2.44 (m, 3H), 2.24 (q, 1H), 2.01-1.11 (m, 15H), 1.06 (s, 9H), 0.83-0.78 (m, 1H).

Compound 128: MS: m/z 833.3 (M++1); ¹H NMR (CDCl₃) δ 10.37 (s, 1H), 8.07 (d, 1H), 7.56-7.22 (m, 5H), 6.89 (d, 1H), 5.96 (s, 1H), 5.57-5.49 (m, 1H), 5.21-5.17 (m, 1H), 4.96-4.83 (m, 1H), 4.72 (dd, 1H), 4.67 (d, 1H), 4.18-4.03 (m, 2H), 2.90-2.79 (m, 1H), 2.69 (s, 3H), 2.64-2.46 (m, 2H), 2.22 (q, 1H), 1.97-1.04 (m, 15H), 1.04 (s, 9H), 0.96-0.87 (m, 1H).

Compound 129: MS: m/z 836.3 (M++1); ¹H NMR (CDCl₃) δ 10.29 (s, 1H), 7.88 (d, 1H), 7.53-7.50 (m, 1H), 7.49 (dd, 1H), 7.19 (s, 1H), 6.65 (s, 1H), 6.04 (s, 1H), 5.70-5.50 (m, 1H), 5.12-4.48 (m, 4H), 4.19-3.98 (m, 2H), 2.95-2.58 (m, 3H), 2.48 (s, 3H), 2.32-2.12 (m, 1H), 1.97-1.18 (m, 15H), 1.00 (s, 9H), 0.98-0.86 (m, 1H).

Compound 130: MS: m/z 832.2 (M++1); ¹H NMR (CDCl₃) δ 10.20 (s, 1H), 7.84 (dd, 1H), 7.52 (dd, 1H), 7.39 (, 1H), 7.38-7.26 (m, 2H), 6.62 (s, 1H), 6.05 (s, 1H), 5.60 (q, 1H), 4.83 (dd, 1H), 4.67 (dd, 1H), 4.55 (dd, 1H), 4.36 (d, 1H), 4.08 (dd, 1H), 2.81-2.50 (m, 3H), 2.48 (s, 3H), 2.45-2.37 (m, 1H), 2.18 (q, 1H), 1.99-0.87 (m, 15H).

Compound 131: MS: m/z 888.3 (M++1); ¹H NMR (CDCl₃) δ 10.36 (s, 1H), 8.23 (d, 1H), 7.41 (s, 1H), 7.30 (m, 2H), 7.11 (s, 1H), 6.16 (s, 1H), 5.68 (q, 1H), 5.23 (d, 1H), 4.98 (dd, 1H), 4.75 (brs, 1H), 4.54 (d, 1H), 4.36-4.11 (m, 3H), 3.39-3.27 (m, 1H), 2.96-2.63 (m, 3H), 2.54 (s, 3H), 2.25 (q, 1H), 1.89-0.93 (m, 30H).

Compound 132: MS: m/z 888.3 (M++1); ¹H NMR (CDCl₃) δ 10.24 (s, 1H), 8.37 (d, 1H), 7.74-7.51 (m, 2H), 7.48-7.42 (m, 1H), 7.22 (s, 1H), 7.12 (s, 1H), 6.17 (s, 1H), 5.70 (q, 1H), 5.28 (d, 1H), 4.99 (dd, 1H), 4.76 (dd, 1H), 4.58 (d, 1H), 4.52 (brs, 1H), 4.35-4.16 (m, 2H), 3.40-3.35 (m, 1H), 2.79-2.43 (m, 3H), 2.25 (q, 1H), 1.95-1.23 (m, 29H), 0.87-0.76 (m, 3H).

Compound 133: MS: m/z 887.3 (M++1); ¹H NMR (CDCl₃) δ 10.37 (s, 1H), 8.59 (s, 1H), 8.22 (d, 1H), 7.81 (d, 1H), 7.58-7.42 (m, 3H), 6.95-6.89 (m, 2H), 6.09 (s, 1H), 5.68 (q, 1H), 5.32 (d, 1H), 4.99 (m, 1H), 4.74 (m, 1H), 4.54 (d, 1H), 4.39-4.22 (m, 1H), 4.14-4.11 (m, 1H), 2.90 (m, 1H), 2.78 (m, 2H), 2.55 (m, 1H), 2.27 (q, 1H), 1.90-1.10 (m, 21H), 1.45 (s, 9H), 0.94-0.83 (m, 2H).

Compound 134: MS: m/z 901.3 (M++1); ¹H NMR (CDCl₃) δ 10.21 (s, 1H), 8.8.51 (s, 1H), 8.23 (d, 1H), 7.81 (d, 1H), 7.59-7.43 (m, 3H), 7.13 (s, 1H), 6.90 (d, 1H), 6.09 (s, 1H), 5.68 (q, 1H), 5.22 (d, 1H), 4.99 (dd, 1H), 4.76 (m, 1H), 4.55 (d, 1H), 4.39-4.22 (m, 1H), 4.14-4.11 (m, 1H), 2.78 (m, 2H), 2.55 (m, 1H), 2.27 (q, 1H), 1.90-0.83 (m, 23H), 1.46 (s, 9H).

Compound 135: MS: m/z 888.3 (M++1).
Compound 136: MS: m/z 902.3 (M++1).
Compound 137: MS: m/z 899.4 (M++1).
Compound 138: MS: m/z 885.3 (M++1); ¹H NMR (CDCl₃) δ 10.36 (s, 1H), 8.17 (d, 1H), 7.58 (m, 2H), 7.42-7.33 (m, 2H), 6.63 (m, 1H), 6.07 (s, 1H), 5.67 (q, 1H), 5.29 (d, 1H), 4.97 (dd, 1H), 4.77 (m, 1H), 4.57 (m, 1H), 4.42-4.03 (m, 3H), 2.89 (m, 1H), 2.75 (m, 5H), 2.52 (m, 1H), 2.27 (q, 1H), 1.91-0.82 (m, 32H).

Compound 139: MS: m/z 803.3 (M++1).
Compound 140: MS: m/z 817.3 (M++1).
Compound 141: MS: m/z 831.3 (M++1); ¹H NMR (CDCl₃) δ 10.33 (s, 1H), 8.05 (s, 1H), 7.56-7.48 (m, 3H), 6.06 (s, 1H), 5.62 (q, 1H), 5.15 (dd, 1H), 4.91 (dd, 1H), 4.75 (dd, 1H), 4.59 (d, 1H), 4.35-4.02 (m, 3H), 2.96-2.88 (m, 1H), 2.74-2.65 (m, 2H), 2.53 (s, 3H), 2.24 (q, 1H), 1.96-0.89 (m, 24H).

EXAMPLES 142 AND 143

Synthesis of [4-Cyclopropanesulfonylaminocarbonyl-2,15-dioxo-18-(2-phenyl-benzo[4,5]furo[3,2-b]pyridin-4-yloxy)-3,16-diaza-tricyclo[14.3.0.04,6]nonadec-7-en-14-yl]-carbamic acid tert-butyl ester (Compound 142) and [4-Cyclopropanesulfonylaminocarbonyl-2,15-dioxo-18-(2-phenyl-benzo[4,5]furo[3,2-b]pyridin-4-yloxy)-3,16-diaza-tricyclo[14.3.0.04,6]nonadec-7-en-14-yl]-carbamic acid cyclopentyl ester (Compound 143)

Compounds 142 and 143 were prepared via the route shown below:

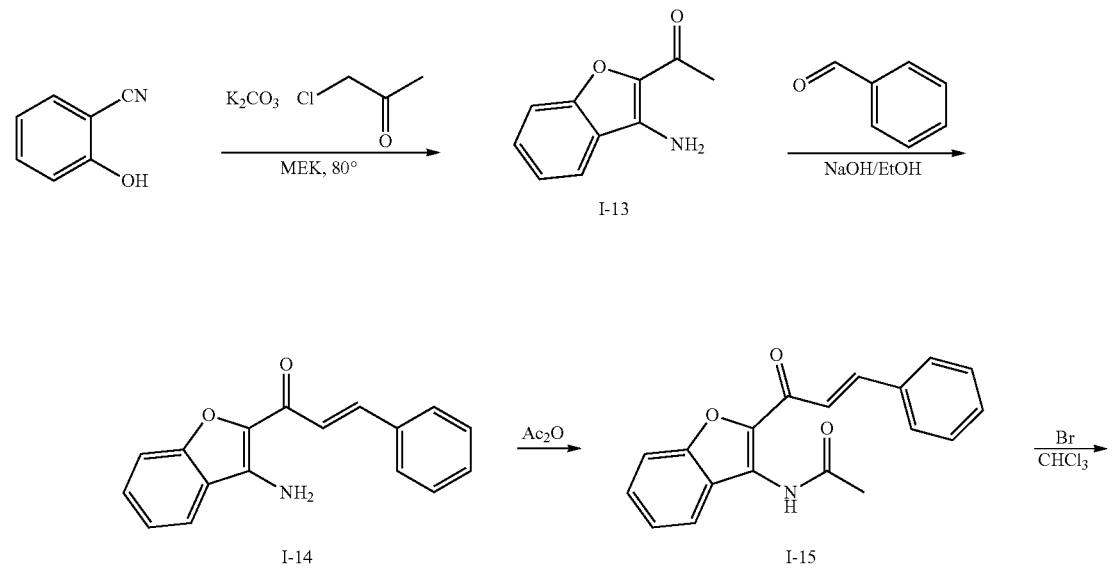

127
128
-continued
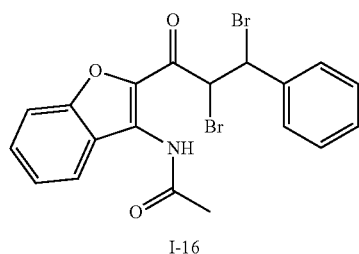
I-16
CH₃CO₂⁻K⁺
Acetone
→
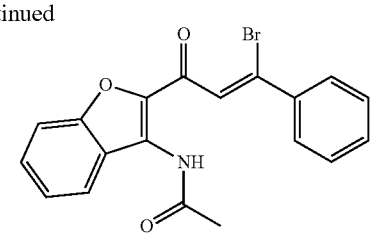
I-17
HOAc/H₃PO₄
Reflux, 5 h
→
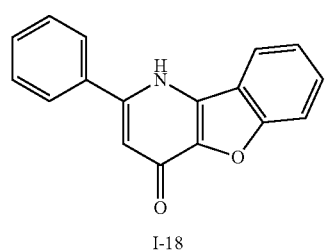
I-18
POCl₃
Reflux, 3 h
→
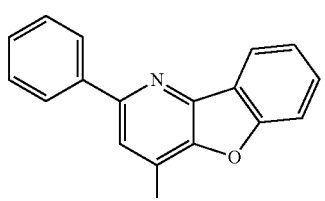
I-19
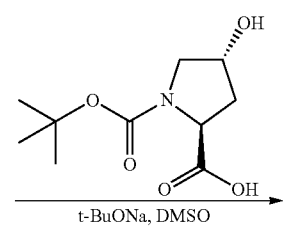
t-BuONa, DMSO
→
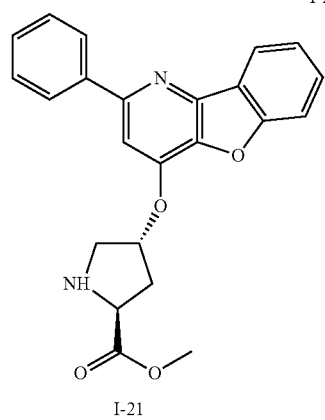
I-20
SOCl₂
MeOH
→
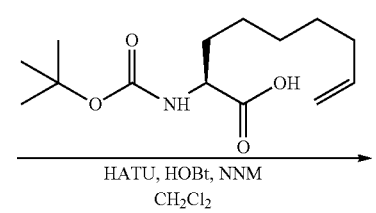
I-21
HATU, HOBt, NNM
CH₂Cl₂
→

-continued
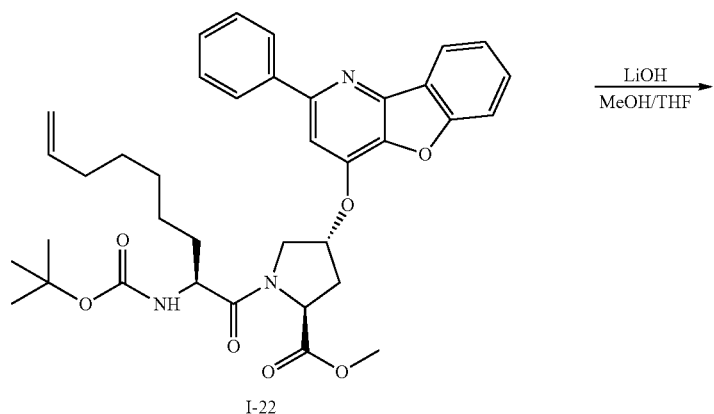
I-22
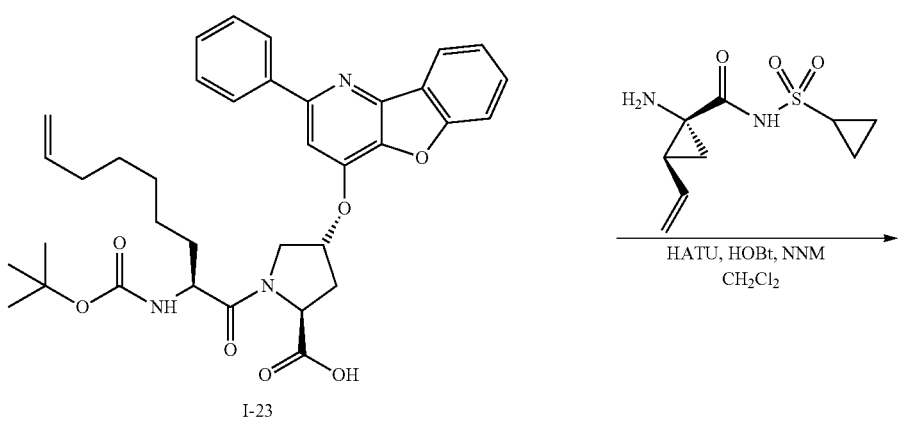
I-23
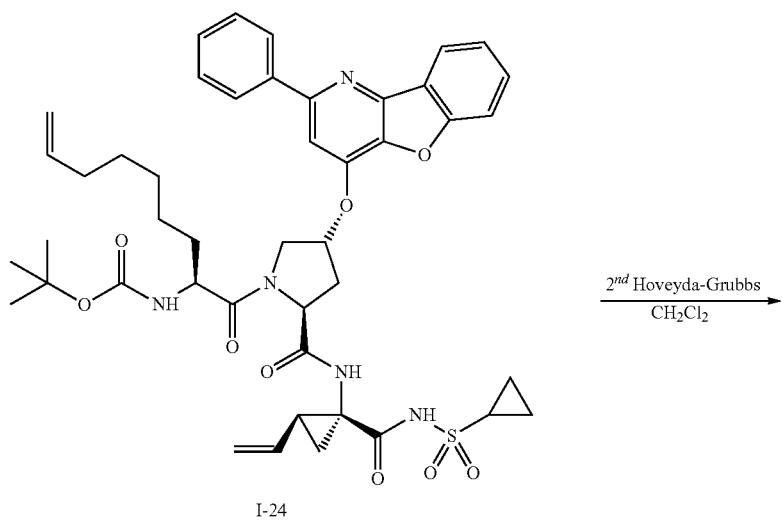
I-24

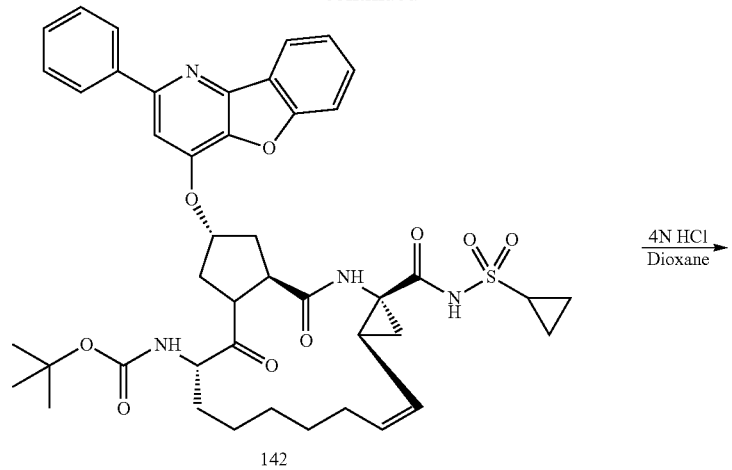

142

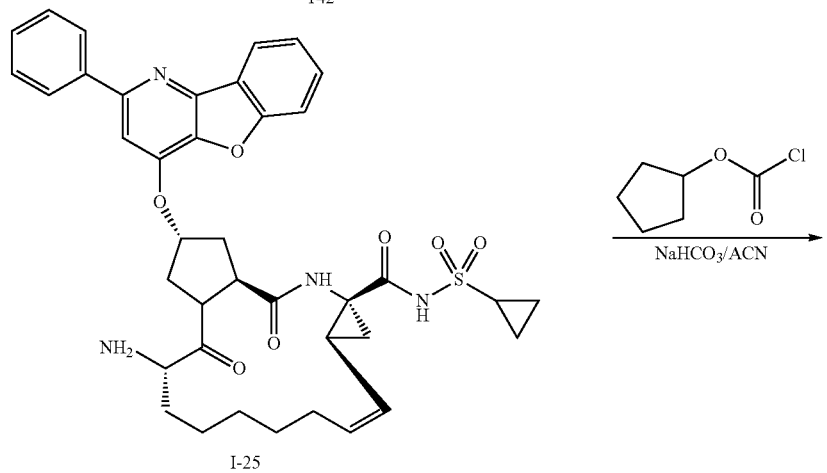

I-25

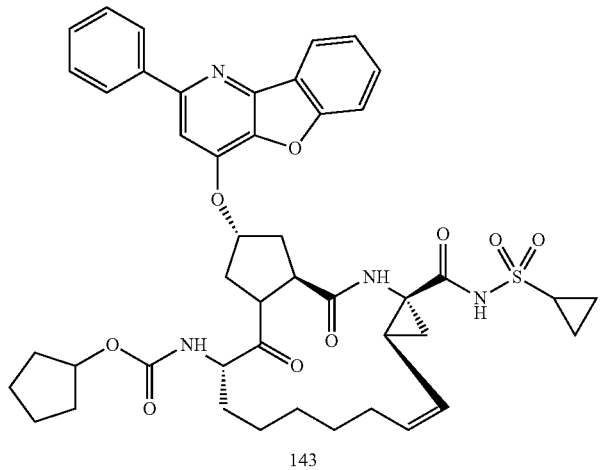

143

To a solution of 2-hydroxybenzonitrile (30 g, 251.6 mmol) in ethyl methyl ketone (320 mL) was added potassium carbonate (69.6 g, 755.5 mmol). After stirred at room temperature for 30 min, chloroacetone (34.95 g, 377.8 mmol) was added to the resulting mixture and then the solution was heated at 100° C. for overnight. Finally, the reaction solvent was removed under reduced pressure and the resulting solid was washed with water and ethyl ether to give I-13 (31 g, 70.3% yield) MS: m/z 176.0 (M$^+$+1); $^1$H NMR (CDCl$_3$) δ 7.59 (d, 1H), 7.46 (dd, 1H), 7.41 (d, 1H), 7.24 (dd, 1H), 2.50 (s, 3H).

To a solution of 2-acetyl-3-aminobenzofuran I-13 (2.17 g, 12.38 mmol) and benzaldehyde (1.31 g, 12.38 mmol) in ethanol (30 mL) at 5~10° C. was added an aqueous solution of sodium hydroxide (70%, 5 mL) dropwise under constant stirring. After stirred for overnight, a bright yellow solid of crude product was suspended in the reaction solution. The solid was filtrated, collected, and re-crystallized from ethanol to afford silky needles I-14 (2.7 g, 90%). MS: m/z 264.0 (M$^+$+1); $^1$H NMR (CDCl$_3$) δ 7.83 (d, 1H), 7.71 (dd, 2H), 7.64 (d, 1H), 7.62 (d, 1H), 7.58-7.39 (m, 5H), 7.29-7.24 (m, 1H), 5.83 (broad, 2H).

Intermediate I-14 (1.32 g, 5.0 mmol) was suspended in acetic anhydride (10 mL) and stirred on a warmed water-bath. After stirred overnight, the reaction mixture was poured into ice-water. The suspended crude product was separated and collected, and then re-crystallized from ethanol to give I-15 (1.52 g, 90%). MS: m/z 306.0 (M$^+$+1); $^1$H NMR (CDCl$_3$) δ 8.58 (d, 1H), 7.91 (d, 1H), 7.72 (m, 3H), 7.54-7.44 (m, 5H), 7.34-7.7.28 (m, 1H), 2.35 (s, 3H).

A solution of intermediate I-15 (1.22 g, 4.0 mmol) in CHCl$_3$ (20 mL) was added dropwise to a solution of bromine (0.72 g 4.5 mmol) in CHCl$_3$ (15 mL) slowly. After stirred overnight, the reaction mixture was quenched with ice water. The suspended solid was separated, collected, and re-crystallized from ethanol/H$_2$O to afford I-16 (1.12 g, 60%). MS: m/z 465.9 (M$^+$+1); $^1$H NMR (CDCl$_3$) δ 10.22 (brs, 1H), 8.63 (d, 1H), 7.61-7.25 (m, 8H), 5.92 (d, 1H), 5.62 (d, 1H), 2.37 (s, 3H).

To a solution of I-16 (0.93 g, 2.0 mmol) in acetone (25 mL) was added anhydrous potassium acetate (0.2 g, 2.0 mmol). After stirred overnight, the reaction mixture was poured into cold water. A suspended solid was separated, collected, and re-crystallized from ethanol to give monobromide-compound I-17 (0.46 g, 60%). MS: m/z 385.9 (M$^+$+1); $^1$H NMR (CDCl$_3$) δ 10.50 (brs, 1H), 8.54 (d, 1H), 8.48 (s, 1H), 7.93 (m, 2H), 7.56-7.46 (m, 5H), 7.36-7.31 (m, 1H), 2.35 (s, 3H).

Compound I-17 (0.35 g, 1.0 mmol) in acetic acid (5 mL) and orthophosphoric acid (5 mL) was refluxed for 5 hr. The reaction mixture was cooled to room temperature, poured into an ice water and stirred for additional 30 min. A suspended solid was separated, collected, and re-crystallized from DMF to give I-18 (0.2 g, 80%). MS: m/z 262.0 (M$^+$+1).

A solution of I-18 (1.0 g, 3.8 mmol) and phosphorus oxychloride (POCl$_3$) (10 mL) was refluxed for 2 hours. After the solution was cooled and thoroughly concentrated, the resulting residue was quenched with 10% sodium hydroxide and extracted with methylene chloride (20 mL×3). The organic layer was collected, dried over sodium sulfate, and concentrated. The crude product was recrystallized from CH$_2$Cl$_2$ and n-hexane to afford I-19 (0.7 g, 75%). MS: m/z 279.9 (M$^+$+1); $^1$H NMR (CDCl$_3$) δ 8.45 (d, 1H), 8.09 (d, 2H), 7.84 (s, 1H), 7.71-7.64 (m, 2H), 7.56-7.47 (m, 4H).

To a suspension of Boc-trans-4-hydroxy-L-proline (0.53 g, 2.3 mmol) in DMSO (10 mL) was added t-BuONa (0.49 g, 5.08 mmol) at 0° C. After warmed to room temperature and stirred for 1 h, intermediate I-19 (0.64 g, 2.3 mmol) was added slowly at 10° C. The reaction mixture was stirred for 4 h and then quenched with 10% HCl aqueous solution to pH 6~7. The crude solid was filtrated, washed with water, and dried under vacuum to give I-20 (0.94 g, 86.3%). MS: m/z 475.1 (M$^+$+1); $^1$H NMR (CDCl$_3$) δ 8.27 (d, 1H), 7.97 (m, 2H), 7.86-7.76 (m, 3H), 7.66-7.44 (m, 4H), 5.81 (s, 1H), 4.47 (m, 1H), 4.03-3.89 (m, 2H), 2.81 (m, 1H), 2.50 (q, 1H).

To a solution of I-20 (1.1 g, 2.3 mmol) in MeOH (20 mL) was added SOCl$_2$ (1.17 g, 9.9 mmol) at room temperature. After refluxed for 1 hour, the reaction solvent was removed under vacuum to give crude compound I-21 which was used in the next step without further purification. MS: m/z 389.1 (M$^+$+1).

To a solution of I-21 (0.78 g, 2.0 mmol), 2-(1H-7-Azabenzotriazol-1-yl)-1,1,3,3-tetramethyl uronium hexafluorophosphate methanaminium (HATU, 1.12 g, 3.0 mmol), N-Hydroxybenzotriazole (HOBT, 0.4 g, 3.0 mmol), and 2-tert-butoxycarbonylamino-non-8-enoic acid (1.19 g, 5.2 mmol) in CH$_2$Cl$_2$ (20 mL) was added NMM (1.0 g, 9.9 mmol) at room temperature. After the mixture was stirred overnight, it was concentrated under vacuum. The residue was purified by silica gel column chromatography to give compound I-22 (1.02 g, 80.7%). MS: m/z 642.3 (M$^+$+1); $^1$H NMR (CDCl$_3$) δ 8.24 (d, 1H), 8.05 (d, 2H), 7.58 (m, 2H), 7.56-7.41 (m, 4H), 7.28 (d, 1H), 5.83-5.76 (q, 1H), 5.71 (s, 1H), 5.24 (d, 1H), 5.01-4.82 (m, 2H), 4.76 (dd, 1H), 4.75-4.34 (m, 2H), 4.03 (m, 1H), 3.77 (s, 3H), 2.78 (m, 1H), 2.36 (q, 1H), 2.01 (m, 2H), 1.75 (m, 1H), 1.54 (m, 1H), 1.42 (m, 6H), 1.31 (s, 9H).

To a solution of I-22 (1.0 g, 1.6 mmol) in THF (20 mL) was added 0.5 M LiOH (5.7 mL, 2.9 mmol) at room temperature. After the reaction mixture was stirred overnight, it was acidified by 10% HCl to pH<7 and concentrated under vacuum to give a solid product, which was filtered and washed with water to give I-23. MS: m/z 628.1 (M$^+$+1); $^1$H NMR (CDCl$_3$) δ 8.34 (brs, 1H), 8.04 (d, 2H), 7.62 (m, 2H), 7.60-7.41 (m, 4H), 7.28 (m, 2H), 5.81-5.72 (q, 1H), 5.70 (s, 1H), 5.29 (d, 1H), 5.00-4.87 (m, 3H), 4.48 (m, 2H), 4.01 (m, 1H), 2.77 (m, 2H), 1.98 (m, 2H), 1.72 (m, 1H), 1.61 (m, 1H), 1.44 (m, 6H), 1.33 (s, 9H).

NMM (0.12 g, 1.2 mmol) was added to a solution of compound I-23 (0.26 g, 0.41 mmol), HATU (0.31 g, 0.81 mmol), HOBT (0.084 g, 0.61 mmol), and cyclopropanesulfonic acid (1-amino-2-vinyl-cyclopropanecarbonyl)-amide (0.094 g, 0.41 mmol) in CH$_2$Cl$_2$ (10 mL) at room temperature. After the reaction mixture was stirred overnight, it was concentrated under vacuum. The residue was purified by silica gel column chromatography to give compound I-24 (0.15 g, 45%). MS: m/z 804.3 (M$^+$+1); $^1$H NMR (CDCl$_3$) δ 10.22 (s, 1H), 8.35 (d, 1H), 8.01 (d, 2H), 7.59 (d, 2H), 7.48-7.30 (m, 5H), 7.04 (s, 1H), 5.78 (m, 3H), 5.35 (d, 1H), 5.23 (d, 1H), 5.15 (d, 1H), 4.93 (m, 2H), 4.53 (dd, 1H), 4.41-4.30 (m, 2H), 4.05 (m, 1H), 2.91 (m, 1H), 2.61 (m, 2H), 2.14 (dd, 1H), 2.04 (m, 3H), 1.91-1.52 (m, 3H), 1.45-1.22 (18H), 1.21 (m, 2H).

To a solution of compound I-24 (100 mg, 0.12 mmol) in CH$_2$Cl$_2$ was added Hoveyda-Grubbs 2nd generation catalyst (35 mg, 0.056 mmol) under N$_2$ at room temperature, and then the reaction mixture was heated to 40° C. and stirred for 24 hours. The reaction mixture was concentrated and purified by column to give compound 142 (30 mg, 31%). MS: m/z 812.3 (M$^+$+1); $^1$H NMR (CDCl$_3$) δ 10.29 (s, 1H), 8.28 (d, 1H), 8.04 (d, 2H), 7.61-7.41 (m, 7H), 7.00 (s, 1H), 5.69 (m, 2H), 5.19 (d, 1H), 4.97 (dd, 1H), 4.67 (m, 2H), 4.31 (m, 1H), 4.05 (m, 1H), 2.89 (m, 1H), 2.70 (m, 2H), 2.55 (m, 1H), 2.29 (q, 1H), 1.89-1.11 (m, 13H), 1.19 (s, 9H), 0.97-0.86 (m, 2H).

To a solution of compound 142 (0.1 g, 0.14 mmol) in CH$_2$Cl$_2$ (5 mL) was added an excessive amount of 4 N HCl solution in dioxane (2 mL) at room temperature. After stirred for 4 hr, HCl, dioxane and CH$_2$Cl$_2$ was removed by evaporated to give crude compound I-25 which was used in the next step without further purification. MS: m/z 712.3 (M$^+$+1).

I-25 was dissolved in acetonitrile (2 mL) and then saturated NaHCO$_3$ (1 mL) was added. The reaction mixture was stirred for 10 min. Cyclepentyl chloroformate (0.02 g, 0.15 mmol) was added to the reaction mixture at room temperature. After stirred for additional 2 hours, the reaction mixture was quenched by saturated NaHCO$_3$ and extracted by CH$_2$Cl$_2$. The residue was purified by silica gel column chromatography to give compound 143 (0.1 g, 87%). MS: m/z 824.3 (M$^+$+1); $^1$H NMR (CDCl$_3$) δ 10.26 (s, 1H), 8.29 (d, 1H), 8.07 (d, 2H), 7.62-7.32 (m, 7H), 7.00 (s, 1H), 5.75 (s, 1H), 5.70 (q, 1H), 5.22 (d, 1H), 4.99 (dd, 1H), 4.75 (m, 2H), 4.56 (d, 1H), 4.32 (m, 1H), 4.05 (m, 1H), 2.89 (m, 1H), 2.70 (m, 2H), 2.52 (m, 1H), 2.29 (q, 1H), 1.91-0.85 (m, 23H).

EXAMPLE 144-253

Syntheses of Compound 144-253

Each of Compounds 144-253 was prepared in a manner similar to those described in Examples 142 and 143.

Compound 144: MS: m/z 7887.3 (M⁺+1); ¹H NMR (CDCl₃) δ 10.36 (s, 1H), 8.40 (s, 1H), 8.21 (d, 1H), 8.08 (dd, 1H), 7.56-7.11 (m, 7H), 6.80 (s, 1H), 5.63 (m, 2H), 4.93 (m, 1H), 4.79 (m, 1H), 4.31 (m, 2H), 4.05 (m, 1H), 3.45 (s, 3H), 2.87 (m, 1H), 2.70 (m, 2H), 2.52 (m, 1H), 2.25 (q, 1H), 1.91-0.84 (m, 15H).

Compound 145: MS: m/z 872.3 (M⁺+1).

Compound 146: MS: m/z 770.3 (M⁺+1); ¹H NMR (CDCl₃) δ 10.35 (s, 1H), 8.25 (d, 1H), 8.00 (d, 2H), 7.56-7.25 (m, 7H), 6.66 (s, 1H), 5.69 (m, 2H), 5.45 (d, 1H), 4.95 (dd, 1H), 4.70 (m, 1H), 4.40-4.28 (m, 2H), 4.05 (m, 1H), 3.52 (s, 3H), 2.88 (m, 1H), 2.70 (m, 2H), 2.51 (m, 1H), 2.30 (q, 1H), 1.87-1.09 (m, 13H), 0.97-0.84 (m, 2H).

Compound 147: MS: m/z 697.2 (M⁺+1); ¹H NMR (CDCl₃) δ 10.37 (s, 1H), 8.24 (d, 1H), 8.04 (d, 2H), 7.56-7.31 (m, 8H), 5.63 (m, 2H), 4.97 (dd, 1H), 4.63 (m, 1H), 4.09 (m, 1H), 3.96 (m, 1H), 2.84 (m, 1H), 2.62 (m, 2H), 2.6-2.03 (m, 4H), 1.95-0.84 (m, 15H).

Compound 148: MS: m/z 872.3 (M⁺+1); ¹H NMR (CDCl₃) δ 10.29 (s, 1H), 8.09 (dd, 1H), 7.69 (d, 1H), 7.48-7.14 (m, 7H), 5.71 (m, 2H), 5.31 (d, 1H), 4.98 (dd, 1H), 4.74 (m, 1H), 4.55 (d, 1H), 4.36 (m, 1H), 4.05 (m, 2H), 3.96 (s, 3H), 2.89 (m, 1H), 2.68 (m, 2H), 2.52 (m, 1H), 2.28 (q, 1H), 2.00-0.88 (m, 23H).

Compound 149: MS: m/z 818.2 (M⁺+1).

Compound 150: MS: m/z 802.2 (M⁺+1); ¹H NMR (CDCl₃) δ 10.23 (s, 1H), 8.08 (dd, 1H), 7.68 (d, 1H), 7.49 (d, 1H), 7.39-7.13 (m, 6H), 6.10 (d, 1H), 5.72 (m, 2H), 4.95 (dd, 1H), 4.63 (m, 1H), 4.17 (d, 1H), 4.06 (m, 1H), 3.92 (s, 3H), 2.89 (m, 1H), 2.69 (m, 2H), 2.46 (m, 1H), 2.26 (q, 1H), 1.94-0.86 (m, 15H), 1.91 (s, 3H).

Compound 151: MS: m/z 854.3 (M⁺+1); ¹H NMR (CDCl₃) δ 10.26 (s, 1H), 8.27 (d, 1H), 8.03 (d, 2H), 7.59 (m, 3H), 7.45 (dd, 1H), 7.01 (d, 2H), 6.88 (m, 1H), 5.74 (m, 2H), 5.19 (d, 1H), 4.96 (m, 2H), 4.75 (s, 1H), 4.53 (d, 1H), 4.32 (m, 1H), 4.04 (m, 1H), 3.87 (s, 3H), 2.89 (m, 1H), 2.69 (m, 2H), 2.46 (m, 1H), 2.27 (q, 1H), 1.90-1.12 (m, 21H), 0.92-0.87 (m, 2H).

Compound 152: MS: m/z 842.3 (M⁺+1).

Compound 153: MS: m/z 854.3 (M⁺+1); ¹H NMR (CDCl₃) δ 10.31 (s, 1H), 8.58 (s, 1H), 8.43 (m, 1H), 7.85 (d, 1H), 7.59 (m, 2H), 7.37 (m, 3H), 7.12 (dd, 1H), 7.01 (d, 1H), 5.65 (m, 2H), 5.31 (d, 1H), 4.94 (dd, 1H), 4.72 (m, 2H), 4.53 (d, 1H), 4.37 (m, 1H), 4.07 (m, 1H), 3.87 (s, 3H), 2.88 (m, 1H), 2.66 (m, 2H), 2.50 (m, 1H), 2.28 (q, 1H), 1.88-0.82 (m, 23H).

Compound 154: MS: m/z 854.3 (M⁺+1); ¹H NMR (CDCl₃) δ 10.29 (s, 1H), 8.50 (s, 1H), 8.29 (d, 1H), 7.63 (s, 1H), 7.56 (m, 3H), 7.43 (m, 2H), 7.28 (m, 1H), 7.11 (s, 1H), 6.98 (dd, 1H), 5.74 (s, 1H), 5.69 (q, 1H), 5.29 (d, 1H), 4.94 (dd, 1H), 4.73 (m, 1H), 4.57 (d, 1H), 4.34 (m, 1H), 4.04 (m, 1H), 3.92 (s, 3H), 2.88 (m, 1H), 2.68 (m, 2H), 2.51 (m, 1H), 2.29 (q, 1H), 1.87-0.84 (m, 23H).

Compound 155: MS: m/z 842.3 (M⁺+1); ¹H NMR (CDCl₃) δ 10.28 (s, 1H), 8.28 (d, 1H), 7.85 (d, 1H), 7.57 (m, 2H), 7.40 (m, 3H), 7.14 (dd, 1H), 7.01 (d, 2H), 5.68 (q, 1H), 5.58 (s, 1H), 5.19 (d, 1H), 4.92 (dd, 1H), 4.67 (m, 2H), 4.33 (m, 1H), 4.03 (m, 1H), 3.87 (s, 3H), 2.89 (m, 1H), 2.68 (m, 2H), 2.54 (m, 1H), 2.28 (q, 1H), 1.90-1.11 (m, 13H), 1.21 (s, 9H), 0.97-0.87 (m, 2H).

Compound 156: MS: m/z 854.3 (M⁺+1); ¹H NMR (CDCl₃) δ 10.24 (s, 1H), 8.59 (s, 1H), 8.04 (m, 2H), 7.84 (d, 1H), 7.49-7.28 (m, 4H), 7.08 (d, 1H), 6.91 (s, 1H), 5.72 (s, 1H), 5.68 (q, 1H), 5.21 (d, 1H), 4.97 (dd, 1H), 4.71-4.67 (m, 2H), 4.56 (d, 1H), 4.36 (m, 1H), 4.05 (s, 3H), 4.04 (m, 1H), 2.90 (m, 1H), 2.69 (m, 2H), 2.54 (m, 1H), 2.31 (q, 1H), 1.96-1.06 (m, 21H), 0.95-0.83 (m, 2H).

Compound 157: MS: m/z 838.3 (M⁺+1); ¹H NMR (CDCl₃) δ 10.30 (s, 1H), 8.59 (s, 1H), 8.27 (d, 1H), 7.92 (d, 2H), 7.57 (m, 2H), 7.44 (m, 1H), 7.26-7.17 (m, 3H), 5.68 (s, 1H), 5.64 (q, 1H), 5.37 (d, 1H), 4.96 (m, 1H), 4.76 (m, 1H), 4.67 (m, 1H), 4.56 (d, 1H), 4.36 (m, 1H), 4.04 (m, 1H), 2.89 (m, 1H), 2.69 (m, 2H), 2.53 (m, 1H), 2.40 (s, 3H), 2.31 (q, 1H), 1.94-1.07 (m, 21H), 0.95-0.83 (m, 2H).

Compound 158: MS: m/z 842.3 (M⁺+1); ¹H NMR (CDCl₃) δ 10.31 (s, 1H), 8.26 (d, 1H), 8.05 (m, 2H), 7.58 (m, 2H), 7.43 (m, 1H), 7.25-7.19 (m, 4H), 5.72 (s, 1H), 5.68 (q, 1H), 5.35 (d, 1H), 4.96 (dd, 1H), 4.75-4.69 (m, 2H), 4.56 (d, 1H), 4.36 (m, 1H), 4.04 (m, 1H), 2.87 (m, 1H), 2.67 (m, 2H), 2.50 (m, 1H), 2.28 (q, 1H), 1.91-1.07 (m, 21H), 0.97-0.84 (m, 2H).

Compound 159: MS: m/z 872.3 (M⁺+1).

Compound 160: MS: m/z 872.1 (M⁺+1); ¹H NMR (CDCl₃) δ 10.48 (s, 1H), 8.02 (m, 2H), 7.68 (d, 1H), 7.47 (d, 1H), 7.23-7.17 (m, 4H), 5.74 (m, 2H), 5.68 (q, 1H), 5.23 (d, 1H), 4.97 (dd, 1H), 4.76 (s, 1H), 4.67 (m, 1H), 4.54 (d, 1H), 4.33 (m, 1H), 4.04 (m, 1H), 3.93 (s, 3H), 2.89 (m, 1H), 2.67 (m, 2H), 2.52 (m, 1H), 2.27 (q, 1H), 1.92-1.06 (m, 21H), 0.97-0.84 (m, 2H).

Compound 161: MS: m/z 860.2 (M⁺+1); ¹H NMR (CDCl₃) δ 10.34 (s, 1H), 8.01 (m, 2H), 7.67 (d, 1H), 7.47 (d, 1H), 7.29-7.16 (m, 5H), 5.68 (m, 2H), 5.23 (d, 1H), 4.95 (dd, 1H), 4.69-4.63 (m, 2H), 4.31 (m, 1H), 4.04 (m, 1H), 3.92 (s, 3H), 2.88 (m, 1H), 2.67 (m, 2H), 2.54 (m, 1H), 2.27 (q, 1H), 1.92-0.83 (m, 15H), 1.20 (s, 9H).

Compound 162: MS: m/z 856.1 (M⁺+1); ¹H NMR (CDCl₃) δ 10.23 (s, 1H), 8.03 (m, 2H), 7.66 (d, 1H), 7.48 (d, 1H), 7.32 (s, 1H), 7.29-7.15 (m, 5H), 5.73 (m, 2H), 4.92 (dd, 1H), 4.69 (m, 2H), 4.31 (d, 1H), 4.06 (m, 1H), 3.91 (s, 3H), 2.85 (m, 1H), 2.68 (m, 2H), 2.44 (m, 1H), 2.20 (q, 1H), 1.93-0.83 (m, 15H).

Compound 163: MS: m/z 854.2 (M⁺+1); ¹H NMR (CDCl₃) δ 10.30 (s, 1H), 8.60 (s, 1H), 8.01 (m, 2H), 7.68 (d, 1H), 7.46 (m, 4H), 7.15 (m, 2H), 5.71 (s, 1H), 5.68 (q, 1H), 5.37 (d, 1H), 4.96 (dd, 1H), 4.67 (s, 1H), 4.64 (m, 1H), 4.55 (d, 1H), 4.36 (m, 1H), 4.03 (m, 1H), 3.93 (s, 3H), 2.88 (m, 1H), 2.68 (m, 2H), 2.52 (m, 1H), 2.28 (q, 1H), 1.94-1.07 (m, 21H), 0.97-0.84 (m, 2H).

Compound 164: MS: m/z 830.4 (M⁺+1); ¹H NMR (CDCl₃) δ 10.33 (s, 1H), 8.25 (d, 1H), 8.04 (m, 2H), 7.57 (m, 2H), 7.42 (m, 1H), 7.25-7.14 (m, 4H), 5.68 (m, 2H), 5.25 (d, 1H), 4.92 (dd, 1H), 4.66 (m, 2H), 4.32 (m, 1H), 4.05 (m, 1H), 2.87 (m, 1H), 2.68 (m, 2H), 2.55 (m, 1H), 2.28 (q, 1H), 1.91-1.06 (m, 13H), 1.20 (s, 9H), 0.97-0.84 (m, 2H).

Compound 165: MS: m/z 868.2 (M⁺+1); ¹H NMR (CDCl₃) δ 10.29 (s, 1H), 8.53 (s, 1H), 8.13 (d, 1H), 7.91 (m, 2H), 7.58 (m, 1H), 7.19 (m, 1H), 7.00 (m, 3H), 5.72 (s, 1H), 5.68 (q, 1H), 5.28 (d, 1H), 4.95 (dd, 1H), 4.79 (s, 1H), 4.68 (m, 1H), 4.53 (d, 1H), 4.37 (m, 1H), 4.05 (m, 1H), 3.91 (s, 3H), 2.88 (m, 1H), 2.66 (m, 2H), 2.50 (m, 1H), 2.40 (s, 3H), 2.25 (q, 1H), 1.90-1.06 (m, 21H), 0.97-0.83 (m, 2H).

Compound 166: MS: m/z 868.3 (M⁺+1); ¹H NMR (CDCl₃) δ 10.30 (s, 1H), 8.59 (s, 1H), 7.98 (m, 2H), 7.71 (s, 1H), 7.46 (d, 1H), 7.27 (m, 2H), 7.15 (m, 2H), 5.71 (s, 1H), 5.68 (q, 1H), 5.29 (d, 1H), 4.94 (dd, 1H), 4.78 (s, 1H), 4.67 (m, 1H), 4.54 (d, 1H), 4.36 (m, 1H), 4.04 (m, 1H), 3.93 (s, 3H), 2.88 (m, 1H), 2.68 (m, 2H), 2.53 (m, 1H), 2.40 (s, 3H), 2.28 (q, 1H), 1.92-1.08 (m, 21H), 0.97-0.83 (m, 2H).

Compound 167: MS: m/z 872.4 (M⁺+1); ¹H NMR (CDCl₃) δ 10.29 (s, 1H), 8.51 (s, 1H), 8.08 (d, 1H), 8.01 (m, 2H), 7.15 (d, 2H), 7.04 (m, 3H), 5.73 (s, 1H), 5.69 (q, 1H), 5.30 (d, 1H), 4.95 (dd, 1H), 4.79 (s, 1H), 4.65 (m, 1H), 4.53 (d, 1H), 4.37 (m, 1H), 4.04 (m, 1H), 3.91 (s, 3H), 2.88 (m, 1H), 2.66 (m, 2H), 2.50 (m, 1H), 2.28 (q, 1H), 1.90-1.05 (m, 21H), 0.97-0.83 (m, 2H).

Compound 168: MS: m/z 826.4 (M⁺+1); ¹H NMR (CDCl₃) δ 10.23 (s, 1H), 8.28 (d, 1H), 7.94 (d, 2H), 7.56 (m, 2H), 7.42

(m, 1H), 7.28 (m, 3H), 7.03 (s, 1H), 5.68 (m, 2H), 5.21 (d, 1H), 4.94 (dd, 1H), 4.67 (m, 2H), 4.32 (m, 1H), 4.05 (m, 1H), 2.89 (m, 1H), 2.68 (m, 2H), 2.55 (m, 1H), 2.55 (s, 3H), 2.35 (q, 1H), 1.94-1.07 (m, 13H), 1.20 (s, 9H), 0.97-0.84 (m, 2H).

Compound 169: MS: m/z 858.3, 859.3 (M$^+$+1); $^1$H NMR (CDCl$_3$) δ 10.35 (s, 1H), 8.58 (s, 1H), 8.24 (d, 1H), 8.00 (m, 2H), 7.57 (m, 2H), 7.45 (m, 3H), 7.25 (s, 1H), 5.71 (s, 1H), 5.66 (q, 1H), 5.41 (d, 1H), 4.96 (dd, 1H), 4.75 (m, 2H), 4.55 (d, 1H), 4.35 (m, 1H), 4.04 (m, 1H), 2.87 (m, 1H), 2.69 (m, 2H), 2.57 (m, 1H), 2.28 (q, 1H), 1.92-0.83 (m, 23H).

Compound 170: MS: m/z 772.2 (M$^+$+1); $^1$H NMR (CDCl$_3$) δ 10.31 (s, 1H), 8.22 (d, 1H), 8.00 (m, 2H), 7.59 (m, 2H), 7.41 (m, 1H), 7.20-7.10 (m, 4H), 6.12 (d, 1H), 5.72 (m, 2H), 4.96 (dd, 1H), 4.64 (m, 1H), 4.55 (m, 1H), 4.40 (d, 1H), 4.01 (m, 1H), 2.88 (m, 1H), 2.66 (m, 2H), 2.50 (m, 1H), 2.26 (q, 1H), 1.92-1.05 (m, 13H), 1.91 (s, 3H), 0.97-0.85 (m, 2H).

Compound 171: MS: m/z 768.2 (M$^+$+1); $^1$H NMR (CDCl$_3$) δ 10.29 (s, 1H), 8.26 (d, 1H), 7.93 (d, 2H), 7.57 (m, 2H), 7.42 (m, 1H), 7.27 (m, 4H), 6.16 (d, 1H), 5.69 (m, 2H), 4.94 (dd, 1H), 4.67 (m, 1H), 4.57 (m, 1H), 4.40 (d, 1H), 4.05 (m, 1H), 2.89 (m, 1H), 2.68 (m, 2H), 2.51 (m, 1H), 2.39 (s, 3H), 2.30 (q, 1H), 1.94-1.05 (m, 13H), 1.92 (s, 3H), 0.97-0.84 (m, 2H).

Compound 172: MS: m/z 788.2 (M$^+$+1); $^1$H NMR (CDCl$_3$) δ 10.32 (s, 1H), 8.22 (d, 1H), 8.01 (m, 2H), 7.57 (m, 2H), 7.42 (m, 1H), 7.22-7.11 (m, 4H), 5.72 (m, 2H), 5.39 (d, 1H), 4.96 (dd, 1H), 4.71 (m, 1H), 4.39 (m, 2H), 4.04 (m, 1H), 3.54 (s, 3H), 2.89 (m, 1H), 2.71 (m, 2H), 2.54 (m, 1H), 2.25 (q, 1H), 1.91-1.06 (m, 13H), 0.93-0.83 (m, 2H).

Compound 173: MS: m/z 822.2 (M$^+$+1); $^1$H NMR (CDCl$_3$) δ 10.15 (s, 1H), 8.27 (d, 1H), 7.91 (d, 2H), 7.59 (m, 2H), 7.44 (m, 1H), 7.27 (m, 3H), 7.15 (d, 1H), 7.07 (s, 1H), 5.75 (s, 1H), 5.69 (q, 1H), 4.91 (dd, 1H), 4.68 (m, 2H), 4.32 (d, 1H), 4.06 (m, 1H), 2.89 (m, 1H), 2.68 (m, 2H), 2.41 (m, 1H), 2.39 (s, 3H), 2.21 (q, 1H), 1.96-1.08 (m, 13H), 0.96-0.83 (m, 2H).

Compound 174: MS: m/z 826.2 (M$^+$+1); $^1$H NMR (CDCl$_3$) δ 10.21 (s, 1H), 8.22 (d, 1H), 8.02 (m, 2H), 7.59 (m, 2H), 7.41 (m, 1H), 7.24-7.13 (m, 5H), 5.73 (s, 1H), 5.67 (q, 1H), 4.89 (dd, 1H), 4.72 (m, 2H), 4.31 (d, 1H), 4.05 (m, 1H), 2.87 (m, 1H), 2.69 (m, 2H), 2.47 (m, 1H), 2.24 (q, 1H), 1.93-1.04 (m, 13H), 0.93-0.82 (m, 2H).

Compound 175: MS: m/z 842.3 (M$^+$+1); $^1$H NMR (CDCl$_3$) δ 10.30 (s, 1H), 8.58 (s, 1H), 8.26 (d, 1H), 8.10 (dd, 1H), 7.61-7.14 (m, 7H), 6.91 (s, 1H), 5.67 (m, 2H), 5.38 (d, 1H), 4.96 (dd, 1H), 4.70 (m, 1H), 4.56 (d, 1H), 4.36 (m, 1H), 4.06 (m, 1H), 2.88 (m, 1H), 2.69 (m, 2H), 2.51 (m, 1H), 2.28 (q, 1H), 1.87-0.88 (m, 23H).

Compound 176: MS: m/z 844.3 (M$^+$+1); $^1$H NMR (CDCl$_3$) δ 10.28 (s, 1H), 8.00 (m, 3H), 7.42 (d, 1H), 7.37 (d, 1H), 7.19 (m, 3H), 6.98 (s, 1H), 5.68 (m, 2H), 5.19 (d, 1H), 4.96 (dd, 1H), 4.66 (m, 2H), 4.30 (m, 1H), 4.04 (m, 1H), 2.89 (m, 1H), 2.67 (m, 2H), 2.52 (s, 3H), 2.51 (m, 1H), 2.26 (q, 1H), 1.94-1.05 (m, 13H), 1.20 (s, 9H), 0.98-0.83 (m, 2H).

Compound 177: MS: m/z 840.2 (M$^+$+1); $^1$H NMR (CDCl$_3$) δ 10.25 (s, 1H), 8.00 (m, 3H), 7.42 (d, 1H), 7.35-7.11 (m, 6H), 5.73 (s, 1H), 5.69 (q, 1H), 4.93 (dd, 1H), 4.66 (m, 2H), 4.32 (d, 1H), 4.04 (m, 1H), 2.89 (m, 1H), 2.70 (m, 2H), 2.51 (s, 3H), 2.48 (m, 1H), 2.23 (q, 1H), 1.95-1.04 (m, 13H), 0.96-0.82 (m, 2H).

Compound 178: MS: m/z 784.2 (M$^+$+1); $^1$H NMR (CDCl$_3$) δ 10.33 (s, 1H), 8.27 (d, 1H), 7.92 (d, 2H), 7.55 (m, 2H), 7.41 (m, 1H), 7.27 (m, 4H), 5.70 (m, 2H), 5.45 (d, 1H), 4.95 (dd, 1H), 4.67 (m, 1H), 4.36 (m, 2H), 4.06 (m, 1H), 3.49 (s, 3H), 2.89 (m, 1H), 2.69 (m, 2H), 2.51 (m, 1H), 2.39 (s, 3H), 2.26 (q, 1H), 1.96-1.06 (m, 13H), 0.97-0.83 (m, 2H).

Compound 179: MS: m/z 856.3 (M$^+$+1); $^1$H NMR (CDCl$_3$) δ 10.28 (s, 1H), 7.92 (d, 2H), 7.69 (d, 1H), 7.44 (d, 1H), 7.29 (d, 2H), 7.15 (s, 1H), 7.05 (dd, 1H), 6.97 (s, 1H), 5.68 (m, 2H), 5.22 (d, 1H), 4.95 (dd, 1H), 4.62 (m, 2H), 4.30 (m, 1H), 4.03 (m, 1H), 3.93 (s, 3H), 2.87 (m, 1H), 2.66 (m, 2H), 2.54 (m, 1H), 2.41 (s, 3H), 2.29 (q, 1H), 1.94-0.82 (m, 15H), 1.21 (s, 9H).

Compound 180: MS: m/z 814.3 (M$^+$+1); $^1$H NMR (CDCl$_3$) δ 10.35 (s, 1H), 7.92 (d, 2H), 7.63 (d, 1H), 7.42 (d, 1H), 7.33-7.21 (m, 4H), 7.10 (dd, 1H), 5.66 (m, 2H), 5.41 (d, 1H), 4.94 (dd, 1H), 4.65 (m, 1H), 4.37 (m, 2H), 4.03 (m, 1H), 3.91 (s, 3H), 3.50 (s, 3H), 2.87 (m, 1H), 2.66 (m, 2H), 2.51 (m, 1H), 2.41 (s, 3H), 2.25 (q, 1H), 1.94-1.07 (m, 13H), 0.93-0.83 (m, 2H).

Compound 181: MS: m/z 852.2 (M$^+$+1); $^1$H NMR (CDCl$_3$) δ 10.19 (s, 1H), 7.91 (d, 2H), 7.71 (d, 1H), 7.48 (d, 1H), 7.30-7.15 (m, 5H), 7.13 (dd, 1H), 5.66 (s, 1H), 5.64 (q, 1H), 4.94 (dd, 1H), 4.65 (m, 2H), 4.30 (d, 1H), 4.03 (m, 1H), 3.93 (s, 3H), 2.84 (m, 1H), 2.67 (m, 2H), 2.46 (m, 1H), 2.40 (s, 3H), 2.22 (q, 1H), 1.95-0.84 (m, 15H).

Compound 182: MS: m/z 798.3 (M$^+$+1); $^1$H NMR (CDCl$_3$) δ 10.33 (s, 1H), 7.92 (d, 2H), 7.72 (d, 1H), 7.43 (d, 1H), 7.39 (s, 1H), 7.21 (m, 3H), 7.11 (dd, 1H), 6.18 (d, 1H), 5.70 (q, 1H), 5.64 (s, 1H), 4.94 (dd, 1H), 4.66 (dd, 1H), 4.56 (m, 1H), 4.39 (d, 1H), 4.02 (m, 1H), 3.93 (s, 3H), 2.84 (m, 1H), 2.68 (m, 2H), 2.47 (m, 1H), 2.39 (s, 3H), 2.25 (q, 1H), 1.95-0.83 (m, 15H), 1.91 (s, 3H).

Compound 183: MS: m/z 802.2 (M$^+$+1); $^1$H NMR (CDCl$_3$) δ 10.39 (s, 1H), 7.96 (m, 3H), 7.44 (m, 2H), 7.35 (m, 1H), 7.14 (m, 3H), 5.66 (m, 2H), 5.41 (d, 1H), 4.92 (dd, 1H), 4.61 (m, 1H), 4.30 (m, 2H), 4.00 (m, 1H), 3.50 (s, 3H), 2.89 (m, 1H), 2.72 (m, 2H), 2.51 (s, 3H), 2.50 (m, 1H), 2.26 (q, 1H), 1.93-1.06 (m, 13H), 0.97-0.83 (m, 2H).

Compound 184: MS: m/z 786.2 (M$^+$+1); $^1$H NMR (CDCl$_3$) δ 10.36 (s, 1H), 7.96 (m, 3H), 7.42 (m, 2H), 7.32 (m, 1H), 7.15 (m, 3H), 6.12 (d, 1H), 5.69 (q, 1H), 5.65 (s, 1H), 4.94 (dd, 1H), 4.64 (m, 1H), 4.54 (m, 1H), 4.38 (d, 1H), 3.98 (m, 1H), 2.88 (m, 1H), 2.71 (m, 2H), 2.50 (m, 1H), 2.49 (s, 3H), 2.27 (q, 1H), 1.92-0.82 (m, 15H), 1.91 (s, 3H).

Compound 185: MS: m/z 812.3 (M$^+$+1); $^1$H NMR (CDCl$_3$) δ 10.37 (s, 1H), 7.96 (m, 3H), 7.41 (d, 1H), 7.36 (d, 1H), 7.25 (m, 1H), 7.10 (m, 3H), 6.19 (d, 1H), 5.71 (q, 1H), 5.64 (s, 1H), 4.95 (dd, 1H), 4.66 (m, 1H), 4.48 (m, 2H), 3.99 (m, 1H), 2.89 (m, 1H), 2.70 (m, 2H), 2.51 (m, 1H), 2.50 (s, 3H), 2.27 (q, 1H), 1.91-1.10 (m, 14H), 0.97-0.80 (m, 2H), 0.80-0.68 (m, 4H).

Compound 186: MS: m/z 856.3 (M$^+$+1); $^1$H NMR (CDCl$_3$) δ 10.28 (s, 1H), 8.00 (m, 3H), 7.42 (d, 1H), 7.37 (d, 1H), 7.25-7.13 (m, 3H), 7.04 (s, 1H), 5.72 (s, 1H), 5.69 (q, 1H), 5.23 (d, 1H), 4.97 (dd, 1H), 4.77 (s, 1H), 4.67 (m, 1H), 4.55 (d, 1H), 4.35 (m, 1H), 4.04 (m, 1H), 2.89 (m, 1H), 2.68 (m, 2H), 2.52 (s, 3H), 2.51 (m, 1H), 2.25 (q, 1H), 1.93-1.06 (m, 21H), 0.97-0.83 (m, 2H).

Compound 187: MS: m/z 830.2 (M$^+$+1); $^1$H NMR (CDCl$_3$) δ 10.29 (s, 1H), 8.01 (d, 2H), 7.93 (d, 1H), 7.50 (m, 4H), 7.29 (m, 2H), 7.07 (s, 1H), 5.67 (m, 2H), 5.19 (d, 1H), 4.94 (dd, 1H), 4.67 (m, 2H), 4.30 (m, 1H), 4.04 (m, 1H), 2.89 (m, 1H), 2.69 (m, 2H), 2.52 (m, 1H), 2.28 (q, 1H), 1.94-1.05 (m, 13H), 1.19 (s, 9H), 0.97-0.84 (m, 2H).

Compound 188: MS: m/z 842.2 (M$^+$+1); $^1$H NMR (CDCl$_3$) δ 10.27 (s, 1H), 8.02 (d, 2H), 7.93 (d, 1H), 7.52 (m, 4H), 7.32 (s, 1H), 7.26 (m, 1H), 7.08 (s, 1H), 5.68 (s, 1H), 5.66 (q, 1H), 5.22 (d, 1H), 4.92 (dd, 1H), 4.71 (m, 2H), 4.57 (d, 1H), 4.33 (m, 1H), 4.05 (m, 1H), 2.89 (m, 1H), 2.68 (m, 2H), 2.53 (m, 1H), 2.28 (q, 1H), 1.95-0.83 (m, 23H).

Compound 189: MS: m/z 882.4 (M$^+$+1).

Compound 190: MS: m/z 884.2 (M$^+$+1); $^1$H NMR (CDCl$_3$) δ 10.29 (s, 1H), 7.96 (m, 3H), 7.54 (m, 1H), 7.36-7.26 (m, 5H), 5.70 (m, 2H), 5.27 (d, 1H), 4.95 (dd, 1H), 4.74 (m, 1H), 4.53 (d, 1H), 4.32 (m, 1H), 4.05 (m, 2H), 2.95 (m, 2H), 2.69 (m, 2H), 2.52 (m, 1H), 2.28 (q, 1H), 1.94-0.83 (m, 23H), 1.29 (d, 6H).

Compound 191: MS: m/z 898.2 (M$^+$+1).

Compound 192: MS: m/z 880.2 (M$^+$+1); $^1$H NMR (CDCl$_3$) δ 10.31 (s, 1H), 8.28 (d, 1H), 7.95 (d, 2H), 7.50 (m, 4H), 7.42 (dd, 1H), 7.27 (s, 1H), 7.21 (s, 1H), 5.68 (s, 1H), 5.65 (q, 1H), 5.35 (d, 1H), 4.94 (dd, 1H), 4.72 (m, 2H), 4.57 (d, 1H), 4.35 (m, 1H), 4.04 (m, 1H), 2.88 (m, 1H), 2.68 (m, 2H), 2.53 (m, 1H), 2.28 (q, 1H), 1.93-1.05 (m, 21H), 1.36 (s, 9H), 0.97-0.82 (m, 2H).

Compound 193: MS: m/z 894.2 (M$^+$+1); $^1$H NMR (CDCl$_3$) δ 10.21 (s, 1H), 8.28 (d, 1H), 7.95 (d, 2H), 7.52 (m, 4H), 7.41 (dd, 1H), 7.34 (s, 1H), 7.26 (s, 1H), 5.70 (s, 1H), 5.65 (q, 1H), 5.41 (d, 1H), 4.95 (dd, 1H), 4.75 (m, 2H), 4.57 (d, 1H), 4.36 (m, 1H), 4.05 (m, 1H), 2.70 (m, 2H), 2.50 (m, 1H), 2.29 (q, 1H), 1.93-0.82 (m, 23H), 1.46 (s, 3H), 1.36 (s, 9H).

Compound 194: MS: m/z 857.3 (M$^+$+1).

Compound 195: MS: m/z 857.3 (M$^+$+1).

Compound 196: MS: m/z 784.3 (M$^+$+1); $^1$H NMR (CDCl$_3$) δ 10.20 (s, 1H), 8.27 (d, 1H), 7.88 (d, 1H), 7.57 (m, 2H), 7.39 (m, 3H), 7.13 (dd, 1H), 7.01 (d, 2H), 6.14 (d, 1H), 5.68 (q, 1H), 5.62 (s, 1H), 4.97 (dd, 1H), 4.64 (m, 2H), 4.41 (d, 1H), 4.07 (m, 1H), 3.87 (s, 3H), 2.87 (m, 1H), 2.67 (m, 2H), 2.45 (m, 1H), 2.25 (q, 1H), 1.93-0.85 (m, 15H), 1.92 (s, 3H).

Compound 197: MS: m/z 856.3 (M$^+$+1); $^1$H NMR (CDCl$_3$) δ 10.34 (s, 1H), 8.03 (s, 1H), 8.00 (d, 2H), 7.45 (d, 1H), 7.35 (d, 1H), 7.16 (m, 2H), 7.00 (d, 2H), 5.71 (s, 1H), 5.69 (q, 1H), 5.23 (d, 1H), 4.95 (dd, 1H), 4.62 (m, 2H), 4.30 (m, 1H), 4.03 (m, 1H), 3.86 (s, 3H), 2.88 (m, 1H), 2.66 (m, 2H), 2.51 (s, 3H), 2.50 (m, 1H), 2.31 (q, 1H), 1.91-0.82 (m, 15H), 1.22 (s, 9H).

Compound 198: MS: m/z 784.2 (M$^+$+1).

Compound 199: MS: m/z 798.3 (M$^+$+1); $^1$H NMR (CDCl$_3$) δ 10.37 (s, 1H), 7.96 (m, 3H), 7.58 (s, 1H), 7.43 (d, 1H), 7.32 (d, 1H), 7.16 (s, 1H), 6.97 (d, 2H), 6.24 (d, 1H), 5.69 (q, 1H), 5.64 (s, 1H), 4.96 (dd, 1H), 4.66 (m, 1H), 4.55 (m, 1H), 4.40 (d, 1H), 4.02 (m, 1H), 3.84 (s, 3H), 2.87 (m, 1H), 2.68 (m, 2H), 2.49 (s, 3H), 2.50 (m, 1H), 2.28 (q, 1H), 1.91-0.83 (m, 15H), 1.91 (s, 3H).

Compound 200: MS: m/z 852.2 (M$^+$+1); $^1$H NMR (CDCl$_3$) δ 10.26 (s, 1H), 8.03 (s, 1H), 7.96 (d, 2H), 7.52 (s, 1H), 7.45 (d, 1H), 7.34 (d, 1H), 7.23 (s, 1H), 6.98 (d, 2H), 5.67 (s, 1H), 5.64 (q, 1H), 5.21 (m, 1H), 4.93 (dd, 1H), 4.67 (m, 2H), 4.30 (d, 1H), 4.04 (m, 1H), 3.85 (s, 3H), 2.87 (m, 1H), 2.66-2.40 (m, 3H), 2.51 (s, 3H), 2.22 (q, 1H), 1.95-0.82 (m, 15H).

Compound 201: MS: m/z 814.3 (M$^+$+1); $^1$H NMR (CDCl$_3$) δ 10.41 (s, 1H), 7.98 (m, 3H), 7.60 (s, 1H), 7.43 (d, 1H), 7.33 (d, 1H), 7.16 (s, 1H), 6.98 (d, 2H), 5.64 (m, 2H), 5.29 (m, 2H), 4.93 (dd, 1H), 4.69 (m, 1H), 4.36 (m, 1H), 4.01 (m, 1H), 3.84 (s, 3H), 3.42 (s, 3H), 2.87 (m, 1H), 2.66 (m, 2H), 2.50 (m, 1H), 2.49 (s, 3H), 2.25 (q, 1H), 1.94-0.82 (m, 15H).

Compound 202: MS: m/z 838.2 (M$^+$+1); $^1$H NMR (CDCl$_3$) δ 10.23 (s, 1H), 8.26 (d, 1H), 8.00 (d, 2H), 7.60 (m, 2H), 7.44 (m, 2H), 7.23 (m, 2H), 7.01 (d, 2H), 5.73 (s, 1H), 5.67 (q, 1H), 4.94 (dd, 1H), 4.68 (m, 2H), 4.32 (d, 1H), 4.07 (m, 1H), 3.86 (s, 3H), 2.86 (m, 1H), 2.67 (m, 2H), 2.41 (m, 1H), 2.23 (q, 1H), 1.94-1.08 (m, 13H), 0.94-0.87 (m, 2H).

Compound 203: MS: m/z 842.3 (M$^+$+1); $^1$H NMR (CDCl$_3$) δ 10.30 (s, 1H), 8.28 (d, 1H), 7.63 (s, 1H), 7.57 (m, 3H), 7.42 (m, 2H), 7.25 (m, 1H), 7.08 (s, 1H), 6.97 (dd, 1H), 5.71 (m, 2H), 5.22 (d, 1H), 4.92 (dd, 1H), 4.64 (m, 2H), 4.31 (m, 1H), 4.00 (m, 1H), 3.91 (s, 3H), 2.89 (m, 1H), 2.69 (m, 2H), 2.55 (m, 1H), 2.29 (q, 1H), 1.85-0.83 (m, 15H), 1.19 (s, 9H).

Compound 204: MS: m/z 784.2 (M$^+$+1); $^1$H NMR (CDCl$_3$) δ 10.28 (s, 1H), 8.26 (d, 1H), 7.62 (s, 1H), 7.58 (m, 3H), 7.41 (m, 2H), 7.25 (m, 2H), 6.96 (dd, 1H), 6.13 (m, 1H), 5.71 (q, 1H), 5.68 (m, 1H), 4.95 (dd, 1H), 4.63 (t, 1H), 4.59 (m, 1H), 4.41 (d, 1H), 4.04 (m, 1H), 3.90 (s, 3H), 2.88 (m, 1H), 2.71 (m, 2H), 2.52 (m, 1H), 2.29 (q, 1H), 1.92-1.1.05 (m, 13H), 1.91 (s, 3H), 0.97-0.84 (m, 2H).

Compound 205: MS: m/z 801.3 (M$^+$+1); $^1$H NMR (CDCl$_3$) δ 10.34 (s, 1H), 8.25 (d, 1H), 7.61 (s, 1H), 7.57 (m, 3H), 7.39-7.25 (m, 4H), 6.93 (dd, 1H), 5.70 (m, 2H), 5.44 (d, 1H), 4.94 (dd, 1H), 4.70 (m, 1H), 4.39 (d, 1H), 4.32 (m, 1H), 4.03 (m, 1H), 3.90 (s, 3H), 3.48 (s, 3H), 2.88 (m, 1H), 2.70 (m, 2H), 2.52 (m, 1H), 2.26 (q, 1H), 1.89-0.82 (m, 15H).

Compound 206: MS: m/z 838.2 (M$^+$+1); $^1$H NMR (CDCl$_3$) δ 10.19 (s, 1H), 8.27 (d, 1H), 7.62 (s, 1H), 7.58 (m, 3H), 7.41 (m, 2H), 7.25 (m, 3H), 6.97 (dd, 1H), 5.71 (s, 1H), 5.63 (q, 1H), 4.92 (dd, 1H), 4.64 (m, 2H), 4.33 (d, 1H), 4.05 (m, 1H), 3.90 (s, 3H), 2.88 (m, 1H), 2.69 (m, 2H), 2.46 (m, 1H), 2.23 (q, 1H), 1.94-1.1.03 (m, 13H), 0.95-0.84 (m, 2H).

Compound 207: MS: m/z 800.2 (M$^+$+1); $^1$H NMR (CDCl$_3$) δ 10.24 (s, 1H), 8.27 (d, 1H), 7.86 (d, 1H), 7.55 (m, 2H), 7.42 (m, 3H), 7.12 (m, 2H), 7.00 (d, 1H), 5.68 (q, 1H), 5.62 (s, 1H), 5.47 (d, 1H), 4.92 (dd, 1H), 4.68 (m, 1H), 4.40 (m, 2H), 4.04 (m, 1H), 3.87 (s, 3H), 3.50 (s, 3H), 2.89 (m, 1H), 2.68 (m, 2H), 2.50 (m, 1H), 2.25 (q, 1H), 1.91-1.03 (m, 13H), 0.98-0.82 (m, 2H).

Compound 208: MS: m/z 838.2 (M$^+$+1); $^1$H NMR (CDCl$_3$) δ 10.19 (s, 1H), 8.27 (d, 1H), 7.82 (d, 1H), 7.57 (m, 2H), 7.39 (m, 5H), 7.12 (dd, 1H), 7.02 (d, 1H), 5.63 (q, 1H), 5.60 (s, 1H), 4.90 (dd, 1H), 4.70 (m, 2H), 4.32 (d, 1H), 4.03 (m, 1H), 3.85 (s, 3H), 2.86 (m, 1H), 2.71-2.52 (m, 2H), 2.39 (m, 1H), 2.20 (q, 1H), 1.94-0.84 (m, 15H).

Compound 209: MS: m/z 896.4 (M$^+$+1); $^1$H NMR (CDCl$_3$) δ 10.20 (s, 1H), 8.31 (d, 1H), 7.99 (d, 2H), 7.58 (m, 2H), 7.42 (m, 1H), 7.30-7.22 (m, 2H), 7.01 (d, 2H), 5.68 (s, 1H), 5.66 (q, 1H), 5.37 (d, 1H), 4.96 (dd, 1H), 4.78-4.51 (m, 4H), 4.37 (m, 1H), 4.06 (m, 1H), 2.69 (m, 2H), 2.51 (m, 1H), 2.28 (q, 1H), 1.94-0.83 (m, 23H), 1.46 (s, 3H), 1.37 (d, 6H).

Compound 210: MS: m/z 882.4 (M$^+$+1); $^1$H NMR (CDCl$_3$) δ 10.24 (s, 1H), 8.27 (d, 1H), 7.98 (d, 2H), 7.58 (m, 2H), 7.42 (m, 1H), 7.24 (m, 1H), 7.01 (d, 2H), 6.89 (s, 1H), 5.68 (s, 1H), 5.66 (q, 1H), 5.22 (d, 1H), 4.97 (dd, 1H), 4.78-4.52 (m, 4H), 4.36 (m, 1H), 4.04 (m, 1H), 2.88 (m, 1H), 2.68 (m, 2H), 2.54 (m, 1H), 2.29 (q, 1H), 1.94-1.05 (m, 21H), 1.37 (d, 6H), 0.97-0.83 (m, 2H)

Compound 211: MS: m/z 922.4 (M$^+$+1); $^1$H NMR (CDCl$_3$) δ 10.13 (s, 1H), 8.26 (d, 1H), 8.10 (d, 1H), 7.59 (m, 2H), 7.42 (m, 1H), 7.35-7.25 (m, 3H), 7.03 (s, 1H), 5.77 (s, 1H), 5.66 (q, 1H), 5.20 (d, 1H), 4.99 (dd, 1H), 4.71 (m, 2H), 4.56 (d, 1H), 4.35 (m, 1H), 4.03 (m, 1H), 2.70 (m, 2H), 2.50 (m, 1H), 2.29 (q, 1H), 1.90-0.84 (m, 23H), 0.85 (s, 3H).

Compound 212: MS: m/z 892.4 (M$^+$+1); $^1$H NMR (CDCl$_3$) δ 10.36 (s, 1H), 8.59 (s, 1H), 8.25 (d, 1H), 8.18 (d, 2H), 7.73 (d, 2H), 7.58 (m, 2H), 7.45 (m, 1H), 7.34 (s, 1H), 5.74 (s, 1H), 5.68 (q, 1H), 5.39 (d, 1H), 4.94 (dd, 1H), 4.72 (m, 2H), 4.55 (d, 1H), 4.31 (m, 1H), 4.04 (m, 1H), 2.86 (m, 1H), 2.67 (m, 2H), 2.49 (m, 1H), 2.26 (q, 1H), 1.91-1.05 (m, 23H).

Compound 213: MS: m/z 880.4 (M$^+$+1); $^1$H NMR (CDCl$_3$) δ 10.36 (s, 1H), 8.26 (d, 1H), 8.16 (d, 2H), 7.74 (d, 2H), 7.59 (m, 2H), 7.45 (m, 1H), 7.30 (m, 2H), 5.71 (s, 1H), 5.66 (q, 1H), 5.25 (d, 1H), 4.95 (dd, 1H), 4.71 (m, 1H), 4.65 (d, 1H), 4.28 (m, 1H), 4.03 (m, 1H), 2.87 (m, 1H), 2.70 (m, 2H), 2.51 (m, 1H), 2.27 (q, 1H), 1.92-1.06 (m, 13H), 1.19 (s, 9H), 0.97-0.82 (m, 2H).

Compound 214: MS: m/z 780.2 (M$^+$+1).

Compound 215: MS: m/z 822.2 (M$^+$+1).

Compound 216: MS: m/z 910.3 (M$^+$+1); $^1$H NMR (CDCl$_3$) δ 10.30 (s, 1H), 8.15 (d, 2H), 7.75 (d, 2H), 7.61 (s, 1H), 7.47 (d, 1H), 7.25-7.15 (m, 3H), 5.72 (s, 1H), 5.68 (q, 1H), 5.18 (d, 1H), 4.98 (dd, 1H), 4.67 (m, 2H), 4.28 (m, 1H), 4.04 (m, 1H), 3.93 (s, 3H), 2.89 (m, 1H), 2.69 (m, 2H), 2.52 (m, 1H), 2.28 (q, 1H), 1.91-0.85 (m, 15H), 1.20 (s, 9H).

Compound 217: MS: m/z 922.3 (M$^+$+1); $^1$H NMR (CDCl$_3$) δ 10.28 (s, 1H), 8.17 (m, 3H), 7.74 (d, 2H), 7.26 (m, 1H), 7.17 (s, 1H), 7.02 (m, 2H), 5.77 (s, 1H), 5.69 (q, 1H), 5.20 (d, 1H), 4.96 (dd, 1H), 4.77 (s, 1H), 4.69 (m, 1H), 4.54 (d, 1H), 4.33 (m, 1H), 4.04 (m, 1H), 3.92 (s, 3H), 2.89 (m, 1H), 2.71 (m, 2H), 2.52 (m, 1H), 2.28 (q, 1H), 1.90-1.05 (m, 21H), 0.97-0.83 (m, 2H).

Compound 218: MS: m/z 892.4 (M$^+$+1); $^1$H NMR (CDCl$_3$) δ 10.29 (s, 1H), 8.35 (s, 1H), 8.28 (d, 1H), 8.24 (d, 1H), 7.59 (m, 4H), 7.44 (m, 1H), 7.33 (s, 1H), 7.15 (s, 1H), 5.80 (s, 1H), 5.67 (q, 1H), 5.27 (d, 1H), 4.95 (dd, 1H), 4.70 (m, 2H), 4.58 (d, 1H), 4.30 (m, 1H), 4.06 (m, 1H), 2.88 (m, 1H), 2.70 (m, 2H), 2.54 (m, 1H), 2.28 (q, 1H), 1.92-0.83 (m, 23H).

Compound 219: MS: m/z 880.2 (M$^+$+1); $^1$H NMR (CDCl$_3$) δ 10.31 (s, 1H), 8.34 (s, 1H), 8.28 (d, 1H), 8.20 (d, 1H), 7.60 (m, 4H), 7.45 (m, 1H), 7.29 (s, 1H), 7.13 (s, 1H), 5.77 (s, 1H), 5.67 (q, 1H), 5.19 (m, 1H), 4.94 (dd, 1H), 4.67 (m, 2H), 4.26 (m, 1H), 4.05 (m, 1H), 2.88 (m, 1H), 2.71 (m, 2H), 2.53 (m, 1H), 2.29 (q, 1H), 1.90-0.83 (m, 15H), 1.18 (s, 9H).

Compound 220: MS: m/z 892.2 (M$^+$+1); $^1$H NMR (CDCl$_3$) δ 10.29 (s, 1H), 8.39 (d, 1H), 8.06 (d, 2H), 7.88 (s, 1H), 7.71 (d, 1H), 7.45 (m, 3H), 7.36 (s, 1H), 7.18 (s, 1H), 5.68 (s, 1H), 5.65 (q, 1H), 5.33 (d, 1H), 4.93 (dd, 1H), 4.72 (m, 2H), 4.67 (d, 1H), 4.36 (m, 1H), 4.05 (m, 1H), 2.88 (m, 1H), 2.70 (m, 2H), 2.53 (m, 1H), 2.28 (q, 1H), 1.92-0.84 (m, 23H).

Compound 221: MS: m/z 880.4 (M$^+$+1); $^1$H NMR (CDCl$_3$) δ 10.30 (s, 1H), 8.39 (d, 1H), 8.04 (d, 2H), 7.87 (s, 1H), 7.69 (d, 1H), 7.48 (m, 3H), 7.33 (s, 1H), 7.25 (s, 1H), 5.67 (m, 2H), 5.21 (d, 1H), 4.94 (dd, 1H), 4.68 (m, 2H), 4.30 (m, 1H), 4.04 (m, 1H), 2.88 (m, 1H), 2.69 (m, 2H), 2.52 (m, 1H), 2.28 (q, 1H), 1.93-0.84 (m, 15H), 1.17 (s, 9H).

Compound 222: MS: m/z 814.3 (M$^+$+1); $^1$H NMR (CDCl$_3$) δ 10.29 (s, 1H), 8.46 (s, 1H), 8.27 (d, 1H), 7.47 (m, 3H), 7.41 (m, 1H), 7.33 (s, 1H), 7.16 (d, 1H), 7.05 (s, 1H), 6.56 (d, 1H), 5.69 (m, 2H), 5.24 (d, 1H), 4.95 (dd, 1H), 4.66 (m, 1H), 4.58 (d, 1H), 4.38 (m, 1H), 4.05 (m, 1H), 2.89 (m, 1H), 2.70 (m, 2H), 2.34 (m, 1H), 2.29 (q, 1H), 1.90-1.06 (m, 21H), 0.96-0.83 (m, 2H).

Compound 223: MS: m/z 802.2 (M$^+$+1); $^1$H NMR (CDCl$_3$) δ 10.30 (s, 1H), 8.28 (d, 1H), 7.54 (m, 3H), 7.42 (m, 1H), 7.29 (s, 1H), 7.20 (d, 1H), 7.08 (s, 1H), 6.56 (d, 1H), 5.66 (m, 2H), 5.15 (d, 1H), 4.95 (dd, 1H), 4.69 (m, 2H), 4.30 (m, 1H), 4.05 (m, 1H), 2.89 (m, 1H), 2.68 (m, 2H), 2.35 (m, 1H), 2.29 (q, 1H), 1.89-1.04 (m, 13H), 1.19 (s, 9H), 0.97-0.83 (m, 2H).

Compound 224: MS: m/z 848.2 (M$^+$+1); $^1$H NMR (CDCl$_3$) δ 10.30 (s, 1H), 8.08 (d, 1H), 7.58 (m, 1H), 7.39 (d, 1H), 7.14 (s, 1H), 7.12-6.95 (m, 4H), 5.70 (m, 2H), 5.20 (d, 1H), 4.95 (dd, 1H), 4.66 (m, 1H), 4.59 (d, 1H), 4.33 (m, 1H), 4.03 (m, 1H), 3.91 (s, 3H), 2.90 (m, 1H), 2.66 (m, 2H), 2.52 (m, 1H), 2.28 (q, 1H), 1.89-1.06 (m, 13H), 1.24 (s, 9H), 0.94-0.83 (m, 2H).

Compound 225: MS: m/z 760.2 (M$^+$+1); $^1$H NMR (CDCl$_3$) δ 10.35 (s, 1H), 8.25 (d, 1H), 7.55 (m, 3H), 7.40 (m, 1H), 7.27 (m, 2H), 7.16 (d, 1H), 6.54 (d, 1H), 5.66 (m, 2H), 5.42 (d, 1H), 4.94 (dd, 1H), 4.67 (m, 1H), 4.46 (d, 1H), 4.35 (m, 1H), 4.04 (m, 1H), 3.50 (s, 3H), 2.89 (m, 1H), 2.66 (m, 2H), 2.33 (m, 1H), 2.26 (q, 1H), 1.92-0.83 (m, 15H).

Compound 226: MS: m/z 798.2 (M$^+$+1); $^1$H NMR (CDCl$_3$) δ 10.20 (s, 1H), 8.25 (d, 1H), 7.55 (m, 3H), 7.41 (m, 1H), 7.27 (m, 3H), 7.16 (d, 1H), 6.56 (d, 1H), 5.66 (m, 2H), 4.94 (dd, 1H), 4.67 (m, 2H), 4.35 (m, 1H), 4.05 (m, 1H), 2.88 (m, 1H), 2.66 (m, 2H), 2.43 (m, 1H), 2.26 (q, 1H), 1.96-0.83 (m, 15H).

Compound 227: MS: m/z 744.2 (M$^+$+1); $^1$H NMR (CDCl$_3$) δ 10.31 (s, 1H), 8.21 (d, 1H), 7.55 (m, 3H), 7.39 (m, 1H), 7.33-7.25 (m, 2H), 7.12 (d, 1H), 6.56 (d, 1H), 6.16 (d, 1H), 5.66 (q, 1H), 5.62 (s, 1H), 4.94 (dd, 1H), 4.62 (m, 1H), 4.59 (m, 1H), 4.41 (d, 1H), 4.06 (m, 1H), 2.87 (m, 1H), 2.68 (m, 2H), 2.50 (m, 1H), 2.26 (q, 1H), 1.95-0.83 (m, 15H), 1.90 (s, 3H).

Compound 228: MS: m/z 857.3 (M$^+$+1).

Compound 229: MS: m/z 830.3 (M$^+$+1); $^1$H NMR (CDCl$_3$) δ 10.25 (s, 1H), 8.26 (d, 1H), 7.59 (m, 2H), 7.43 (m, 2H), 7.25 (m, 2H), 7.19 (m, 1H), 7.06 (m, 1H), 5.76 (s, 1H), 5.72 (q, 1H), 5.18 (m, 1H), 4.97 (dd, 1H), 4.68 (m, 2H), 4.56 (d, 1H), 4.30 (m, 1H), 4.04 (m, 1H), 2.90 (m, 1H), 2.70 (m, 2H), 2.39 (m, 1H), 2.27 (q, 1H), 1.90-0.80 (m, 23H).

Compound 230: MS: m/z 860.3 (M$^+$+1); $^1$H NMR (CDCl$_3$) δ 10.28 (s, 1H), 8.10 (d, 1H), 7.58 (d, 1H), 7.39 (d, 1H), 7.18 (s, 1H), 7.09-6.97 (m, 4H), 5.72 (s, 1H), 5.68 (q, 1H), 5.24 (d, 1H), 4.95 (dd, 1H), 4.80 (s, 1H), 4.65 (m, 1H), 4.54 (d, 1H), 4.32 (m, 1H), 4.03 (m, 1H), 3.91 (s, 3H), 2.94 (m, 1H), 2.68 (m, 2H), 2.54 (m, 1H), 2.28 (q, 1H), 1.90-1.05 (m, 21H), 0.95-0.84 (m, 2H).

Compound 231: MS: m/z 848.2 (M$^+$+1); $^1$H NMR (CDCl$_3$) δ 10.26 (s, 1H), 7.64 (d, 1H), 7.60 (d, 1H), 7.48 (d, 1H), 7.40 (d, 1H), 7.20 (s, 1H), 7.15 (m, 2H), 6.88 (s, 1H), 5.65 (m, 2H), 5.10 (d, 1H), 4.96 (dd, 1H), 4.63 (m, 2H), 4.31 (m, 1H), 4.04 (m, 1H), 3.94 (s, 3H), 2.86 (m, 1H), 2.68 (m, 2H), 2.56 (m, 1H), 2.29 (q, 1H), 1.94-0.83 (m, 15H), 1.22 (s, 9H).

Compound 232: MS: m/z 836.2 (M$^+$+1); $^1$H NMR (CDCl$_3$) δ 10.29 (s, 1H), 7.89 (dd, 1H), 7.60 (d, 1H), 7.50 (dd, 1H), 7.40 (d, 1H), 7.22 (m, 2H), 7.10 (m, 1H), 7.00 (s, 1H), 5.68 (m, 2H), 5.18 (m, 1H), 4.95 (dd, 1H), 4.66 (m, 2H), 4.29 (m, 1H), 4.04 (m, 1H), 2.88 (m, 1H), 2.67 (m, 2H), 2.53 (m, 1H), 2.26 (q, 1H), 1.92-0.83 (m, 15H), 1.20 (s, 9H).

Compound 233: MS: m/z 806.2 (M$^+$+1); $^1$H NMR (CDCl$_3$) δ 10.36 (s, 1H), 8.05 (d, 1H), 7.59 (d, 1H), 7.38 (m, 2H), 7.14-6.97 (m, 4H), 5.70 (m, 2H), 5.64 (d, 1H), 4.96 (dd, 1H), 4.65 (m, 1H), 4.58 (m, 2H), 4.04 (m, 1H), 3.90 (s, 3H), 3.58 (s, 3H), 2.89 (m, 1H), 2.68 (m, 2H), 2.53 (m, 1H), 2.25 (q, 1H), 1.88-0.82 (m, 15H).

Compound 234: MS: m/z 860.2 (M$^+$+1); $^1$H NMR (CDCl$_3$) δ 10.31 (s, 1H), 7.63 (d, 1H), 7.60 (d, 1H), 7.45 (d, 1H), 7.40 (d, 1H), 7.20 (m, 2H), 7.10 (m, 2H), 5.69 (s, 1H), 5.67 (q, 1H), 5.30 (d, 1H), 4.94 (dd, 1H), 4.78 (s, 1H), 4.64 (m, 1H), 4.55 (d, 1H), 4.36 (m, 1H), 4.04 (m, 1H), 3.94 (s, 3H), 2.89 (m, 1H), 2.68 (m, 2H), 2.53 (m, 1H), 2.26 (q, 1H), 1.93-1.04 (m, 21H), 0.97-0.82 (m, 2H).

Compound 235: MS: m/z 844.2 (M$^+$+1); $^1$H NMR (CDCl$_3$) δ 10.24 (s, 1H), 8.04 (d, 1H), 7.58 (d, 1H), 7.39 (d, 1H), 7.31 (m, 2H), 7.18 (s, 1H), 7.08 (m, 3H), 5.70 (s, 1H), 5.67 (q, 1H), 4.86 (dd, 1H), 4.64 (m, 2H), 4.26 (d, 1H), 4.02 (m, 1H), 3.90 (s, 3H), 2.84 (m, 1H), 2.65 (m, 2H), 2.44 (m, 1H), 2.20 (q, 1H), 1.91-0.83 (m, 15H).

Compound 236: MS: m/z 832.2 (M$^+$+1); $^1$H NMR (CDCl$_3$) δ 10.27 (s, 1H), 8.22 (d, 1H), 7.58 (m, 2H), 7.44 (m, 1H), 7.29 (m, 1H), 7.10 (s, 1H), 6.94 (d, 1H), 6.90 (s, 1H), 5.69 (m, 2H), 5.18 (d, 1H), 4.93 (dd, 1H), 4.67 (m, 2H), 4.28 (m, 1H), 4.05 (m, 1H), 2.85 (m, 1H), 2.68 (m, 2H), 2.55 (s, 3H), 2.54 (m, 1H), 2.28 (q, 1H), 1.91-0.83 (m, 15H), 1.19 (s, 9H).

Compound 237: MS: m/z 844.3 (M$^+$+1); $^1$H NMR (CDCl$_3$) δ 10.23 (s, 1H), 8.22 (d, 1H), 7.58 (m, 2H), 7.40 (m, 1H), 7.29 (m, 2H), 6.96 (d, 1H), 6.84 (s, 1H), 5.69 (s, 1H), 5.66 (q, 1H), 5.20 (d, 1H), 4.94 (dd, 1H), 4.73 (s, 1H), 4.67 (m, 1H), 4.58 (d, 1H), 4.35 (m, 1H), 4.05 (m, 1H), 2.89 (m, 1H), 2.68 (m, 2H), 2.56 (s, 3H), 2.54 (m, 1H), 2.26 (q, 1H), 1.91-0.83 (m, 23H).

Compound 238: MS: m/z 844.3 (M$^+$+1); $^1$H NMR (CDCl$_3$) δ 10.26 (s, 1H), 8.22 (d, 1H), 7.55 (m, 2H), 7.43 (m, 2H), 7.18 (m, 1H), 6.93 (s, 1H), 6.75 (s, 1H), 5.70 (m, 2H), 5.21 (d, 1H), 4.94 (dd, 1H), 4.78 (s, 1H), 4.63 (m, 1H), 4.53 (d, 1H), 4.35

(m, 1H), 4.05 (m, 1H), 2.89 (m, 1H), 2.67 (m, 2H), 2.53 (s, 3H), 2.52 (m, 1H), 2.26 (q, 1H), 1.92-1.04 (m, 21H), 0.95-0.83 (m, 2H).

Compound 239: MS: m/z 790.2 (M$^+$+1); $^1$H NMR (CDCl$_3$) δ 10.34 (s, 1H), 8.20 (d, 1H), 7.54 (m, 2H), 7.38 (m, 2H), 7.28 (s, 1H), 7.14 (s, 1H), 6.73 (s, 1H), 5.68 (m, 2H), 5.43 (d, 1H), 4.94 (dd, 1H), 4.65 (m, 1H), 4.39 (m, 2H), 4.04 (m, 1H), 3.58 (s, 3H), 2.89 (m, 1H), 2.68 (m, 2H), 2.51 (s, 3H), 2.50 (m, 1H), 2.28 (q, 1H), 1.93-1.06 (m, 13H), 0.94-0.82 (m, 2H).

Compound 240: MS: m/z 828.2 (M$^+$+1); $^1$H NMR (CDCl$_3$) δ 10.18 (s, 1H), 8.22 (d, 1H), 7.56 (m, 2H), 7.40 (m, 2H), 7.20 (s, 2H), 7.08 (s, 1H), 6.76 (d, 1H), 5.71 (s, 1H), 5.66 (q, 1H), 4.94 (dd, 1H), 4.66 (m, 2H), 4.29 (d, 1H), 4.04 (m, 1H), 2.88 (m, 1H), 2.65 (m, 2H), 2.53 (s, 3H), 2.45 (m, 1H), 2.23 (q, 1H), 1.96-1.05 (m, 13H), 0.95-0.83 (m, 2H).

Compound 241: MS: m/z 778.1 (M$^+$+1); $^1$H NMR (CDCl$_3$) δ 10.38 (s, 1H), 7.89 (dd, 1H), 7.58 (d, 2H), 7.44 (dd, 1H), 7.35 (d, 1H), 7.24 (m, 2H), 7.05 (m, 1H), 6.18 (d, 1H), 5.71 (q, 1H), 5.62 (s, 1H), 4.95 (dd, 1H), 4.63 (m, 1H), 4.50 (m, 1H), 4.40 (d, 1H), 4.00 (m, 1H), 2.88 (m, 1H), 2.66 (m, 2H), 2.53 (m, 1H), 2.22 (q, 1H), 1.96-0.82 (m, 15H), 1.91 (s, 3H).

Compound 242: MS: m/z 846.4 (M$^+$+1).

Compound 243: MS: m/z 858.3 (M$^+$+1); $^1$H NMR (CDCl$_3$) δ 10.28 (s, 1H), 8.24 (d, 1H), 7.57 (m, 2H), 7.42 (m, 2H), 7.19 (s, 1H), 7.08 (s, 1H), 6.79 (d, 1H), 5.66 (m, 2H), 5.24 (d, 1H), 4.96 (m, 1H), 4.78 (s, 1H), 4.67 (m, 1H), 4.55 (d, 1H), 4.35 (m, 1H), 4.03 (m, 1H), 2.85 (m, 3H), 2.67 (m, 2H), 2.53 (m, 1H), 2.28 (q, 1H), 1.94-0.84 (m, 26H).

Compound 244: MS: m/z 872.3 (M$^+$+1); $^1$H NMR (CDCl$_3$) δ 10.13 (s, 1H), 8.24 (d, 1H), 7.53 (m, 2H), 7.41 (m, 2H), 7.19 (s, 1H), 6.99 (s, 1H), 6.79 (d, 1H), 5.69 (m, 2H), 5.23 (d, 1H), 4.98 (dd, 1H), 4.77 (s, 1H), 4.65 (m, 1H), 4.55 (d, 1H), 4.35 (m, 1H), 4.04 (m, 1H), 2.87 (q, 2H), 2.68 (m, 2H), 2.53 (m, 1H), 2.29 (q, 1H), 1.94-0.84 (m, 26H), 0.83 (s, 3H).

Compound 245: MS: m/z 831.2 (M$^+$+1); $^1$H NMR (CDCl$_3$) δ 10.21 (s, 1H), 8.26 (d, 1H), 7.90 (d, 2H), 7.58 (m, 2H), 7.46 (d, 2H), 7.00 (s, 1H), 5.69 (m, 2H), 5.09 (d, 1H), 4.99 (dd, 1H), 4.62 (m, 3H), 4.27 (m, 1H), 4.05 (m, 1H), 2.89 (m, 1H), 2.70 (m, 2H), 2.56 (m, 1H), 2.29 (q, 1H), 1.94-0.84 (m, 23H).

Compound 246: MS: m/z 761.4 (M$^+$+1); $^1$H NMR (CDCl$_3$) δ 10.21 (s, 1H), 8.17 (d, 1H), 7.80 (d, 3H), 7.56 (m, 2H), 7.41 (d, 2H), 6.58 (s, 1H), 5.61 (m, 2H), 5.21 (d, 1H), 4.65 (m, 2H), 4.24 (m, 1H), 4.05 (m, 1H), 2.89 (m, 1H), 2.70 (m, 2H), 2.56-2.21 (m, 2H), 1.94-0.84 (m, 15H), 1.87 (s, 3H).

Compound 247: MS: m/z 803.4 (M$^+$+1).

Compound 248: MS: m/z 845.3 (M$^+$+1).

Compound 249: MS: m/z 917.2 (M$^+$+1); $^1$H NMR (CDCl$_3$) δ 10.22 (s, 1H), 8.08 (d, 1H), 7.78 (s, 1H), 7.40 (s, 1H), 7.06 (s, 1H), 6.97 (m, 2H), 5.64 (m, 2H), 5.32 (d, 1H), 4.94 (dd, 1H), 4.70 (m, 2H), 4.54 (d, 1H), 4.34 (dd, 1H), 4.08 (m, 1H), 3.83 (s, 3H), 3.18 (m, 1H), 2.73-2.43 (m, 2H), 2.33 (q, 1H), 2.15-1.20 (m, 30H), 0.83 (s, 3H).

Compound 250: MS: m/z 905.4 (M$^+$+1).

Compound 251: MS: m/z 901.3 (M$^+$+1).

Compound 252: MS: m/z 917.4 (M$^+$+1).

Compound 253: MS: m/z 903.3 (M$^+$+1).

EXAMPLE 254

Synthesis of [4-Cyclopropanesulfonylaminocarbonyl-18-(2-fluoro-benzo[4,5]furo[3,2-b]quinolin-11-yloxy)-2,15-dioxo-3,16-diaza-tricyclo[14.3.0.04,6]nonadec-14-yl]-carbamic acid cyclopentyl ester (Compound 254).

Compound 254 was prepared via the route shown below.

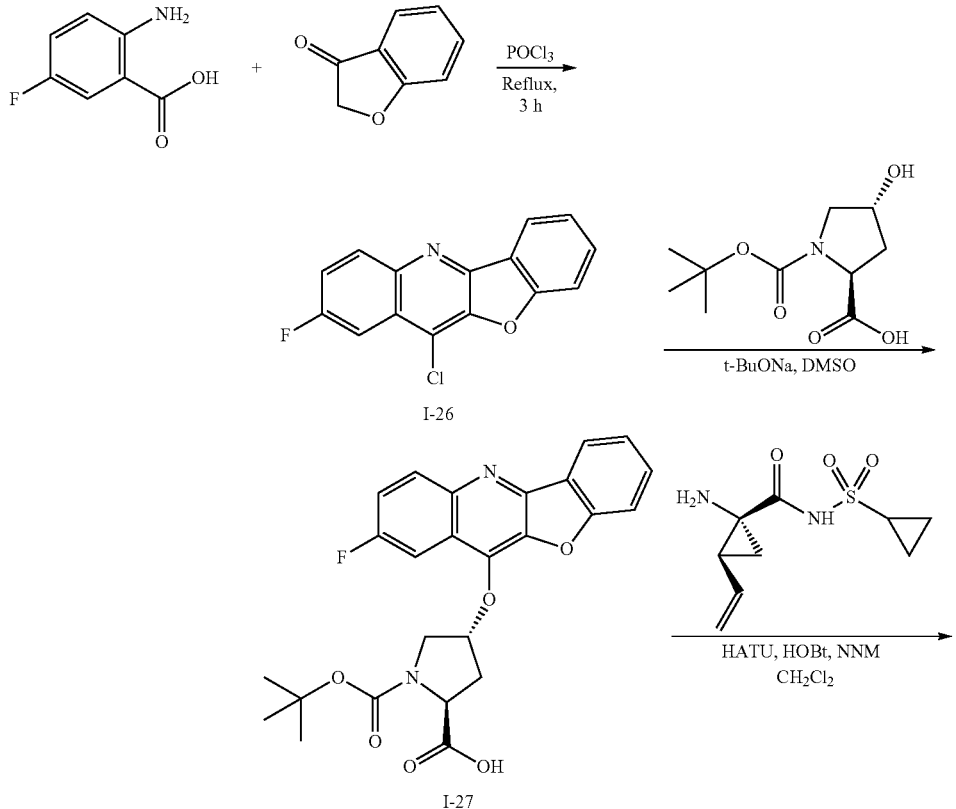

-continued
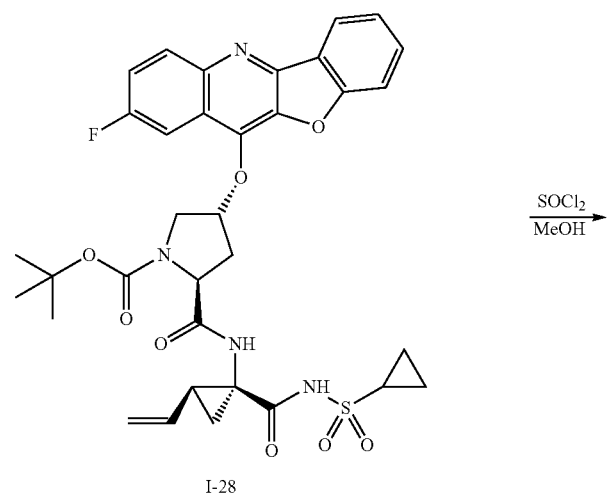
I-28
SOCl2 / MeOH →
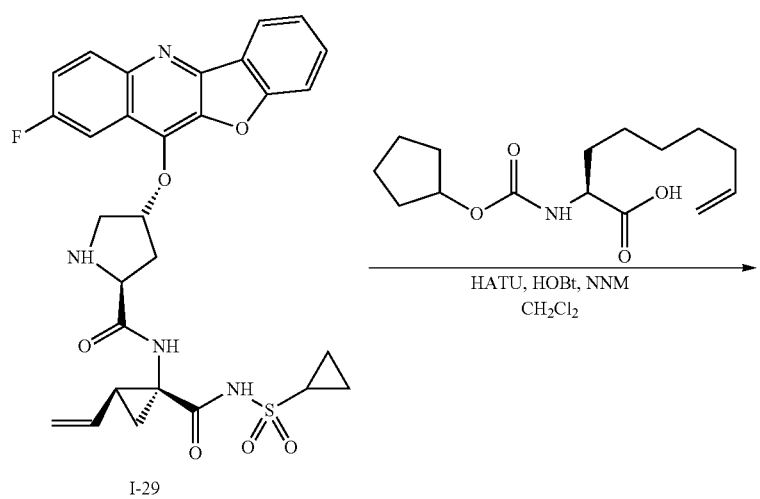
I-29
HATU, HOBt, NNM
CH2Cl2 →
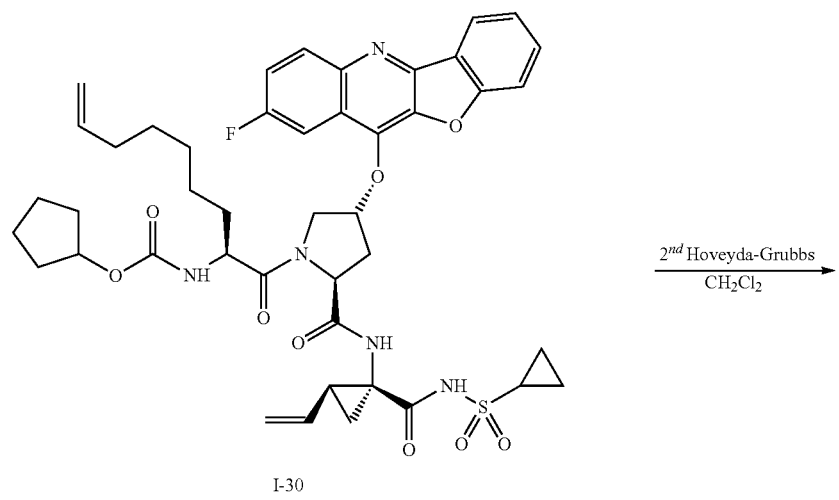
I-30
2nd Hoveyda-Grubbs
CH2Cl2 →

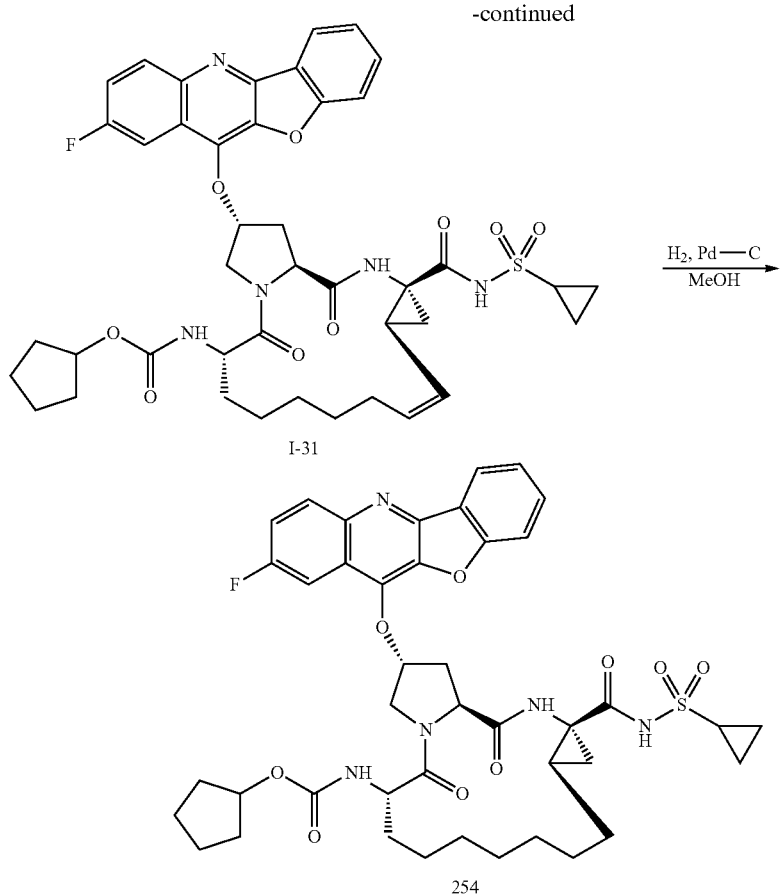

To a suspension of Boc-trans-4-hydroxy-L-proline (0.53 g, 2.30 mmol) in DMSO (10 mL) was added t-BuONa (0.49 g, 5.08 mmol) at 0° C. After warmed to room temperature and stirred for additional 1 hour, intermediate I-26 (0.62 g, 2.31 mmol) was added slowly at 10° C. The reaction mixture was stirred for 4 h and then quenched with 10% HCl aqueous solution to pH 6-7. The crude suspension solid was filtrated, washed with water and dried under vacuum to give I-27 (0.92 g, 86%). MS: m/z 467.1 (M$^+$+1).

To a solution of I-27 (0.90 g, 1.93 mmol), HATU (58.9 g, 1.55 mmol), HOBt (7.0 g, 0.52 mmol) and NMM (38.3 g, 3.86 mmol) in CH$_2$Cl$_2$ (10 mL) was dropwisely added a mixture of cyclopropanesulfonic acid (1-amino-2-vinyl-cyclopropanecarbonyl)-amide (54.0 g, 2.03 mmol) and NMM (0.19 g, 1.93 mmol) dissolved in CH$_2$Cl$_2$ at 5° C. After warmed to room temperature and stirred for another 16 h, the reaction mixture was filtrated, concentrated and purified by silica gel column chromatography to afford a crude product I-28 (0.89 g, 80% yield). MS: m/z 679.1 (M$^+$+1).

Compound I-28 (1.20 g, 1.77 mmol) was dissolved in MeOH (18 mL) at room temperature and then cooled the solution using an ice bath. To the reaction mixture was added thionyl chloride (0.39 mL, 5.30 mmol) dropwisely. After removal of the ice-bath, the reaction mixture was heated at 65° C. for 1 h. The resulting solution was cooled to 40° C., filtrated, and washed with cold MeOH and ether to afford light yellow powder to give white powder I-29 without further purification used at next reaction step. MS: m/z 579.1 (M$^+$+1).

To a solution of 2-cyclopentyloxycarbonylamino-non-8-enoic acid (0.87 g, 2.34 mmol), HATU (1.16 g, 3.05 mmol) and HOBt (0.14 g, 1.02 mmol) in CH$_2$Cl$_2$ (10 mL) was dropwisely added a mixture of I-29 (1.18 g, 2.03 mmol) and NMM (0.49 g, 4.87 mmol) dissolved in DMF (10 mL) at 5° C. After warmed to room temperature and stirred for additional 16 h, 10% HCl (1 mL) was added and the reaction mixture was concentrated. The residue was cooled to 5° C. and washed with 5% HCl (aq) (10 mL×2) and NaHCO$_3$ (aq) (10 ml×2) sequentially to give a light yellow solid. The solid was dissolved in MeOH (10 mL) and further precipitated by added small portion ether slowly to afford I-30 (1.51 g, 88% yield). MS: m/z 844.3 (M$^+$+1).

A solution of compound I-30 (0.50 g, 0.59 mmol) in CH$_2$Cl$_2$ (120 mL) was degassed by bubbling nitrogen for 1 h. Hoveyda-Grubb's 2$^{nd}$ generation catalyst (48 mg, 0.076 mmol) was added, and then the reaction mixture was heated at 40° C. for 16 h. After completion of the reaction indicated by HPLC, the reaction mixture was cooled to 30° C., concentrated and purified by silica gel column chromatography to give product I-31 (0.30 g, 62% yield). MS: m/z 816.3 (M$^+$+1); $^1$H NMR (CDCl$_3$) δ 10.33 (s, 1H), 8.30 (d, 1H), 8.11 (dd, 1H), 7.88 (dd, 1H), 7.67-7.56 (m, 2H), 7.46 (dd, 1H), 7.43-7.30 (m, 2H), 6.12 (s, 1H), 5.64 (q, 1H), 5.22 (d, 1H), 4.92 (dd, 1H), 4.77 (d, 1H), 4.66 (dd, 1H), 4.32-4.22 (m, 1H), 4.04 (dd, 1H), 2.93-2.46 (m, 3H), 2.31 (q, 1H), 1.92-0.80 (m, 25H).

To a solution of compound I-31 (50 mg, 0.061 mmol) in MeOH (10 mL) was added 5% Pd—C (5 mg) at room temperature under N$_2$. Then, the reaction mixture was stirred in the atmosphere of hydrogen under 60 psi pressure at room temperature for 4 h. The reaction mixture was filtrated and purified by column chromatography to give compound 254

(27.6 mg, 55%). MS: m/z 818.3 (M$^+$+1); $^1$H NMR (CDCl$_3$) δ 10.50 (s, 1H), 8.28 (d, 1H), 8.13 (dd, 1H), 7.80 (dd, 1H), 7.65-7.57 (m, 2H), 7.45 (dd, 1H), 7.39-7.30 (m, 2H), 6.11 (s, 1H), 5.25 (d, 1H), 4.96 (brs, 1H), 4.68 (dd, 1H), 4.60 (d, 1H), 4.37 (dd, 1H), 4.14 (dd, 1H), 3.02-2.57 (m, 3H), 1.92-0.80 (m, 29H).

EXAMPLE 255-281

Syntheses of Compound 255-281

Each of Compounds 255-280 was prepared in a manner similar to that described in Example 254.

Compound 255: MS: m/z 764.2 (M$^+$+1); $^1$H NMR (CDCl$_3$) δ 10.47 (s, 1H), 7.88-7.84 (m, 3H), 7.70 (s, 1H), 7.56 (dd, 1H), 7.37 (m, 1H), 7.18 (m, 1H), 6.20 (d, 1H), 5.97 (s, 1H), 5.64 (q, 1H), 4.94 (dd, 1H), 4.68 (m, 1H), 4.61 (d, 1H), 4.44 (m, 1H), 4.02 (m, 1H), 2.85 (m, 2H), 2.70 (m, 1H), 2.58 (m, 1H), 2.25 (q, 1H), 1.92 (s, 3H), 1.90-1.03 (m, 15H).

Compound 256: MS: m/z 815.6 (M$^+$+1); $^1$H NMR (CDCl$_3$) δ 10.31 (s, 1H), 8.32 (d, 1H), 8.25 (m, 1H), 7.81 (dd, 1H), 7.64 (m, 2H), 7.46 (dd, 1H), 7.23-7.12 (m, 2H), 6.20 (s, 1H), 5.66 (q, 1H), 5.16 (d, 1H), 4.98 (dd, 1H), 4.75-4.64 (m, 3H), 4.31 (m, 1H), 4.08 (m, 1H), 2.88 (m, 1H), 2.78 (m, 2H), 2.55 (m, 1H), 2.29 (q, 1H), 1.92-0.84 (m, 23H).

Compound 257: MS: m/z 804.1 (M$^+$+1); $^1$H NMR (CDCl$_3$) δ 10.52 (s, 1H), 8.29 (d, 1H), 8.03-7.97 (m, 2H), 7.82 (dd, 1H), 7.63-7.42 (m, 3H), 7.21 (m, 1H), 5.97 (s, 1H), 5.60 (q, 1H), 5.44 (d, 1H), 4.85 (dd, 1H), 4.66 (m, 2H), 4.29 (m, 1H), 4.02 (m, 1H), 3.88-3.62 (m, 2H), 2.87-2.58 (m, 5H), 2.33 (q, 1H), 1.90-0.78 (m, 15H), 0.97 (s, 6H).

Compound 258: MS: m/z 806.1 (M$^+$+1); $^1$H NMR (CDCl$_3$) δ 10.36 (s, 1H), 8.28 (d, 1H), 8.07 (m, 1H), 7.84 (s, 1H), 7.62 (m, 3H), 7.44 (m, 2H), 7.18 (m, 1H), 6.06 (s, 1H), 5.67 (q, 1H), 4.96 (dd, 1H), 4.80 (d, 1H), 4.60 (m, 1H), 4.41 (m, 1H), 4.10 (m, 2H), 3.66 (m, 1H), 3.39 (m, 2H), 3.22 (s, 3H), 2.91-2.58 (m, 4H), 2.20 (q, 1H), 1.90-0.86 (m, 15H).

Compound 259: MS: m/z 788.1 (M$^+$+1); $^1$H NMR (CDCl$_3$) δ 10.51 (s, 1H), 8.28 (d, 1H), 7.94 (m, 1H), 7.86 (s, 1H), 7.64 (d, 1H), 7.60-7.43 (m, 4H), 7.16 (m, 1H), 6.00 (s, 1H), 5.85 (m, 1H), 5.62 (m, 2H), 5.30-5.19 (m, 2H), 4.93 (dd, 1H), 4.66 (m, 1H), 4.58-4.36 (m, 3H), 4.02 (m, 1H), 2.87-2.56 (m, 4H), 2.26 (q, 1H), 1.86-0.86 (m, 15H).

Compound 260: MS: m/z 762.2 (M$^+$+1); $^1$H NMR (CDCl$_3$) δ 10.63 (s, 1H), 8.26 (d, 1H), 8.10 (s, 1H), 7.88 (d, 1H), 7.67-7.44 (m, 4H), 6.84 (s, 1H), 5.89 (s, 1H), 5.68 (q, 1H), 5.38 (d, 1H), 4.97 (dd, 1H), 4.76 (m, 1H), 4.58 (d, 1H), 4.21 (m, 1H), 3.96 (m, 1H), 3.66 (s, 3H), 2.91-2.60 (m, 4H), 2.25 (q, 1H), 1.89-0.89 (m, 15H).

Compound 261: MS: m/z 704.2 (M$^+$+1); $^1$H NMR (CD$_3$OD) δ 9.26 (s, 1H), 8.47 (d, 1H), 8.26 (m, 1H), 8.15 (dd, 1H), 7.97-7.82 (m, 3H), 7.66 (m, 1H), 6.54 (s, 1H), 5.74 (q, 1H), 5.13 (dd, 1H), 4.60 (d, 1H), 4.35 (m, 2H), 3.72-3.58 (m, 2H), 2.97-2.81 (m, 3H), 2.51 (m, 1H), 2.33 (q, 1H), 1.99-1.06 (m, 15H).

Compound 262: MS: m/z 818.3 (M$^+$+1); $^1$H NMR (CDCl$_3$) δ 10.42 (s, 1H), 8.30 (d, 1H), 8.12 (m, 1H), 7.86 (m, 1H), 7.49-7.33 (m, 5H), 6.10 (s, 1H), 5.66 (m, 2H), 5.08-4.66 (m, 4H), 4.28 (m, 1H), 4.03 (m, 1H), 3.86-3.58 (m, 4H), 2.86-2.57 (m, 4H), 2.34 (q, 1H), 2.03-0.87 (m, 17H).

Compound 263: MS: m/z 780.2 (M$^+$+1); $^1$H NMR (CDCl$_3$) δ 10.60 (s, 1H), 8.04-7.92 (m, 3H), 7.78 (m, 1H), 7.56 (dd, 1H), 7.38 (m, 1H), 6.94 (m, 1H), 5.89 (s, 1H), 5.67 (q, 1H), 5.40 (d, 1H), 4.95 (dd, 1H), 4.76 (m, 1H), 4.57 (d, 1H), 4.20 (m, 1H), 3.97 (m, 1H), 3.64 (s, 3H), 2.94-2.63 (m, 4H), 2.23 (q, 1H), 1.88-1.09 (m, 15H).

Compound 264: MS: m/z 931.3 (M$^+$+1); $^1$H NMR (CDCl$_3$) δ 10.43 (s, 1H), 8.30 (d, 1H), 8.10 (m, 1H), 7.86 (d, 1H), 7.62-7.34 (m, 5H), 6.08 (s, 1H), 5.60 (q, 1H), 5.38 (s, 1H), 4.90-4.62 (m, 4H), 4.26 (m, 1H), 4.03 (m, 1H), 3.64 (m, 2H), 3.15 (m, 2H), 2.85-2.55 (m, 4H), 2.33 (q, 1H), 1.83-0.86 (m, 19H), 1.44 (s, 9H).

Compound 265: MS: m/z 780.2 (M$^+$+1); $^1$H NMR (CDCl$_3$) δ 10.45 (s, 1H), 8.29 (d, 1H), 8.05 (m, 1H), 7.78 (d, 1H), 7.63-7.25 (m, 4H), 6.04 (m, 2H), 5.63 (q, 1H), 4.91 (dd, 1H), 4.72-4.63 (m, 3H), 4.43-4.32 (m, 2H), 4.02 (m, 1H), 3.78-3.58 (m, 1H), 2.85-2.35 (m, 6H), 2.03-0.86 (m, 15H).

Compound 266: MS: m/z 776.3 (M$^+$+1); $^1$H NMR (CDCl$_3$) δ 10.56 (s, 1H), 8.24 (d, 1H), 8.00 (s, 1H), 7.87-7.79 (m, 2H), 7.61-7.42 (m, 4H), 7.06 (m, 1H), 5.93 (s, 1H), 5.61 (q, 1H), 5.44 (m, 1H), 4.91 (dd, 1H), 4.68 (m, 1H), 4.25-3.96 (m, 4H), 2.86-2.57 (m, 4H), 2.29 (q, 1H), 1.81-0.88 (m, 18H).

Compound 267: MS: m/z 812.2 (M$^+$+1); $^1$H NMR (CDCl$_3$) δ 10.47 (s, 1H), 8.27 (d, 1H), 7.90 (m, 1H), 7.81 (m, 2H), 7.76-7.43 (m, 4H), 7.17 (m, 1H), 6.03-5.85 (m, 2H), 5.61 (q, 1H), 4.88 (dd, 1H), 4.72-4.61 (m, 2H), 4.25-3.98 (m, 4H), 2.86-2.58 (m, 4H), 2.30 (q, 1H), 1.84-0.88 (m, 15H).

Compound 268: MS: m/z 832.2 (M$^+$+1); $^1$H NMR (CDCl$_3$) δ 10.50 (s, 1H), 8.35-8.29 (m, 1H), 8.15-8.01 (m, 1H), 7.84-7.32 (m, 5H), 7.13-7.03 (m, 1H), 6.10 (s, 1H), 5.54 (m, 1H), 5.36 (m, 1H), 5.05-4.83 (m, 2H), 4.74-4.65 (m, 1H), 4.36 (m, 1H), 4.14-4.05 (m, 1H), 2.88-2.51 (m, 4H), 2.12-0.88 (m, 24H).

Compound 269: MS: m/z 834.3 (M$^+$+1).

Compound 270: MS: m/z 792.2 (M$^+$+1).

Compound 271: MS: m/z 822.2 (M$^+$+1); $^1$H NMR (CDCl$_3$) δ 10.38 (s, 1H), 8.09 (m, 1H), 7.99 (dd, 1H), 7.83 (dd, 1H), 7.58 (dd, 1H), 7.41-7.25 (m, 3H), 6.15 (s, 1H), 5.59 (q, 1H), 5.16 (d, 1H), 4.89 (dd, 1H), 4.78-4.67 (m, 2H), 4.25 (m, 1H), 4.07 (m, 1H), 2.77-2.70 (m, 3H), 2.57 (m, 1H), 2.30 (q, 1H), 1.90-0.82 (m, 15H), 1.23 (s, 9H).

Compound 272: MS: m/z 822.2 (M$^+$+1); $^1$H NMR (CDCl$_3$) δ 10.37 (s, 1H), 8.10 (m, 1H), 7.98 (dd, 1H), 7.83 (dd, 1H), 7.58 (dd, 1H), 7.42-7.27 (m, 2H), 7.19 (s, 1H), 6.16 (s, 1H), 5.62 (q, 1H), 5.11 (d, 1H), 4.92 (dd, 1H), 4.78-4.67 (m, 2H), 4.24 (m, 1H), 4.07 (m, 1H), 2.86-2.77 (m, 3H), 2.56 (m, 1H), 2.32 (q, 1H), 1.90-0.82 (m, 15H), 1.23 (s, 9H).

Compound 273: MS: m/z 850.3, 852.3 (M$^+$+1).

Compound 274: MS: m/z 834.2 (M$^+$+1); $^1$H NMR (CDCl$_3$) δ 10.43 (s, 1H), 8.08 (m, 1H), 7.95 (dd, 1H), 7.91 (dd, 1H), 7.56 (dd, 1H), 7.50 (s, 1H), 7.37-7.31 (m, 2H), 6.05 (s, 1H), 5.58 (q, 1H), 5.39 (d, 1H), 4.72-4.67 (m, 4H), 4.27 (m, 1H), 4.03 (m, 1H), 2.89-2.67 (m, 3H), 2.55 (m, 1H), 2.29 (q, 1H), 1.90-0.87 (m, 23H).

Compound 275: MS: m/z 780.2 (M$^+$+1); $^1$H NMR (CDCl$_3$) δ 10.61 (s, 1H), 8.06-7.92 (m, 3H), 7.75 (m, 1H), 7.55 (dd, 1H), 7.39 (m, 1H), 6.90 (m, 1H), 5.89 (s, 1H), 5.66 (q, 1H), 5.44 (d, 1H), 4.94 (dd, 1H), 4.77 (m, 1H), 4.58 (d, 1H), 4.20 (m, 1H), 3.96 (m, 1H), 3.65 (s, 3H), 2.93-2.67 (m, 4H), 2.24 (q, 1H), 1.87-1.09 (m, 15H).

Compound 276: MS: m/z 818.1 (M$^+$+1); $^1$H NMR (CDCl$_3$) δ 10.35 (s, 1H), 8.05 (m, 1H), 7.96 (dd, 1H), 7.75 (dd, 1H), 7.57-7.52 (m, 2H), 7.39-7.32 (m, 3H), 6.06 (s, 1H), 5.60 (q, 1H), 4.85-4.73 (m, 2H), 4.55-4.48 (m, 2H), 4.06 (m, 1H), 2.83 (m, 2H), 2.69 (m, 1H), 2.50 (m, 1H), 2.23 (q, 1H), 1.85-1.05 (m, 15H).

Compound 277: MS: m/z 856.3 (M$^+$+1).

Compound 278: MS: m/z 764.2 (M$^+$+1); $^1$H NMR (CDCl$_3$) δ 10.49 (s, 1H), 7.94-7.82 (m, 3H), 7.72 (s, 1H), 7.55 (dd, 1H), 7.38 (m, 1H), 7.17 (m, 1H), 6.21 (d, 1H), 5.99 (s, 1H), 5.62 (q, 1H), 4.94 (dd, 1H), 4.68 (m, 1H), 4.61 (d, 1H), 4.45 (m, 1H), 4.02 (m, 1H), 2.85 (m, 2H), 2.71 (m, 1H), 2.56 (m, 1H), 2.27 (q, 1H), 1.92 (s, 3H), 1.90-1.03 (m, 15H).

Compound 279: MS: m/z 834.3 (M⁺+1); ¹H NMR (CDCl₃) δ 10.43 (s, 1H), 8.05 (m, 1H), 7.96 (dd, 1H), 7.91 (dd, 1H), 7.55 (dd, 1H), 7.48 (s, 1H), 7.37-7.32 (m, 2H), 6.05 (s, 1H), 5.57 (q, 1H), 5.39 (d, 1H), 4.79-4.67 (m, 4H), 4.28 (m, 1H), 4.03 (m, 1H), 2.87-2.67 (m, 3H), 2.54 (m, 1H), 2.29 (q, 1H), 1.90-0.87 (m, 23H).

Compound 280: MS: m/z 818.2 (M⁺+1); ¹H NMR (CDCl₃) δ 10.36 (s, 1H), 8.02 (m, 1H), 7.94 (dd, 1H), 7.71 (dd, 1H), 7.60 (s, 1H), 7.54-7.51 (dd, 1H), 7.42 (d, 1H), 7.36-7.30 (m, 2H), 6.03 (s, 1H), 5.60 (q, 1H), 4.86-4.72 (m, 2H), 4.56-4.48 (m, 2H), 4.05 (m, 1H), 2.84 (m, 2H), 2.68 (m, 1H), 2.48 (m, 1H), 2.23 (q, 1H), 1.88-1.05 (m, 15H).

Compound 281 was prepared similar to the procedure described in Example 1: Compound 281: MS: m/z 901.2 (M⁺+1); ¹H NMR (CDCl₃) δ 10.25 (s, 1H), 8.48 (d, 1H), 7.59 (dd, 1H), 7.39 (d, 1H), 7.32 (dd, 1H), 7.15 (s, 1H), 7.04 (s, 1H), 6.14 (s, 1H), 5.69 (ddd, 1H), 5.04 (m, 2H), 4.72 (m, 1H), 4.56 (m, 2H), 4.24-4.15 (m, 2H), 3.97 (s, 3H), 3.34 (tt, 1H), 2.55 (m, 1H), 2.24-2.26 (m, 1H), 2.01-0.69 (m, 34H).

EXAMPLE 282

Inhibition of NS3/4A Protease

Protein Expression and Purification

A plasmid containing a gene encoding N-terminal His₆-tagged-NS4A$_{(21-32)}$-GSGS-NS3$_{(3-181)}$ was transformed into *E. coli* strain BL21(DE3) pLysS (Novagen) for protein overexpression. Single colony of transformed BL21 (DE3) pLysS was cultured in 200 mL of Lauria-Bertani (LB) medium with Kanamycin and Chloramphenicol at 37° C. overnight. The bacterial culture was transferred into 6 L LB medium (Difco) containing antibiotics and incubated with shaking at 22° C. After the absorbance at 600 nm reached 0.6, the culture was induced with 1 mM isopropyl-1-thio-β-D-galactopyranoside (IPTG) at 22° C. for hours. The culture was subsequently harvested by centrifugation (6,000×g for 15 minutes at 4° C.). Cell pellets were resuspended in 150 mL buffer A (50 mM HEPES, pH 7.4, 0.3 M NaCl, 0.1% (w/v) CHAPS, 10 mM imidazol, 10% (v/v) glycerol). After the mixture was disrupted by four passes through a Microfluidizer operated at 30 psi, the cell debris was removed by centrifugation (58,250×g for 30 minutes at 4° C.). The cell lysate containing His₆-tagged proteins was charged at 3 mL/min onto a 25 mL Ni-NTA (Qiagen) column in the presence of 10 mM imidazole using a gradiFrac system (Pharmacia). The column was washed with 10 column volumes of the lysis buffer. The bound NS4A$_{(21-32)}$-GSGS-NS3$_{(3-181)}$ was eluted with 8 column volumes of buffer A supplemented with 300 mM imidazole. The pooled fractions were further purified by Q-Sepharose column equilibrated with buffer B (50 mM HEPES, pH 7.4, 0.1% (w/v) CHAPS, 10% (v/v) glycerol, 5 mM dithiothreitol (DTT), and 1 M NaCl). The eluant containing NS4A$_{(21-32)}$-GSGS-NS3$_{(3-181)}$ was collected and further purified by size-exclusion chromatography at a flow rate of 0.5 mL/min using the sephacryl-75 column (16×100 cm, Pharmacia) pre-equilibrated with buffer C (50 mM HEPES, pH 7.4, 0.1% (w/v) CHAPS, 5 mM DTT, 10% (v/v) glycerol). The purified protein was frozen and stored at −80° C. before use.

HPLC Microbore Assay

A solution containing 50 mM Tris, pH 7.4, 100 mM NaCl, 20% glycerol, 0.012% CHAPS, 10 mM DTT, 5 μM substrate Ac-Asp-Glu-Asp(EDANS)-Glu-Glu-Abu-ψ-[COOAla]-Ser-Lys(DABCYL)-NH₂ (RET 51, ANASPEC), and 10 μM test compound was prepared. 80 μL of the solution was added to each well of a 96-well plate. Reaction was initiated by addition of 20 μL of 10 nM NS3/4A protease in a buffer containing 50 mM Tris buffer, pH 7.4, 100 mM NaCl, 20% glycerol, and 0.012% CHAPS. The final concentration of NS3/4A protease was 2 nM, which was lower than the Km of substrate RET 51.

The assay solution was incubated for 30 minutes at 30° C. The reaction was then quenched by addition of 100 μL of 1% TFA. 200 μL aliquot was transferred to each well of Agilent 96-well plates.

Reaction products were analyzed using reverse phase HPLC described below. The HPLC system included: Agilent 1100, Degasser G1379A, Binary pump G1312A, Autosampler G1367A, Column thermostated chamber G1316A, Diode array detector G1315B, Column: Agilent, ZORBAX Eclipse XDB-C18, 4.6 mm, 5 μm, P/N 993967-902, Column thermostat: room temperature, injection volume: 100 μL, Solvent A=HPLC grade water+0.09% TFA, Solvent B=HPLC grade acetonitrile+0.09% TFA. Total HPLC running time was 7.6 minutes with a linear gradient from 25 to 50% solvent B in 4 minutes, 50% solvent B for 30 seconds, and a gradient from 50 to 25% solvent B for additional 30 seconds. The column was re-equilibrated with 25% solvent B for 2.6 minutes before next sample was injected. The IC₅₀ value (the concentration at which 50% inhibition of NS3/4A activity was observed) was calculated for each test compound based on the HPLC results.

Compounds 1-281 were tested in the above inhibition assay. The results showed that 274 compounds exhibited IC₅₀ values lower than 20 nM and 7 compounds exhibited IC₅₀ values in the range of 20-100 nM.

In addition, certain compounds of this invention were found to unexpectedly inhibit in an effective manner HCV protease mutants resistant to one or more other HCV drugs.

EXAMPLE 283

HCV Replicon Cell Assay Protocol

Cells containing HCV replicon were maintained in DMEM containing 10% fetal bovine serum (FBS), 1.0 mg/ml of G418, and appropriate supplements (media A).

On day 1, the replicon cell monolayer was treated with a trypsin/EDTA mixture, removed, and was diluted with media A to a final concentration of 48,000 cells/ml. The solution (1 ml) was added to each well of a 24-well tissue culture plate, and cultured overnight in a tissue culture incubator at 37° C. with 5% CO₂.

On day 2, a test compound (in 100% DMSO) was serially diluted by DMEM containing 10% FBS and appropriate supplements (media B). The final concentration of DMSO was maintained at 0.2% throughout the dilution series.

The media on the replicon cell monolayer was removed, and then media B containing various concentrations of compounds was added. Media B without any compound was added to other wells as compound-free controls.

The cells were incubated with a compound or 0.2% DMSO in media B for 72 hours in a tissue culture incubator with 5% CO₂ at 37° C. Then, the media was removed and the replicon cell monolayer was washed once with PBS. RNA extraction reagents from RNeasy kits or TRIZOL reagents were added to the cells immediately to avoid degradation of RNA. Total RNA was extracted according to the instruction provided by manufacturer with modification to improve extraction efficiency and consistency. Finally, total cellular RNA, including HCV replicon RNA, was eluted and stored at −80° C. until further processing.

A TaqMan° real-time RT-PCR quantification assay was set up with two sets of specific primers: one was for HCV and the other was for ACTB (beta-actin). The total RNA was added to the PCR reactions for quantification of both HCV and ACTB RNA in the same PCR well. Experimental failure was flagged and rejected based on the level of ACTB RNA in each well. The level of HCV RNA in each well was calculated according to a standard curve run in the same PCR plate. The percentage of inhibition of HCV RNA level by the compound treatment was calculated using the DMSO or compound-free control as 0% of inhibition. EC50 (concentration at which 50% inhibition of HCV RNA level was achieved) was calculated from the titration curve of any given compound.

Compounds 1-281 were tested in the HCV replicon cell assay. The results showed that 274 compounds exhibited $EC_{50}$ values lower than 20 nM and 7 compound exhibited $EC_{50}$ values in the range of 20-100 nM.

EXAMPLE 284

Pharmacokinetic Study

Male Sprague-Dawley rats (300-400 g) were surgically implanted with polyethylene cannula in the jugular vein for blood sampling while under pentobarbital anesthesia the day before the in-life phase. They were fasted overnight with water ad libitum, and then dosed the next day with a test compound by oral gavage. Serial blood samples were collected from animals until 48 hrs post-dose and heparinized plasma was recovered following centrifugation. The test compound in blood plasma was extracted and determined by liquid chromatography-mass spectrometry analysis (LC-MS/MS).

Standard pharmacokinetic parameters were assessed by non-compartmental analysis using WinNonlin (Version 4.0, Pharsight, Calif., USA). The maximum in the curve of the test compound concentration in blood plasma vs. time is denoted $C_{max}$. The apparent terminal-phase elimination ($t_{1/2}$) were calculated as $\ln(2)/\lambda_z$, where $\lambda_z$ is an elimination rate constant. The area under the concentration vs. time curve from the time of dosing to infinity ($AUC_{(0-inf)}$ was calculated according to the linear trapezoidal rule.

Certain compounds of this invention showed prolonged half-life and high AUC values.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

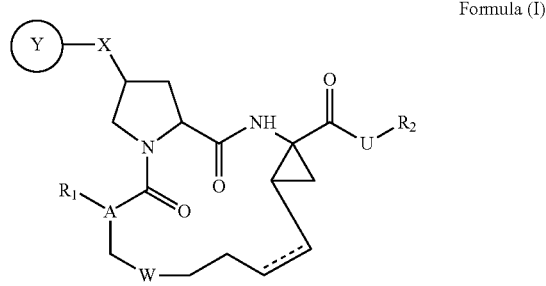

Formula (I)

wherein
$R_1$ is —H, —OH, $C_{1-6}$ alkyl, $C_{1-6}$ alkoxyl, $C_{3-10}$ cycloalkyl, $C_{1-10}$ heterocycloalkyl, aryl, heteroaryl, —Z—R, or —NH—Z—R; in which R is H, or is a moiety selected from $C_{1-6}$ alkyl, $C_{3-10}$ cycloalkyl, $C_{1-10}$ heterocycloalkyl, aryl, and heteroaryl, each of which is optionally mono-, di- or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl; and Z is —C(O)—, —C(O)O—, —C(O)C(O)O—, —C(O)C(O)NH—, —C(O)NR'—, —OC(S)—, —C(S)NR'—, or —C(NH)O—, R' being H, $C_{1-6}$ alkyl, $C_{3-10}$ cycloalkyl, $C_{1-10}$ heterocycloalkyl, aryl, or heteroaryl;
$R_2$ is H, or is a moiety selected from $C_{1-6}$ alkyl, $C_{3-10}$ cycloalkyl, $C_{1-10}$ heterocycloalkyl, aryl, and heteroaryl, each of which is optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl;
A is N or CH;
U is —O—, —NH—, —NH(CO)—, —NHSO—, or —NHSO$_2$—;
W is —(CH$_2$)$_m$—, —NH(CH$_2$)$_n$—, —(CH$_2$)$_n$NH—, —O(CH$_2$)$_n$—, —(CH$_2$)$_n$O—, —S(CH$_2$)$_n$—, —(CH$_2$)$_n$S—, —SO—, —SO(CH$_2$)$_n$—, —(CH$_2$)$_n$SO—, —SO$_2$(CH$_2$)$_n$—, or —(CH$_2$)$_n$SO$_2$—, m being 1,2, or 3 and n being 0, 1, or 2;
X is —O—, —S—, or —NH;
Y is

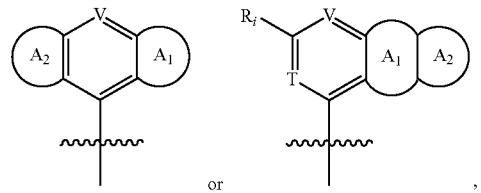

or in which each of V and T, independently, is —CH— or —N—; each of $A_1$ and $A_2$, independently, is a moiety selected from $C_{4-10}$ cycloalkyl, $C_{1-10}$ heterocycloalkyl, aryl, and heteroaryl, each of which is optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl; and $R_i$ is H, halo, nitro, cyano, or amino, or is a moiety selected from $C_{1-6}$ alkyl, $C_{1-6}$ alkoxyl, $C_{2-6}$ alkenyl, $C_{2-6}$ alkynyl, $C_{3-10}$ cycloalkyl, $C_{1-10}$ heterocycloalkyl, aryl, and heteroaryl, each of $C_{1-6}$ alkyl, $C_{1-6}$ alkoxyl, $C_{2-6}$ alkenyl, and $C_{2-6}$ alkynyl being optionally mono-, di- or tri-substituted with halo, nitro, cyano, amino, $C_{1-6}$ alkyl, $C_{1-6}$ alkoxyl, $C_{2-6}$ alkenyl, $C_{2-6}$ alkynyl, $C_{3-10}$ cycloalkyl, $C_{1-10}$ heterocycloalkyl, aryl, or heteroaryl, and each of $C_{3-10}$ cycloalkyl, $C_{1-10}$ heterocycloalkyl, aryl, and heteroaryl being optionally mono-, di- or tri-substituted with halo, nitro, cyano, amino, $C_{1-6}$ alkyl, $C_{1-6}$ alkoxyl, $C_{2-6}$ alkenyl, $C_{2-6}$ alkynyl, $C_{3-10}$ cycloalkyl, $C_{1-10}$ heterocycloalkyl, aryl, or heteroaryl, or optionally fused with $C_{3-10}$ cycloalkyl, $C_{1-10}$ heterocycloalkyl, aryl, or heteroaryl; and ≡≡≡ is a single bond or a double bond.

2. The compound of claim 1, wherein X is O.

3. The compound of claim 1, wherein A is CH and W is —CH$_2$CH$_2$—, —OCH$_2$—, —SCH$_2$—, or —SOCH$_2$—.

4. The compound of claim 1, wherein A is N and W is —CH$_2$CH$_2$—, —OCH$_2$—, —SCH$_2$—, or —SOCH$_2$—.

5. The compound of claim 1, wherein U is —NHSO$_2$—.

6. The compound of claim 1, wherein ≡≡≡ is a double bond.

7. The compound of claim 1, wherein Y is

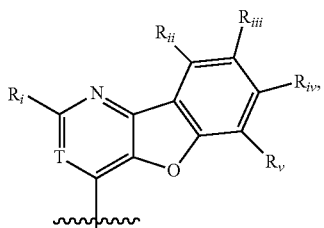

in which T is CH or N and each of $R_i$, $R_{ii}$, $R_{iii}$, $R_{iv}$, and $R_v$, independently, is H, halo, nitro, cyano, amino, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl.

8. The compound of claim 7, wherein $R_i$ is phenyl or thioazolyl optionally substituted with halo, amino, $C_{1-6}$ alkyl, or $C_{1-6}$ alkoxyl.

9. The compound of claim 1, wherein $R_2$ is

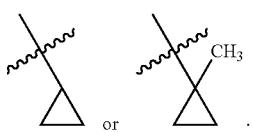

10. The compound of claim 9, wherein Y is

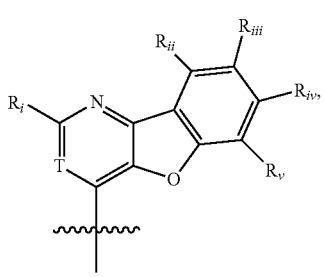

in which T is CH or N; $R_i$ is phenyl or thioazolyl optionally substituted with halo, amino, $C_{1-6}$ alkyl, or $C_{1-6}$ alkoxyl; and each of $R_{ii}$, $R_{iii}$, $R_{iv}$, and $R_v$, independently, is H, halo, nitro, cyano, amino, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl.

11. The compound of claim 1, wherein $R_1$ is —NH—Z—R, in which Z is —C(O)—, —C(O)O—, —C(O)C(O)O—, or —C(O)C(O)NH—.

12. The compound of claim 11, wherein $R_1$ is —NH—C(O)O-t-Bu or —NH—C(O)O-cyclopentyl.

13. The compound of claim 12, wherein $R_2$ is

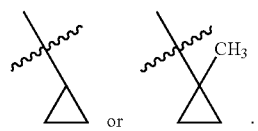

14. The compound of claim 13, wherein Y is

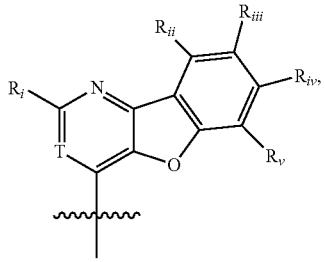

in which T is CH or N; $R_i$ is phenyl or thioazolyl optionally substituted with halo, amino, $C_{1-6}$ alkyl, or $C_{1-6}$ alkoxyl; and each of $R_{ii}$, $R_{iii}$, $R_{iv}$, and $R_v$, independently, is H, halo, nitro, cyano, amino, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl.

15. The compound of claim 14, wherein X is O; A is CH; W is —CH$_2$CH$_2$—, —OCH$_2$—, —SCH$_2$—, or —SOCH$_2$—; U is —NHSO$_2$—; and ≡≡≡ is a double bond.

16. The compound of claim 11, wherein $R_1$ is —NH—C(O)-furyl.

17. The compound of claim 16, wherein $R_2$ is

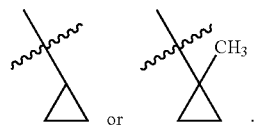

18. The compound of claim 17, wherein Y is

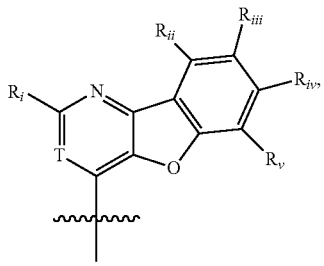

in which T is CH or N; $R_i$ is phenyl or thioazolyl optionally substituted with halo, amino, $C_{1-6}$ alkyl, or $C_{1-6}$ alkoxyl; and each of $R_{ii}$, $R_{iii}$, $R_{iv}$, and $R_v$, independently, is H, halo, nitro, cyano, amino, $C_{1-6}$ alkyl, $C_{1-6}$ alkoxyl, $C_{2-6}$ alkenyl, or $C_{2-6}$ alkynyl, or is a moiety selected from $C_{3-10}$ cycloalkyl, $C_{1-10}$ heterocycloalkyl, aryl, and heteroaryl, each of which is optionally mono-, di-, or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl, or optionally fused with $C_{3-10}$ cycloalkyl, $C_{1-10}$ heterocycloalkyl, aryl, or heteroaryl.

19. The compound of claim 18, wherein X is O; A is CH; W is —CH$_2$CH$_2$—, —OCH$_2$—, —SCH$_2$—, or —SOCH$_2$—; U is —NHSO$_2$—; and ≡≡≡ is a double bond.

20. The compound of claim 1, wherein Y is

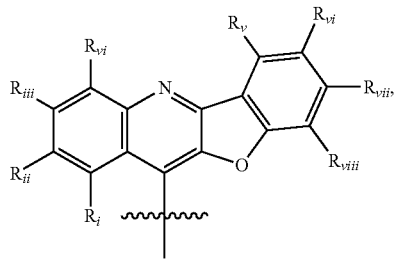

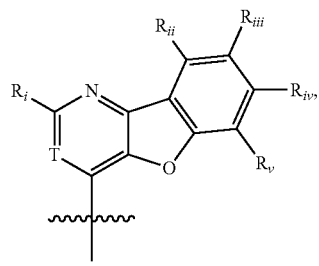

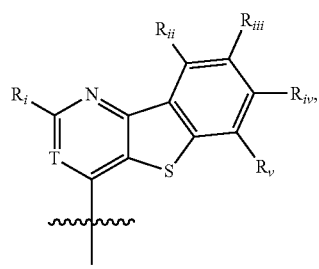

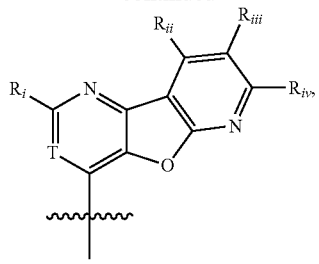

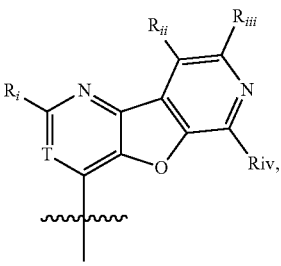

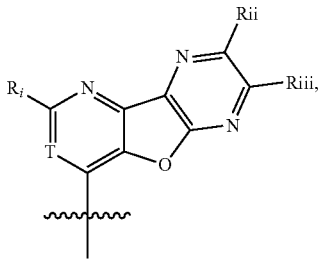

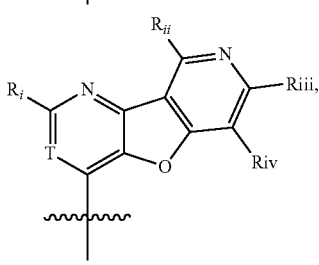

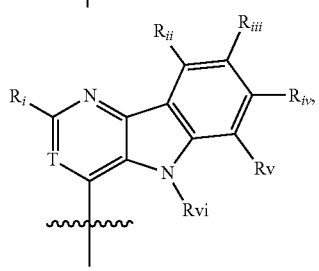

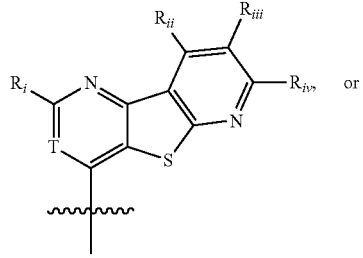 or

-continued

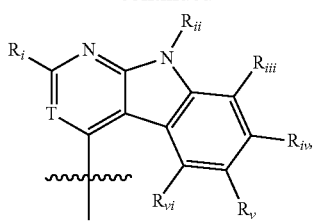

wherein each of $R_i$, $R_{ii}$, $R_{iii}$, $R_{iv}$, $R_v$, and $R_{vi}$, independently, is H, halo, nitro, cyano, amino, $C_{1-6}$ alkyl, $C_{1-6}$ alkoxyl, $C_{2-6}$ alkenyl, $C_{2-6}$ alkynyl, $C_{3-10}$ cycloalkyl, $C_{1-10}$ heterocycloalkyl, aryl, or heteroaryl, each of cycloalkyl, heterocycloalkyl, aryl, and heteroaryl being optionally mono-, di- or tri-substituted with halo, nitro, cyano, amino, $C_{1-6}$ alkyl, $C_{1-6}$ alkoxyl, $C_{2-6}$ alkenyl, $C_{2-6}$ alkynyl, aryl, or heteroaryl; and optionally fused with $C_{3-10}$ cycloalkyl, $C_{1-10}$ heterocycloalkyl, aryl, or heteroaryl.

21. The compound of claim 20, wherein $R_i$, is

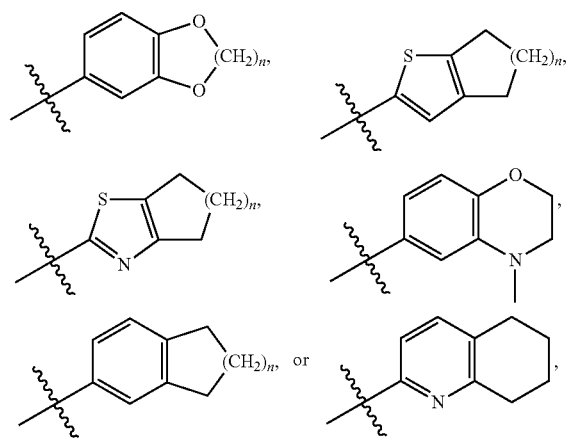

in which n is 1 or 2.

22. The compound of claim 1, wherein the compound is one of the following compounds:

Compound 1

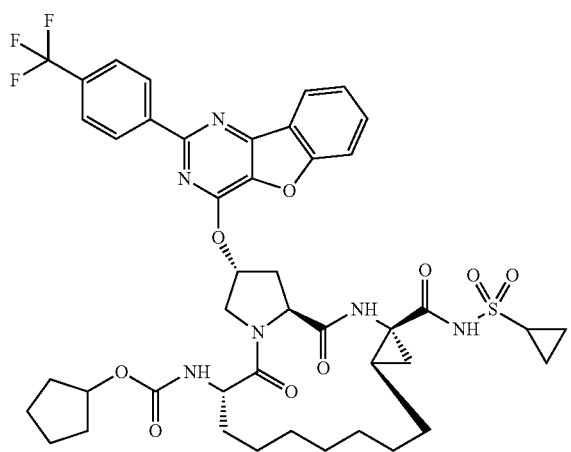

Compound 2

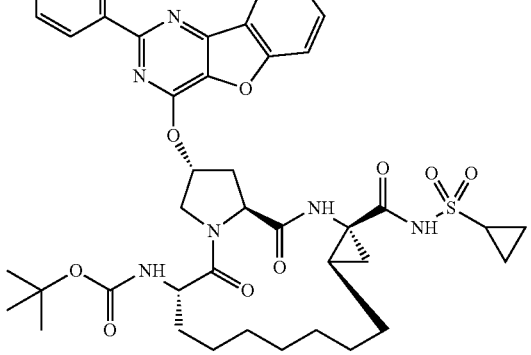

Compound 3

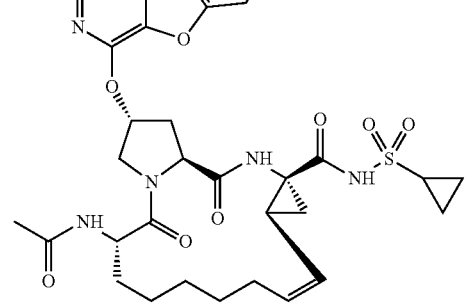

Compound 4

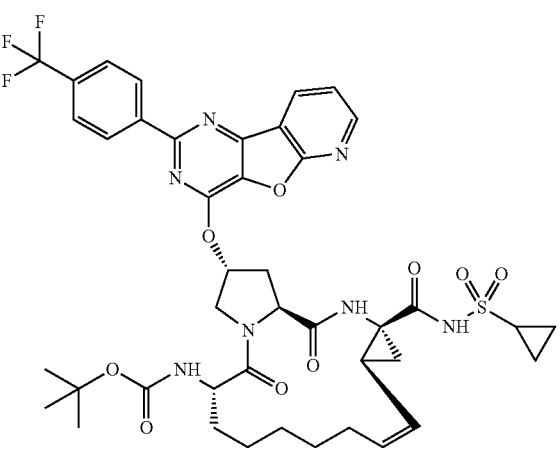

Compound 5
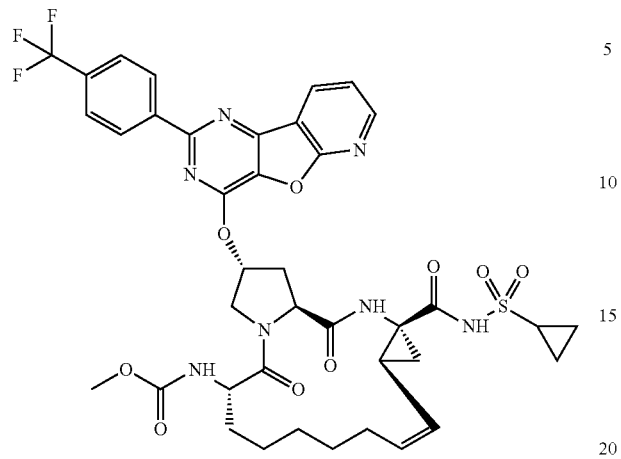
Compound 8
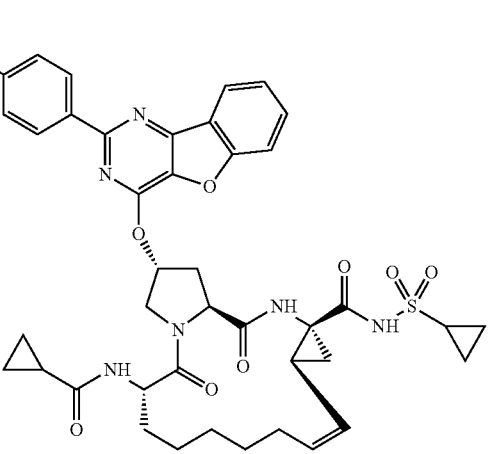
Compound 6
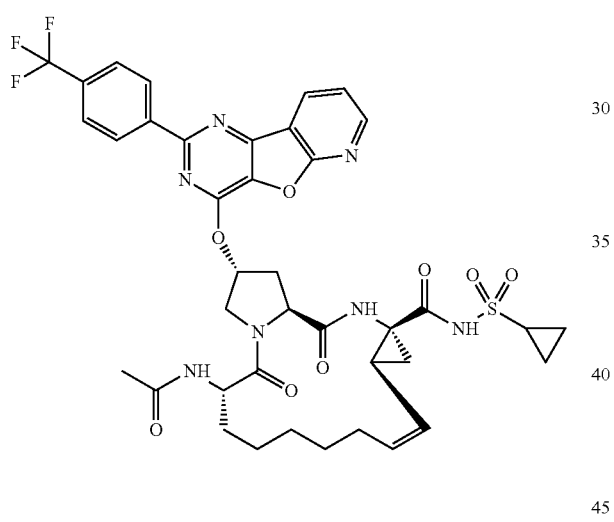
Compound 9
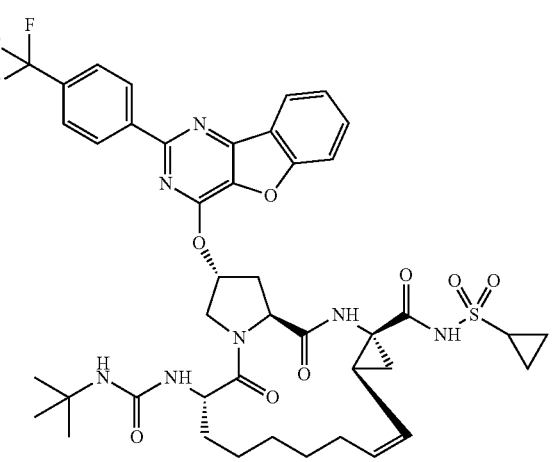
Compound 7
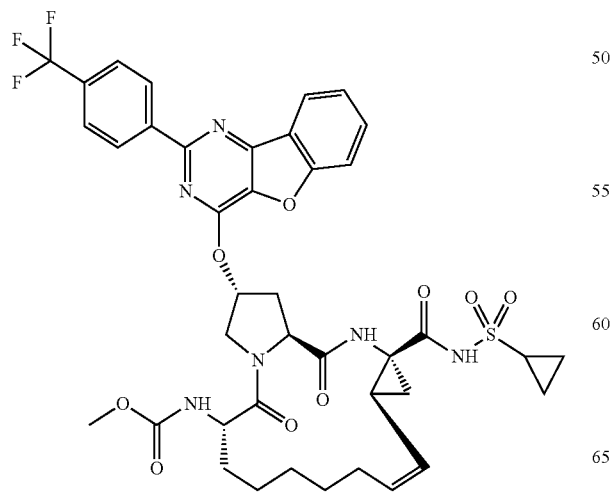
Compound 10
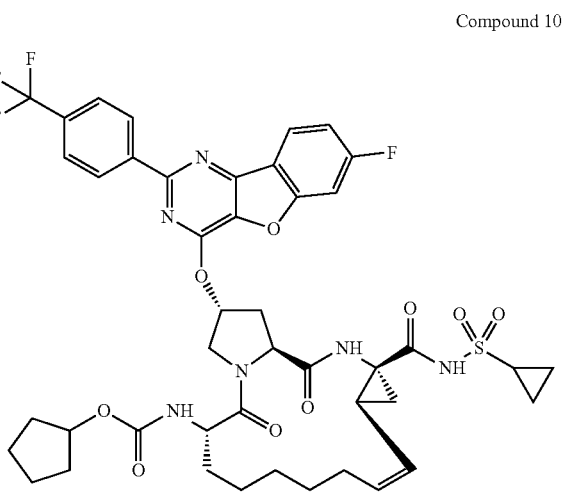

-continued
Compound 11
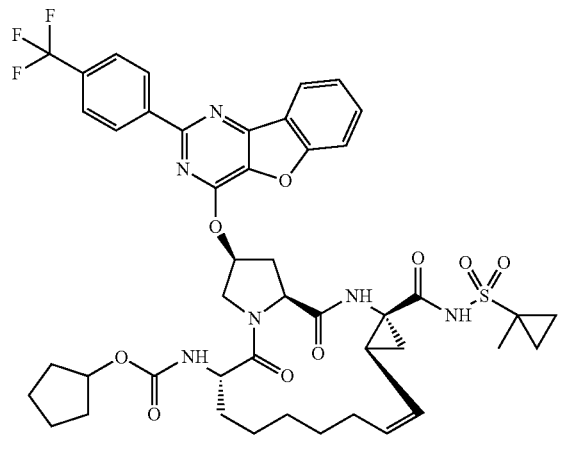
Compound 12
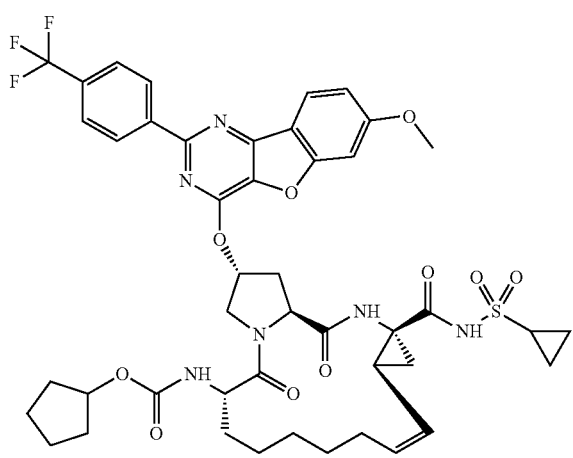
Compound 13
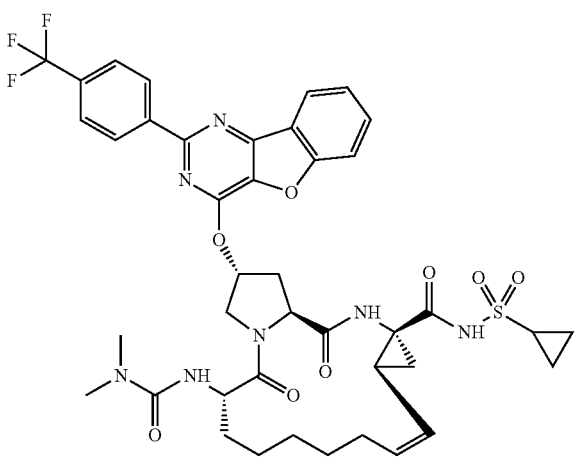
-continued
Compound 14
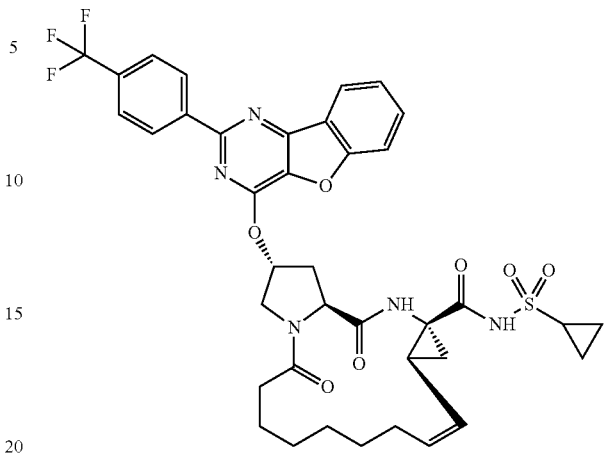
Compound 15
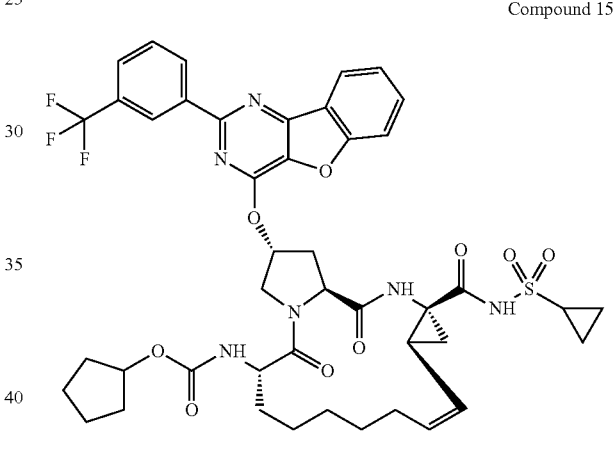
Compound 16
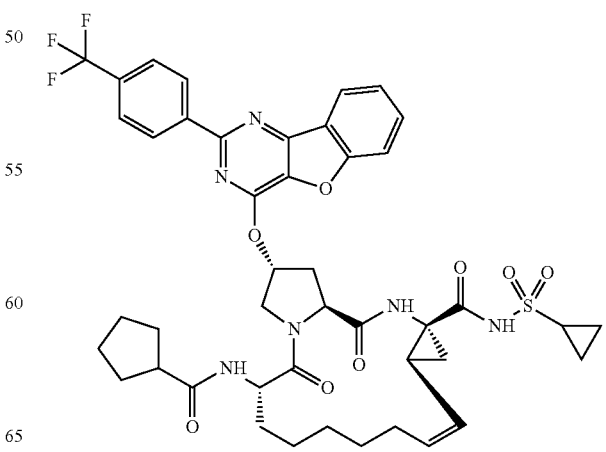

Compound 17
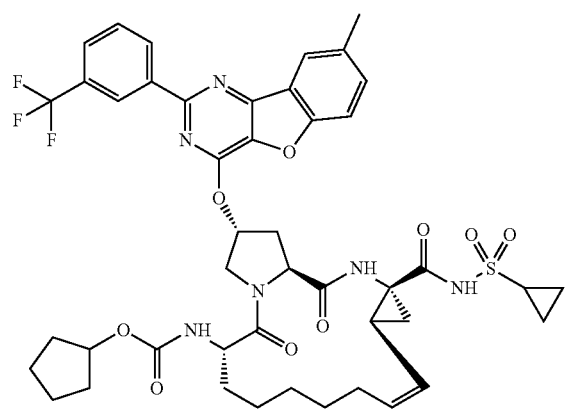
Compound 20
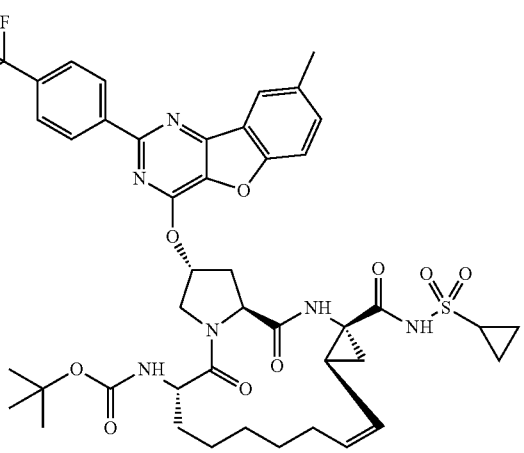
Compound 18
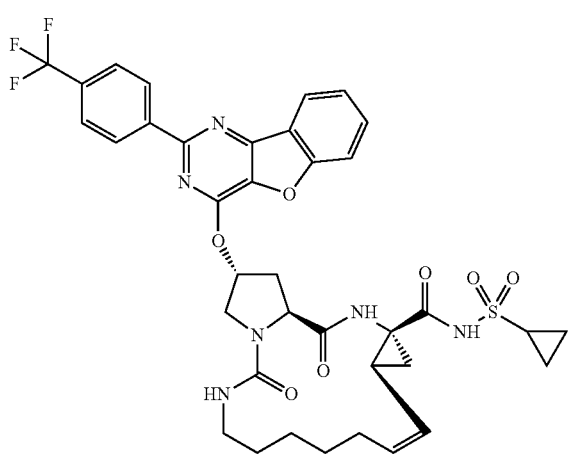
Compound 21
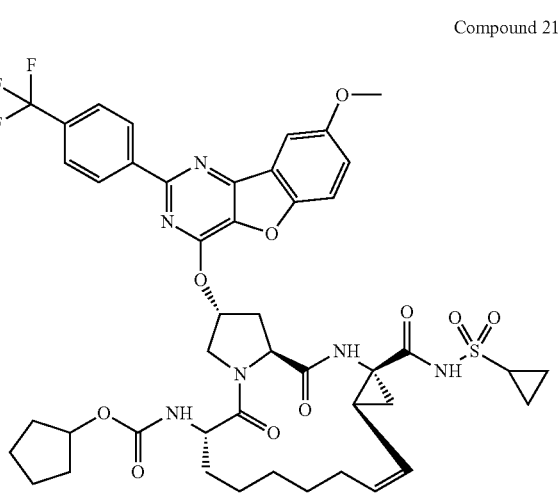
Compound 19
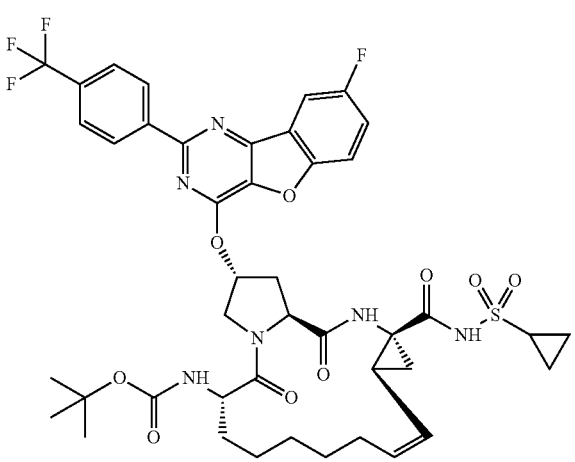
Compound 22
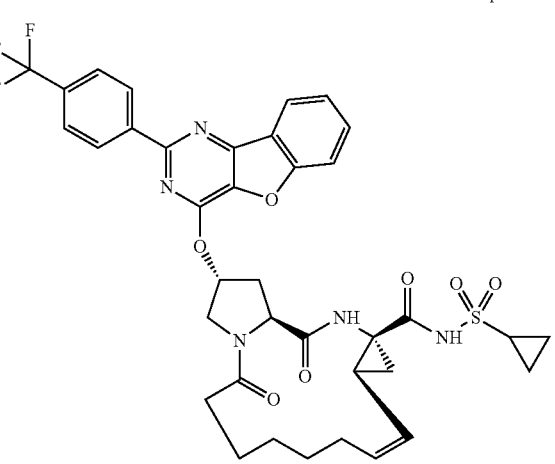

Compound 23
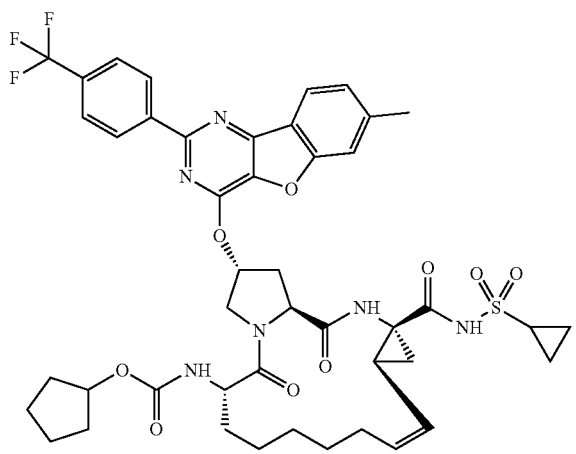
Compound 26
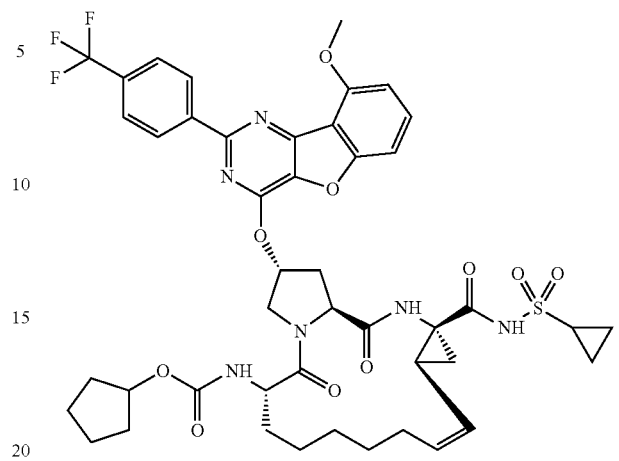
Compound 24
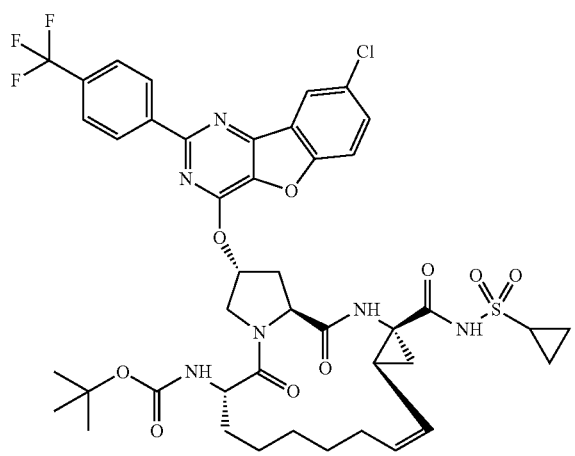
Compound 27
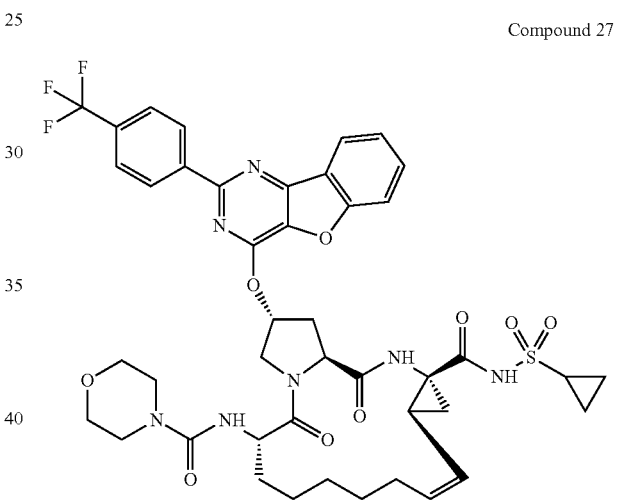
Compound 25
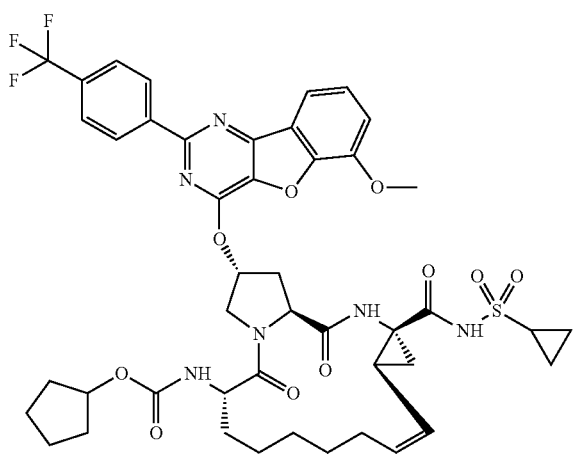
Compound 28
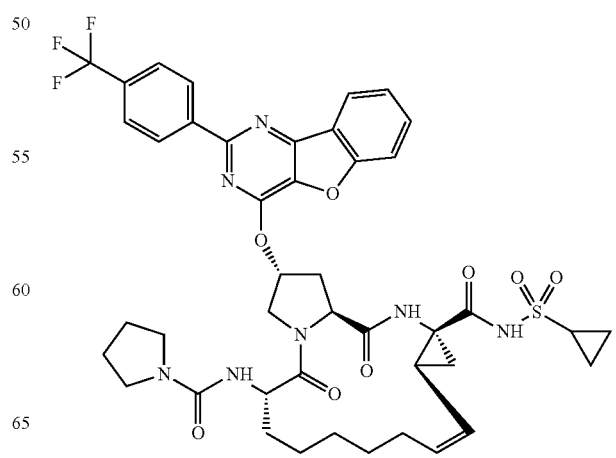

-continued
Compound 29
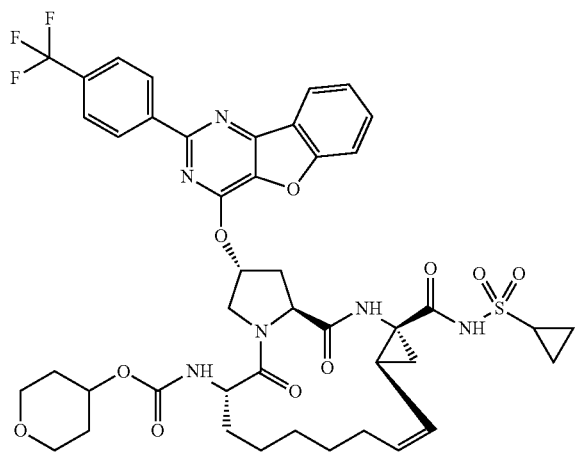
Compound 30
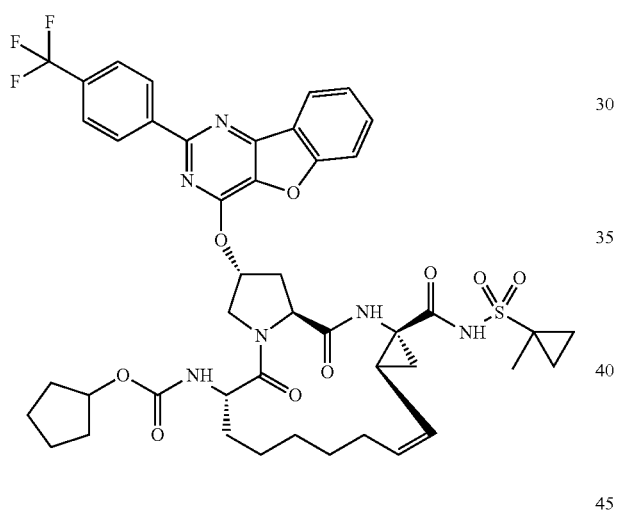
Compound 31
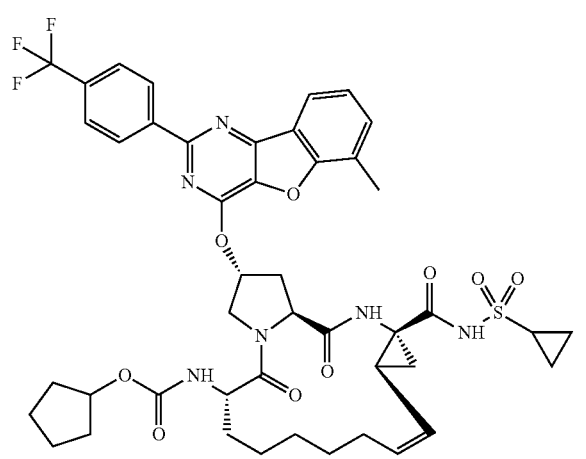
-continued
Compound 32
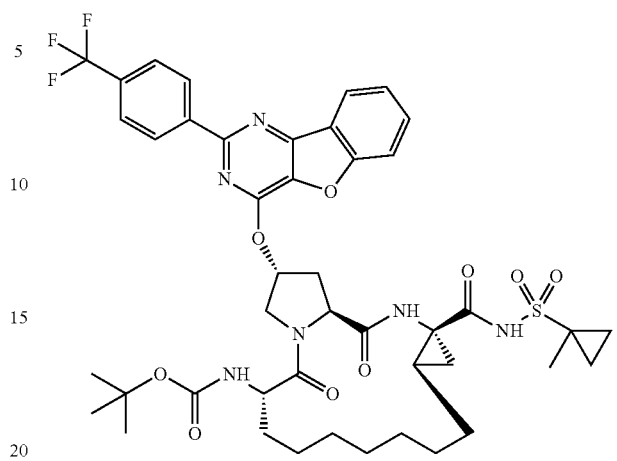
Compound 33
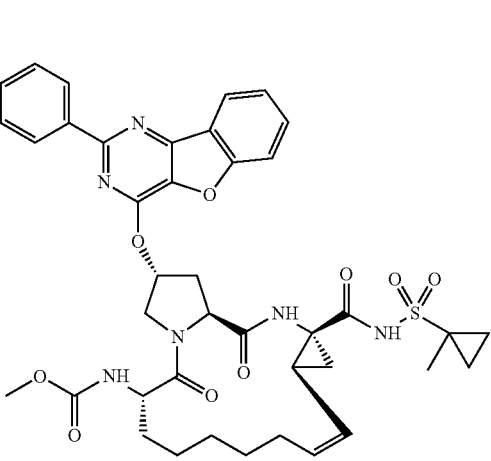
Compound 34
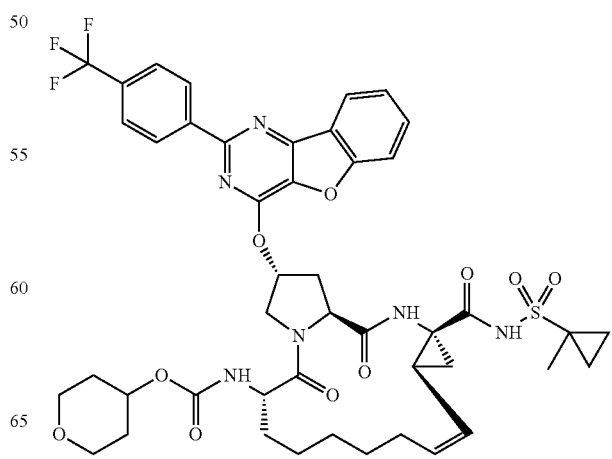

Compound 35
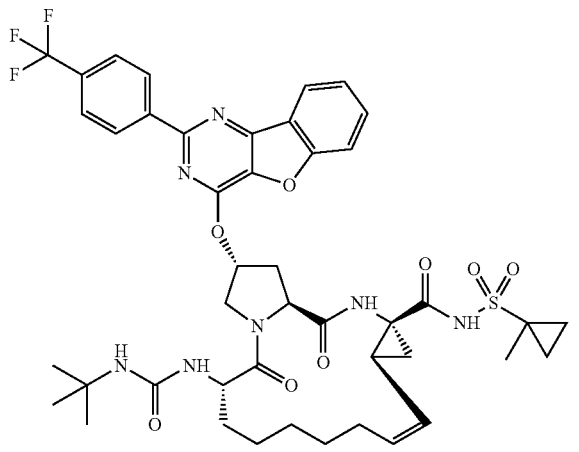
Compound 38
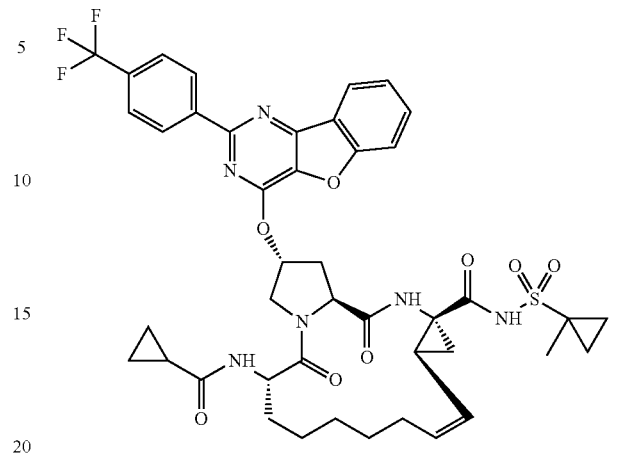
Compound 36
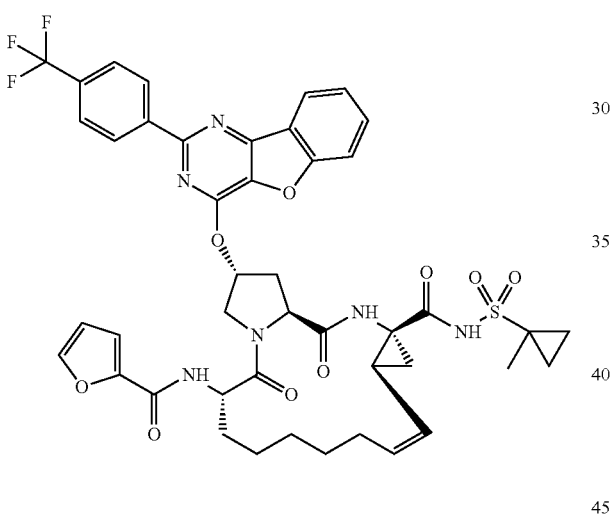
Compound 39
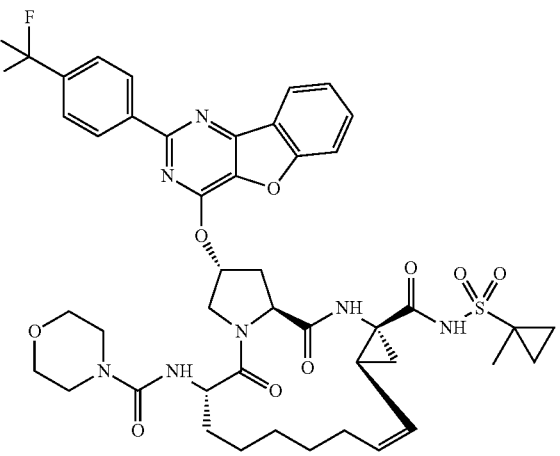
Compound 37
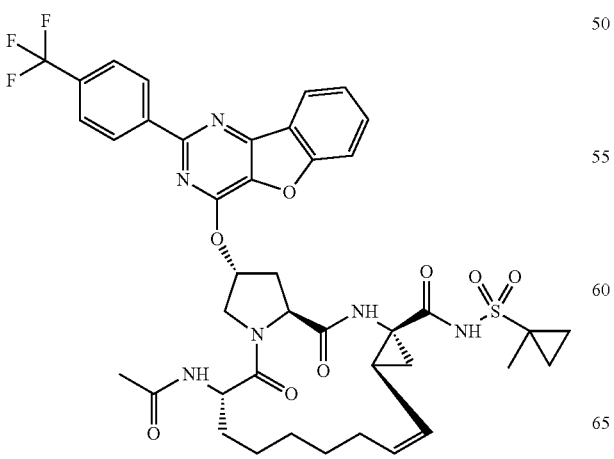
Compound 40
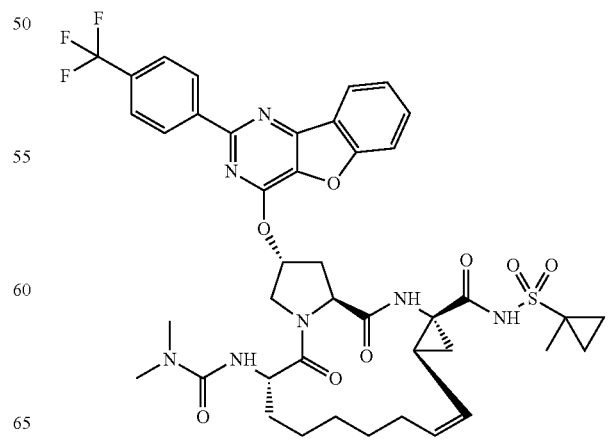

-continued
Compound 41
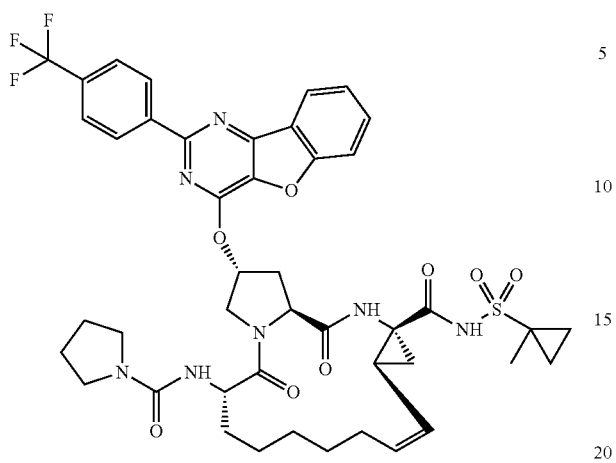
Compound 42
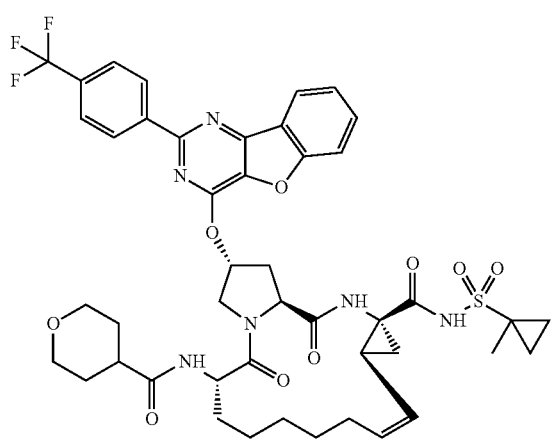
Compound 43
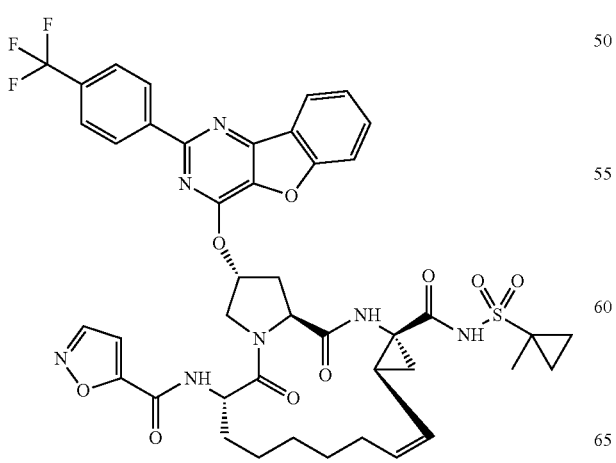
-continued
Compound 44
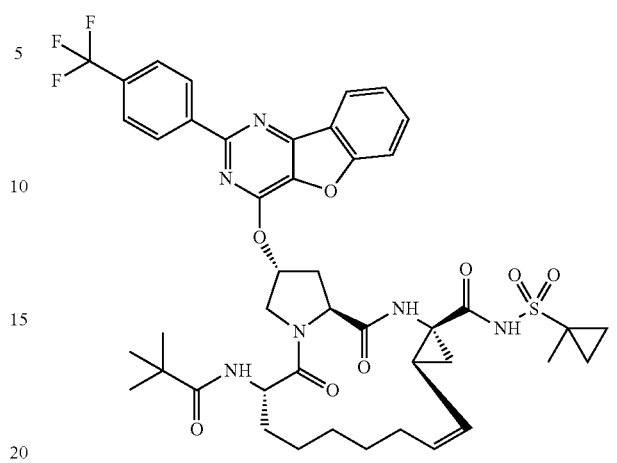
Compound 45
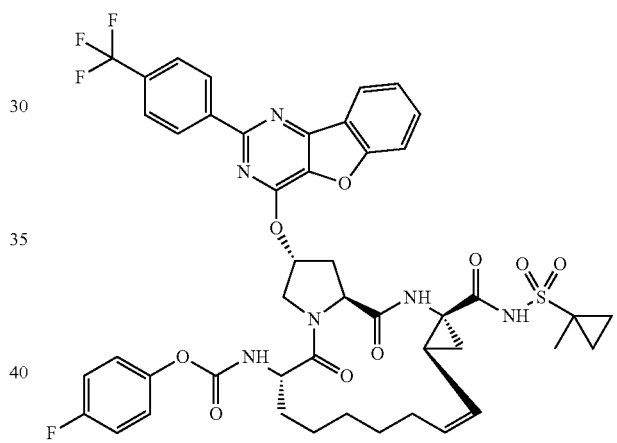
Compound 46
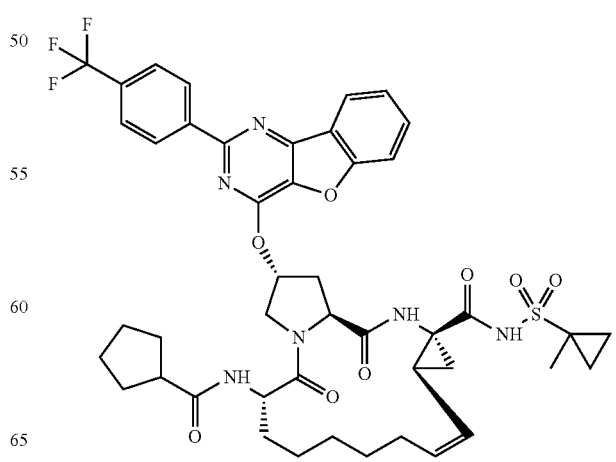

Compound 47
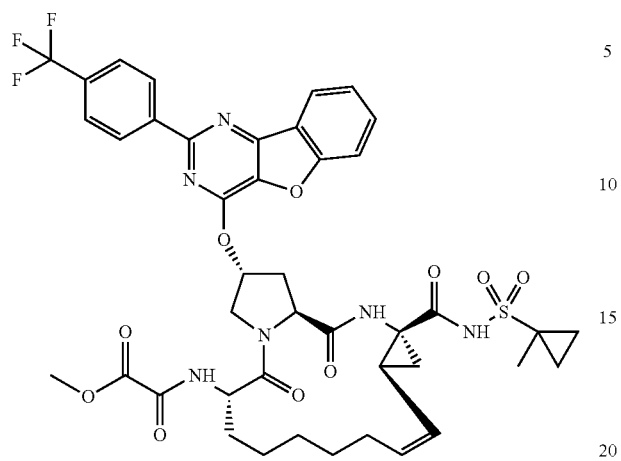
Compound 48
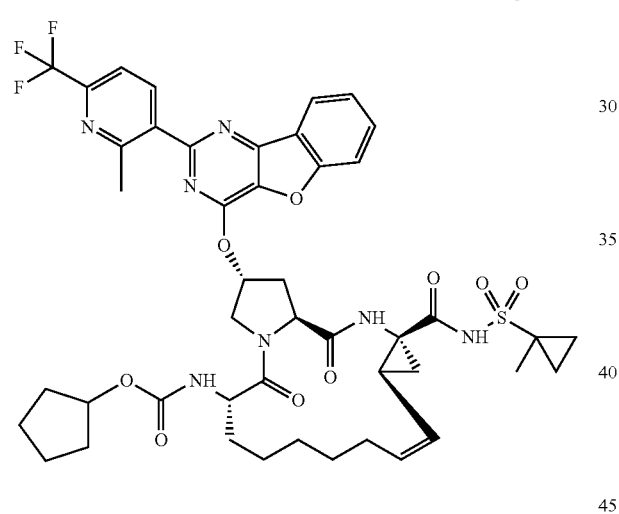
Compound 49
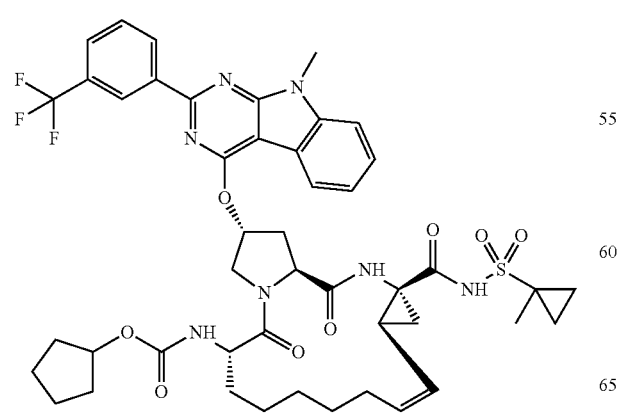
Compound 50
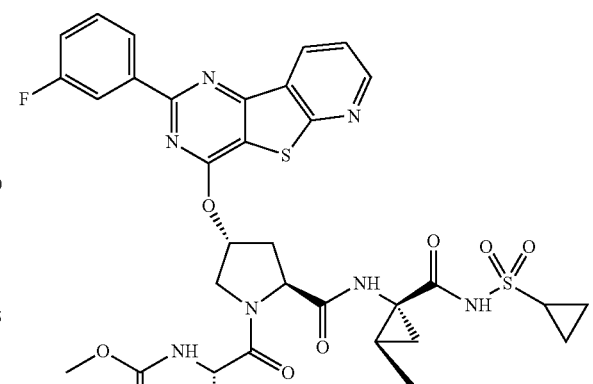
Compound 51
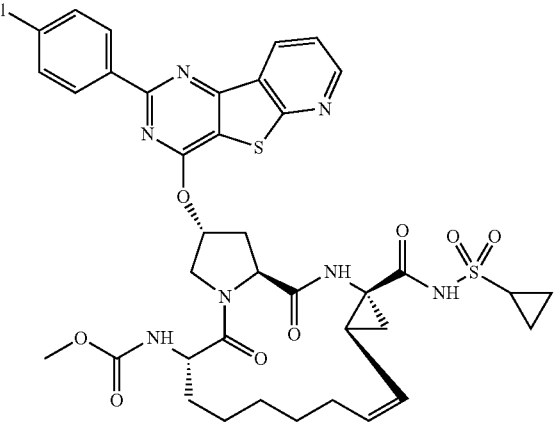
Compound 52
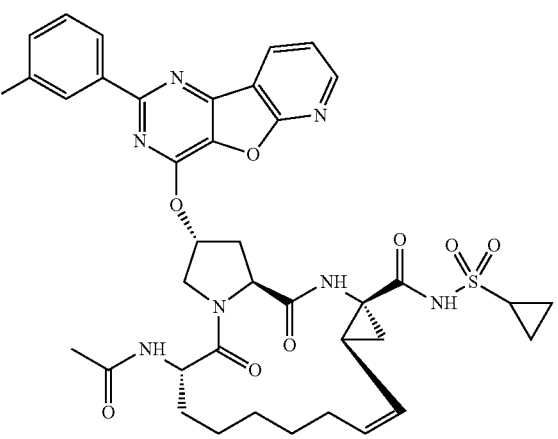

Compound 53
Compound 56
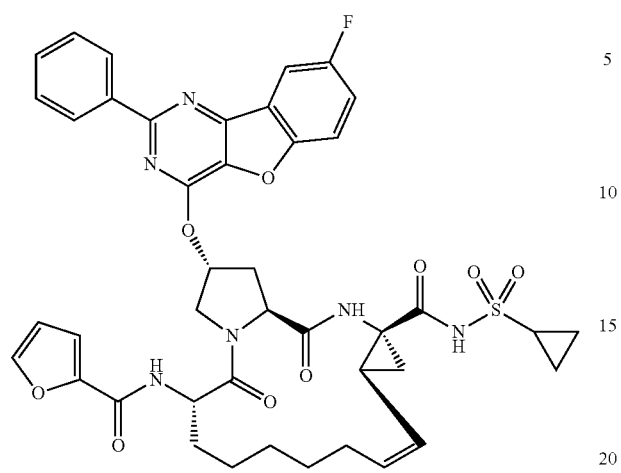
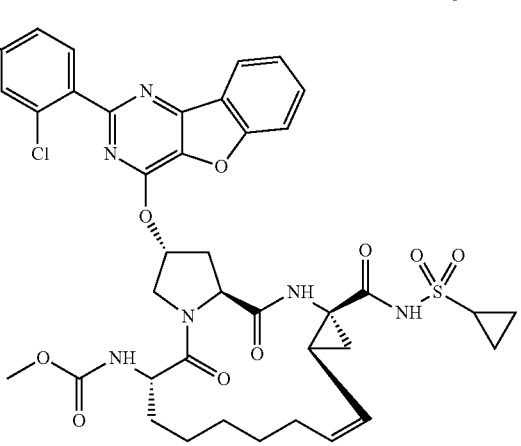
Compound 54
Compound 57
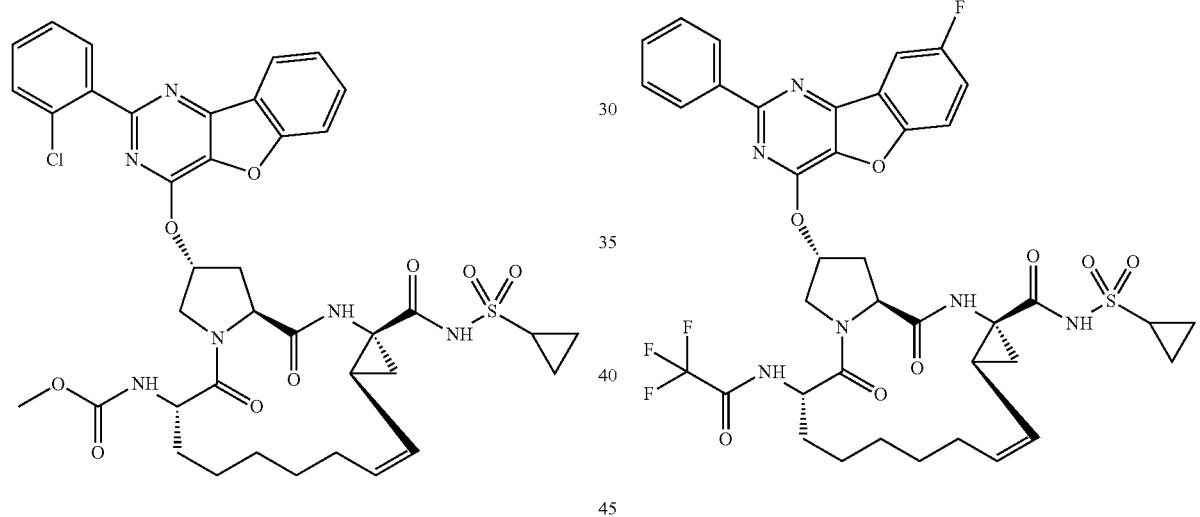
Compound 55
Compound 58
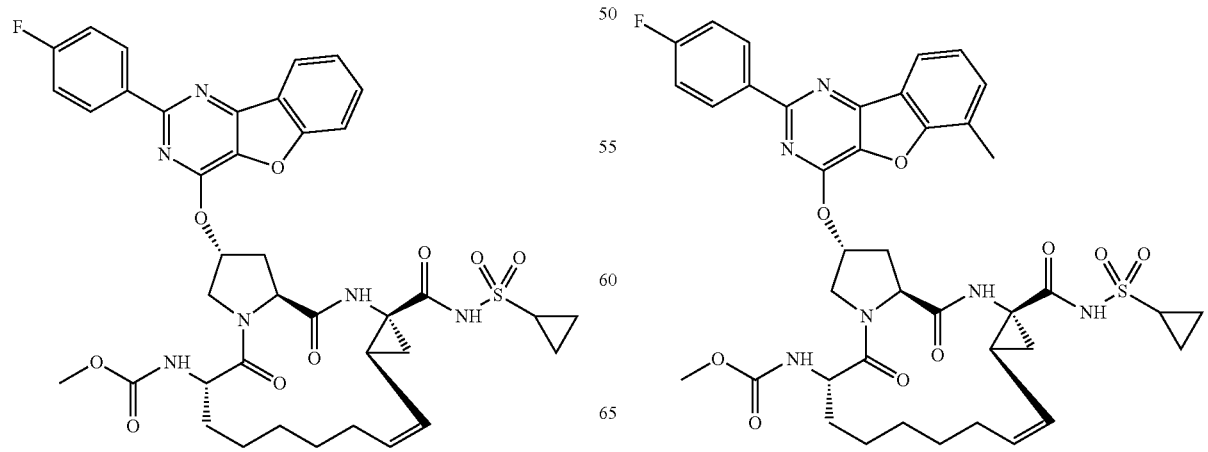

Compound 59
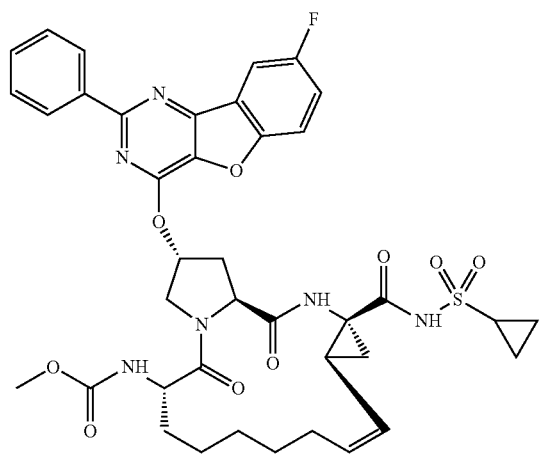
Compound 62
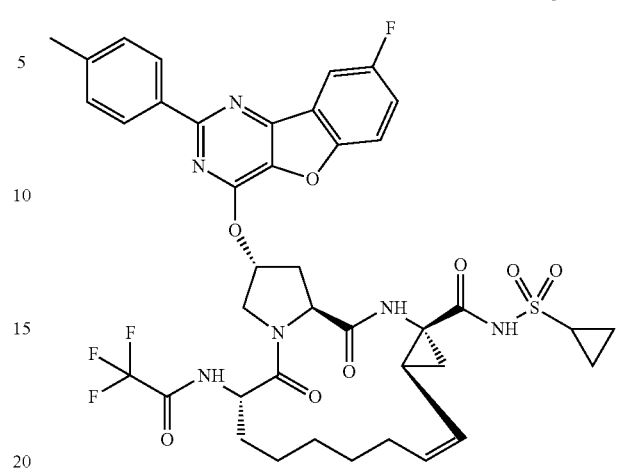
Compound 60
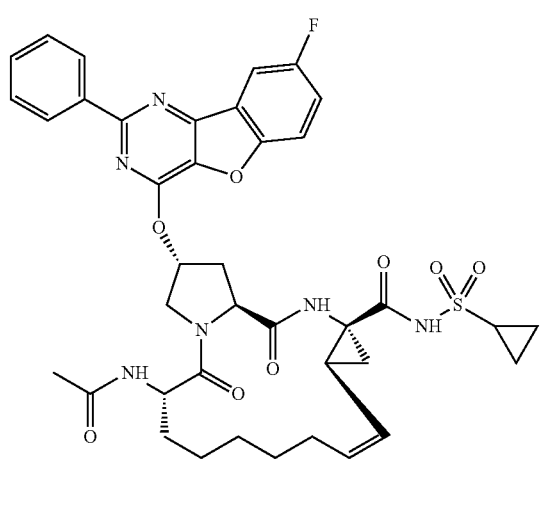
Compound 63
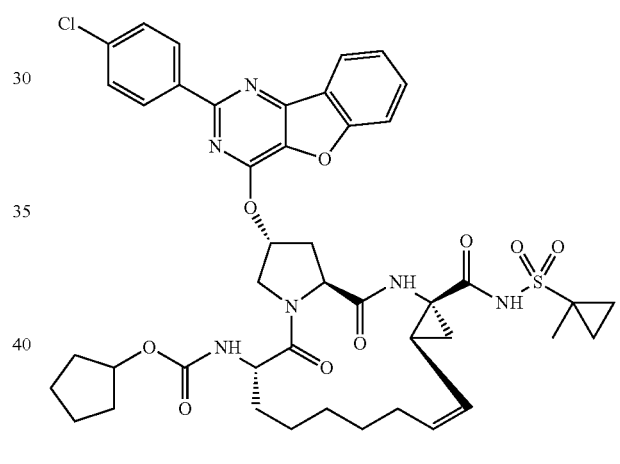
Compound 61
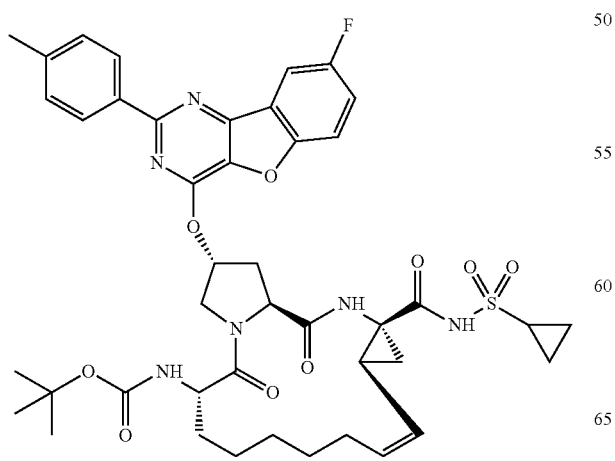
Compound 64
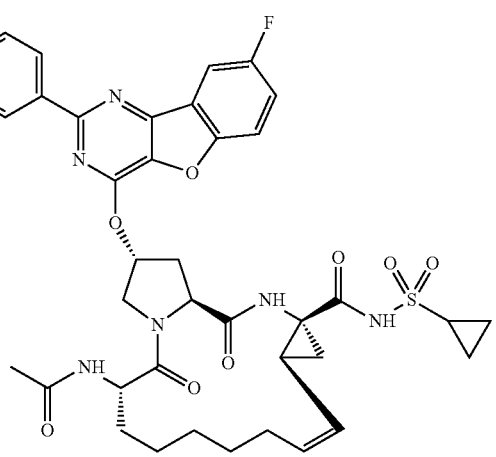

Compound 65
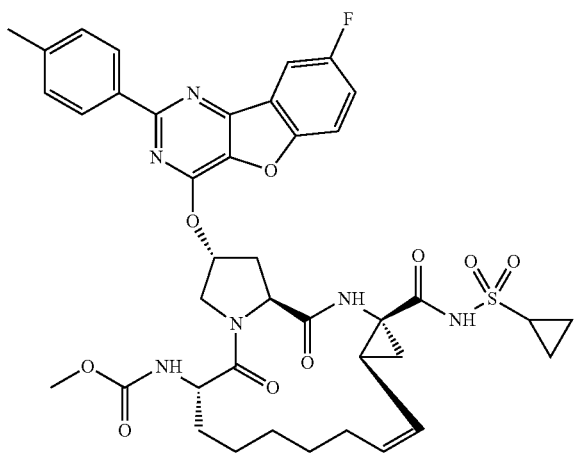
Compound 68
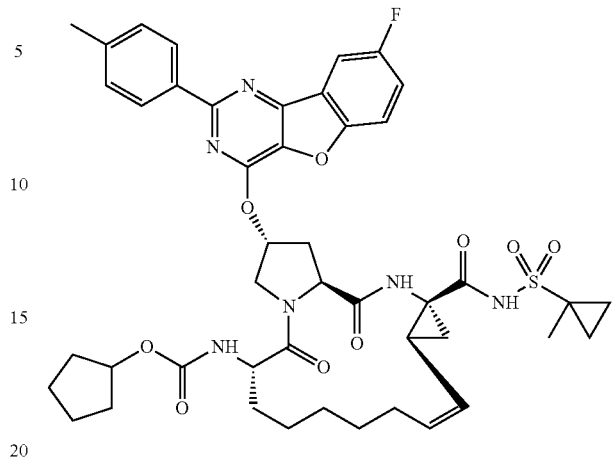
Compound 66
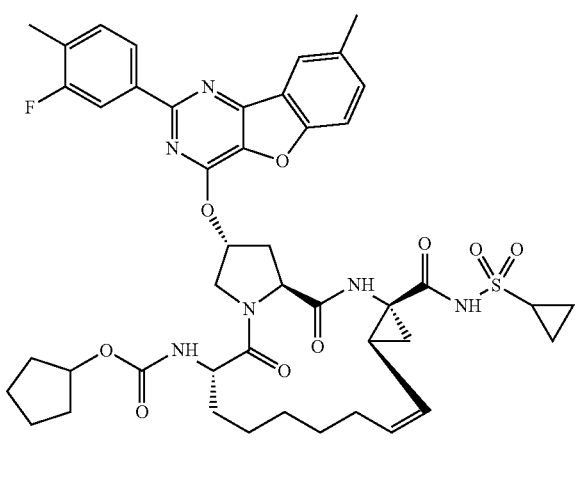
Compound 69
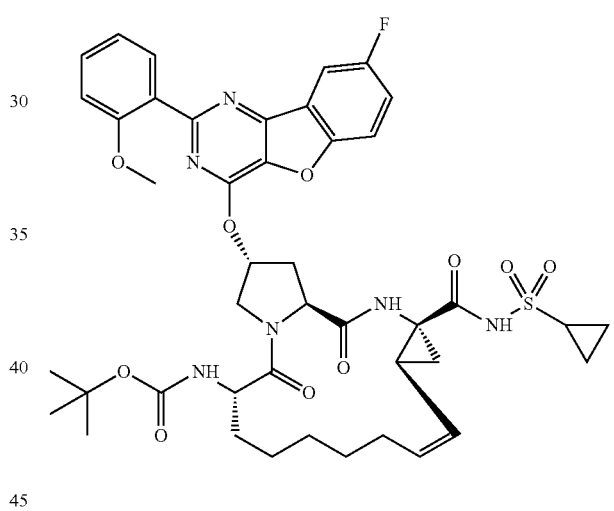
Compound 67
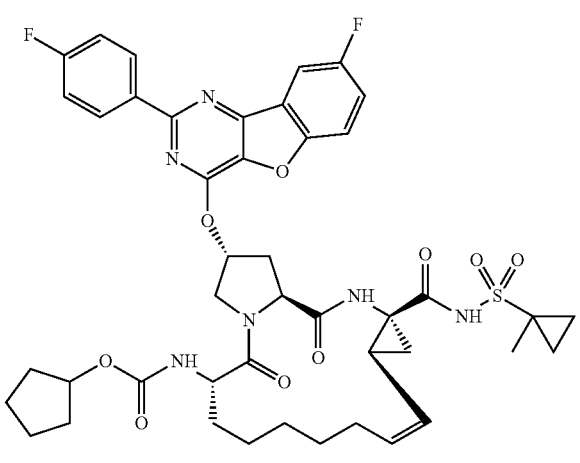
Compound 70
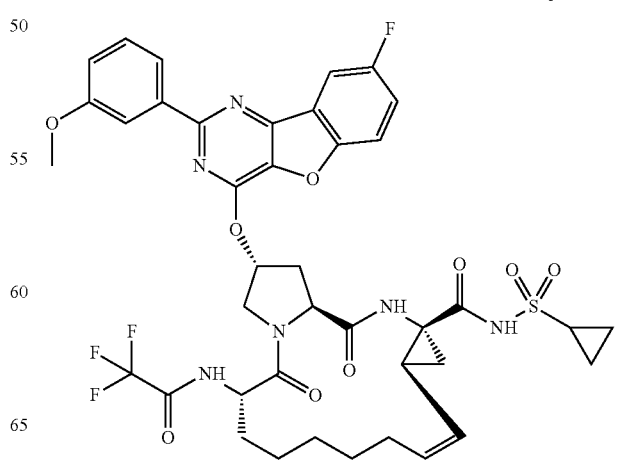

183
-continued
Compound 71
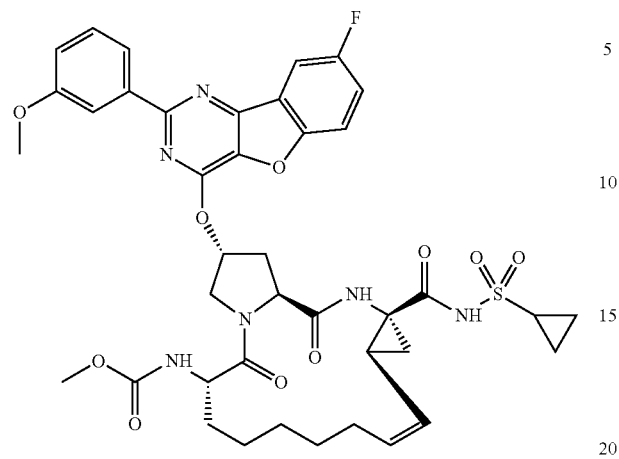
Compound 72
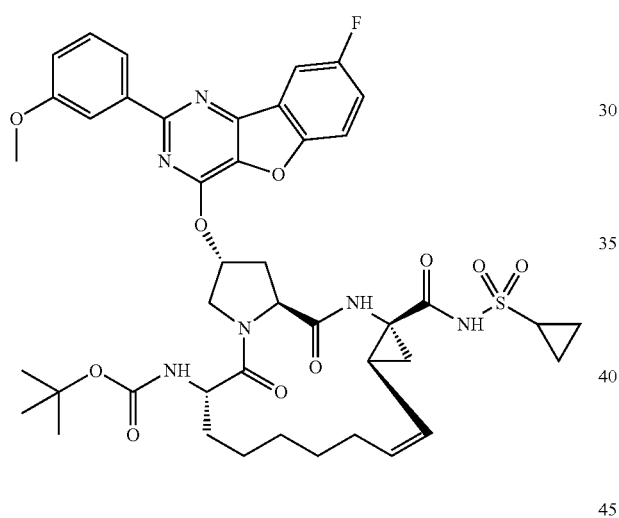
Compound 73
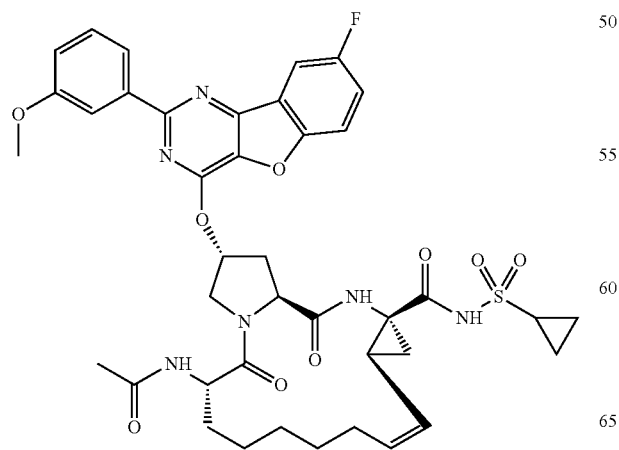
184
-continued
Compound 74
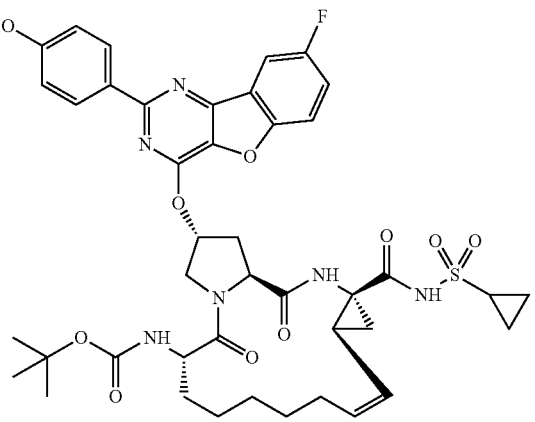
Compound 75
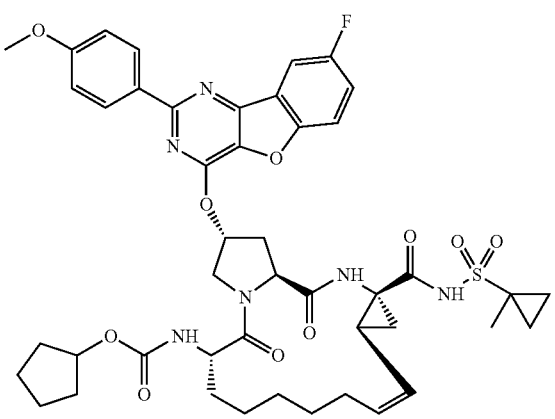
Compound 76
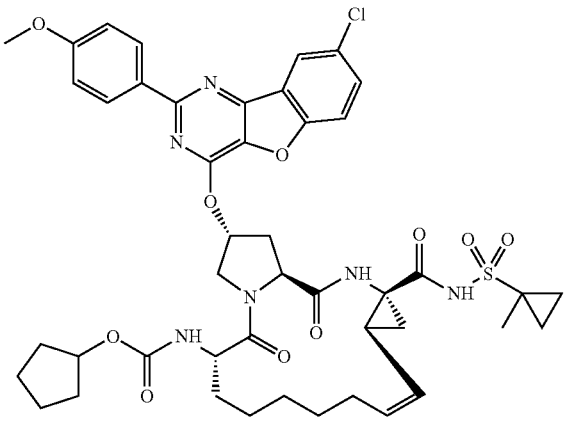

Compound 77
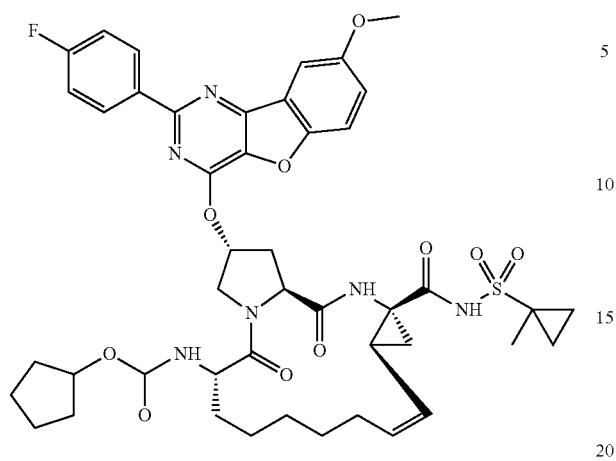
Compound 80
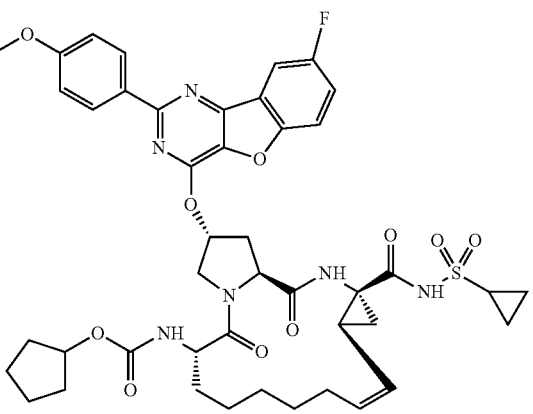
Compound 78
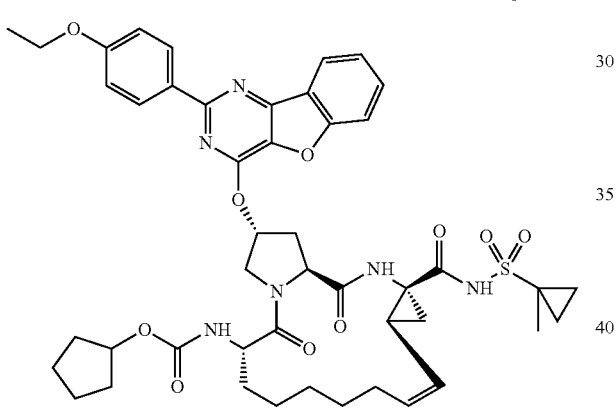
Compound 81
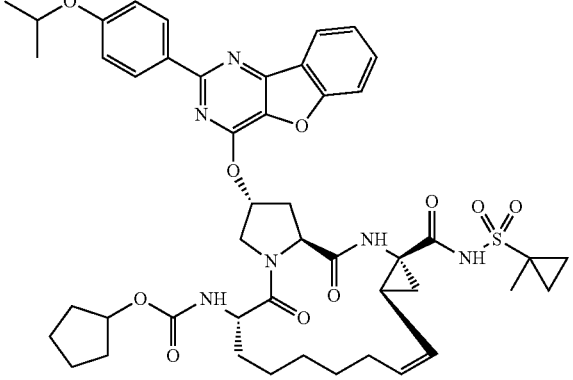
Compound 79
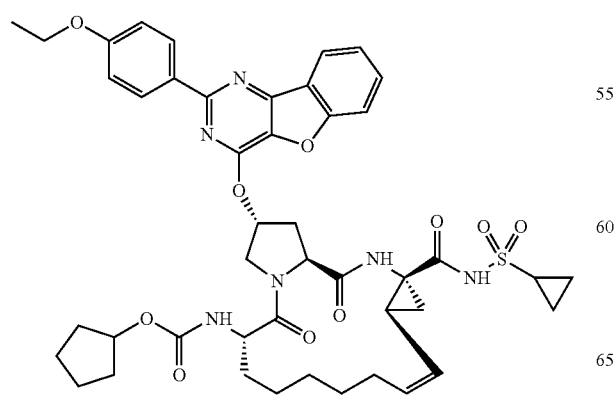
Compound 82
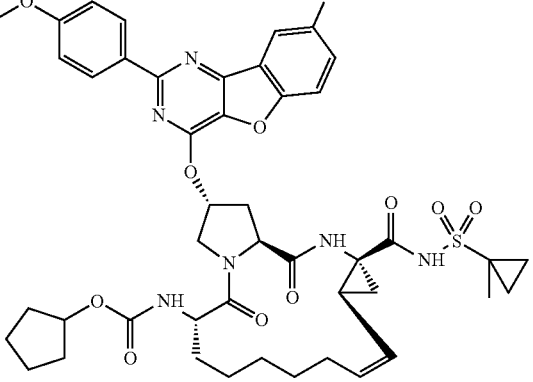

Compound 83
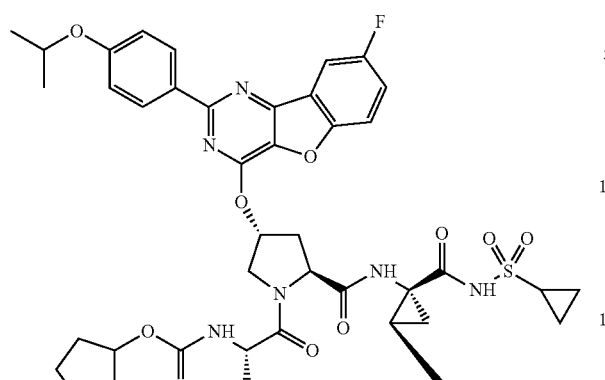
Compound 86
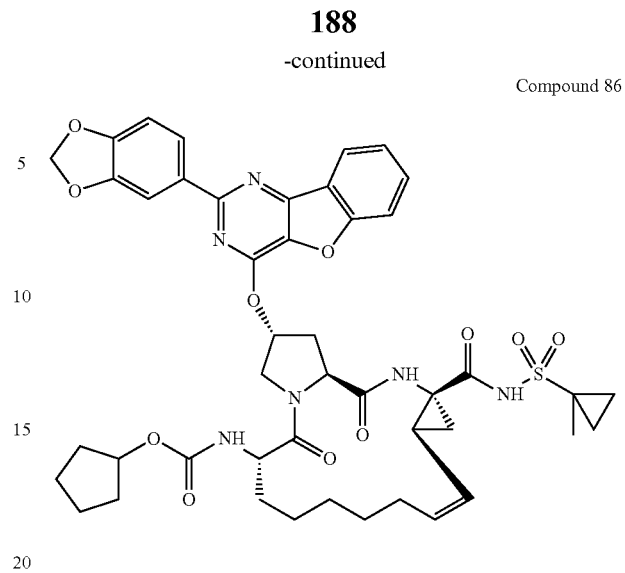
Compound 84
Compound 87
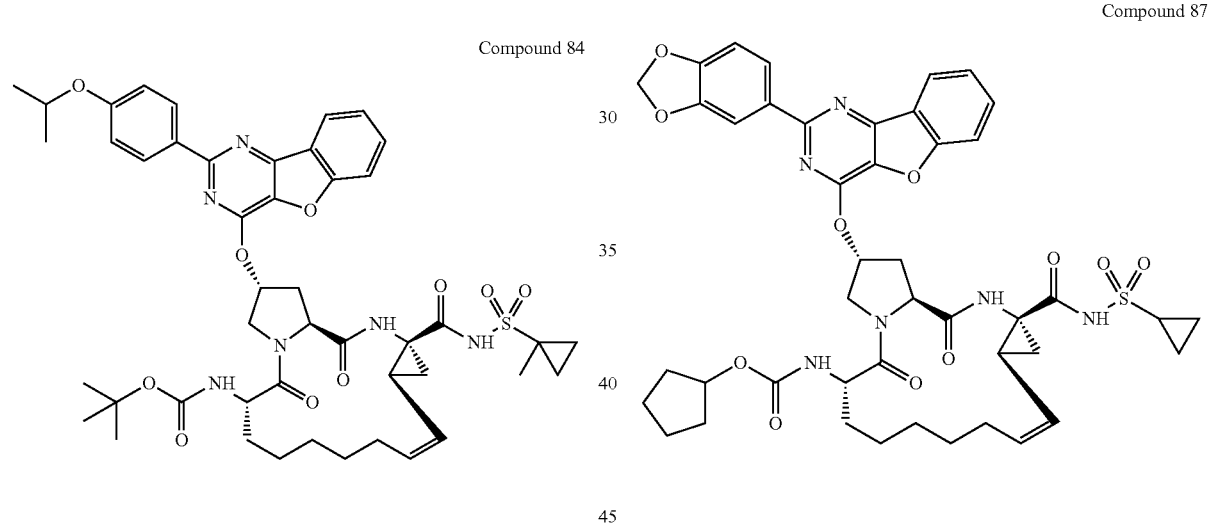
Compound 85
Compound 88
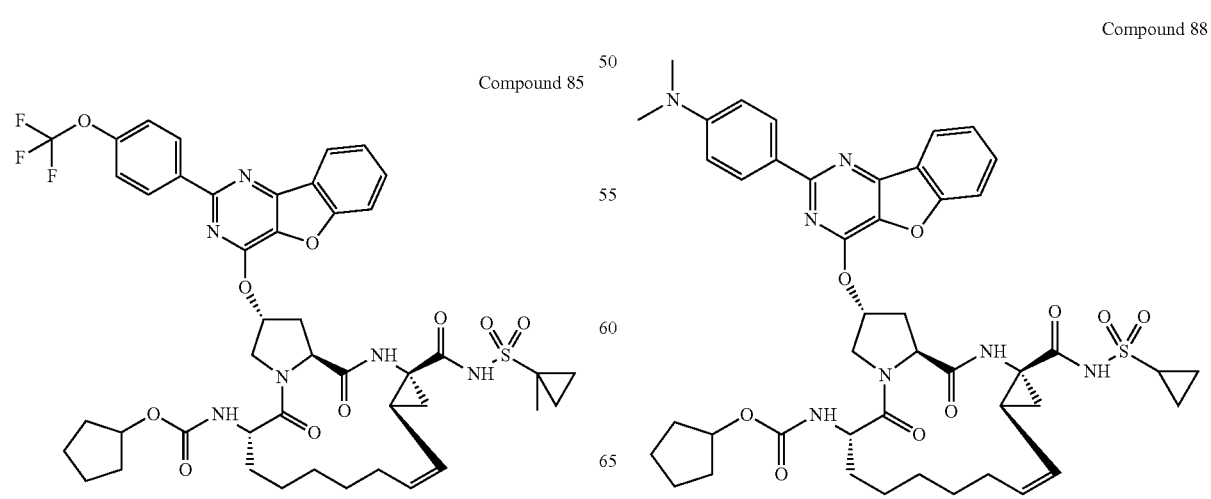

Compound 89
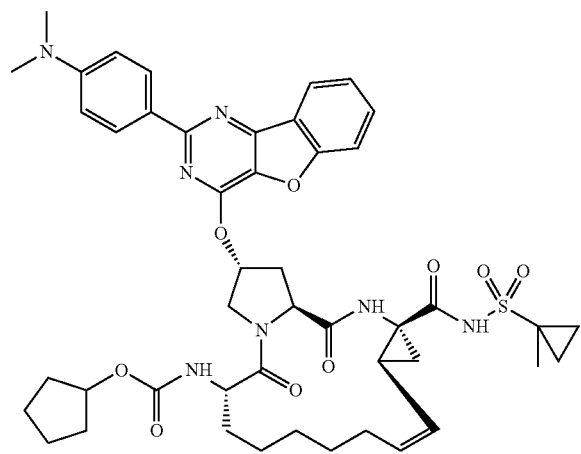
Compound 92
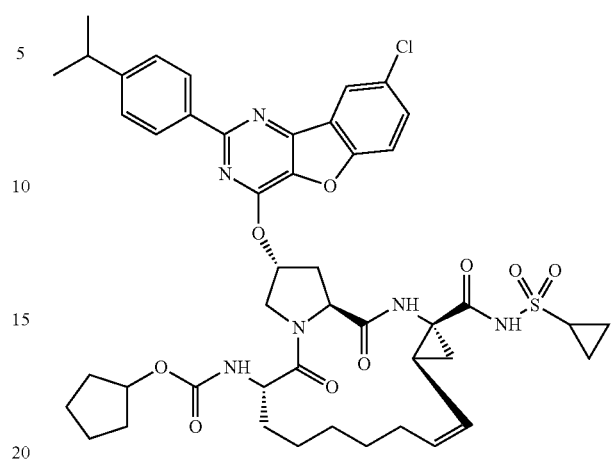
Compound 90
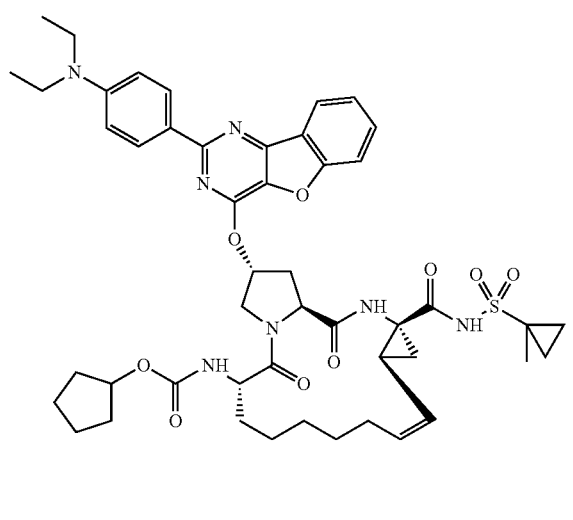
Compound 93
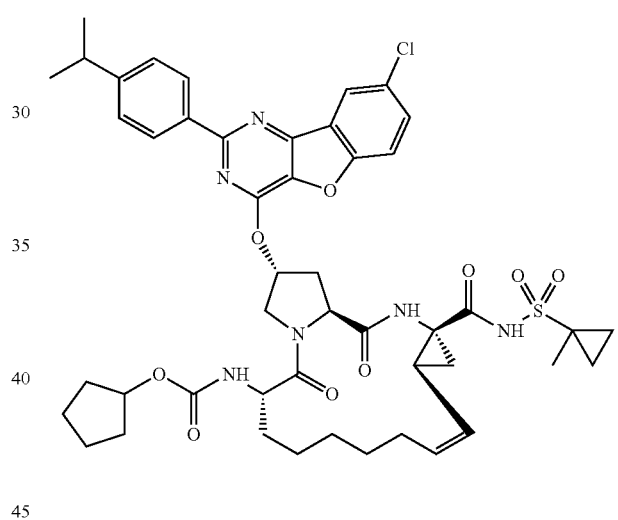
Compound 91
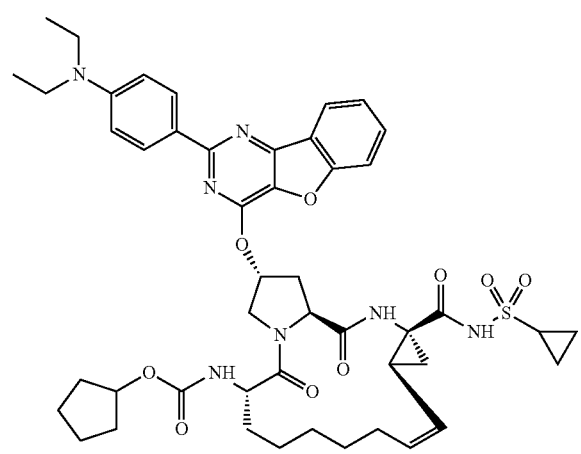
Compound 94
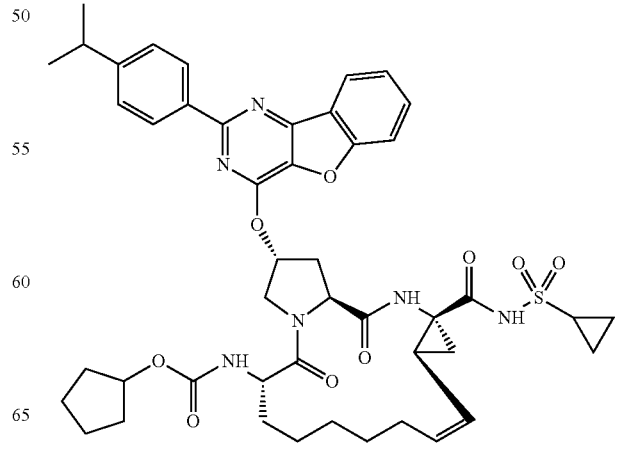

Compound 95
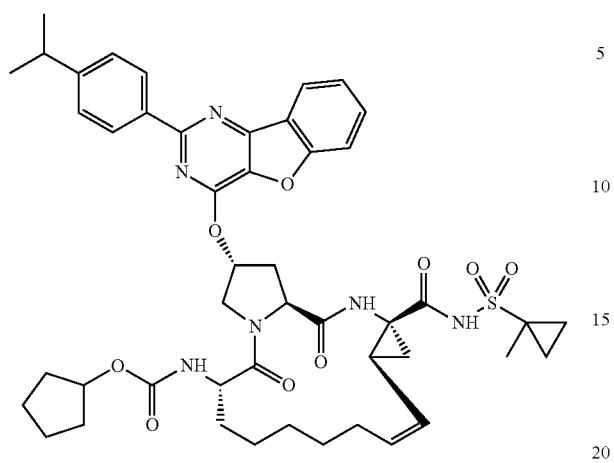
Compound 98
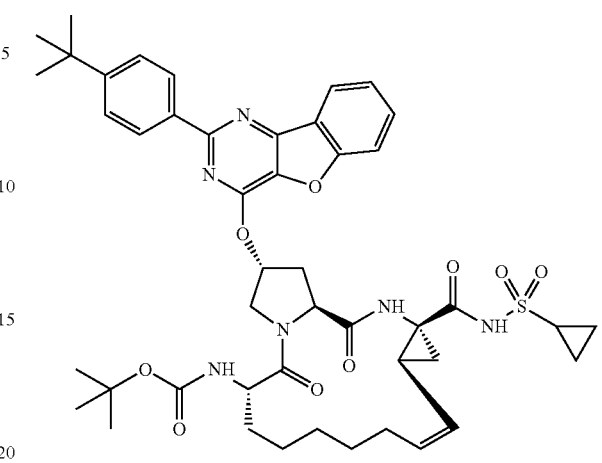
Compound 96
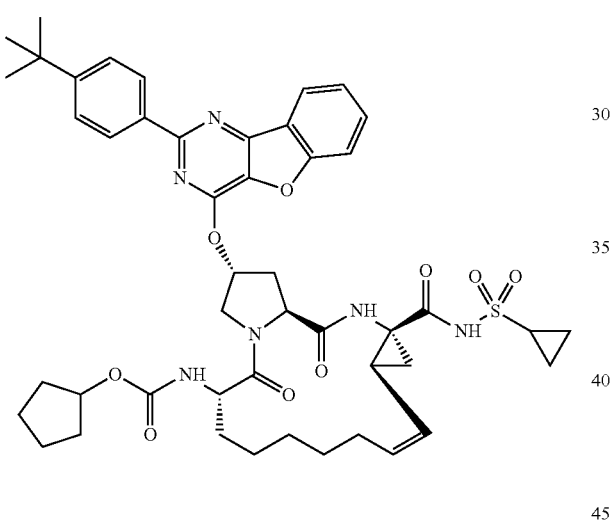
Compound 99
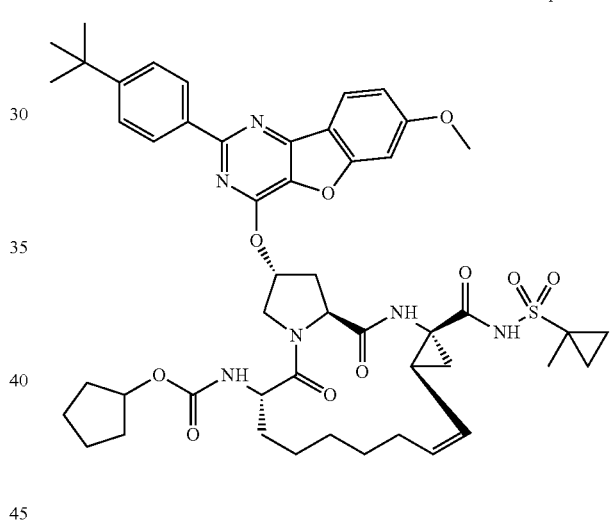
Compound 97
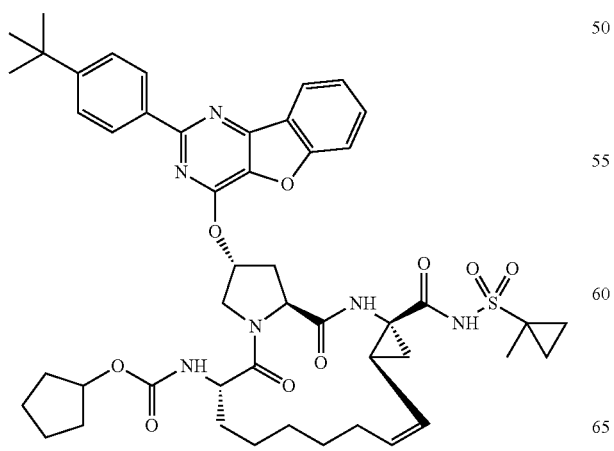
Compound 100
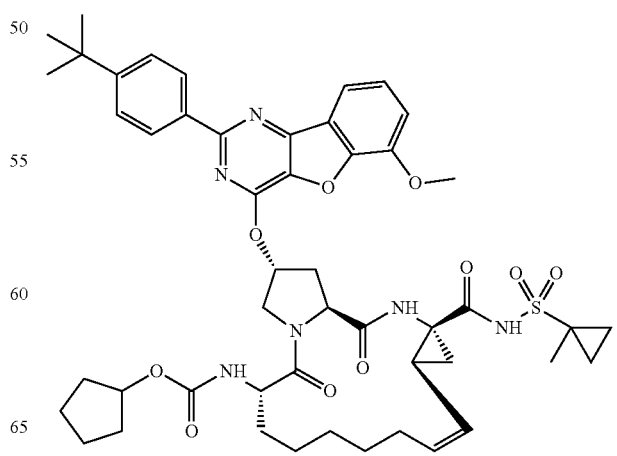

193
-continued
Compound 101
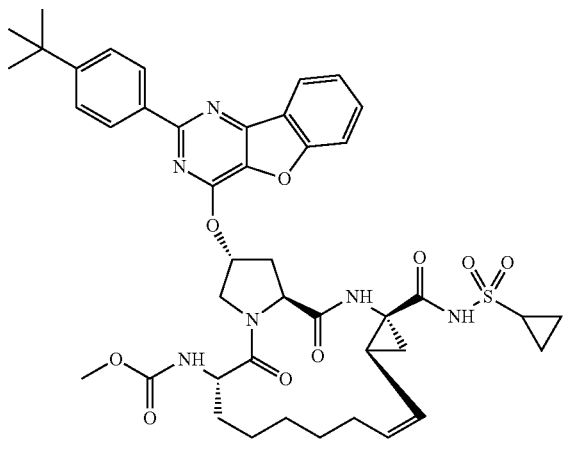
Compound 102
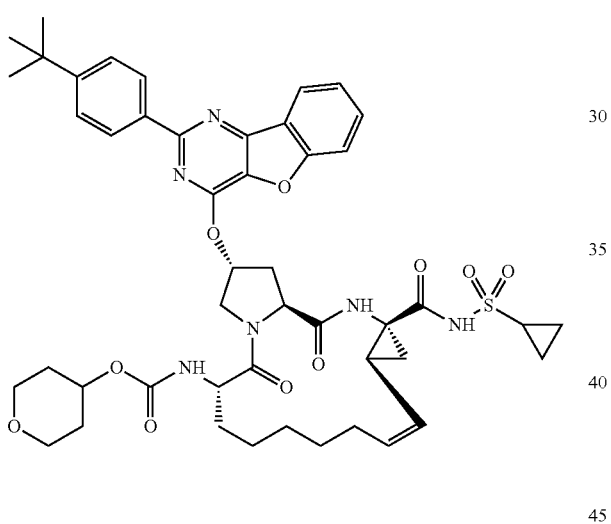
Compound 103
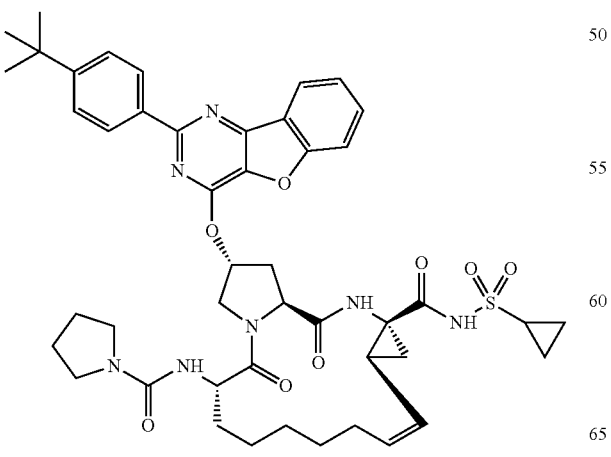
194
-continued
Compound 104
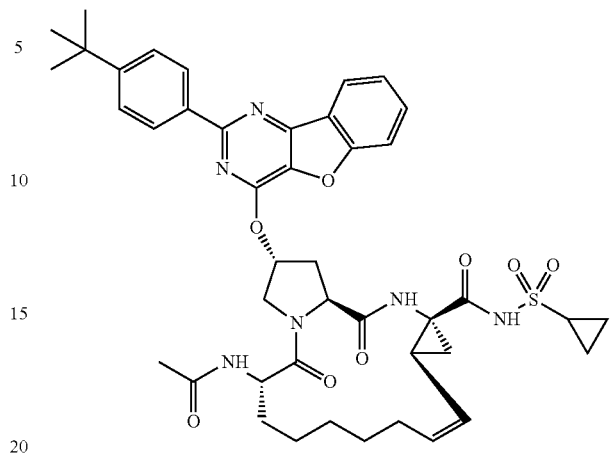
Compound 105
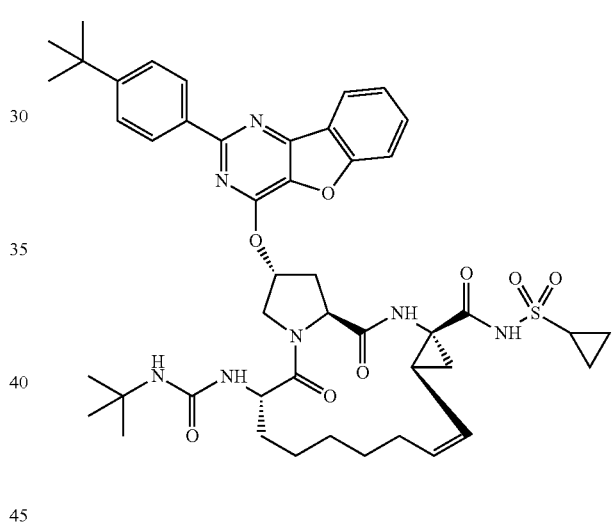
Compound 106
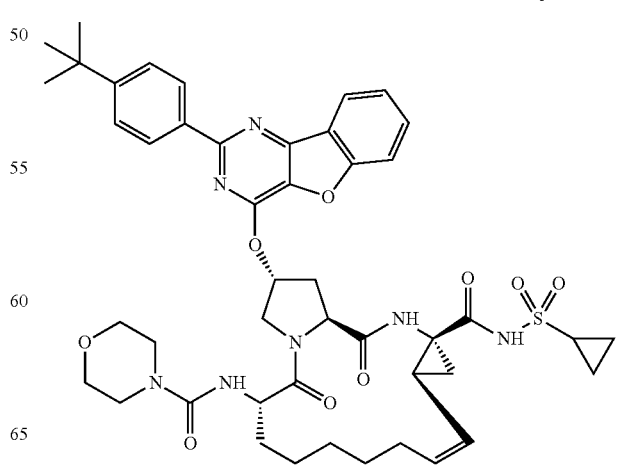

Compound 107
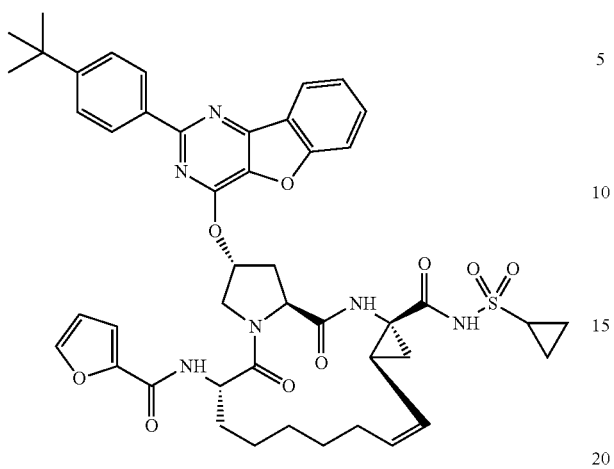
Compound 108
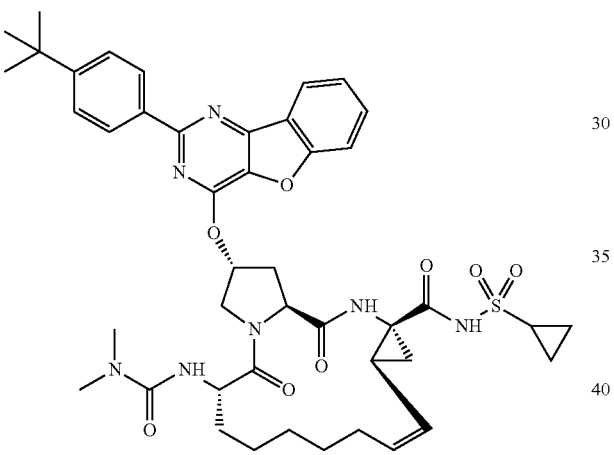
Compound 109
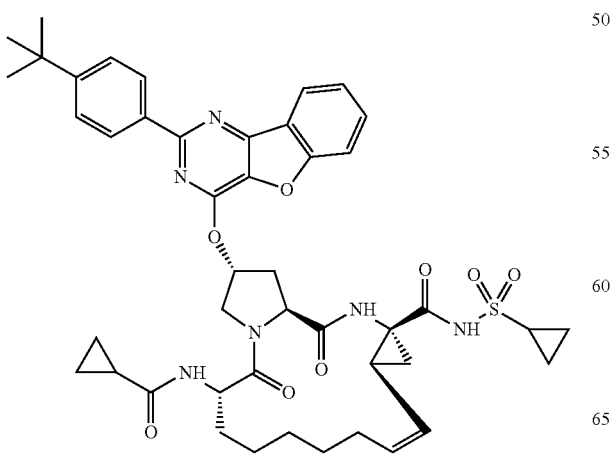
Compound 110
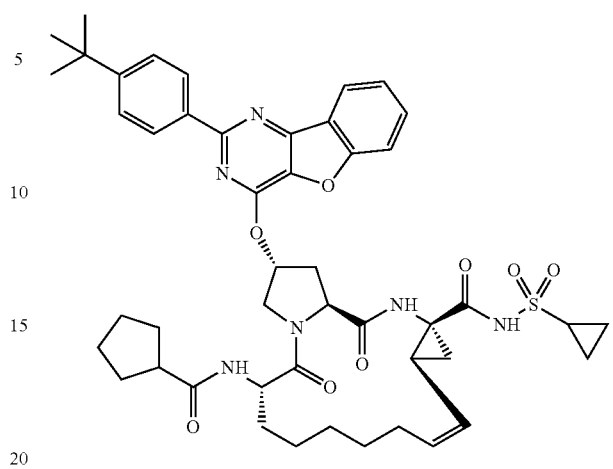
Compound 111
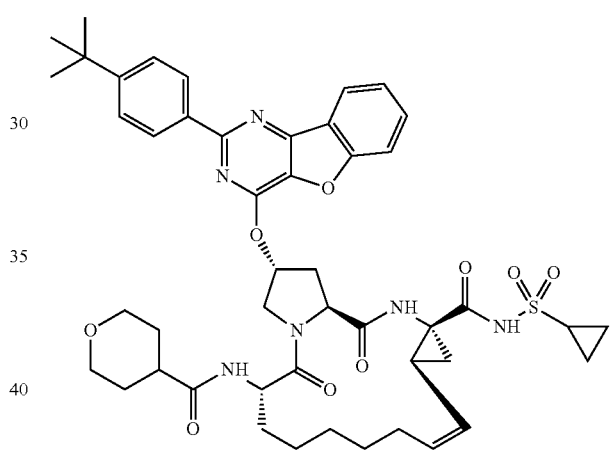
Compound 112
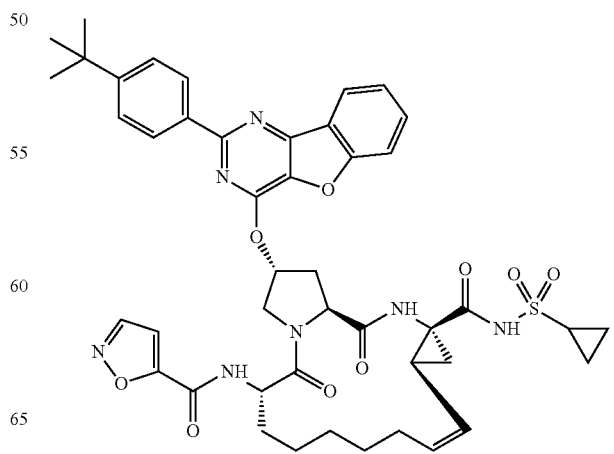

-continued
Compound 113
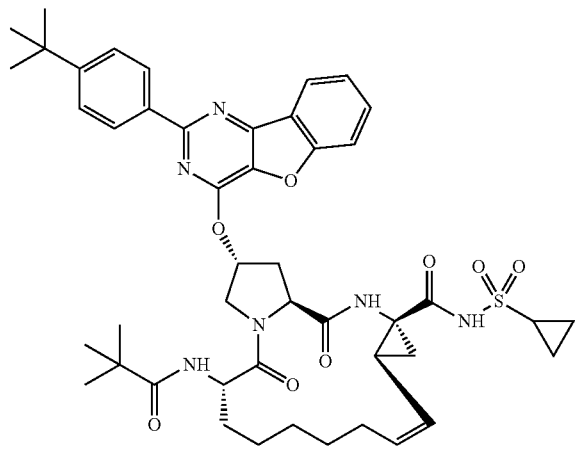
Compound 114
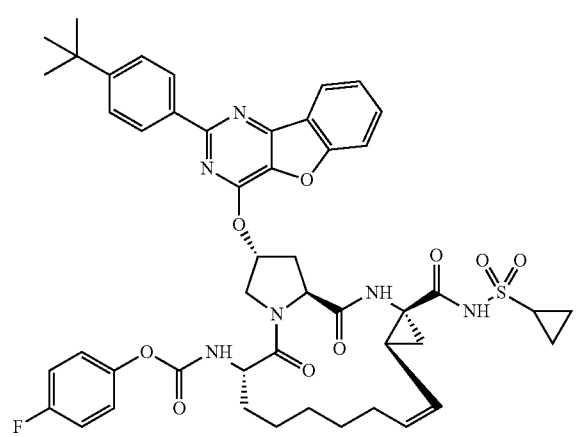
Compound 115
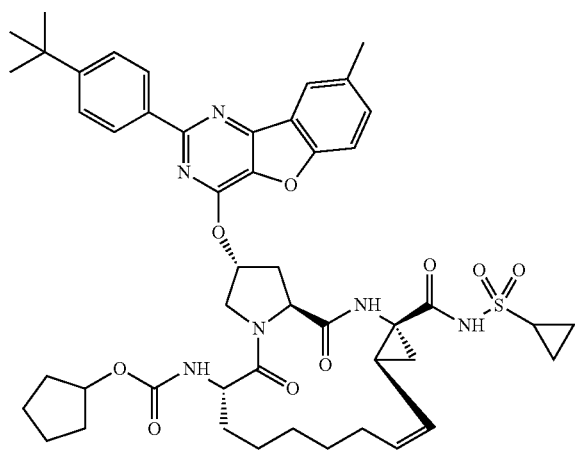
-continued
Compound 116
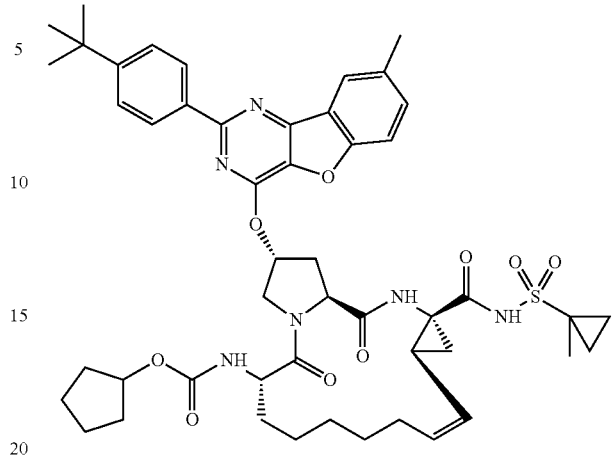
Compound 117
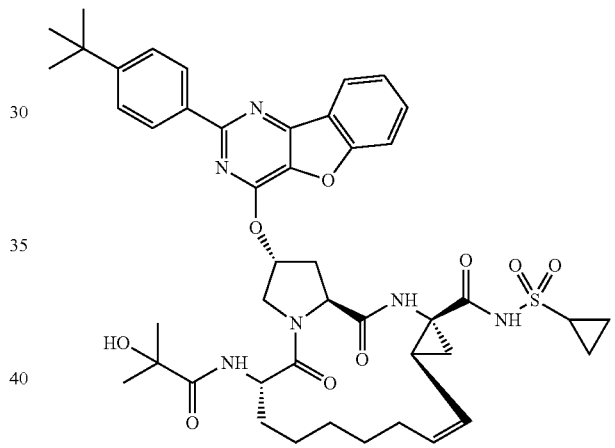
Compound 118
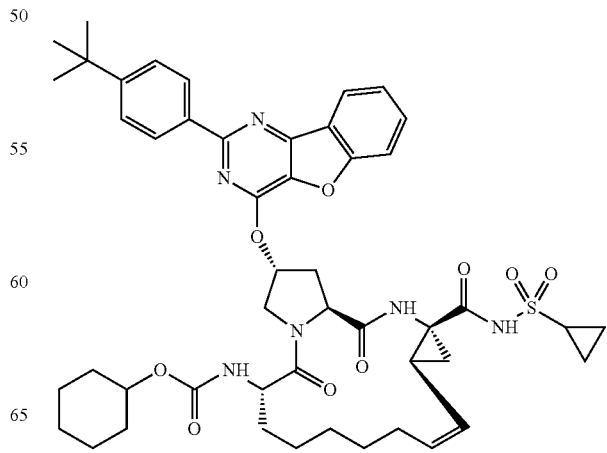

-continued
Compound 119
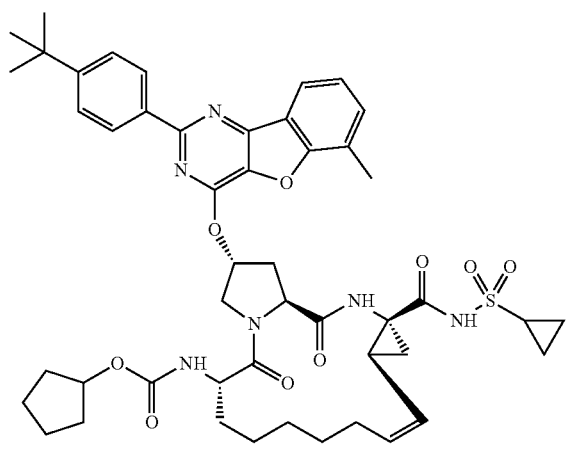
Compound 122
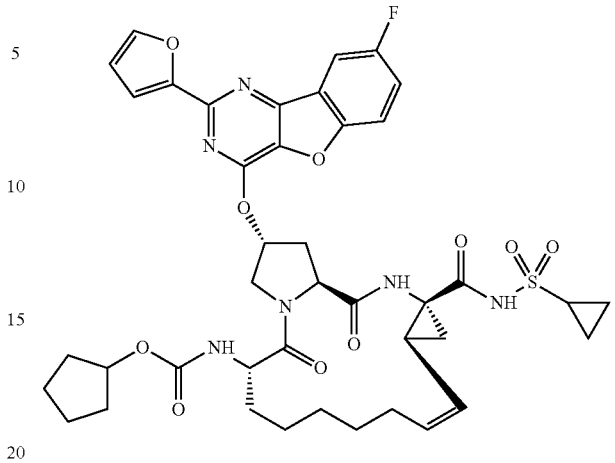
Compound 120
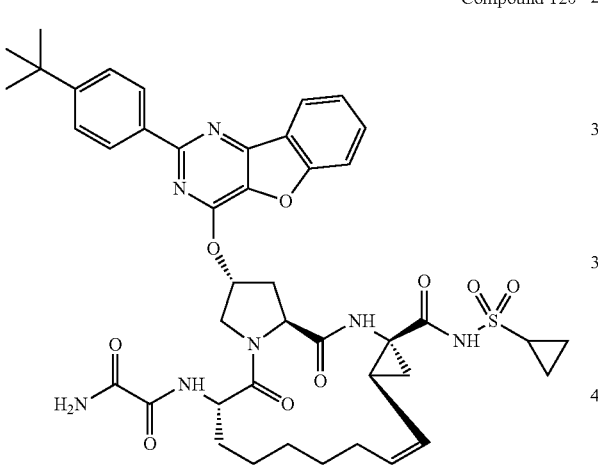
Compound 123
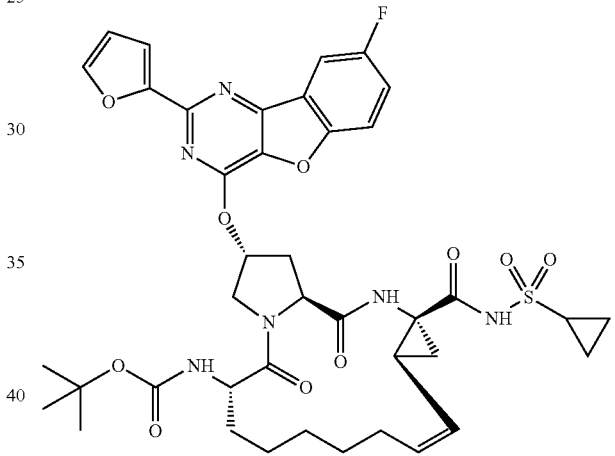
Compound 121
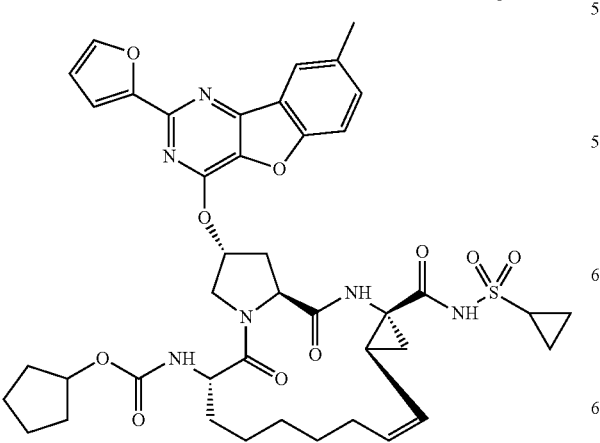
Compound 124
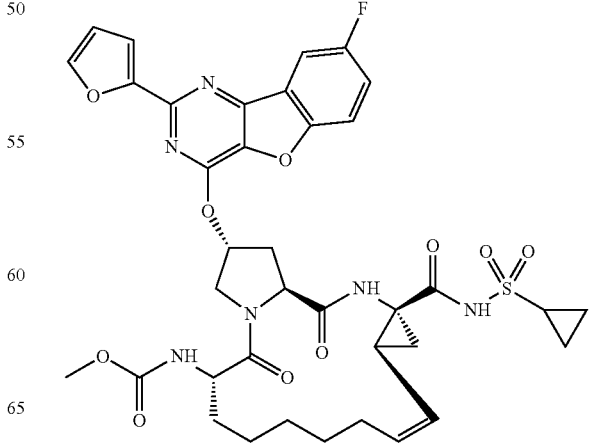

-continued
Compound 125
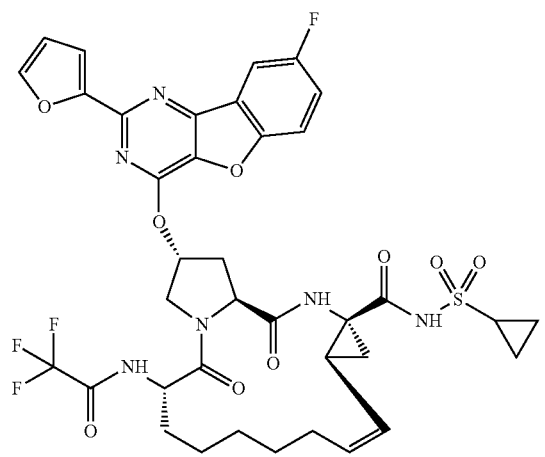
Compound 126
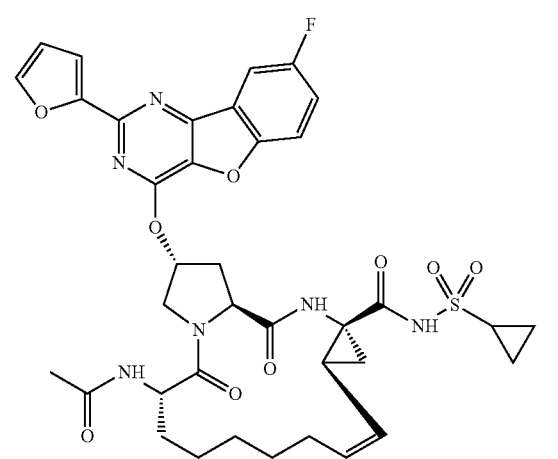
Compound 127
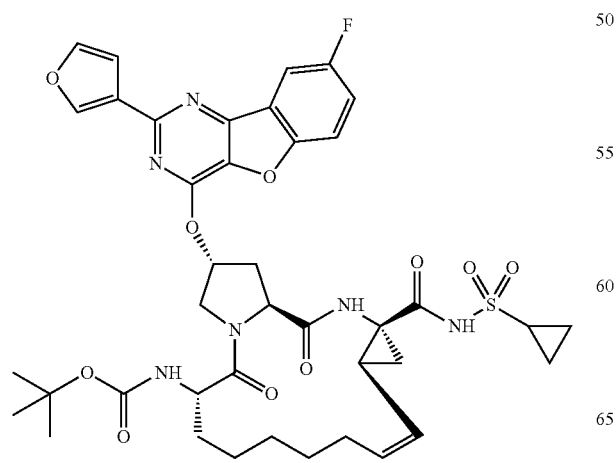
-continued
Compound 128
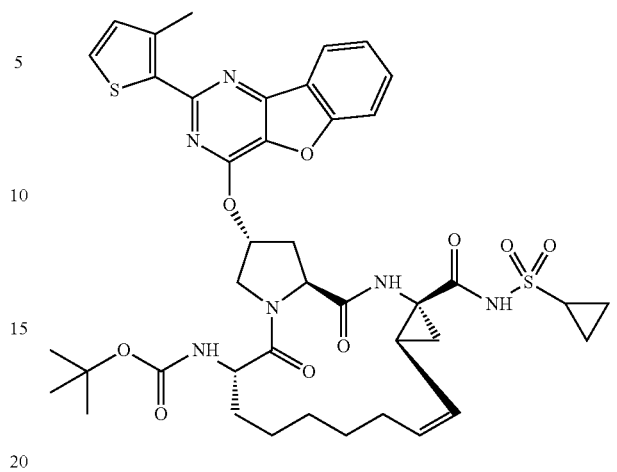
Compound 129
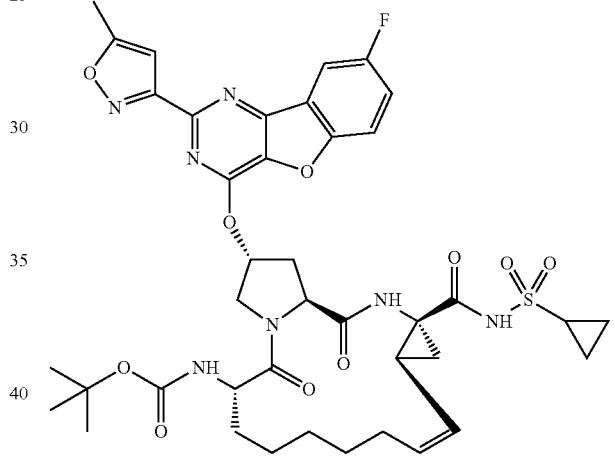
Compound 130
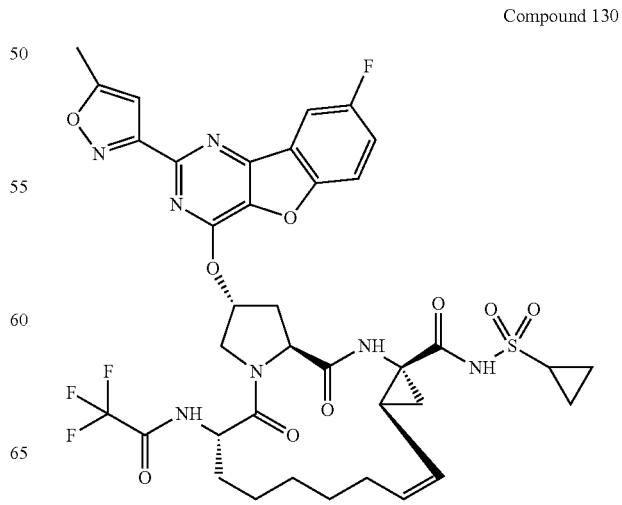

Compound 131
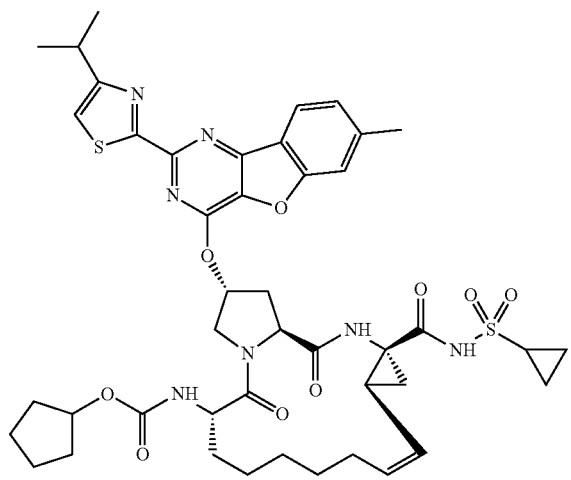
Compound 132
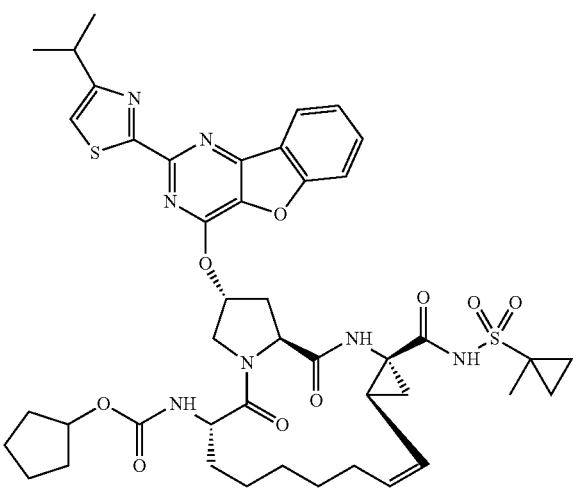
Compound 133
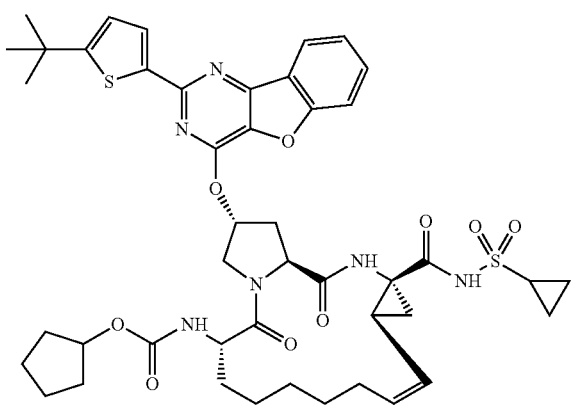
Compound 134
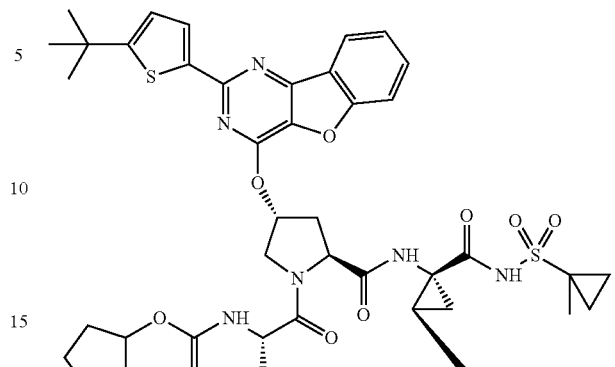
Compound 135
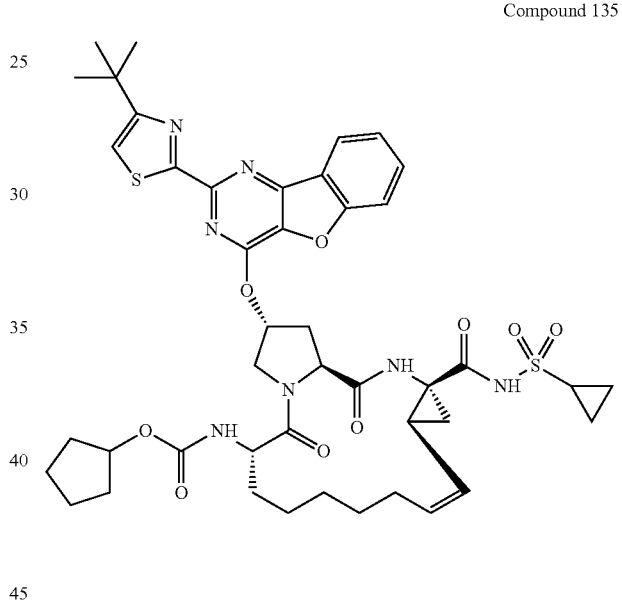
Compound 136
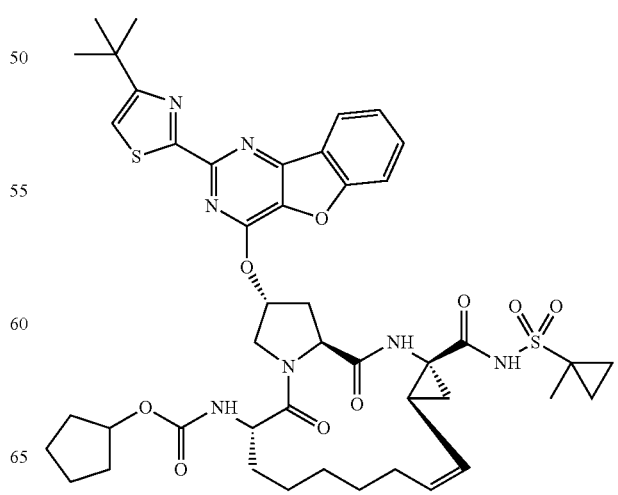

Compound 137
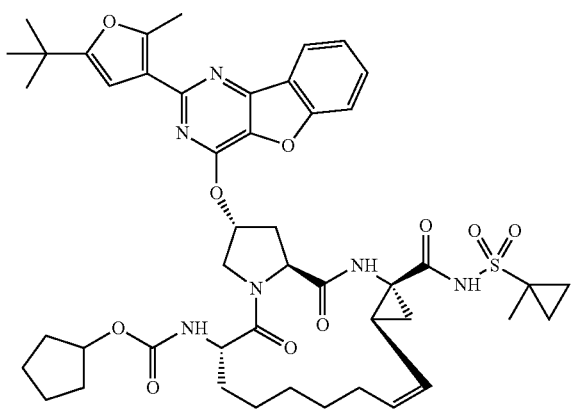
Compound 138
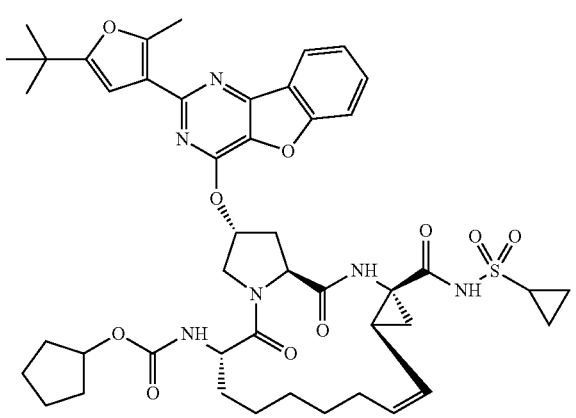
Compound 139
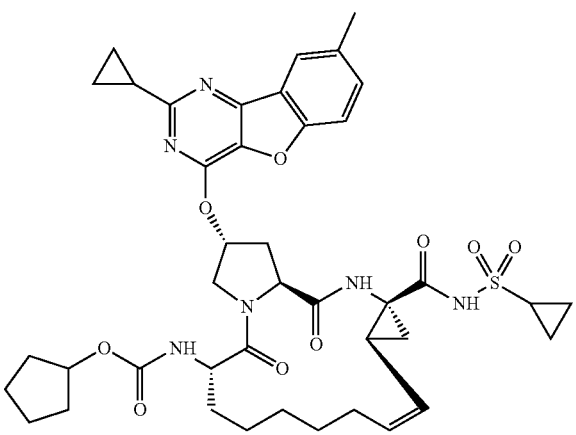
Compound 140
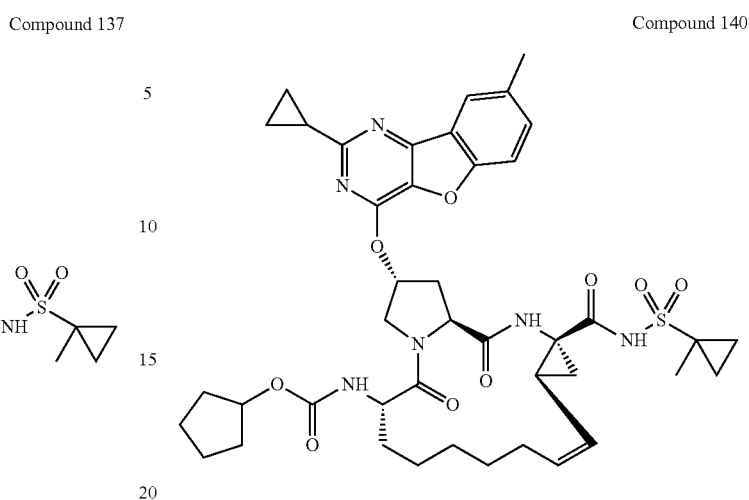
Compound 141
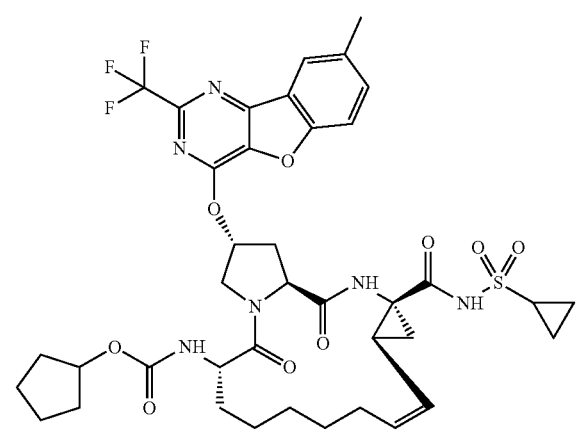
Compound 142
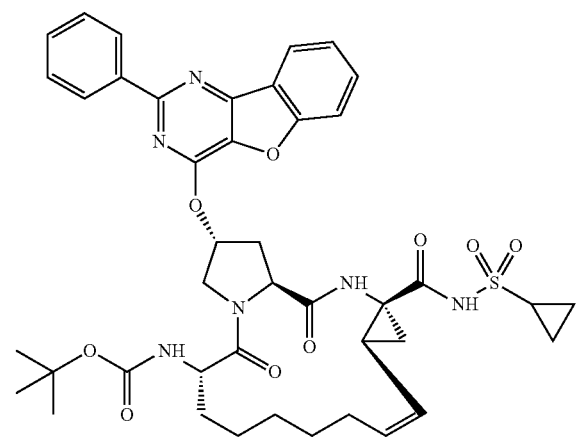

Compound 143
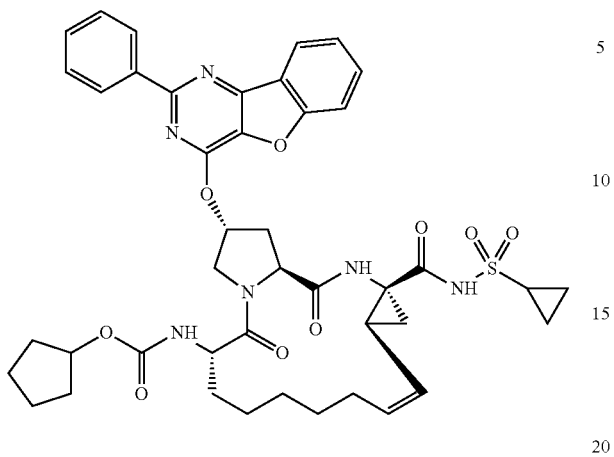
Compound 144
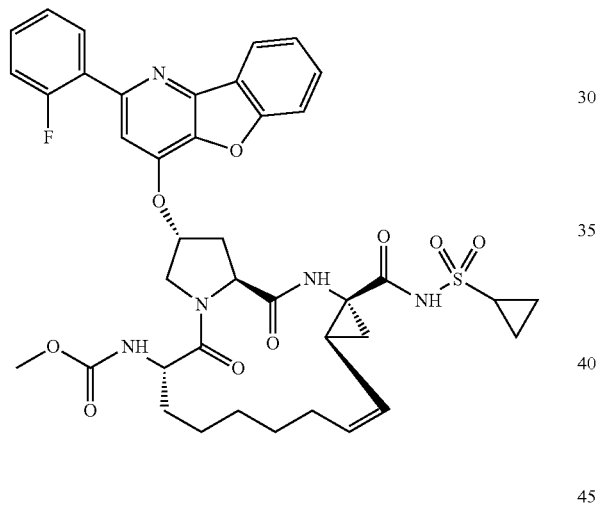
Compound 145
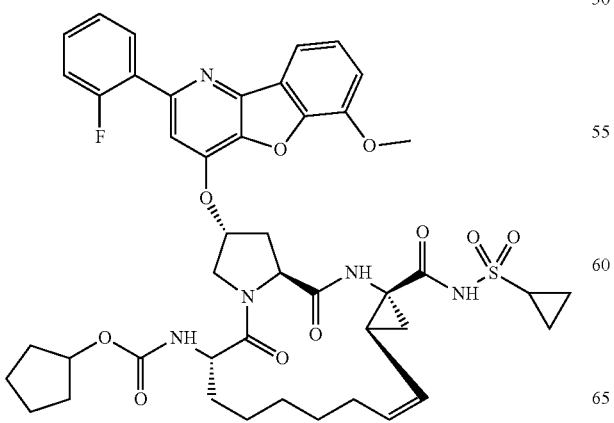
Compound 146
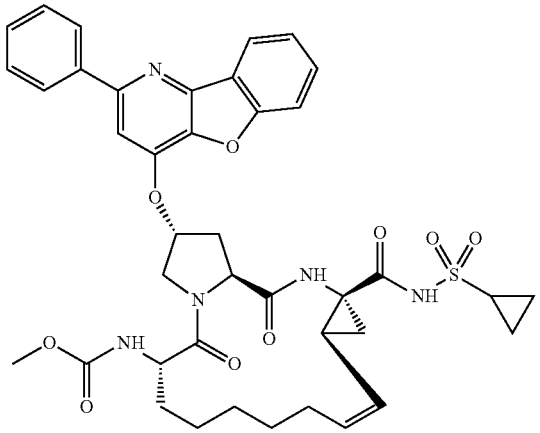
Compound 147
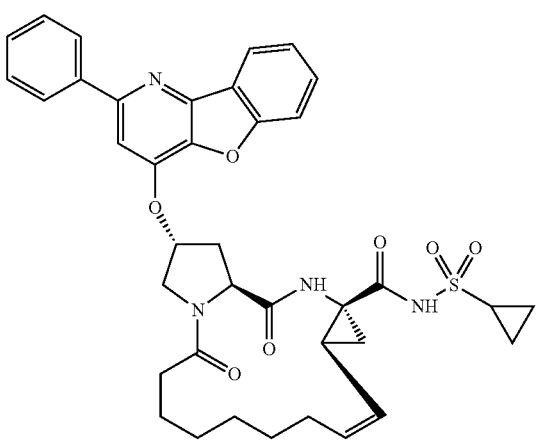
Compound 148
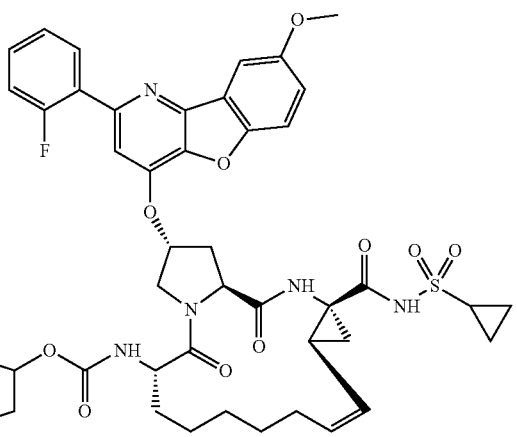

Compound 149
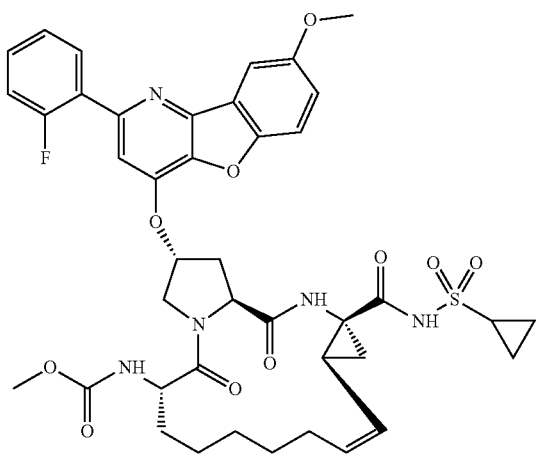
Compound 152
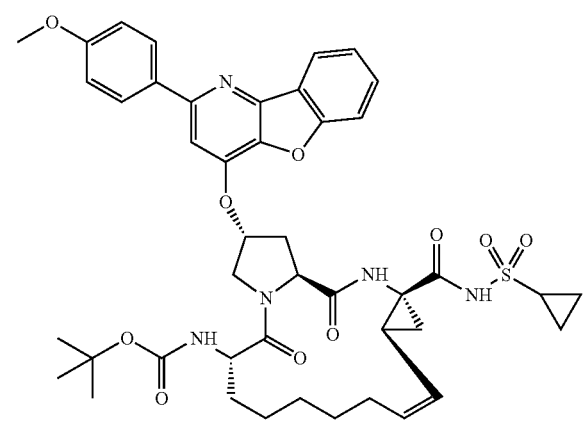
Compound 150
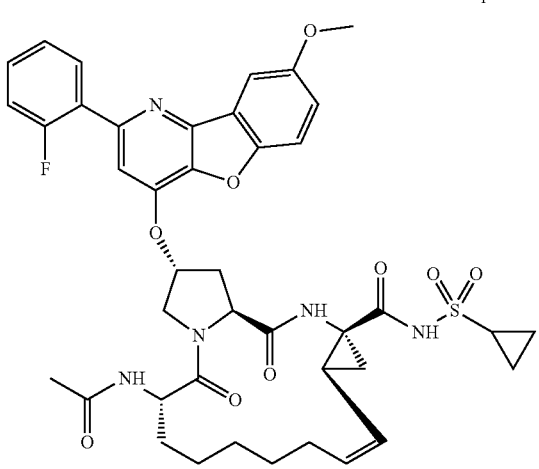
Compound 153
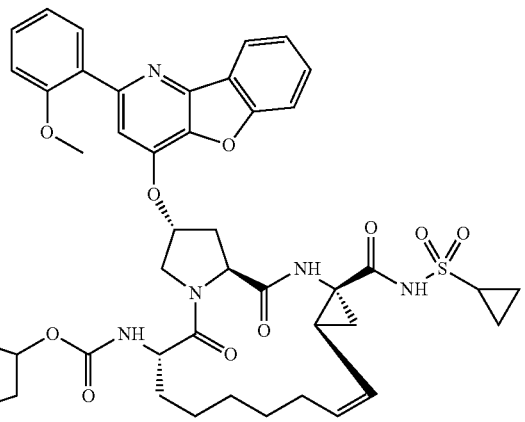
Compound 151
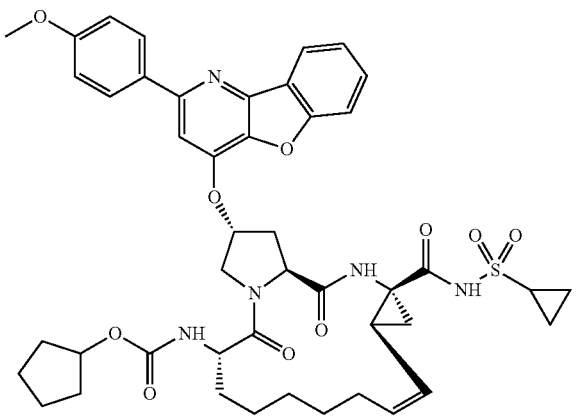
Compound 154
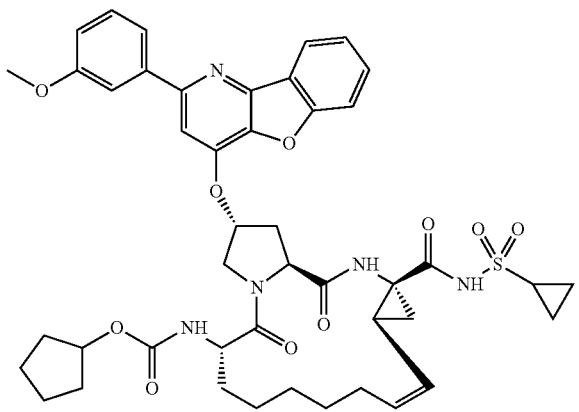

Compound 155
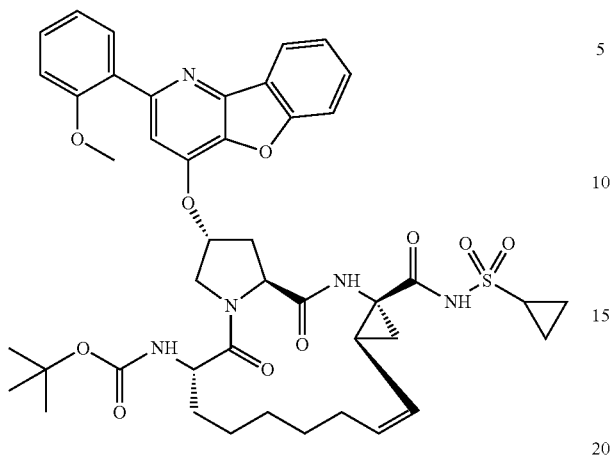
Compound 156
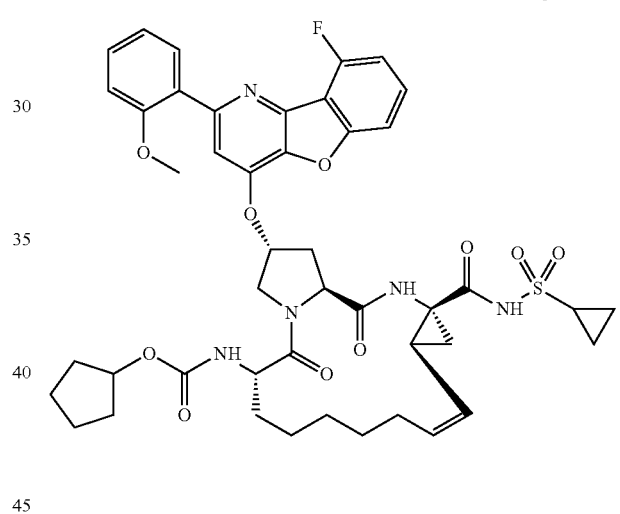
Compound 157
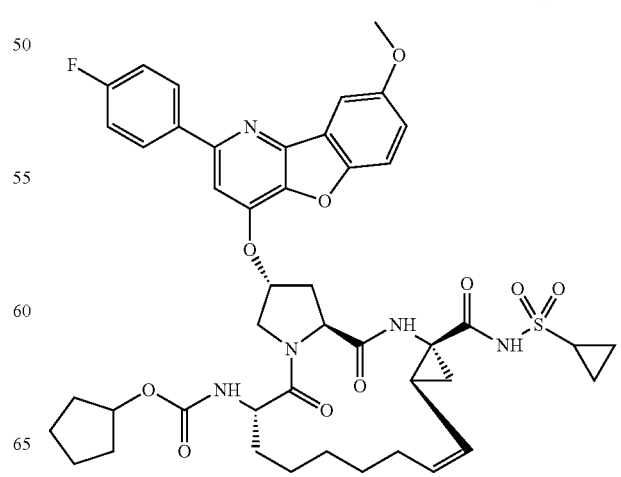
Compound 158
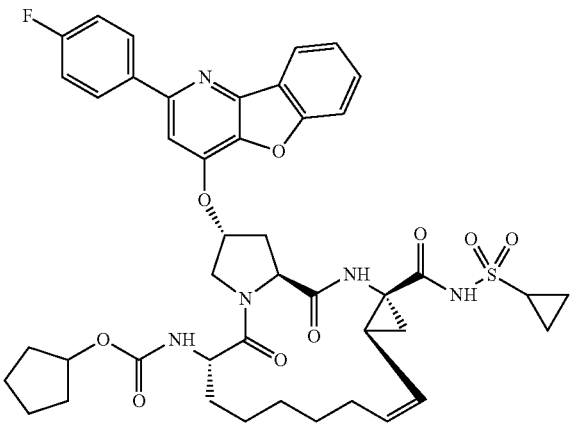
Compound 159
Compound 160

Compound 161
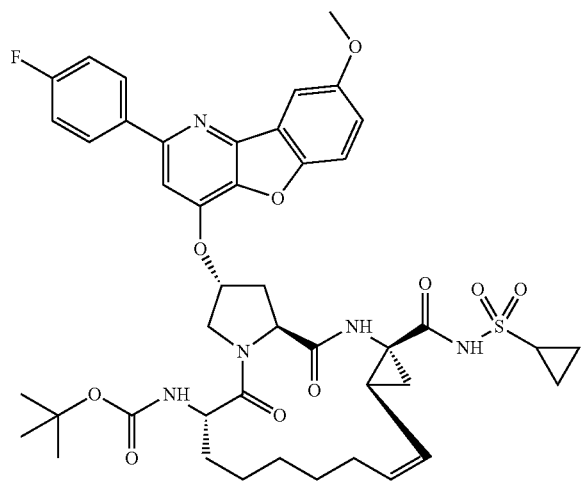
Compound 164
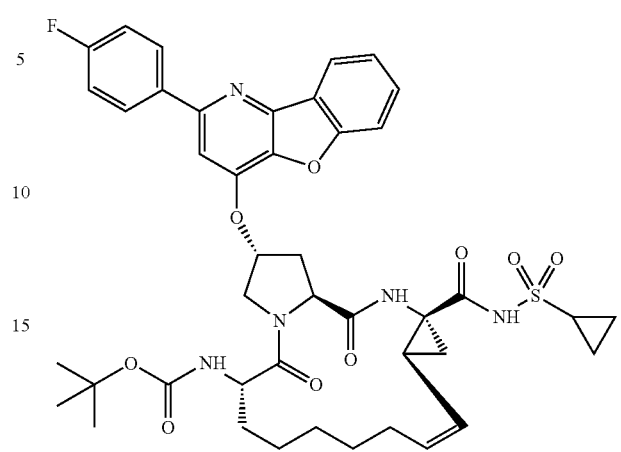
Compound 162
Compound 165
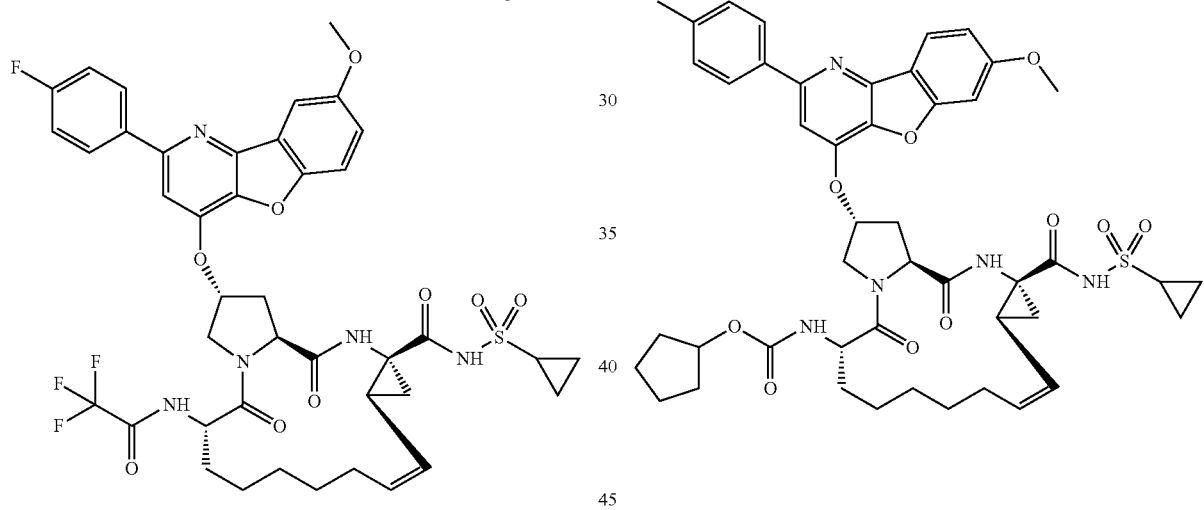
Compound 163
Compound 166
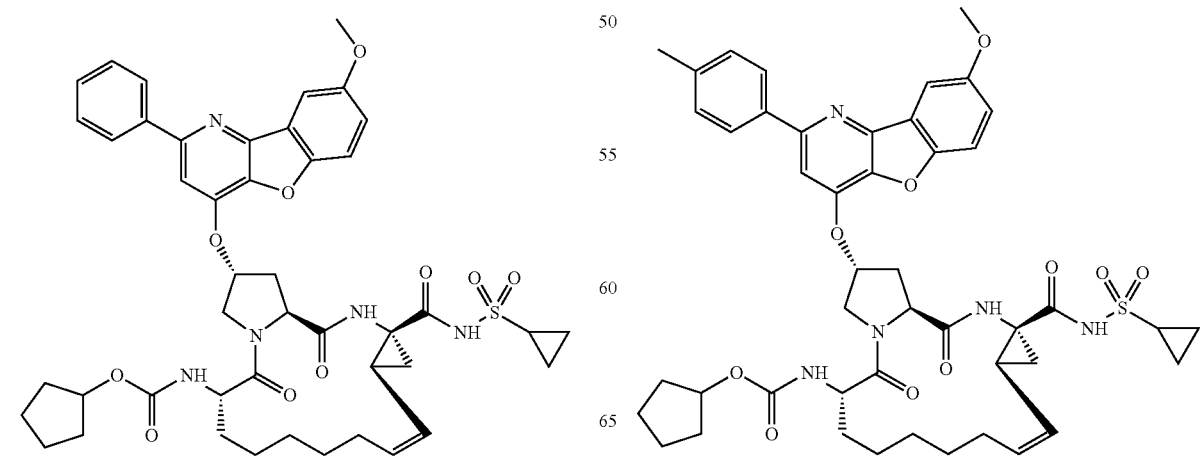

Compound 167
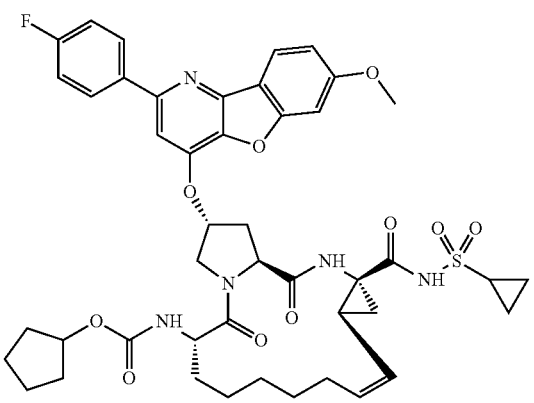
Compound 170
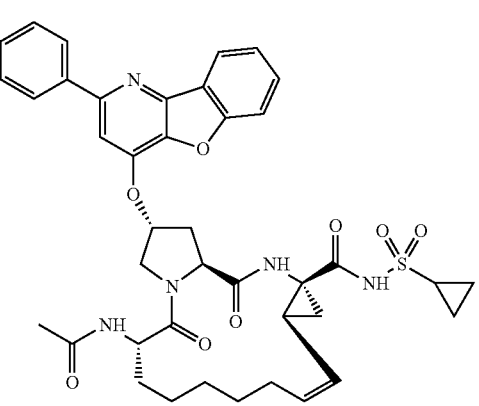
Compound 168
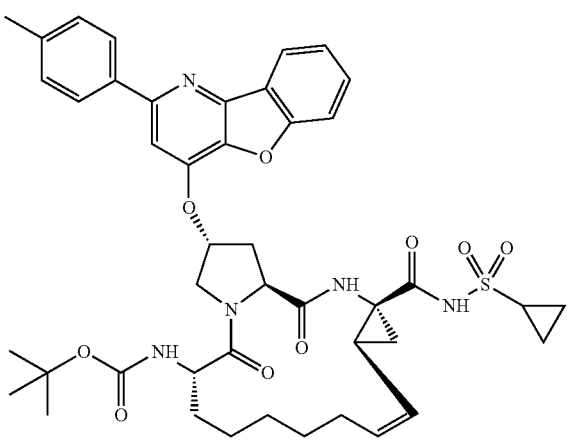
Compound 171
Compound 169
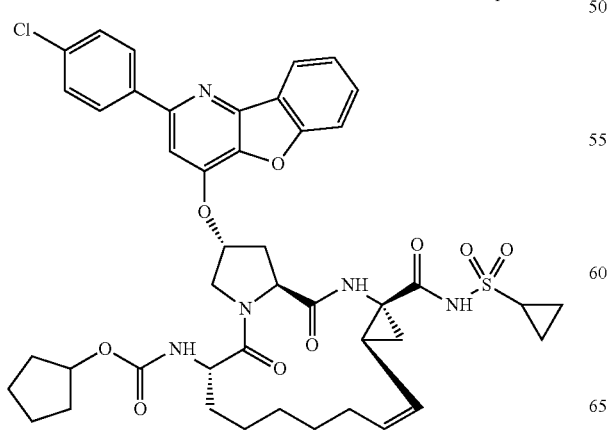
Compound 172

217
-continued
Compound 173
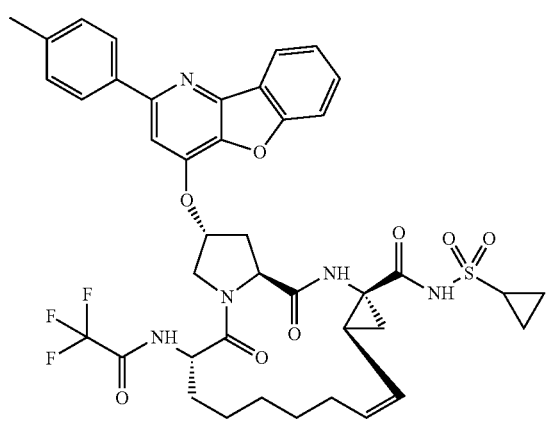
Compound 174
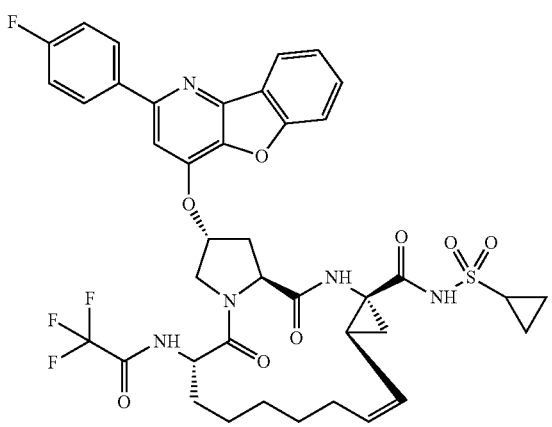
Compound 175
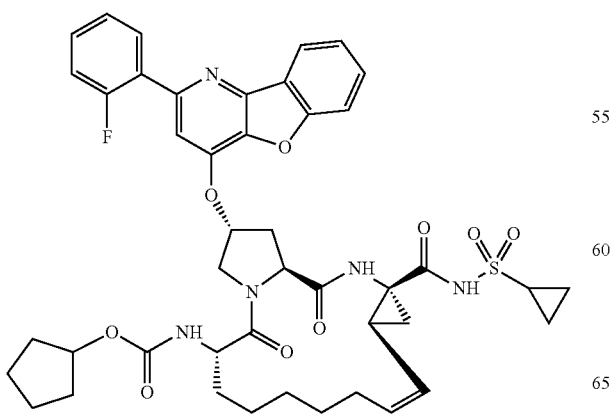
218
-continued
Compound 176
Compound 177
Compound 178
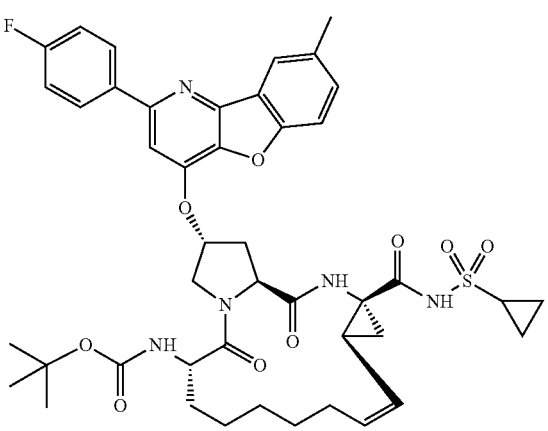

Compound 179
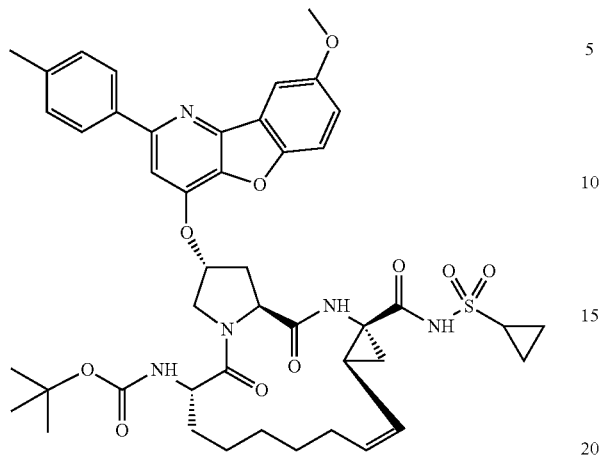
Compound 182
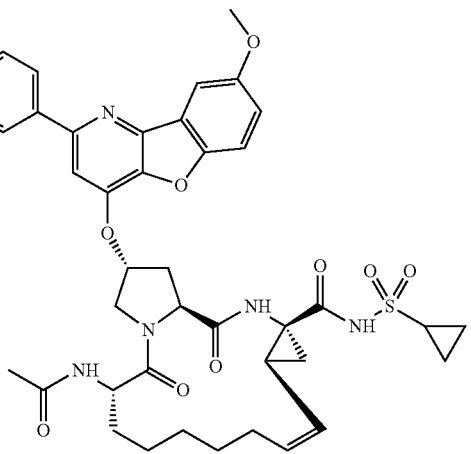
Compound 180
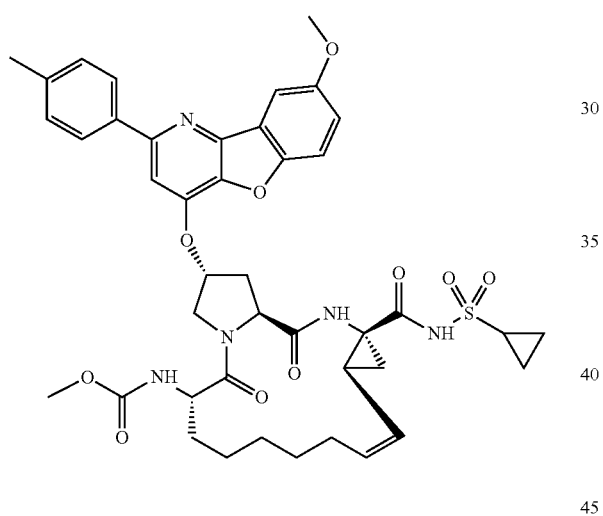
Compound 183
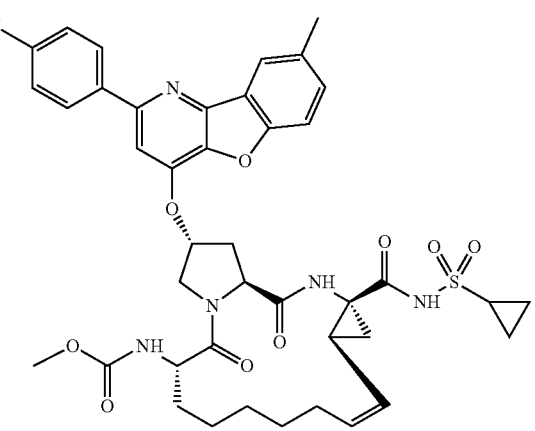
Compound 181
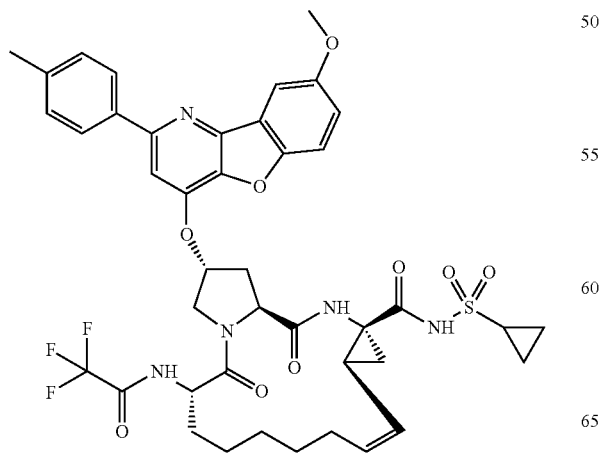
Compound 184
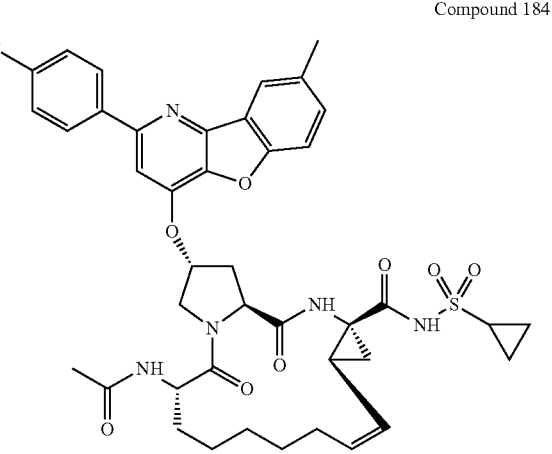

221
-continued
Compound 185
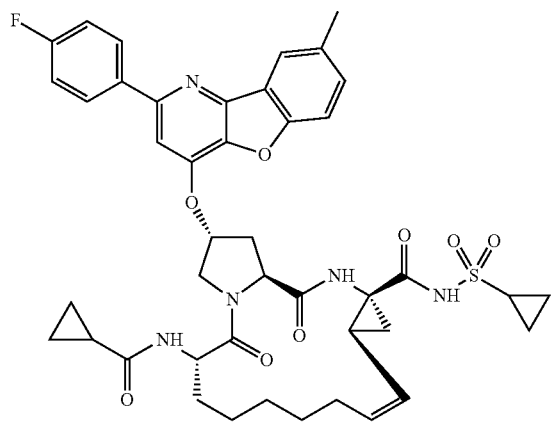
Compound 186
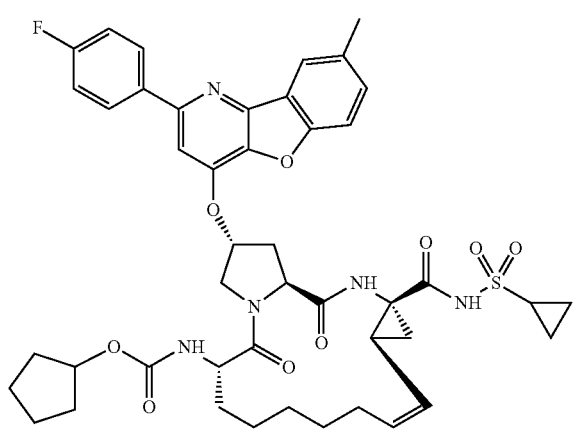
Compound 187
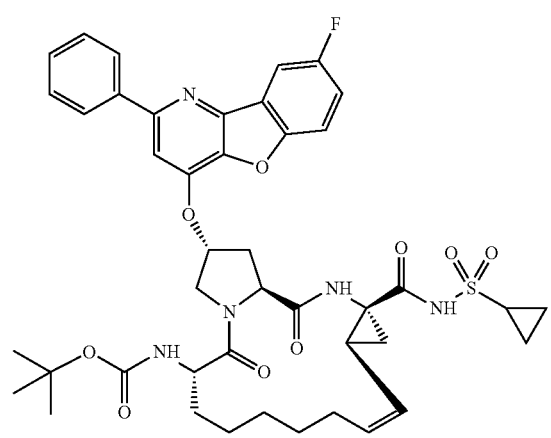
222
-continued
Compound 188
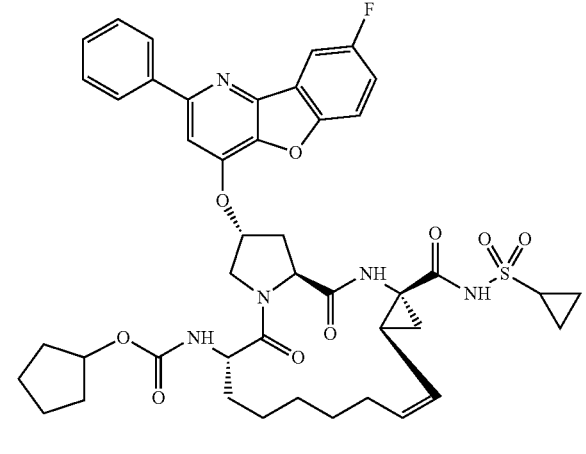
Compound 189
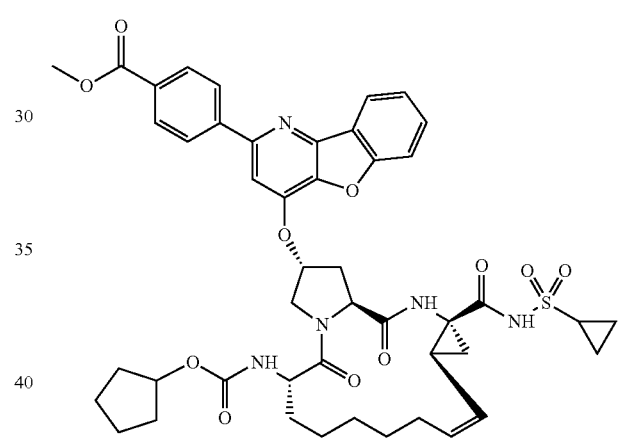
Compound 190
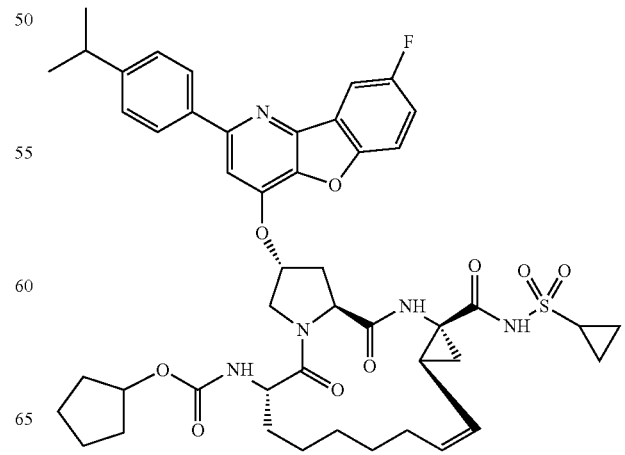

Compound 191
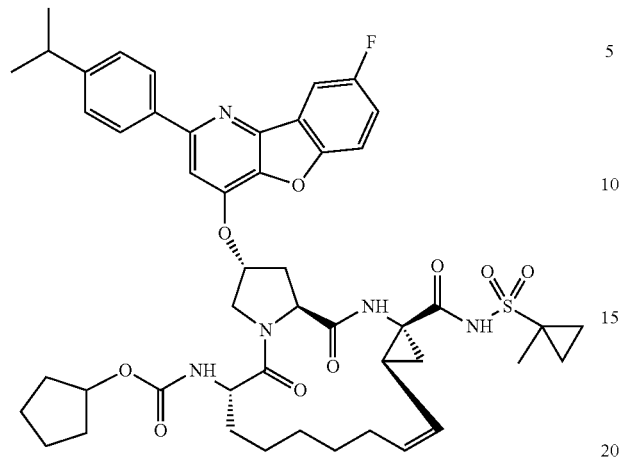
Compound 194
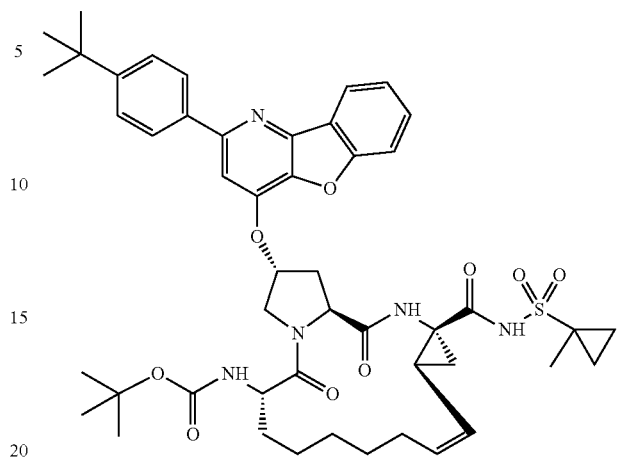
Compound 192
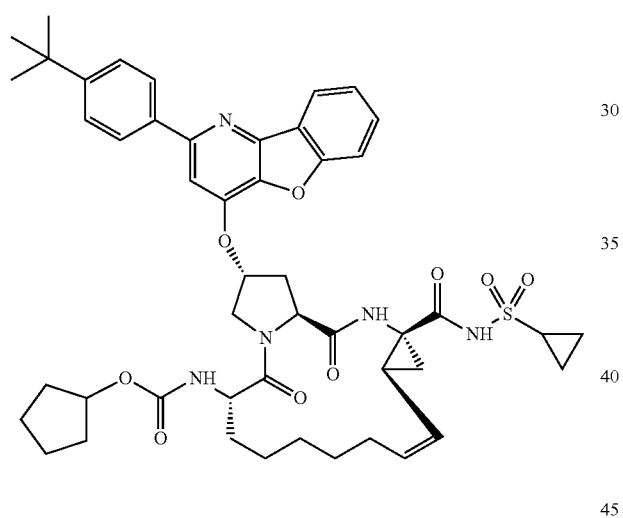
Compound 195
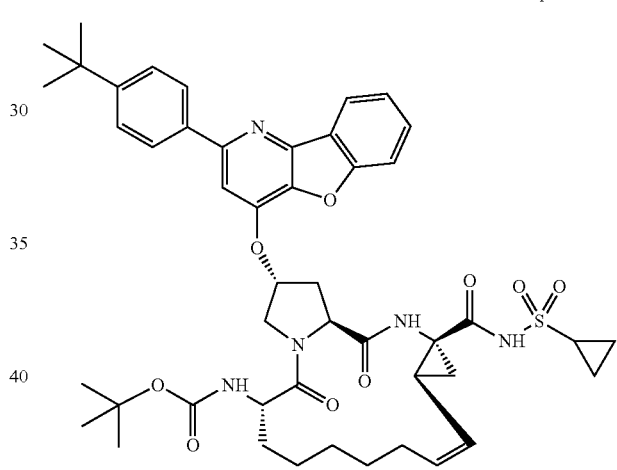
Compound 193
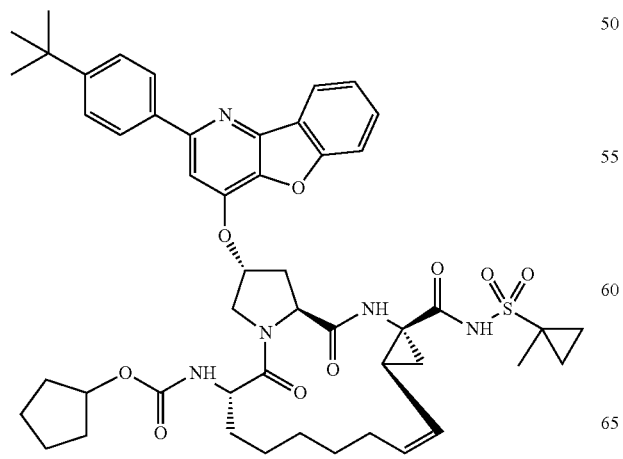
Compound 196
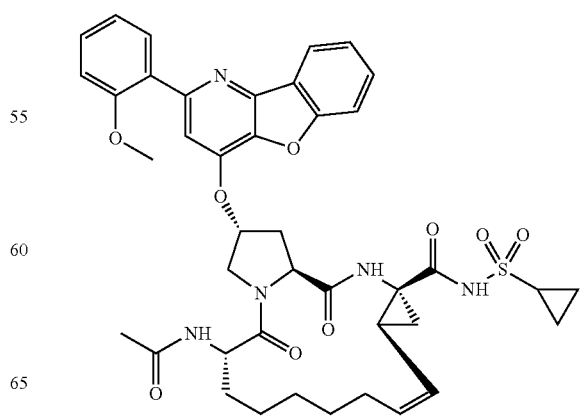

Compound 197
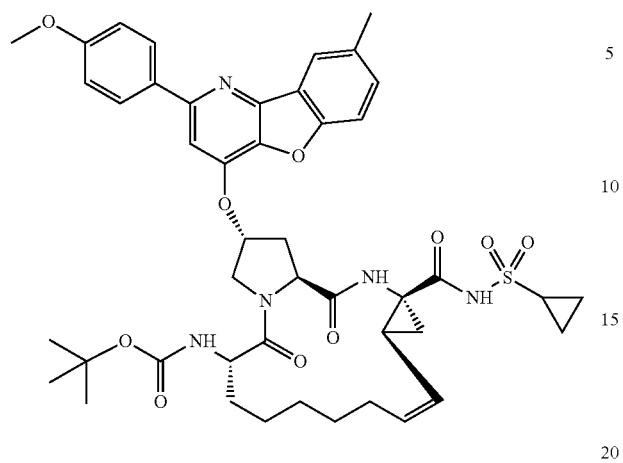
Compound 200
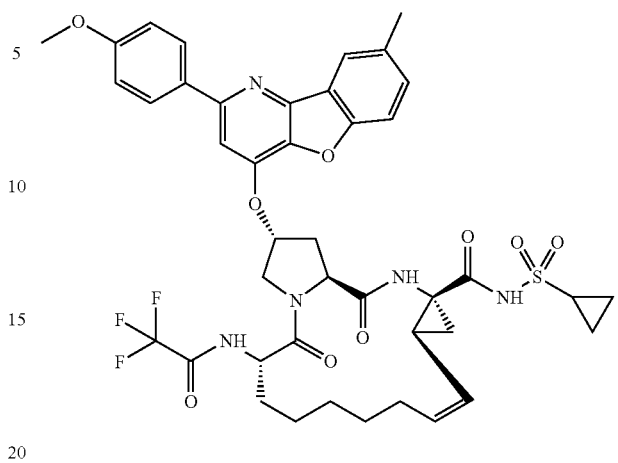
Compound 198
Compound 201
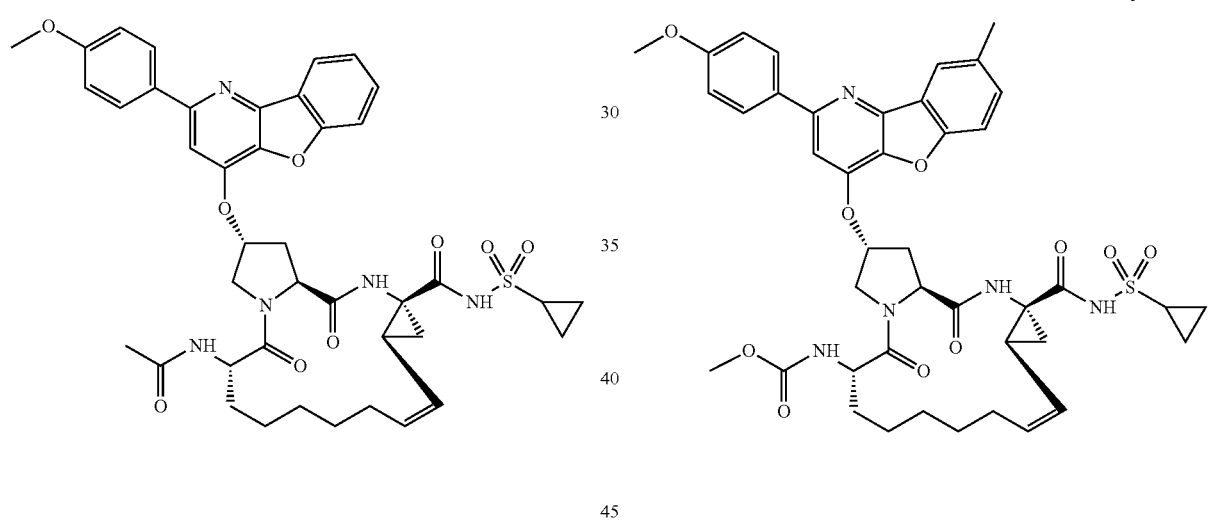
Compound 199
Compound 202
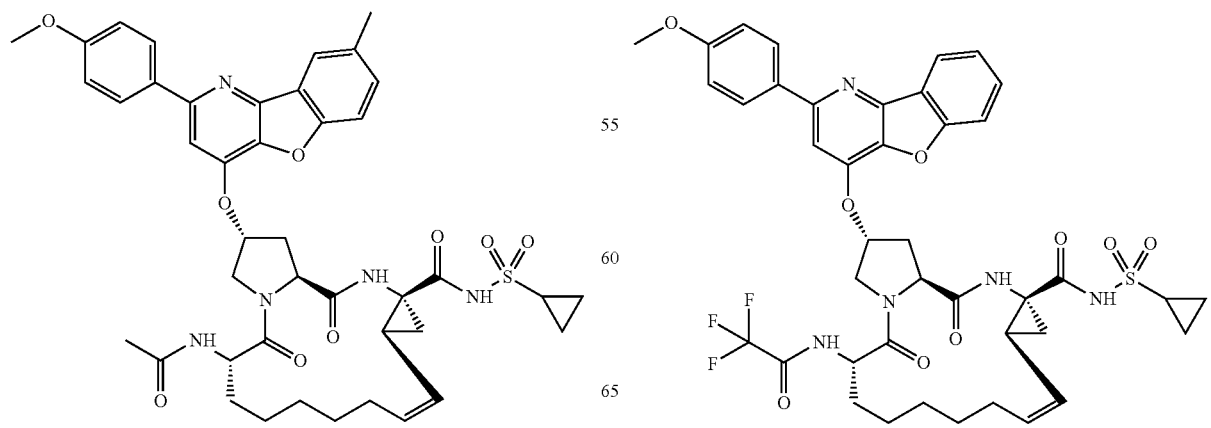

Compound 203
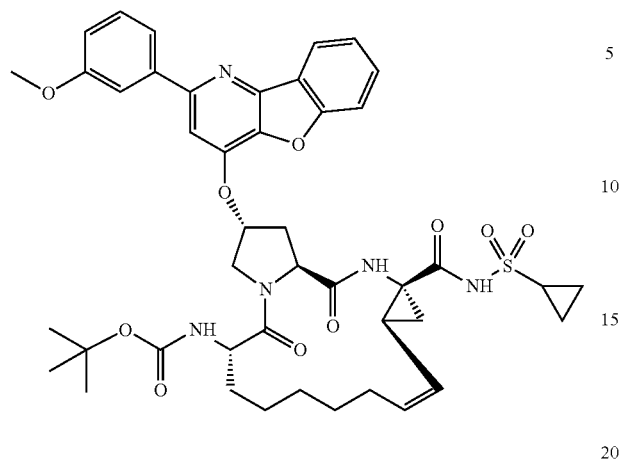
Compound 204
Compound 205
Compound 206
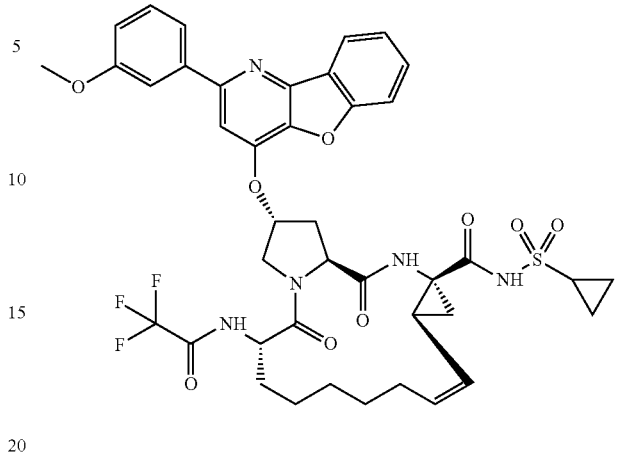
Compound 207
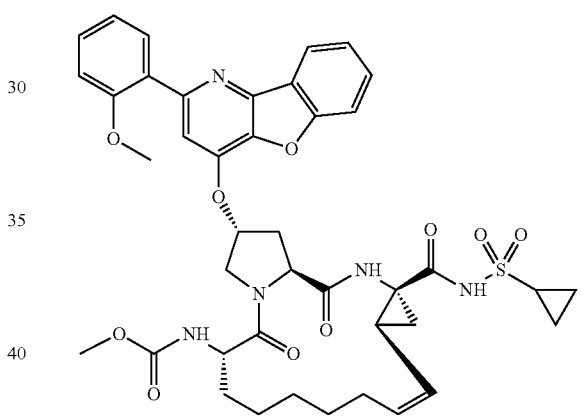
Compound 208
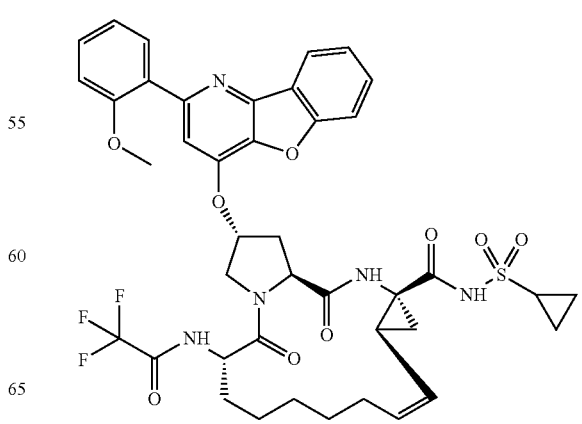

Compound 209
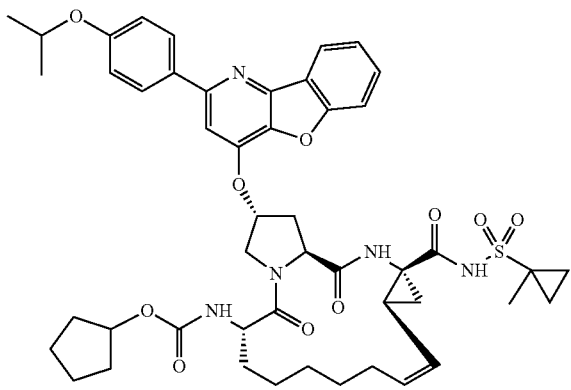
Compound 212
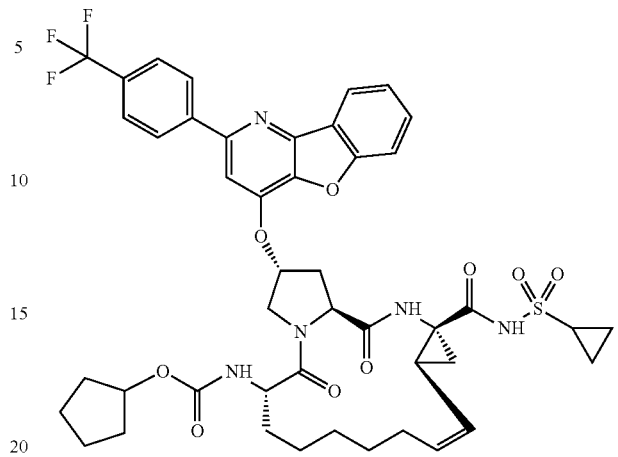
Compound 210
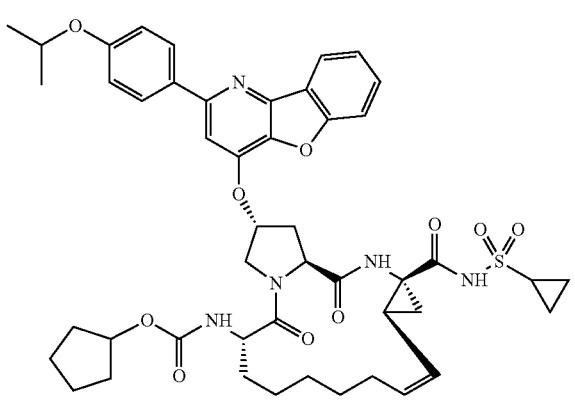
Compound 213
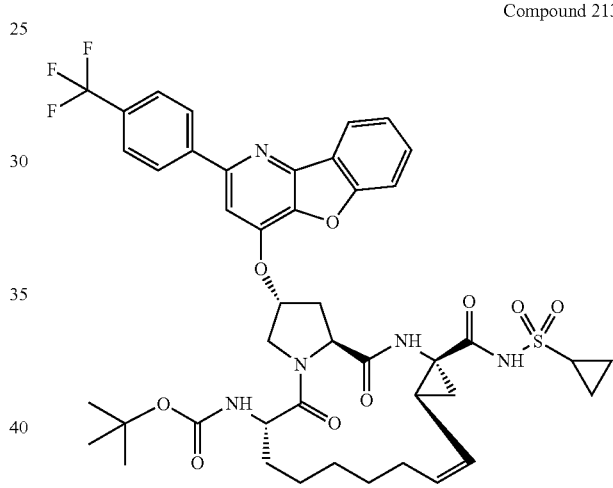
Compound 211
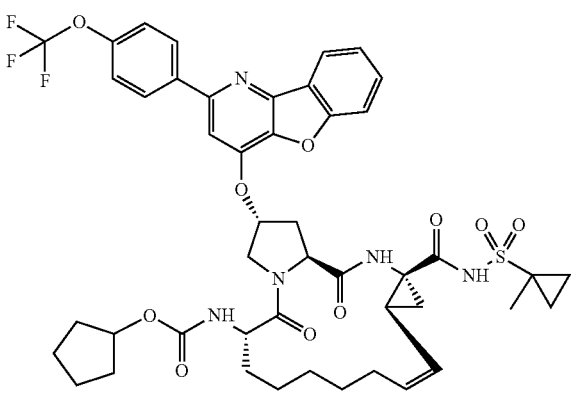
Compound 214
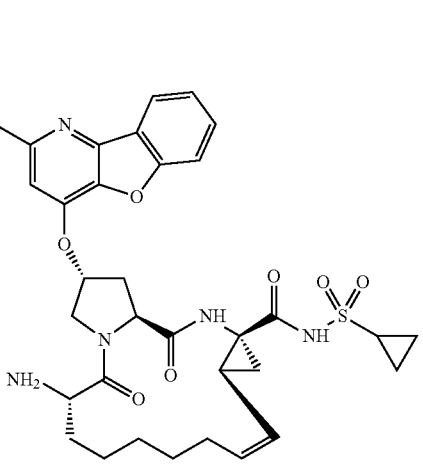

Compound 215
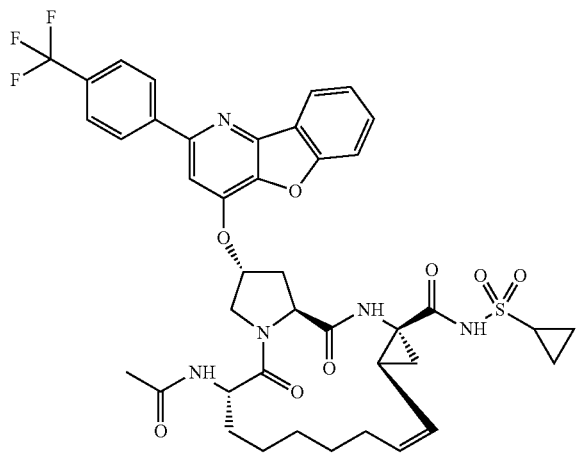
Compound 218
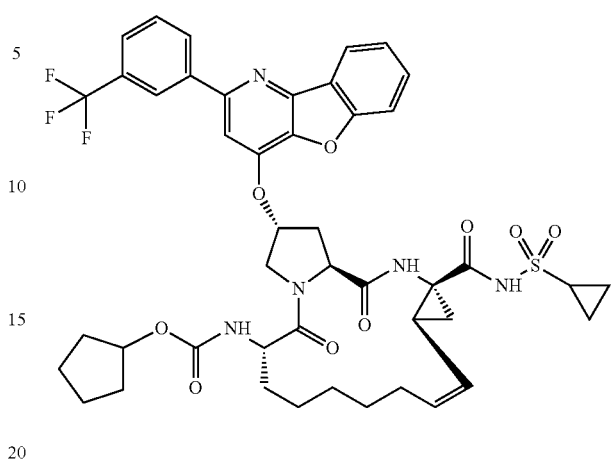
Compound 216
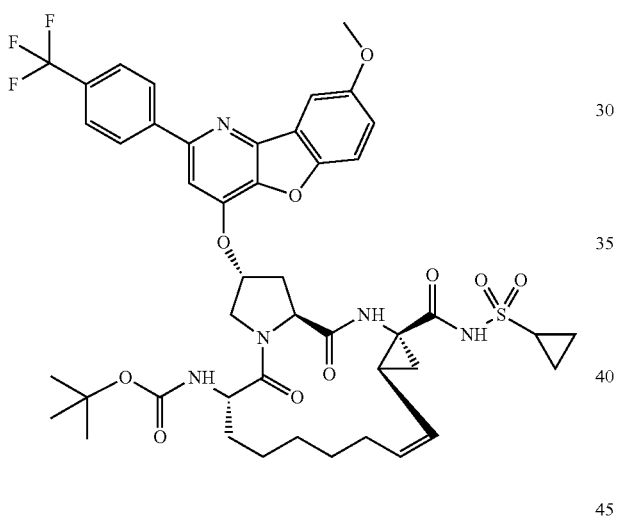
Compound 219
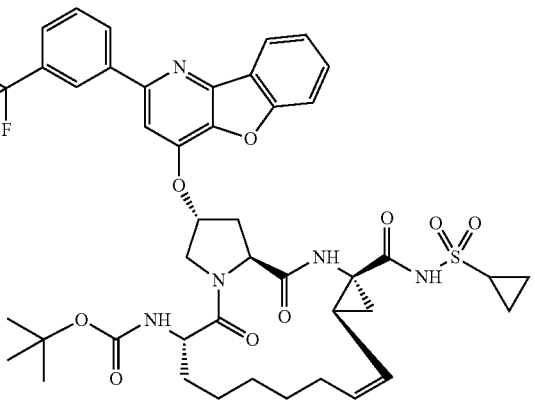
Compound 217
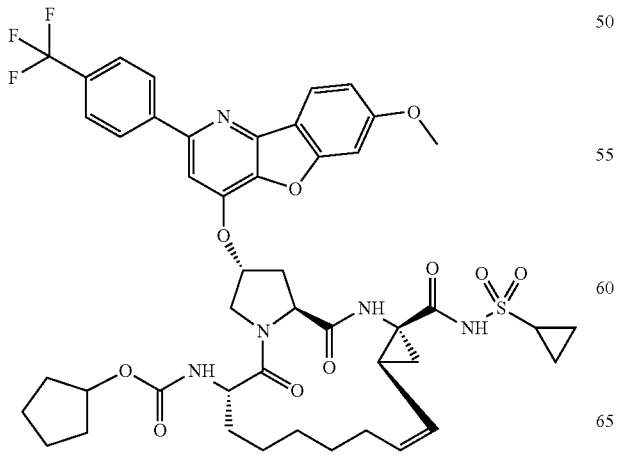
Compound 220
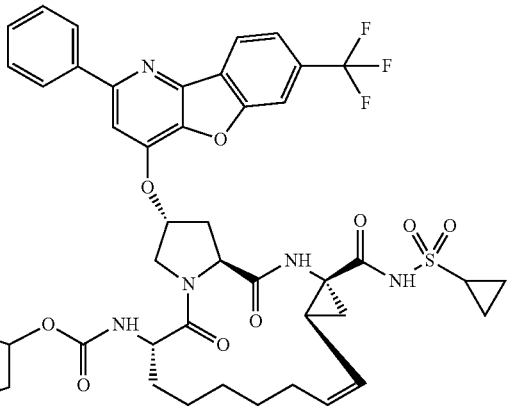

Compound 221
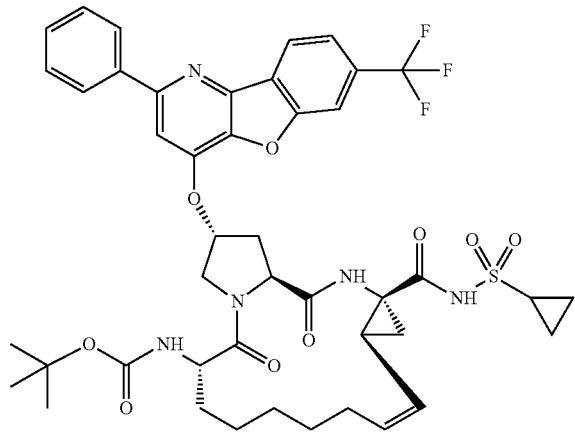
Compound 224
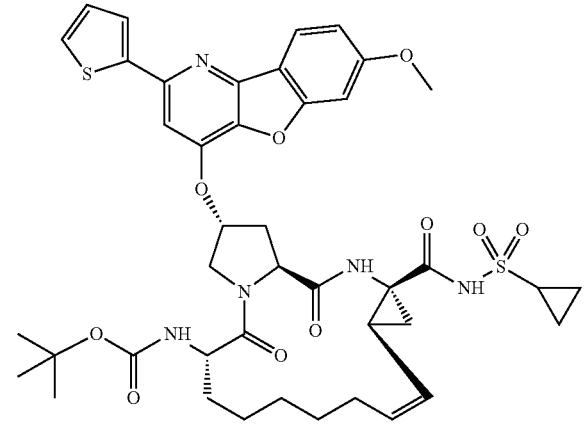
Compound 222
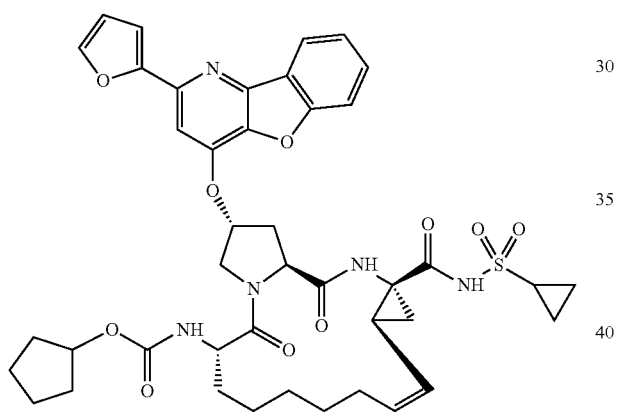
Compound 225
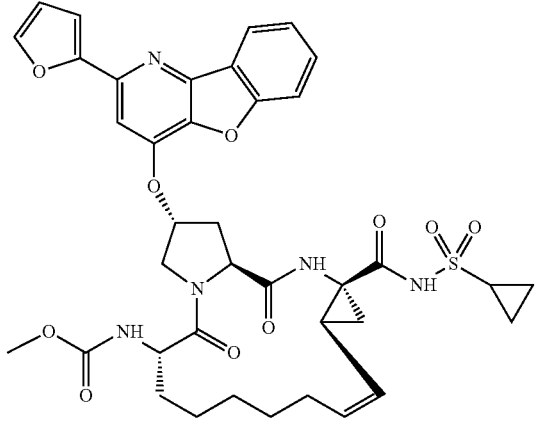
Compound 223
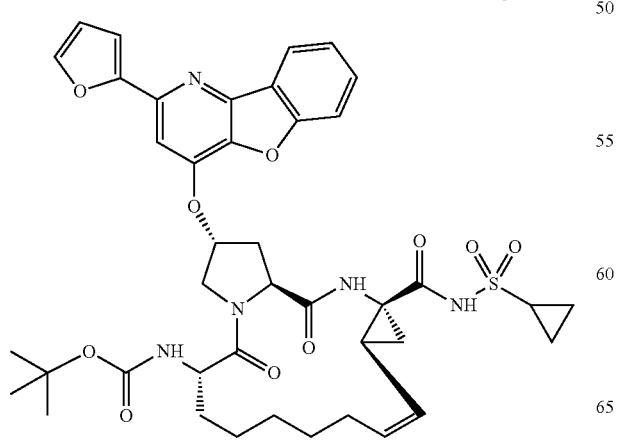
Compound 226
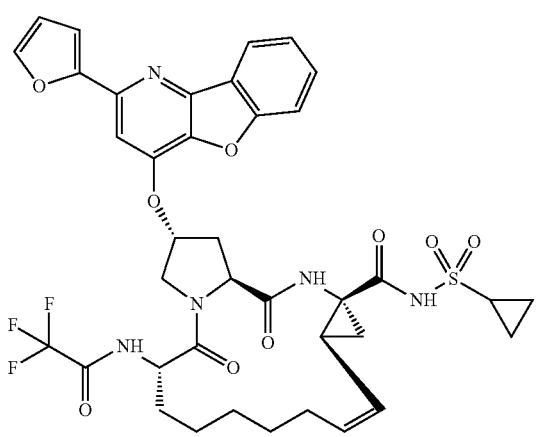

Compound 227
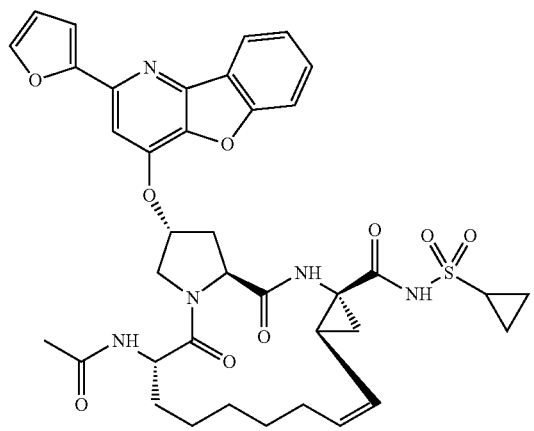
Compound 230
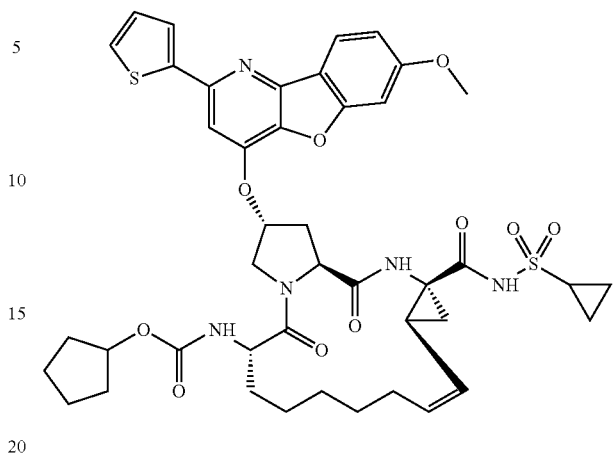
Compound 228
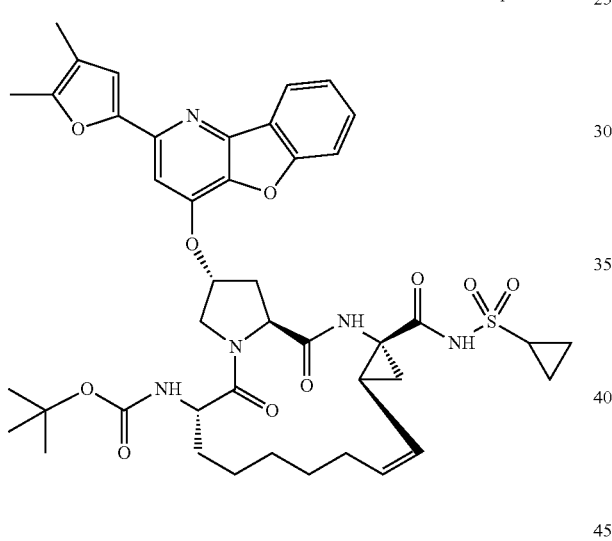
Compound 231
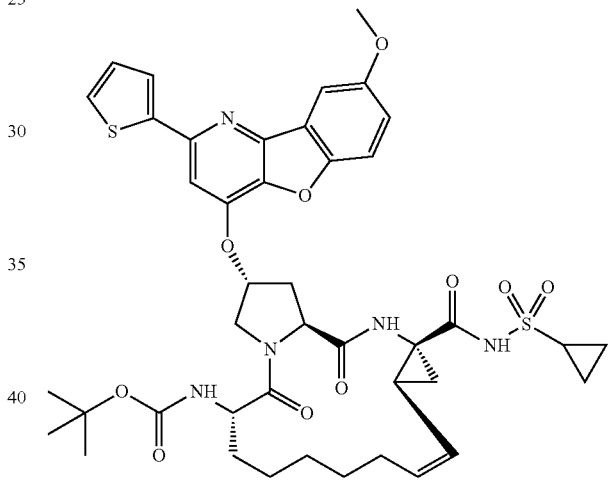
Compound 229
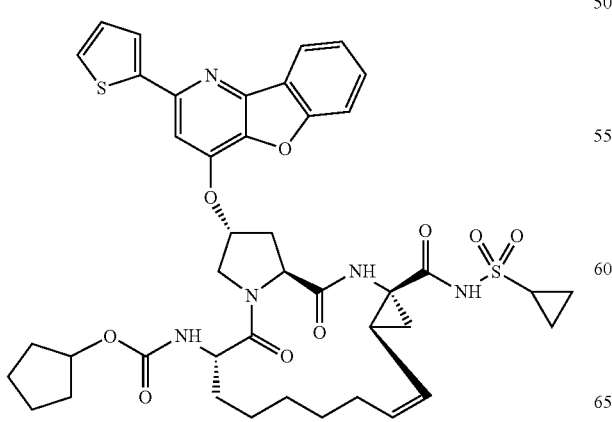
Compound 232
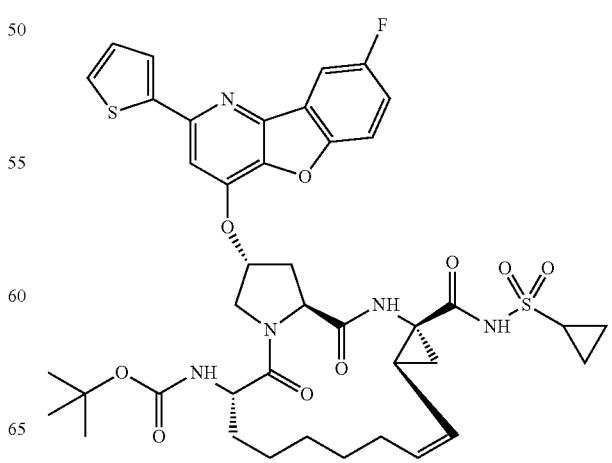

-continued
Compound 233
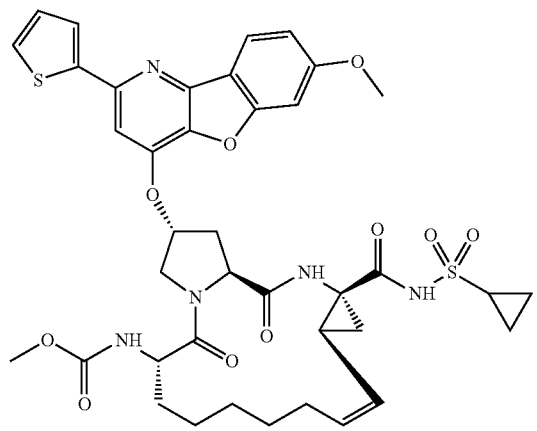
Compound 234
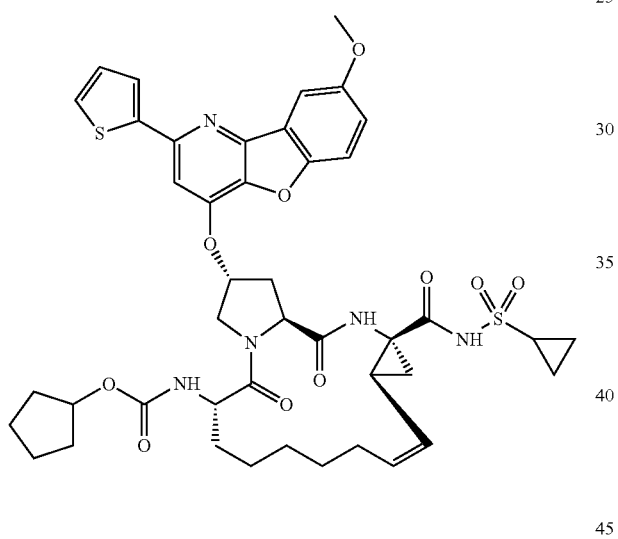
Compound 235
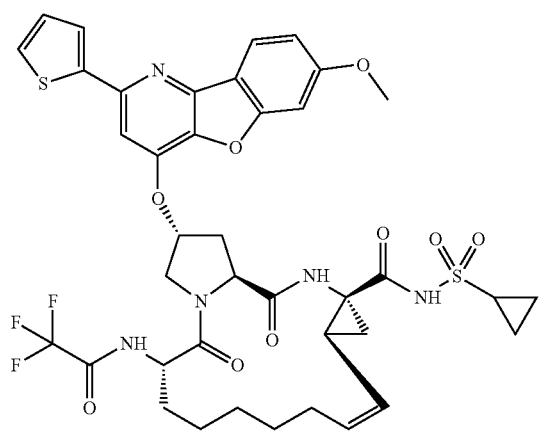
-continued
Compound 236
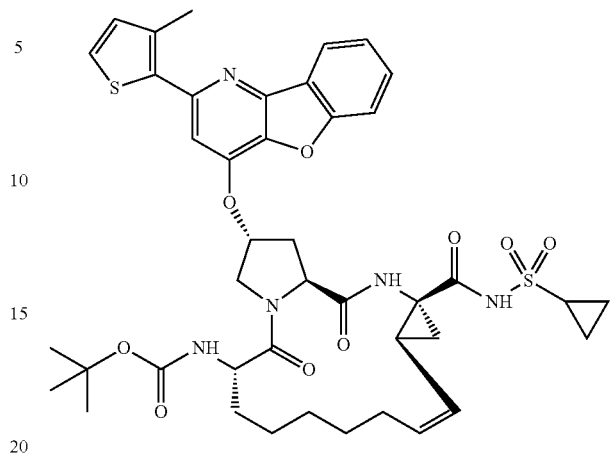
Compound 237
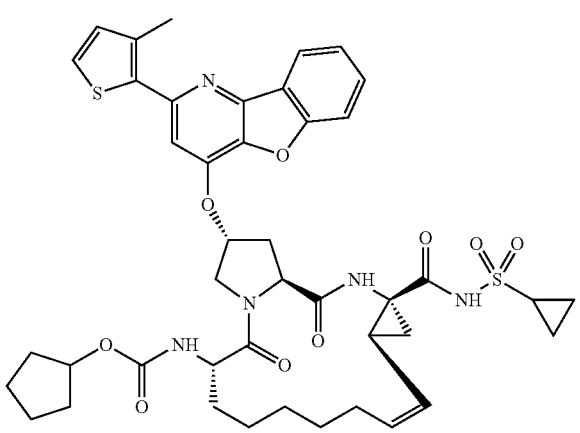
Compound 238
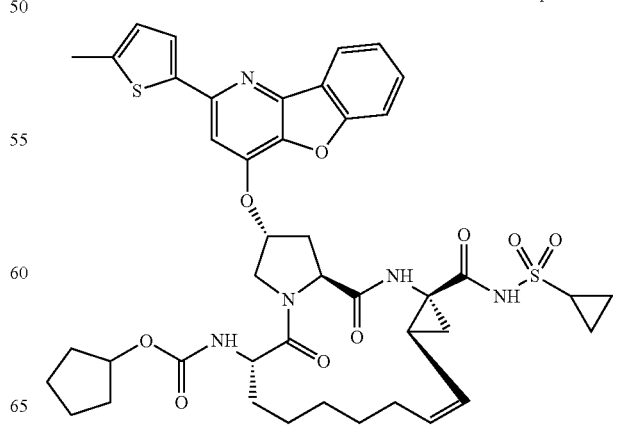

Compound 239
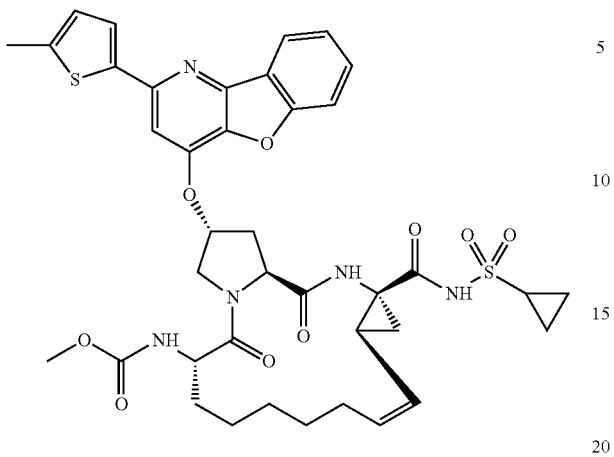
Compound 242
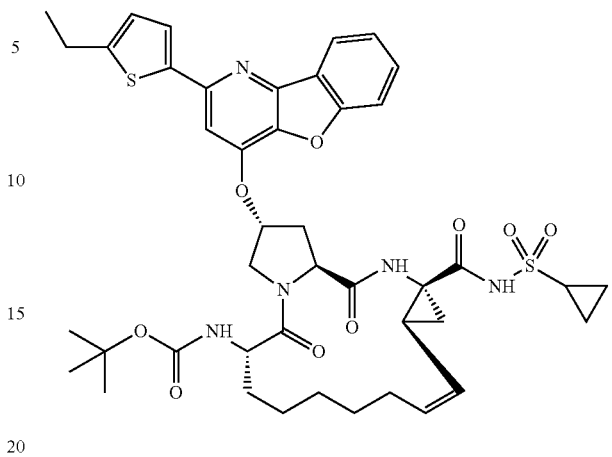
Compound 240
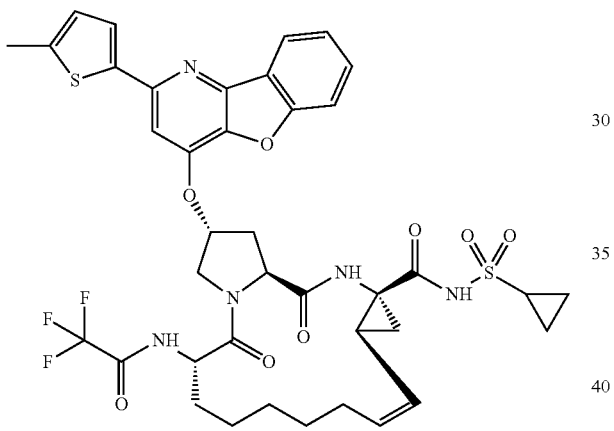
Compound 243
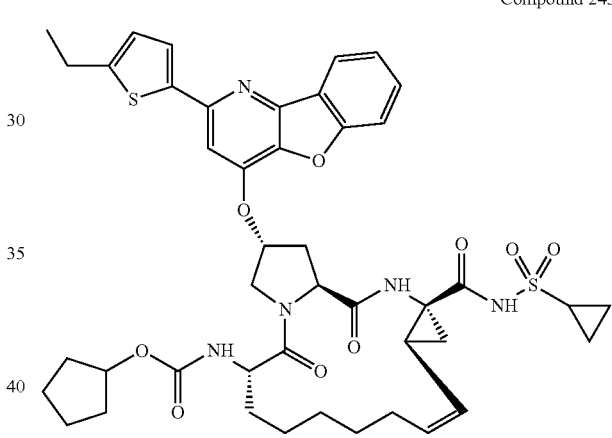
Compound 241
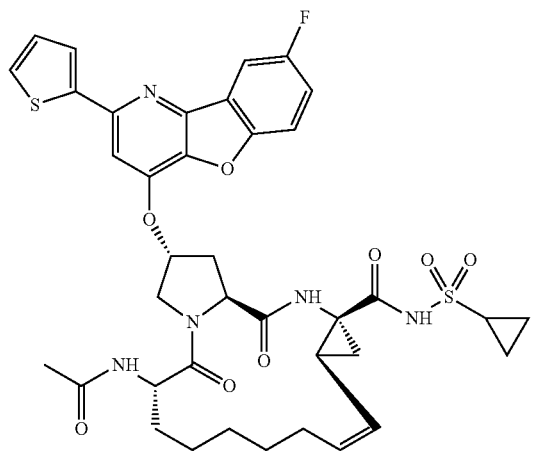
Compound 244
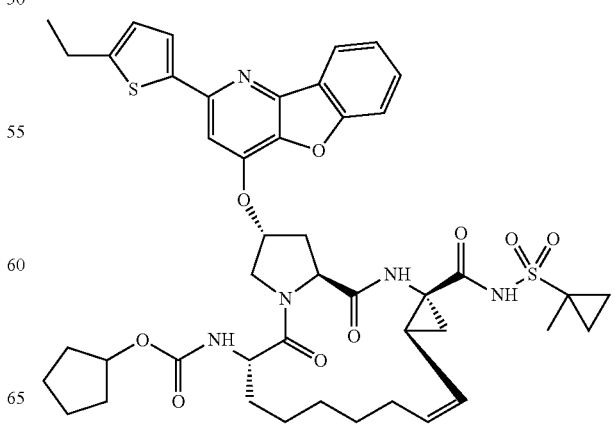

Compound 245
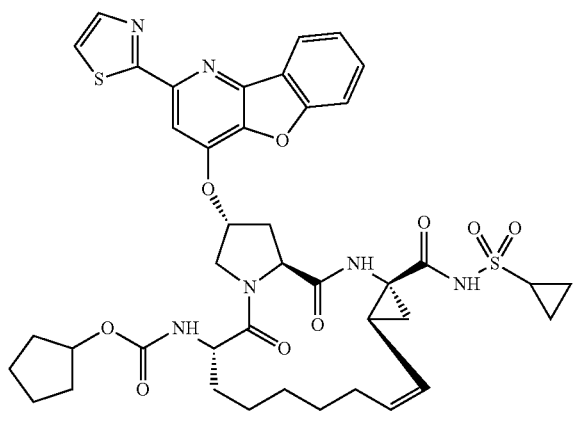
Compound 246
Compound 248
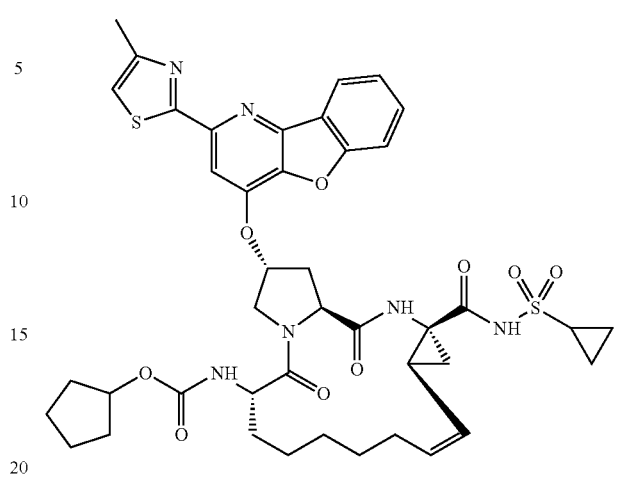
Compound 249
Compound 247
Compound 250
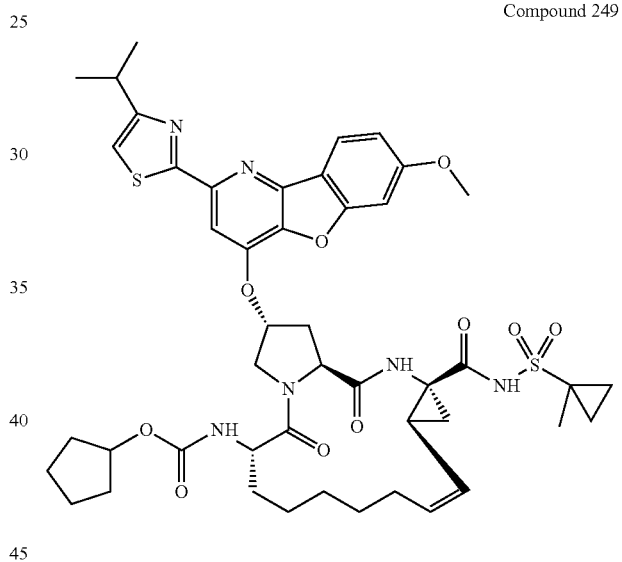
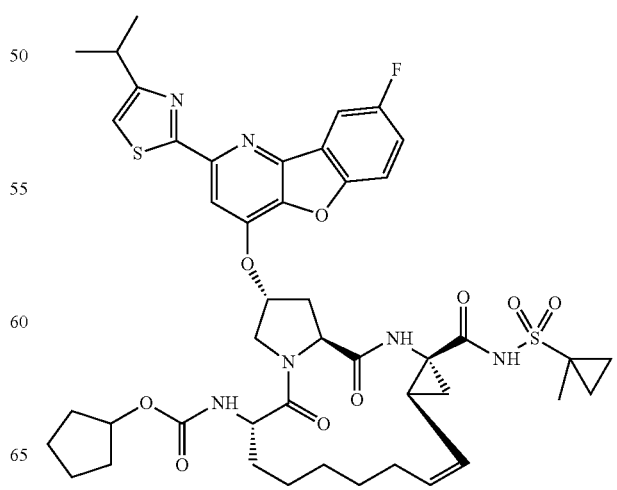

Compound 251
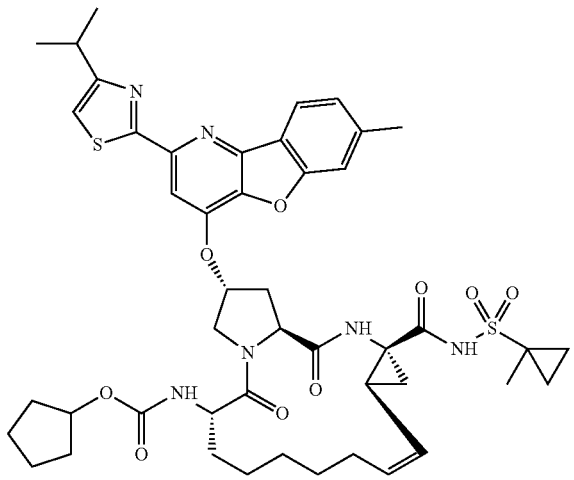
Compound 254
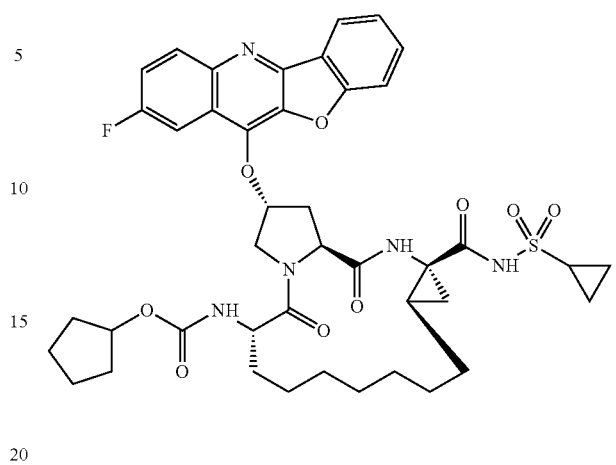
Compound 252
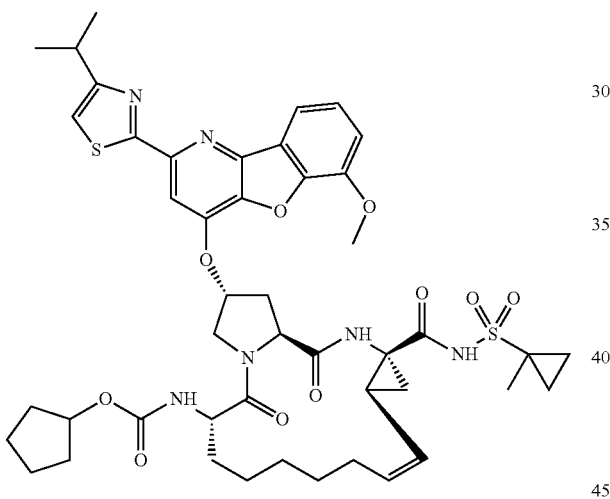
Compound 255
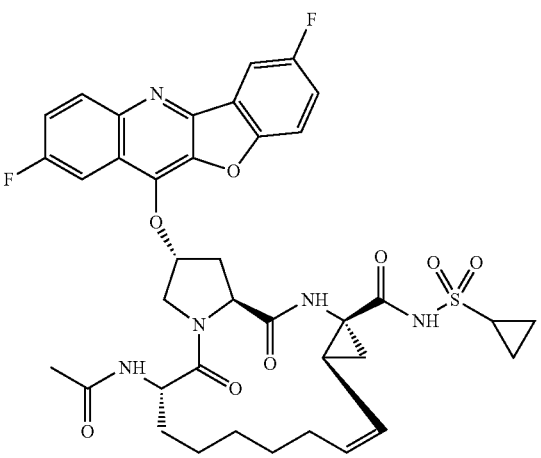
Compound 253
Compound 256
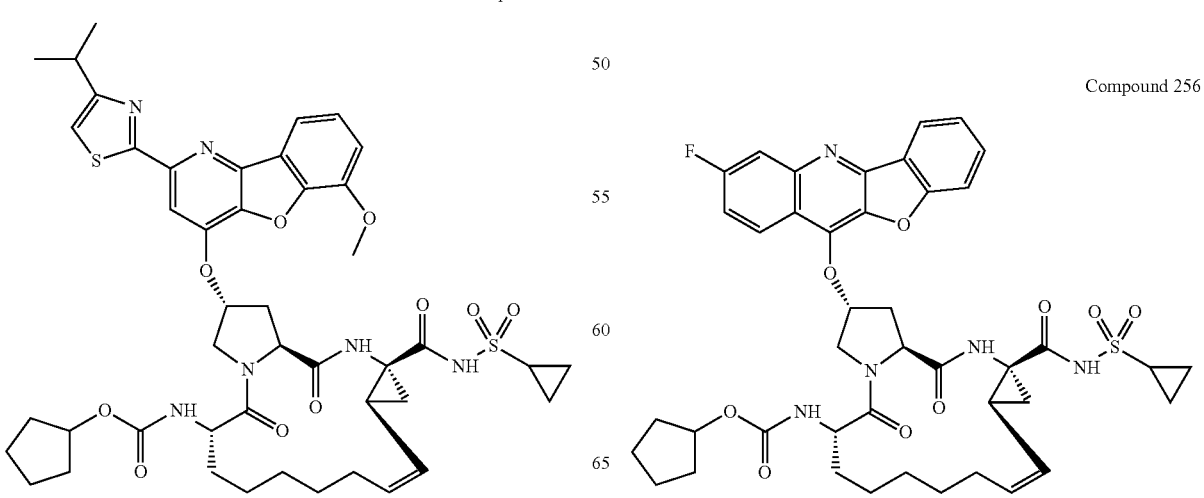

Compound 257
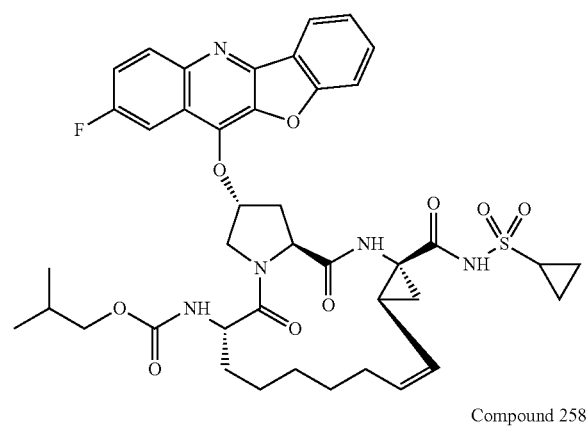
Compound 258
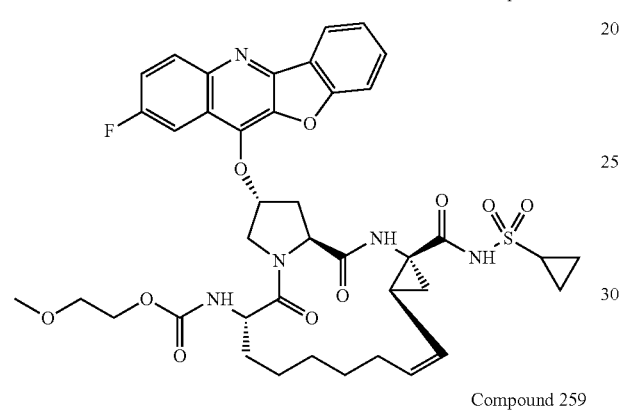
Compound 259
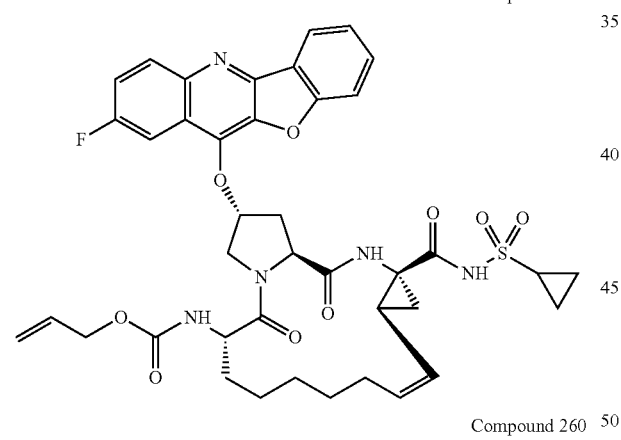
Compound 260
Compound 261
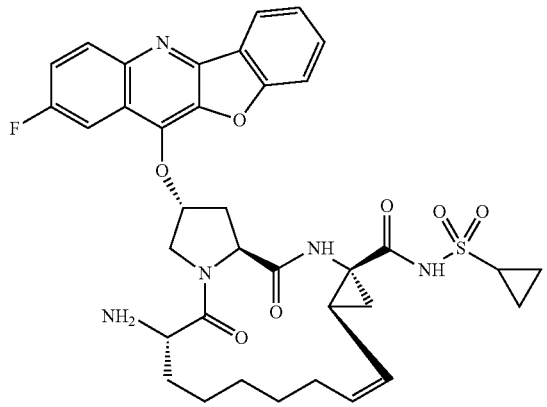
Compound 262
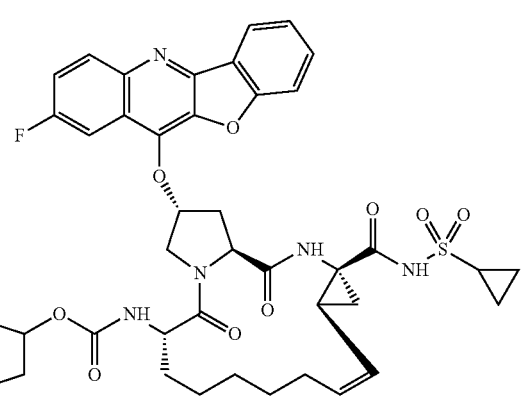
Compound 263
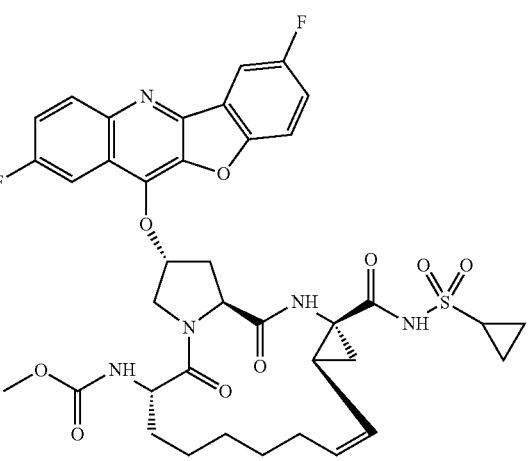

Compound 264
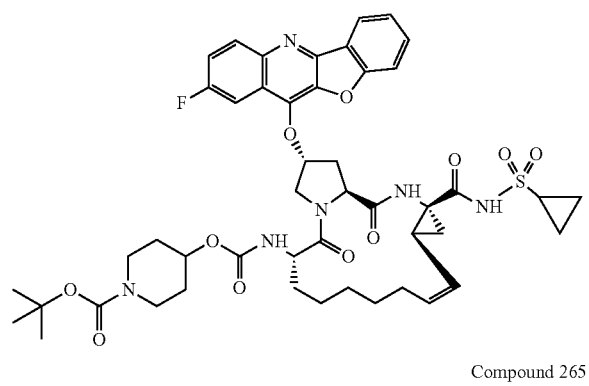
Compound 265
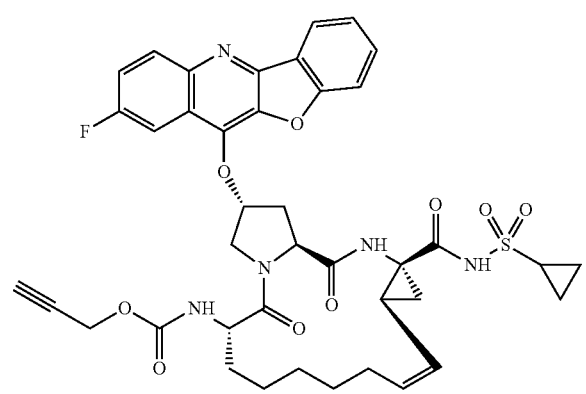
Compound 266
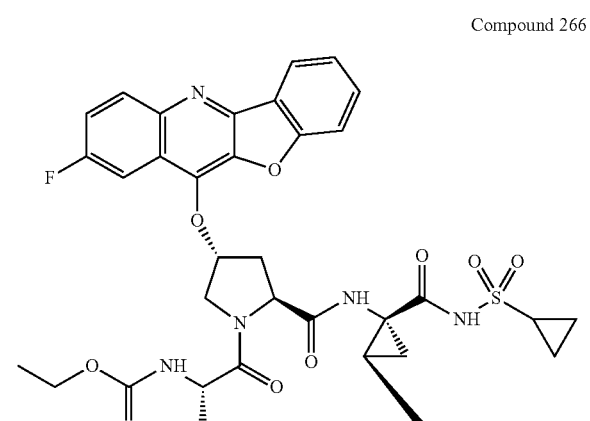
Compound 267
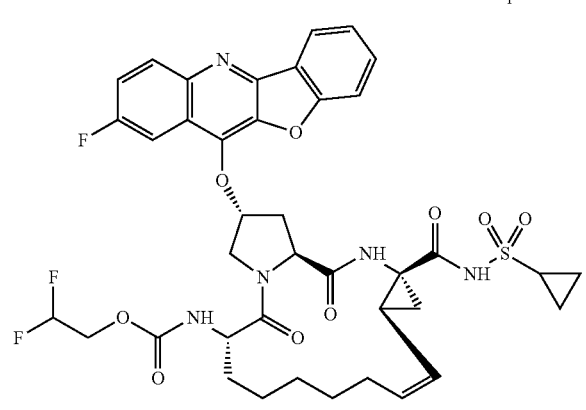
Compound 268
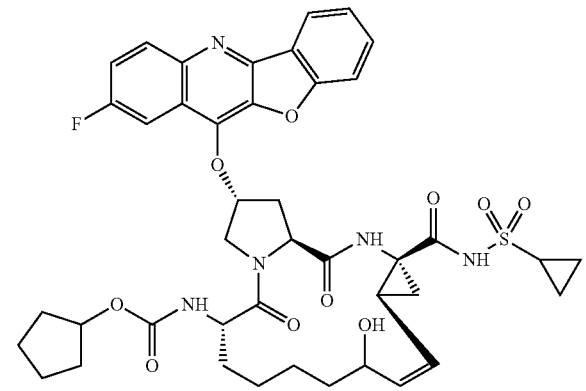
Compound 269
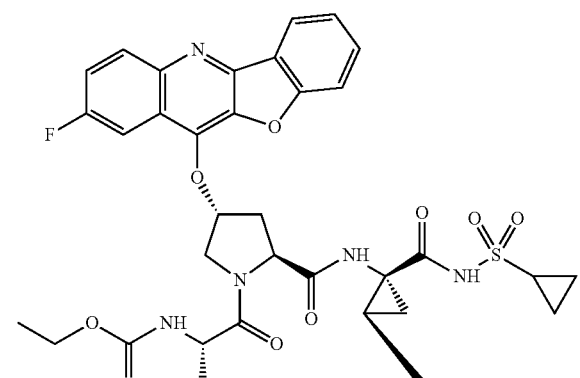
Compound 270
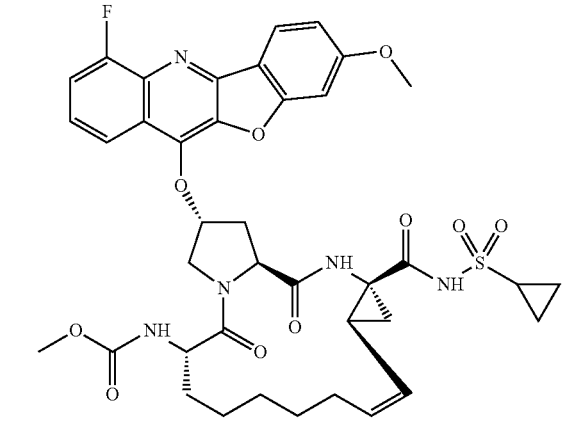

Compound 271
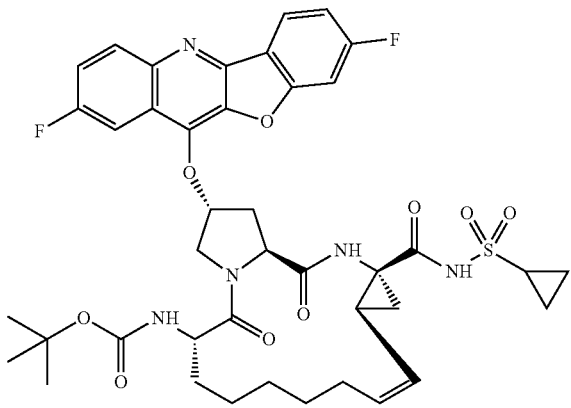
Compound 274
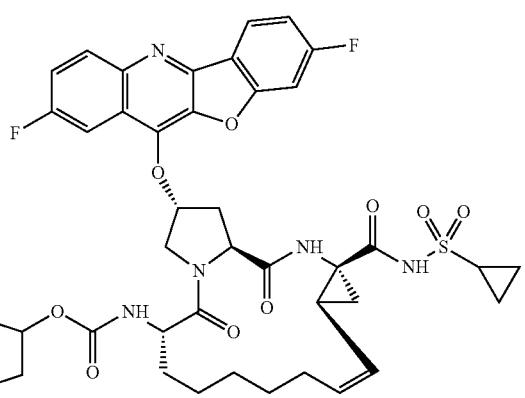
Compound 272
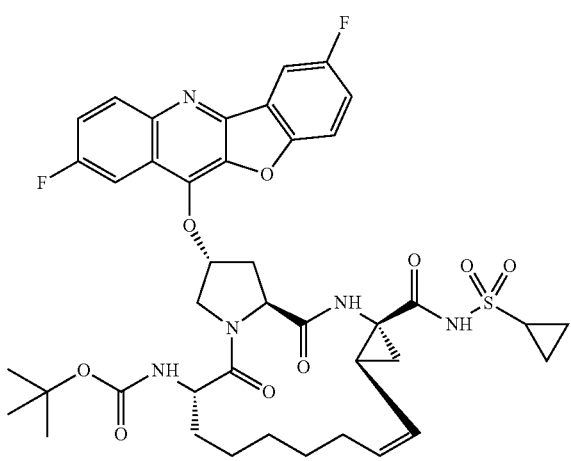
Compound 275
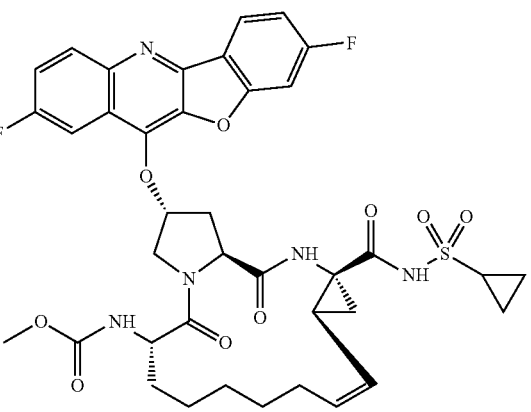
Compound 273
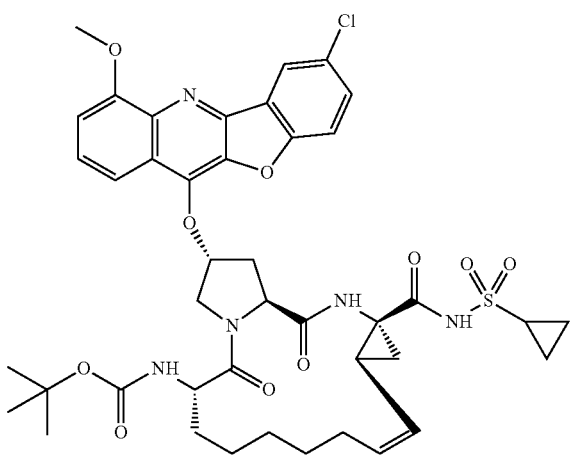
Compound 276
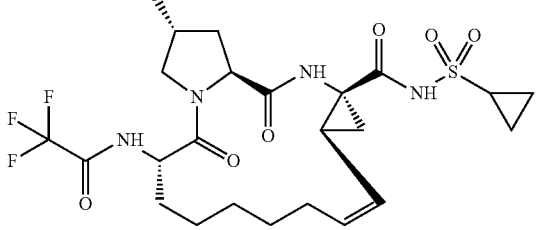

Compound 277

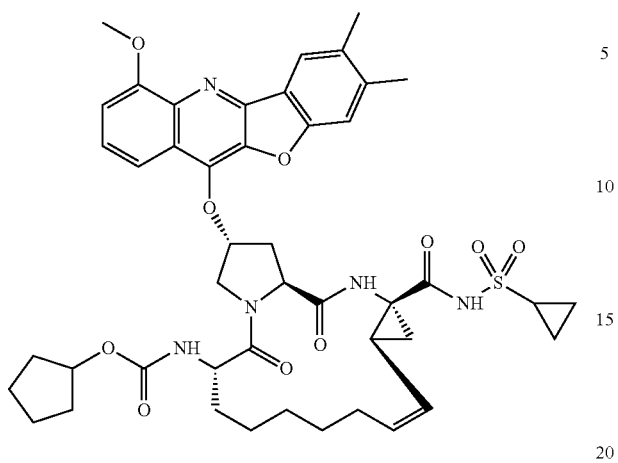

Compound 280

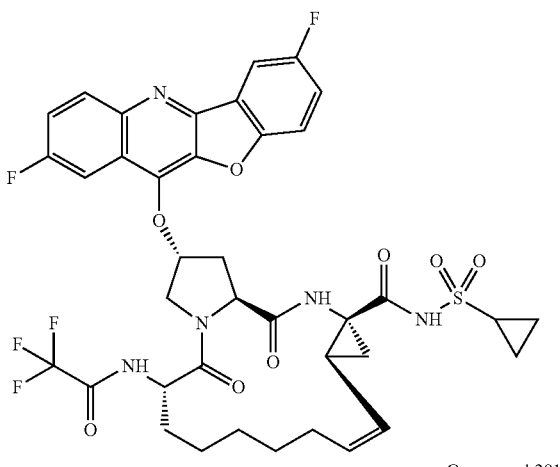

Compound 278

Compound 281

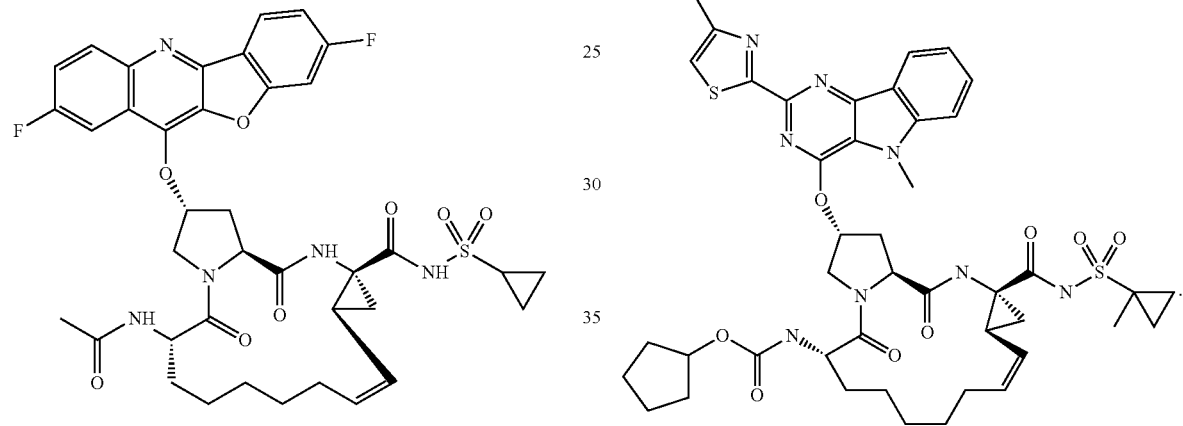

Compound 279

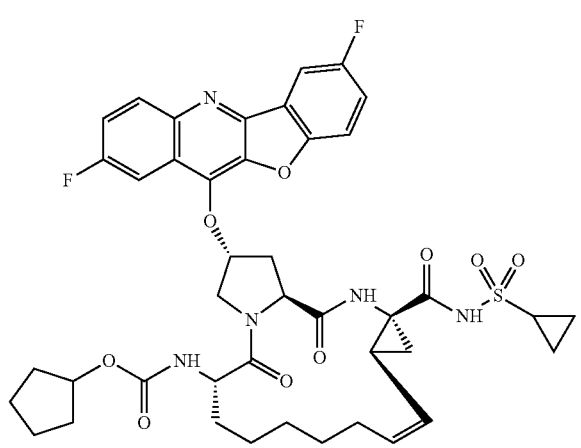

23. A pharmaceutical composition comprising a compound of claim 1 and a pharmaceutically acceptable carrier.

24. A method for treating hepatitis C virus infection, comprising administering to a subject in need thereof a pharmaceutical composition containing an effective amount of a compound of claim 1.

25. The method of claim 24, wherein the composition is administered to the subject once a day.

26. The method of claim 25, wherein the composition is administered orally.

27. The method of claim 24, wherein the compound is one of Compounds 1-281.

28. The compound of claim 22, wherein the compound is one of Compounds 10, 16, 23, 25, 26, 30, 35, 36, 80, 81, 82, 84, 85, 86, 90, 95, 97, 100, 116, and 209.

* * * * *